US006579520B2

(12) United States Patent
Chen et al.

(10) Patent No.: US 6,579,520 B2
(45) Date of Patent: Jun. 17, 2003

(54) IL-17 RELATED MAMMALIAN CYTOKINE POLYPEPTIDES (IL-17E)

(75) Inventors: Jian Chen, Princeton, NJ (US); Ellen Filvaroff, San Francisco, CA (US); Sherman Fong, Alameda, CA (US); Audrey Goddard, San Francisco, CA (US); Paul Godowski, Burlingame, CA (US); Christopher Grimaldi, San Francisco, CA (US); Austin Gurney, Belmont, CA (US); Hanzhong Li, San Mateo, CA (US); Kenneth Hillan, San Francisco, CA (US); Daniel Tumas, Orinda, CA (US); Menno VanLookeren, San Francisco, CA (US); Richard Vandlen, Hillsborough, CA (US); Colin Watanabe, Moraga, CA (US); P. Mickey Williams, Half Moon Bay, CA (US); William I. Wood, Hillsborough, CA (US); Daniel Yansura, Pacifica, CA (US)

(73) Assignee: Genentech, Inc., South San Francisco ( * ) Notice: Subject to any disclaimer, the term of this patent is extended or adjusted under 35 U.S.C. 154(b) by 0 days.

(21) Appl. No.: 09/816,744

(22) Filed: Mar. 22, 2001

(65) Prior Publication Data

US 2003/0003546 A1 Jan. 2, 2003

Related U.S. Application Data

(63) Continuation-in-part of application No. 09/311,832, filed on May 14, 1999.
(60) Provisional application No. 60/253,646, filed on Nov. 28, 2000, provisional application No. 60/244,072, filed on Oct. 26, 2000, provisional application No. 60/242,837, filed on Oct. 24, 2000, provisional application No. 60/213,807, filed on Jun. 22, 2000, provisional application No. 60/191,007, filed on Mar. 21, 2000, provisional application No. 60/175,481, filed on Jan. 11, 2000, provisional application No. 60/172,096, filed on Dec. 23, 1999, provisional application No. 60/138,387, filed on Jun. 9, 1999, provisional application No. 60/134,287, filed on May 14, 1999, provisional application No. 60/131,022, filed on Apr. 26, 1999, provisional application No. 60/130,232, filed on Apr. 21, 1999, provisional application No. 60/113,621, filed on Dec. 23, 1998, and provisional application No. 60/085,579, filed on May 15, 1998.

(51) Int. Cl.[7] ............................................... A61K 45/05

(52) U.S. Cl. ................... 424/85.2; 530/351; 530/387.3; 435/69.7

(58) Field of Search ................... 530/351; 424/85.2; 435/69.7

(56) References Cited

U.S. PATENT DOCUMENTS 5,536,637 A 7/1996 Jacobs

FOREIGN PATENT DOCUMENTS

| WO | WO96/29408 | * | 9/1996 | |
| WO | WO 98/49310 | | 11/1998 | |
| WO | WO 99/03982 | | 1/1999 | |
| WO | WO 99/61617 | | 2/1999 | |
| WO | WO9/14240 | * | 3/1999 | |
| WO | WO 99/32632 | | 7/1999 | |
| WO | WO 99/35267 | | 7/1999 | |
| WO | WO99/46281 | * | 9/1999 | |
| WO | WO99/60127 | * | 11/1999 | |
| WO | WO 00/42187 | * | 7/2000 | ........... C12N/15/24 |
| WO | WO00/53752 | * | 9/2000 | |
| WO | WO00/70050 | * | 11/2000 | |
| WO | WO00/73452 | * | 12/2000 | |

OTHER PUBLICATIONS

Aarvak et al., "IL–17 Is Produced by Some Proinflammatory Th1/Th0 Cells but not by Th2 Cells" *Journal of Immunology* 162:1246–1251 (1999).

Albanesi et al., "IL–17 Is produced by Nickel–Specific T Lymphocytes and Regulates ICAM–1 Expression and Chemokine Production in Human Keratinocytes: Synergistic or Antagonist Effects with IFN–γ and TNF–α" *Journal of Immunology* 162:494–502 (1999).

Altschul et al., "Local alignment statistics" *Methods in Enzymology* 266:460–480 (1996).

Antonysamy et al., "Evidence for a role of IL–17 in organ allograft rejection: IL–17 promotes the functional differentiation of dendritic cell progenitors" *J. Immunol.* 162(1):577–584 (1999).

Antonysamy, M.A. et al., "Evidence for a role of IL–17 in alloimmunity: a novel IL–17 antagonist promotes heart graft survival" *Transplant Proc.* 31(1–2) :93 (1999).

Ashok et al., "The role of nitric oxide in articular cartilage breakdown in osteoarthritis" *Current Opinion in Rheumatology* 10(3):263–268 (1998).

Attur et al., "Interleukin–17 Up–Regulation of Nitric Oxide Production in Human Osteoarthritis Cartilage" *Arthritis and Rheumatism* 40(6):1050–1053 (Jun. 1997).

(List continued on next page.)

Primary Examiner—Lorraine Spector
Assistant Examiner—Dong Jiang
(74) Attorney, Agent, or Firm—Elizabeth M. Barnes

(57) ABSTRACT

The present invention is directed to novel polypeptides having sequence identity with IL-17, IL-17 receptors and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention. Further provided herein are methods for treating degenerative cartilaginous disorders and other inflammatory diseases.

8 Claims, 48 Drawing Sheets

OTHER PUBLICATIONS

BLAST Results A–1—A–1 (Dayhoff).

BLAST Results B–1—B–10 (Dayhoff).

Biesinger et al., "Stable growth transformation of human T lymphocytes by *Herpesvirus saimiri*" *Proc. Natl. Acad. Sci. USA* 89:3116–3119 (Apr. 1992).

Broxmeyer, H.E., "Is Interleukin 17, An Inducible Cytokine That Stimulates Production of Other Cytokines, Merely a Redundant Player in a Sea of Other Biomolecules?" *Journal of Experimental Medicine* 183:2411–2415 (Jun. 1996).

Chabaud et al., "Enhancing Effect of IL–17 on IL–1–Induced IL–6 and Leukemia Inhibitory Factor Production by Rheumatoid Arthritis Synoviocytes and Its Regulation by Th2 Cytokines" *Journal of Immunology* 161:409–414 (1998).

Chabaud et al., "Human Interleukin–17: A T Cell–Derived Proinflammatory Cytokine Produced by the Rheumatoid Synovium" *Arthrtis & Rheumatism* 42(5):963–970 (1999).

Farndale et al., "Improved quantitation and discrimination of sulphated glycosaminoglycans by use of dimethylmethylene Blue" *Biochem. Biophys. Acta* 883:173–177 (1986).

Fleckenstein adn Desrosiers, "*Herpesvirus saimiri* and *Herpesvirus ateles*" In the Herpesviruses, I.B. Roizman, ed., NY:Plenum Publishing Press pp. 253–332 (1982).

Fossiez et al., "Interleukin–17" *Int. Rev. Immunol.* 16(5–6):541–551 (1998).

Fossiez et al., "T Cell Interleukin–17 Induces Stromal Cells to Produce Proinflammatory and Hematopoietic Cytokines" *Journal of Experimental Medicine* 183(6):2593–2603 (Jun. 1996).

Gordon et al., "Molecular immunobiology of macrophages: recent progress" *Current Opinion in Immunology* 7:24–33 (1995).

Gurney et al., "Identification of a new member of the tumor necrosis factor family and its receptor, a human ortholog of mouse GITR" *Current Biology* 9(4):215–218 (Feb. 25, 1999).

Hillier et al., "af37c02.s1 Soares total fetus Nb2HF8 9w *Homo sapiens* cDNA clone 1033826 3'" (Accession No. AA780147) (Feb. 6, 1998).

Hillier et al., "zf01f09.s1 Soares fetal heart NbHH19W *Homo sapiens* cDNA clone 375689 3'" (Accession No. AA033733) (Feb. 4, 1997).

"Isolation of Mouse Mononuclear Cells" *Current Protocols in Immunology*, Coligan et al. eds., John Wiley & Sons, Inc. vol. 1:unit 3.1.2 (1993).

Jovanovic et al., "IL–17 Stimulates the Production and Expression of Proinflammatory Cytokines, IL–β and TNF–α, by Human Macrophages" *J. Immunol* 160:3513–3521 (1998).

Kennedy et al., "Mouse IL–17: A Cytokine preferentially Expressed by αβTCR+CD4–CD8– T Cells" *Journal of Interferon and Cytokine Research* 16(8):611–617 (1996).

Klein et al., "Selection for Genes Encoding Secreted proteins and Receptors" *Proc. Natl. Acad. Sci. USA* 93(14):7108–7113 (1996).

Kotake et al., "IL–17 in synovial fluids from patients with rheumatoid arthritis is a potent stimulator of osteoclastogenesis" *Journal of Clinical investigation* 103(9):1345–1352 (1999).

Lennon et al., "The I.M.A.G.E. Consortium: An Integrated Molecular Analysis of Genomes and Their Expression" *Genomics* (Article #0177) 33:151–152 (1996).

Li et al., "Cloning and characterization of the IL–17B and IL–17C two new members of the IL–17 cytokine family" *Proc. Natl. Acad. Sci. USA* 97(2):773–778 (2000).

Lotz et al., "IL–17 Promotes Cartilage Degradation" *Cytokines* (ACR Abstract Session 10, Oct. 19, 1996, abstract #559) pp. S120 (1996).

March et al., "Cloning, sequence and expression of two distinct human interleukin–1 complementary DNAs" *Nature* 315:641–647 (Jun. 20, 1985).

Martel–Pelletier et al., "Major Signaling Pathways Involved in the IL–17 Induced Nitric Oxide (NO) Production in Human Osteoarthritic Chondrocytes" *Orthopaedic Research Society* (45th Annual Meeting, Feb. 1–4, 1999, pt 2) 24:595 (1999).

Matusevicius et al., "Interleukin–17 mRNA expression in blood and CSF mononuclear cells is augmented in multiple sclerosis" *Multiple Sclerosis* 5:101–104 (1999).

Nielsen et al., "Identification of prokaryotic and eukaryotic signal peptides and prediction of their cleavage sites" *Protein Engineering* 10(1):1–6 (1997).

Rouvier et al., "CTLA–8, Cloned from an Activated T Cell, Bearing AU–Rich Messenger RNA Instability Sequences, and Homologous to a Herpesvirus Saimiri Gene" *Journal of Immunology* 150(12):5445–5456 (Jun. 15, 1993).

Schwarzenberger et al., "IL–17 Stimulates Granulopoiesis in Mice: Use of an Alternate, Novel Gene Therapy–Derived Method for In Vivo Evaluation of Cytokines" *Journal of Immunology* 161:6383–6389 (1998).

Seow, H.F., "Pathogen interactions with cytokines and host defence: an overview" *Vet Immunol. Immunopathol.* 63(1–2):139–148 (1998).

Shalom–Barak et al., "Interleukin–17–induced Gene Expression in Articular Chondrocytes is Associated with Activation of Mitogen–activated Protein Kinases and NF–κB" *Journal of Biological Chemistry* 273(42):27467–27473 (Oct. 16, 1998).

Spencer et al., "The orphan receptor CRF2–4 is an essential subunit of the interleukin 10 receptor" *Journal of Experimental Medicine* 187(4):571–578 (Feb. 16, 1998).

Spriggs, M.K., "Interleukin–17 and Its Receptor" *Journal of Clinical immunology* 17(5):366–369 (1997).

Van Bezooijen et al., "Interleukin–17: A New Bone Acting Cytokine In Vitro" *Journal of Bone and Mineral Research* 14(9):1513–1521 (1999).

Xie et al., "FGF–19, a novel fibroblast growth factor with unique specificity for FGFR4" *Cytokine* 11(10):729–735 (1999).

Xie et al., "Interleukin (IL)–22, a Novel Human Cytokine That Signals through the Interferon Receptor–related proteins CRF2–4 and IL–22R" *Journal of Biological Chemistry* 275(40):31335–31339 (2000).

Yao et al., "Herpesvirus Saimiri Encodes a New Cytokine, IL–17, which Binds to a Novel Cytokine Receptor" *Immunity* 3:811–821 (Dec. 1995).

Yao et al., "Human IL–17: A Novel Cytokine Derived from T Cells" *Journal of Immunology* 155(12):5483–5486 (1995).

Yao et al., "Molecular Characterization of the Human Interleukin (IL)–17 Receptor" *Cytokine* 9(11):794–800 (Nov. 1997).

von Heinje, G., "A new method for predicting signal sequence cleavage sites" *Nucl. Acids. Res.* 14(11):4683–4690 (1986).

Shi, "A novel cytokine receptor–ligand pair: identification, molecular characterization and in vivo immunomodulatory activity" *Journal of Biological Chemistry, American Society of Biological Chemists*, Baltimore 275(25):19167–19176 (Jun. 23, 2000).*

* cited by examiner

FIGURE 1

AGGCGGGCAGCAGCTGCAGGCTGACCTTGCAGCTTGGCGGAATGGACTGGCCTCACAACCTGCTGTTTCTT
CTTACCATTTCCATCTTCCTGGGGCTGGGCCAGCCCAGGAGCCCCAAAAGCAAGAGGAAGGGGCAAGGGCG
GCCTGGGCCCCTGGCCCCTGGCCCTCACCAGGTGCCACTGGACCTGGTGTCACGGATGAAACCGTATGCCC
GCATGGAGGAGTATGAGAGGAACATCGAGGAGATGGTGGCCCAGCTGAGGAACAGCTCAGAGCTGGCCCAG
AGAAAGTGTGAGGTCAACTTGCAGCTGTGGATGTCCAACAAGAGGAGCCTGTCTCCCTGGGGCTACAGCAT
CAACCACGACCCCAGCCGTATCCCCGTGGACCTGCCGGAGGCACGGTGCCTGTGTCTGGGCTGTGTGAACC
CCTTCACCATGCAGGAGGACCGCAGCATGGTGAGCGTGCCGGTGTTCAGCCAGGTTCCTGTGCGCCGCCGC
CTCTGCCCGCCACCGCCCCGCACAGGGCCTTGCCGCCAGCGCGCAGTCATGGAGACCATCGCTGTGGGCTG
CACCTGCATCTTCTGAATCACCTGGCCCAGAAGCCAGGCCAGCAGCCCGAGACCATCCTCCTTGCACCTTT
GTGCCAAGAAAGGCCTATGAAAAGTAAACACTGACTTTTGAAAGCAAG

FIGURE 2

MDWPHNLLFLLTISIFLGLGQPRSPKSKRKGQGRPGPLAPGPHQVPLDLVSRMKPYARMEEYERNIEEMVA
QLRNSSELAQRKCEVNLQLWMSNKRSLSPWGYSINHDPSRIPVDLPEARCLCLGCVNPFTMQEDRSMVSVP
VFSQVPVRRRLCPPPPRTGPCRQRAVMETIAVGCTCIF

FIGURE 3

```
GCCAGGTGTGCAGGCCGCTCCAAGCCCAGCCTGCCCCGCTGCCGCCACCATGACGCTCCTCCCCGGCCTCC
TGTTTCTGACCTGGCTGCACACATGCCTGGCCCACCATGACCCCTCCCTCAGGGGGCACCCCCACAGTCAC
GGTACCCCACACTGCTACTCGGCTGAGGAACTGCCCCTCGGCCAGGCCCCCCCACACCTGCTGGCTCGAGG
TGCCAAGTGGGGCAGGCTTTGCCTGTAGCCCTGGTGTCCAGCCTGGAGGCAGCAAGCCACAGGGGGAGGC
ACGAGAGGCCCTCAGCTACGACCCAGTGCCCGGTGCTGCGGCCGGAGGAGGTGTTGGAGGCAGACACCCAC
CAGCGCTCCATCTCACCCTGGAGATACCGTGTGGACACGGATGAGGACCGCTATCCACAGAAGCTGGCCTT
CGCCGAGTGCCTGTGCAGAGGCTGTATCGATGCACGGACGGGCCGCGAGACAGCTGCGCTCAACTCCGTGC
GGCTGCTCCAGAGCCTGCTGGTGCTGCGCCGCCGGCCCTGCTCCCGCGACGGCTCGGGGCTCCCCACACCT
GGGGCCTTTGCCTTCCACACCGAGTTCATCCACGTCCCCGTCGGCTGCACCTGCGTGCTGCCCCGTTCAGT
GTGACCGCCGAGGCCGTGGGGCCCCTAGACTGGACACGTGTGCTCCCCAGAGGGCACCCCCTATTTATGTG
TATTTATTGTTATTTATATGCCTCCCCCAACACTACCCTTGGGGTCTGGGCATTCCCCGTGTCTGGAGGAC
AGCCCCCCACTGTTCTCCTCATCTCCAGCCTCAGTAGTTGGGGGTAGAAGGAGCTCAGCACCTCTTCCAGC
CCTTAAAGCTGCAGAAAAGGTGTCACACGGCTGCCTGTACCTTGGCTCCCTGTCCTGCTCCCGGCTTCCCT
TACCCTATCACTGGCCTCAGGCCCCGCAGGCTGCCTCTTCCCAACCTCCTTGGAAGTACCCCTGTTTCTTA
AACAATTATTTAAGTGTACGTGTATTATTAAACTGATGAACACATCCCCAAAA
```

FIGURE 4

MTLLPGLLFLTWLHTCLAHHDPSLRGHPHSHGTPHCYSAEELPLGQAPPHLLARGAKWGQALPVALVSSLE
AASHRGRHERPSATTQCPVLRPEEVLEADTHQRSISPWRYRVDTDEDRYPQKLAFAECLCRGCIDARTGRE
TAALNSVRLLQSLLVLRRRPCSRDGSGLPTPGAFAFHTEFIHVPVGCTCVLPRSV

Signal peptide: Amino acids 1-18
Tyrosine kinase phosphorylation site: Amino acids 112-121
N-myristoylation sites: Aminoacids 32-38;55-61;133-139
Leucine zipper pattern: Amino acids 3-25
Homologous region to IL-17: Amino acids 99-195

FIGURE 5

GGCTTGCTGAAAATAAAATCAGGACTCCTAACCTGCTCCAGTCAGCCTGCTTCCACGAGGCCTGTCAGTCA
GTGCCCGACTTGTGACTGAGTGTGCAGTGCCCAGCATGTACCAGGTCAGTGCAGAGGGCTGCCTGAGGGCT
GTGCTGAGAGGGAGAGGAGCAGAGATGCTGCTGAGGGTGGAGGGAGGCCAAGCTGCCAGGTTTGGGGCTGG
GGGCCAAGTGGAGTGAGAAACTGGGATCCCAGGGGGAGGGTGCAGATGAGGGAGCGACCCAGATTAGGTGA
GGACAGTTCTCTCATTAGCCTTTTCCTACAGGTGGTTGCATTCTTGGCAATGGTCATGGGAACCCACACCT
ACAGCCACTGGCCCAGCTGCTGCCCCAGCAAAGGGCAGGACACCTCTGAGGAGCTGCTGAGGTGGAGCACT
GTGCCTGTGCCTCCCCTAGAGCCTGCTAGGCCCAACCGCCACCCAGAGTCCTGTAGGGCCAGTGAAGATGGA
CCCCTCAACAGCAGGGCCATCTCCCCCTGGAGATATGAGTTGGACAGAGACTTGAACCGGCTCCCCCAGGA
CCTGTACCACGCCCGTTGCCTGTGCCCGCACTGCGTCAGCCTACAGACAGGCTCCCACATGGACCCCGGG
GCAACTCGGAGCTGCTCTACCACAACCAGACTGTCTTCTACAGGCGGCCATGCCATGGCGAGAAGGGCACC
CACAAGGGCTACTGCCTGGAGCGCAGGCTGTACCGTGTTTCCTTAGCTTGTGTGTGTGTGCGGCCCCGTGT
GATGGGCTAGCCGGACCTGCTGGAGGCTGGTCCCTTTTTGGGAAACCTGGAGCCAGGTGTACAACCACTTG
CCATGAAGGGCCAGGATGCCCAGATGCTTGGCCCCTGTGAAGTGCTGTCTGGAGCAGCAGGATCCCGGGAC
AGGATGGGGGCTTTGGGGAAAACCTGCACTTCTGCACATTTTGAAAAGAGCAGCTGCTGCTTAGGGCCGC
CGGAAGCTGGTGTCCTGTCATTTTCTCTCAGGAAAGGTTTTCAAAGTTCTGCCCATTTCTGGAGGCCACCA
CTCCTGTCTCTTCCTCTTTTCCCATCCCCTGCTACCCTGGCCCAGCACAGGCACTTTCTAGATATTTCCCC
CTTGCTGGAGAAGAAAGAGCCCCTGGTTTTATTTGTTTGTTTACTCATCACTCAGTGAGCATCTACTTTGG
GTGCATTCTAGTGTAGTTACTAGTCTTTTGACATGGATGATTCTGAGGAGGAAGCTGTTATTGAATGTATA
GAGATTTATCCAAATAAATATCTTTATTTAAAAATGAAAAA

FIGURE 6

MRERPRLGEDSSLISLFLQVVAFLAMVMGTHTYSHWPSCCPSKGQDTSEELLRWSTVPVPPLEPARPNRHP
ESCRASEDGPLNSRAISPWRYELDRDLNRLPQDLYHARCLCPHCVSLQTGSHMDPRGNSELLYHNQTVFYR
RPCHGEKGTHKGYCLERRLYRVSLACVCVRPRVMG

| | |
|---|---|
| Signal peptide: | Amino acids 1-32 |
| N-glycosylation site: | Amino acids 136-140 |
| Tyrosine kinase phosphorylation site: | Amino acids 127-135 |
| N-myristoylation sites: | Amino acids 44-50;150-156 |

FIGURE 7

ATGCTGGTAGCCGGCTTCCTGCTGGCGCTGCCGCCGAGCTGGGCCGCGGGCGCCCCCAGGGCGGGCAGGCG
CCCCGCGCGGCCGCGGGGCTGCGCGGACCGGCCGGAGGAGCTACTGGAGCAGCTGTACGGGCGCCTGGCGG
CCGGCGTGCTCAGTGCCTTCCACCACACGCTGCAGCTGGGGCCGCGTGAGCAGGCGCGCAACGCGAGCTGC
CCGGCAGGGGGCAGGCCCGGCGACCGCCGCTTCCGGCCGCCCACCAACCTGCGCAGCGTGTCGCCCTGGGC
CTACAGAATCTCCTACGACCCGGCGAGGTACCCCAGGTACCTGCCTGAAGCCTACTGCCTGTGCCGGGGCT
GCCTGACCGGGCTGTTCGGCGAGGAGGACGTGCGCTTCCGCAGCGCCCCTGTCTACATGCCCACCGTCGTC
CTGCGCCGCACCCCCGCCTGCGCCGGCGGCCGTTCCGTCTACACCGAGGCCTACGTCACCATCCCCGTGGG
CTGCACCTGCGTCCCCGAGCCGGAGAAGGACGCAGACAGCATCAACTCCAGCATCGACAAACAGGGCGCCA
AGCTCCTGCTGGGCCCCAACGACGCGCCCGCTGGCCCCTGAGGCCGGTCCTGCCCCGGGAGGTCTCCCCGG
CCCGCATCCCGAGGCGCCCAAGCTGGAGCCGCCTGGAGGGCTCGGTCGGCGACCTCTGAAGAGAGTGCACC
GAGCAAACCAAGTGCCGGAGCACCAGCGCCGCCTTTCCATGGAGACTCGTAAGCAGCTTCATCTGACACGG
GCATCCCTGGCTTGCTTTTAGCTACAAGCAAGCAGCGTGGCTGGAAGCTGATGGGAAACGACCCGGCACGG
GCATCCTGTGTGCGGCCCGCATGGAGGGTTTGGAAAAGTTCACGGAGGCTCCCTGAGGAGCCTCTCAGATC
GGCTGCTGCGGGTGCAGGGCGTGACTCACCGCTGGGTGCTTGCCAAAGAGATAGGGACGCATATGCTTTTT
AAAGCAATCTAAAAATAATAATAAGTATAGCGACTATATACCTACTTTTAAAATCAACTGTTTTGAATAGA
GGCAGAGCTATTTTATATTATCAAATGAGAGCTACTCTGTTACATTTCTTAACATATAAACATCGTTTTTT
ACTTCTTCTGGTAGAATTTTTTAAAGCATAATTGGAATCCTTGGATAAATTTTGTAGCTGGTACACTCTGG
CCTGGGTCTCTGAATTCAGCCTGTCACCGATGGCTGACTGATGAAATGGACACGTCTCATCTGACCCACTC
TTCCTTCCACTGAAGGTCTTCACGGGCCTCCAGGTGGACCAAAGGGATGCACAGGCGGCTCGCATGCCCCA
GGGCCAGCTAAGAGTTCCAAAGATCTCAGATTTGGTTTTAGTCATGAATACATAAACAGTCTCAAACTCGC
ACAATTTTTTCCCCCTTTTGAAAGCCACTGGGGCCAATTTGTGGTTAAGAGGTGGTGAGATAAGAAGTGGA
ACGTGACATCTTTGCCAGTTGTCAGAAGAATCCAAGCAGGTATTGGCTTAGTTGTAAGGGCTTTAGGATCA
GGCTGAATATGAGGACAAAGTGGGCCACGTTAGCATCTGCAGAGATCAATCTGGAGGCTTCTGTTTCTGCA
TTCTGCCACGAGAGCTAGGTCCTTGATCTTTTCTTTAGATTGAAAGTCTGTCTCTGAACACAATTATTTGT
AAAAGTTAGTAGTTCTTTTTTAAATCATTAAAAGAGGCTTGCTGAAGGAT

FIGURE 8

MLVAGFLLALPPSWAAGAPRAGRRPARPRGCADRPEELLEQLYGRLAAGVLSAFHHTLQLGPREQARNASC
PAGGRPGDRRFRPPTNLRSVSPWAYRISYDPARYPRYLPEAYCLCRGCLTGLFGEEDVRFRSAPVYMPTVV
LRRTPACAGGRSVYTEAYVTIPVGCTCVPEPEKDADSINSSIDKQGAKLLLGPNDAPAGP

| | |
|---|---|
| Signal peptide: | Amino acids 1-15 |
| N-glycosylation sites: | Amino acids 68-72;181-185 |
| Tyrosine kinase phosphorylation site: | Amino acids 97-106 |
| N-myristoylation sites: | Amino acids 17-23;49-55;74-80; 118-124 |
| Amidation site: | Amino acids 21-25 |

FIGURE 9

CAACTGCACCTCGGTTCTATCGATAGCCACCAGCGCAACATGACAGTGAAGACCCTGCATGGCCCAGCCAT
GGTCAAGTACTTGCTGCTGTCGATATTGGGGCTTGCCTTTCTGAGTGAGGCGGCAGCTCGGAAAATCCCCA
AAGTAGGACATACTTTTTTCCAAAAGCCTGAGAGTTGCCCGCCTGTGCCAGGAGGTAGTATGAAGCTTGAC
ATTGGCATCATCAATGAAAACCAGCGCGTTTCCATGTCACGTAACATCGAGAGCCGCTCCACCTCCCCCTG
GAATTACACTGTCACTTGGGACCCCAACCGGTACCCCTCGGAAGTTGTACAGGCCCAGTGTAGGAACTTGG
GCTGCATCAATGCTCAAGGAAAGGAAGACATCTCCATGAATTCCGTTCCCATCCAGCAAGAGACCCTGGTCGTC
CGGAGGAAGCACCAAGGCTGCTCTGTTTCTTTCCAGTTGGAGAAGGTGCTGGTGACTGTTGGCTGCACCTG
CGTCACCCCTGTCATCCACCATGTGCAGTAAGAGGTGCATATCCACTCAGCTGAAGAAG

FIGURE 10

MTVKTLHGPAMVKYLLLSILGLAFLSEAAARKIPKVGHTFFQKPESCPPVPGGSMKLDIGIINENQRVSMS
RNIESRSTSPWNYTVTWDPNRYPSEVVQAQCRNLGCINAQGKEDISMNSVPIQQETLVVRRKHQGCSVSFQ
LEKVLVTVGCTCVTPVIHHVQ

Signal sequence:            Amino acids 1-30

N-glycosylation site:       Amino acids 83-86

N-myristoylation sites:     Amino acids 106-111;136-141

FIGURE 11

```
CCGGCGATGTCGCTCGTGCTGCTAAGCCTGGCCGCGCTGTGCAGGAGCGCCGTACCCCGAGAGCCGACCGT
TCAATGTGGCTCTGAAACTGGGCCATCTCCAGAGTGGATGCTACAACATGATCTAATCCCCGGAGACTTGA
GGGACCTCCGAGTAGAACCTGTTACAACTAGTGTTGCAACAGGGGACTATTCAATTTTGATGAATGTAAGC
TGGGTACTCCGGGCAGATGCCAGCATCCGCTTGTTGAAGGCCACCAAGATTTGTGTGACGGGCAAAAGCAA
CTTCCAGTCCTACAGCTGTGTGAGGTGCAATTACACAGAGGCCTTCCAGACTCAGACCAGACCCTCTGGTG
GTAAATGGACATTTTCCTACATCGGCTTCCCTGTAGAGCTGAACACAGTCTATTTCATTGGGGCCCATAAT
ATTCCTAATGCAAATATGAATGAAGATGGCCCTTCCATGTCTGTGAATTTCACCTCACCAGGCTGCCTAGA
CCACATAATGAAATATAAAAAAAAGTGTGTCAAGGCCGGAAGCCTGTGGGATCCGAACATCACTGCTTGTA
AGAAGAATGAGGAGACAGTAGAAGTGAACTTCACAACCACTCCCCTGGGAAACAGATACATGGCTCTTATC
CAACACAGCACTATCATCGGGTTTTCTCAGGTGTTTGAGCCACACCAGAAGAAACAAACGCGAGCTTCAGT
GGTGATTCCAGTGACTGGGGATAGTGAAGGTGCTACGGTGCAGCTGACTCCATATTTTCCTACTTGTGGCA
GCGACTGCATCCGACATAAAGGAACAGTTGTGCTCTGCCCACAAACAGGCGTCCCTTTCCCTCTGGATAAC
AACAAAAGCAAGCCGGGAGGCTGGCTGCCTCCTCCTGCTGTCTCTGCTGGTGGCCACATGGGTGCTGGT
GGCAGGGATCTATCTAATGTGGAGGCACGAAAGGATCAAGAAGACTTCCTTTTCTACCACCACACTACTGC
CCCCCATTAAGGTTCTTGTGGTTTACCCATCTGAAATATGTTTCCATCACACAATTTGTTACTTCACTGAA
TTTCTTCAAAACCATTGCAGAAGTGAGGTCATCCTTGAAAAGTGGCAGAAAAGAAAATAGCAGAGATGGG
TCCAGTGCAGTGGCTTGCCACTCAAAAGAAGGCAGCAGACAAAGTCGTCTTCCTTCTTTCCAATGACGTCA
ACAGTGTGTGCGATGGTACCTGTGGCAAGAGCGAGGGCAGTCCCAGTGAGAACTCTCAAGACCTCTTCCCC
CTTGCCTTTAACCTTTTCTGCAGTGATCTAAGAAGCCAGATTCATCTGCACAAATACGTGGTGGTCTACTT
TAGAGAGATTGATACAAAAGACGATTACAATGCTCTCAGTGTCTGCCCCAAGTACCACCTCATGAAGGATG
CCACTGCTTTCTGTGCAGAACTTCTCCATGTCAAGCAGCAGGTGTCAGCAGGAAAAAGATCACAAGCCTGC
CACGATGGCTGCTGCTCCTTGTAG
```

FIGURE 12

MSLVLLSLAALCRSAVPREPTVQCGSETGPSPEWMLQHDLIPGDLRDLRVEPVTTSVATGDYSILMNVSWV
LRADASIRLLKATKICVTGKSNFQSYSCVRCNYTEAFQTQTRPSGGKWTFSYIGFPVELNTVYFIGAHNIP
NANMNEDGPSMSVNFTSPGCLDHIMKYKKKCVKAGSLWDPNITACKKNEETVEVNFTTTPLGNRYMALIQH
STIIGFSQVFEPHQKKQTRASVVIPVTGDSEGATVQLTPYFPTCGSDCIRHKGTVVLCPQTGVPFPLDNNK
SKPGGWLPLLLLSLLVATWVLVAGIYLMWRHERIKKTSFSTTTLLPPIKVLVVYPSEICFHHTICYFTEFL
QNHCRSEVILEKWQKKKIAEMGPVQWLATQKKAADKVVFLLSNDVNSVCDGTCGKSEGSPSENSQDLFPLA
FNLFCSDLRSQIHLHKYVVVYFREIDTKDDYNALSVCPKYHLMKDATAFCAELLHVKQQVSAGKRSQACHD
GCCSL

Signal sequence:                            Amino acids 1-14

Transmembrane domain:                       Amino acids 290-309

N-glycosylation sites:                      Amino acids 67-70;103-106;156-159;
                                            183-186;197-200;283-286 cAMP- and cGMP-dependent protein kinase phosphorylation sites:
                                            Amino acids 228-231;319-322

N-myristoylation site:                      Amino acids 116-121

Amidation site:                             Amino acids 488-491

FIGURE 13

ACACTGGCCAAACAAAAACGAAAGCACTCCGTGCTGGAAGTAGGAGGAGAGTCAGGACTCCCAGGACAGAG
AGTGCACAAACTACCCAGCACAGCCCCCTCCGCCCCCTCTGGAGGCTGAAGAGGGATTCCAGCCCCTGCCA
CCCACAGACACGGGCTGACTGGGGTGTCTGCCCCCCTTGGGGGGGGCAGCACAGGGCCTCAGGCCTGGGT
GCCACCTGGCACCTAGAAGATGCCTGTGCCCTGGTTCTTGCTGTCCTTGGCACTGGGCCGAAGCCCAGTGG
TCCTTTCTCTGGAGAGGCTTGTGGGGCCTCAGGACGCTACCCACTGCTCTCCGGGCCTCTCCTGCCGCCTC
TGGGACAGTGACATACTCTGCCTGCCTGGGGACATCGTGCCTGCTCCGGGCCCCGTGCTGGCGCCTACGCA
CCTGCAGACAGAGCTGGTGCTGAGGTGCCAGAAGGAGACCGACTGTGACCTCTGTCTGCGTGTGGCTGTCC
ACTTGGCCGTGCATGGGCACTGGGAAGAGCCTGAAGATGAGGAAAAGTTTGGAGGAGCAGCTGACTCAGGG
GTGGAGGAGCCTAGGAATGCCTCTCTCCAGGCCCAAGTCGTGCTCTCCTTCCAGGCCTACCCTACTGCCCG
CTGCGTCCTGCTGGAGGTGCAAGTGCCTGCTGCCCTTGTGCAGTTTGGTCAGTCTGTGGGCTCTGTGGTATAT
GACTGCTTCGAGGCTGCCCTAGGGAGTGAGGTACGAATCTGGTCCTATACTCAGCCCAGGTACGAGAAGGA
ACTCAACCACACACAGCAGCTGCCTGCCCTGCCCTGGCTCAACGTGTCAGCAGATGGTGACAACGTGCATC
TGGTTCTGAATGTCTCTGAGGAGCAGCACTTCGGCCTCTCCCTGTACTGGAATCAGGTCCAGGGCCCCCCA
AAACCCCGGTGGCACAAAAACCTGACTGGACCGCAGATCATTACCTTGAACCACACAGACCTGGTTCCCTG
CCTCTGTATTCAGGTGTGGCCTCTGGAACCTGACTCCGTTAGGACGAACATCTGCCCCTTCAGGGAGGACC
CCCGCGCACACCAGAACCTCTGGCAAGCCGCCCGACTGCGACTGCTGACCCTGCAGAGCTGGCTGCTGGAC
GCACCGTGCTCGCTGCCCGCAGAAGCGGCACTGTGCTGGCGGGCTCCGGGTGGGGACCCCTGCCAGCCACT
GGTCCCACCGCTTTCCTGGGAGAACGTCACTGTGGACAAGGTTCTCGAGTTCCCATTGCTGAAAGGCCACC
CTAACCTCTGTGTTCAGGTGAACAGCTCGGAGAAGCTGCAGCTGCAGGAGTGCTTGTGGGCTGACTCCCTG
GGGCCTCTCAAAGACGATGTGCTACTGTTGGAGACACGAGGCCCCCAGGACAACAGATCCCTCTGTGCCTT
GGAACCCAGTGGCTGTACTTCACTACCCAGCAAAGCCTCCACGAGGGCAGCTCGCCTTGGAGAGTACTTAC
TACAAGACCTGCAGTCAGGCCAGTGTCTGCAGCTATGGGACGATGACTTGGGAGCGCTATGGGCCTGCCCC
ATGGACAAATACATCCACAAGCGCTGGGCCCTCGTGTGGCTGGCCTGCCTACTCTTTGCCGCTGCGCTTTC
CCTCATCCTCCTTCTCAAAAAGGATCACGCGAAAGGGTGGCTGAGGCTCTTGAAACAGGACGTCCGCTCGG
GGGCGGCCGCCAGGGGCCGCGCGGCTCTGCTCCTCTACTCAGCCGATGACTCGGGTTTCGAGCGCCTGGTG
GGCGCCCTGGCGTCGGCCCTGTGCCAGCTGCCGCTGCGCGTGGCCGTAGACCTGTGGAGCCGTCGTGAACT
GAGCGCGCAGGGGCCCGTGGCTTGGTTTCACGCGCAGCGGCGCCAGACCCTGCAGGAGGGCGGCGTGGTGG
TCTTGCTCTTCTCTCCCGGTGCGGTGGCGCTGTGCAGCGAGTGGCTACAGGATGGGGTGTCCGGGCCCGGG
GCGCACGGCCCGCACGACGCCTTCCGCGCCTCGCTCAGCTGCGTGCTGCCCGACTTCTTGCAGGGCCGGGC
GCCCGGCAGCTACGTGGGGGCCTGCTTCGACAGGCTGCTCCACCCGGACGCCGTACCCGCCCTTTTCCGCA
CCGTGCCCGTCTTCACACTGCCCTCCCAACTGCCAGACTTCCTGGGGGCCCTGCAGCAGCCTCGCGCCCCG
CGTTCCGGGCGGCTCCAAGAGAGAGCGGAGCAAGTGTCCCGGGCCCTTCAGCCAGCCCTGGATAGCTACTT
CCATCCCCCGGGGACTCCCGCGCCGGGACGCGGGGTGGGACCAGGGGCGGGACCTGGGCGGGGGACGGGA
CTTAAATAAAGGCAGACGCTGTTTTTCTAAAAAAA

FIGURE 14

```
MPVPWFLLSLALGRSPVVLSLERLVGPQDATHCSPGLSCRLWDSDILCLPGDIVPAPGPVLAPTHLQTELV
LRCQKETDCDLCLRVAVHLAVHGHWEEPEDEEKFGGAADSGVEEPRNASLQAQVVLSFQAYPTARCVLLEV
QVPAALVQFGQSVGSVVYDCFEAALGSEVRIWSYTQPRYEKELNHTQQLPALPWLNVSADGDNVHLVLNVS
EEQHFGLSLYWNQVQGPPKPRWHKNLTGPQIITLNHTDLVPCLCIQVWPLEPDSVRTNICPFREDPRAHQN
LWQAARLRLLTLQSWLLDAPCSLPAEAALCWRAPGGDPCQPLVPPLSWENVTVDKVLEFPLLKGHPNLCVQ
VNSSEKLQLQECLWADSLGPLKDDVLLETRGPQDNRSLCALEPSGCTSLPSKASTRAARLGEYLLQDLQS
GQCLQLWDDDLGALWACPMDKYIHKRWALVWLACLLFAAALSLILLLKKDHAKGWLRLLKQDVRSGAAARG
RAALLLYSADDSGFERLVGALASALCQLPLRVAVDLWSRRELSAQGPVAWFHAQRRQTLQEGGVVVLLFSP
GAVALCSEWLQDGVSGPGAHGPHDAFRASLSCVLPDFLQGRAPGSYVGACFDRLLHPDAVPALFRTVPVFT
LPSQLPDFLGALQQPRAPRSGRLQERAEQVSRALQPALDSYFHPPGTPAPGRGVGPGAGPGAGDGT
```

| | |
|---|---|
| signal sequence: | Amino acids 1-20 |
| transmembrane domain: | Amino acids 453-473 |
| N-glycosylation sites: | Amino acids 118-121;186-189;198-201; 211-214;238-241;248-251;334-337; 357-360;391-394 |
| Glycosaminoglycan attachment site: | Amino acids 583-586 |
| cAMP- and cGMP-dependent protein kinase phosphorylation site: | Amino acids 552-555 |
| N-myristoylation sites: | Amino acids 107-112;152-157;319-324; 438-443;516-521;612-617;692-697; 696-701;700-705 |

FIGURE 15

```
CGAGGGCTCCTGCTGGTACTGTGTTCGCTGCTGCACAGCAAGGCCCTGCCACCCACCTTCAGGCCATGCAG
CCATGTTCCGGGAGCCCTAATTGCACAGAAGCCCATGGGGAGCTCCAGACTGGCAGCCCTGCTCCTGCCTC
TCCTCCTCATAGTCATCGACCTCTCTGACTCTGCTGGGATTGGCTTTCGCCACCTGCCCCACTGGAACACC
CGCTGTCCTCTGGCCTCCCACACGGATGACAGTTTCACTGGAAGTTCTGCCTATATCCCTTGCCGCACCTG
GTGGGCCCTCTTCTCCACAAAGCCTTGGTGTGTGCGAGTCTGGCACTGTTCCCGCTGTTTGTGCCAGCATCTGC
TGTCAGGTGGCTCAGGTCTTCAACGGGGCCTCTTCCACCTCCTGGTGCAGAAATCCAAAAAGTCTTCCACA
TTCAAGTTCTATAGGAGACACAAGATGCCAGCACCTGCTCAGAGGAAGCTGCTGCCTCGTCGTCACCTGTC
TGAGAAGAGCCATCACATTTCCATCCCCTCCCCAGACATCTCCCACAAGGGACTTCGCTCTAAAAGGACCC
AACCTTCGGATCCAGAGACATGGGAAAGTCTTCCCAGATTGGACTCACAAAGGCATGGAGGACCCGAGTTC
TCCTTTGATTTGCTGCCTGAGGCCCGGGCTATTCGGGTGACCATATCTTCAGGCCCTGAGGTCAGCGTGCG
TCTTTGTCACCAGTGGGCACTGGAGTGTGAAGAGCTGAGCAGTCCCTATGATGTCCAGAAAATTGTGTCTG
GGGGCCACACTGTAGAGCTGCCTTATGAATTCCTTCTGCCCTGTCTGTGCATAGAGGCATCCTACCTGCAA
GAGGACACTGTGAGGCGCAAAAAATGTCCCTTCCAGAGCTGGCCAGAAGCCTATGGCTCGGACTTCTGGAA
GTCAGTGCACTTCACTGACTACAGCCAGCACACTCAGATGGTCATGGCCCTGACACTCCGCTGCCCACTGA
AGCTGGAAGCTGCCCTCTGCCAGAGGCACGACTGGCATACCCTTTGCAAAGACCTCCCGAATGCCACGGCT
CGAGAGTCAGATGGGTGGTATGTTTTGGAGAAGGTGGACCTGCACCCCAGCTCTGCTTCAAGTTCTCTTT
TGGAAACAGCAGCCATGTTGAATGCCCCCACCAGACTGGGTCTCTCACATCCTGGAATGTAAGCATGGATA
CCCAAGCCCAGCAGCTGATTCTTCACTTCTCCTCAAGAATGCATGCCACCTTCAGTGCTGCCTGGAGCCTC
CCAGGCTTGGGGCAGGACACTTTGGTGCCCCCCGTGTACACTGTCAGCCAGGCCCGGGGCTCAAGCCCAGT
GTCACTAGACCTCATCATTCCCTTCCTGAGGCCAGGGTGCTGTGTCCTGGTGTGGCGGTCAGATGTCCAGT
TTGCCTGGAAGCACCTCTTGTGTCCAGATGTCTCTTACAGACACCTGGGGCTCTTGATCCTGGCACTGCTG
GCCCTCCTCACCCTACTGGGTGTTGTTCTGGCCCTCACCTGCCGGCGCCCACAGTCAGGCCCGGGCCCAGC
GCGGCCAGTGCTCCTCCTGCACGCGGCGGACTCGGAGGCGCAGCGGCGCCTGGTGGGAGCGCTGGCTGAAC
TGCTACGGGCAGCGCTGGGCGGCGGGCGCGACGTGATCGTGGACCTGTGGGAGGGGAGGCACGTGGCGCGCGT
GGGCCCGCTGCCGTGGCTCTGGGCGGCGCGGACGCGCGTAGCGCGGGAGCAGGGCACTGTGCTGCTGCTGT
GGAGCGGCGCCGACCTTCGCCCGGTCAGCGGCCCCGACCCCCGCGCCGCGCCCTGCTCGCCCTGCTCCAC
GCTGCCCCGCGCCCGCTGCTGCTGCTCGCTTACTTCAGTCGCCTCTGCGCCAAGGGCGACATCCCCCCGCC
GCTGCGCGCCCTGCCGCGCTACCGCCTGCTGCGCGACCTGCCGCGTCTGCTGCGGGCGCTGGACGCGCGGC
CTTTCGCAGAGGCCACCAGCTGGGGCCGCCTTGGGGCGCGGCAGCGCAGGCAGAGCCGCCTAGAGCTGTGC
AGCCGGCTTGAACGAGAGGCCGCCCGACTTGCAGACCTAGGTTGAGCAGAGCTCCACCGCAGTCCCGGGTGTCT
```

FIGURE 16

```
MGSSRLAALLLPLLLIVIDLSDSAGIGFRHLPHWNTRCPLASHTDDSFTGSSAYIPCRTWWALFSTKPWCV
RVWHCSRCLCQHLLSGGSGLQRGLFHLLVQKSKKSSTFKFYRRHKMPAPAQRKLLPRRHLSEKSHHISIPS
PDISHKGLRSKRTQPSDPETWESLPRLDSQRHGGPEFSFDLLPEARAIRVTISSGPEVSVRLCHQWALECE
ELSSPYDVQKIVSGGHTVELPYEFLLPCLCIEASYLQEDTVRRKKCPFQSWPEAYGSDFWKSVHFTDYSQH
TQMVMALTLRCPLKLEAALCQRHDWHTLCKDLPNATARESDGWYVLEKVDLHPQLCFKFSFGNSSHVECPH
QTGSLTSWNVSMDTQAQQLILHFSSRMHATFSAAWSLPGLGQDTLVPPVYTVSQARGSSPVSLDLIIPFLR
PGCCVLVWRSDVQFAWKHLLCPDVSYRHLGLLILALLALLTLLGVVLALTCRRPQSGPGPARPVLLLHAAD
SEAQRRLVGALAELLRAALGGGRDVIVDLWEGRHVARVGPLPWLWAARTRVAREQGTVLLLWSGADLRPVS
GPDPRAAPLLALLHAAPRPLLLLAYFSRLCAKGDIPPPLRALPRYRLLRDLPRLLRALDARPFAEATSWGR
LGARQRRQSRLELCSRLEREAARLADLG
```

Signal peptide:                                   Amino acids 1-23

Transmembrane domain:                 Amino acids 455-472

N-glycosylation sites:                 Amino acids 318-322; 347-351; 364-368

Glycosaminoglycan attachment site:   Amino acids 482-486 cAMP- and cGMP-dependent protein kinase phosphorylation sites:
                                                    Amino acids 104-108; 645-649

Tyrosine kinase phosphorylation site:   Amino acids 322-329

N-myristoylation sites:                Amino acids 90-96; 358-364; 470-476

Eukaryotic cobalamin-binding proteins:   Amino acids 453-462

FIGURE 17

GCCAGGCCCTATCTCCCTGCCAGGAGGCCGGAGTGGGGGAGGTCAGACGGGGCGGTTGGAGGGGGAGGGAT
GCCACGCGCTTCTGCCTCAGGTGTTCCTGCGTTGTTTGTCAGTGGAGAGCAGGGAGTGGGGCCAGCCAGCA
GAAACAGTGGGCTGTACAACATCACCTTCAAATATGACAATTGTACCACCTACTTGAATCCAGTGGGGAAG
CATGTGATTGCTGACGCCCAGAATATCACCATCAGCCAGTATGCTTGCCATGACCAAGTGGCAGTCACCAT
TCTTTGGTCCCCAGGGGCCCTCGGCATCGAATTCCTGAAAGGATTTCGGGTAATACTGGAGGAGCTGAAGT
CGGAGGGAAGACAGTGCCAACAACTGATTCTAAAGGATCCGAAGCAGCTCAACAGTAGCTTCAAAAGAACT
GGAATGGAATCTCAACCTTTCCTGAATATGAAATTTGAAACGGATTATTTCGTAAAGGTTGTCCCTTTTCC
TTCCATTAAAAACGAAAGCAATTACCACCCTTTCTTCTTTAGAACCCGAGCCTGTGACCTGTTGTTACAGC
CGGACAATCTAGCTTGTAAACCCTTCTGGAAGCCTCGGAACCTGAACATCAGCCAGCATGGCTCGGACATGC
AGGTGTCCTTCGACCACGCACCGCATGGCTCGGACATGCAGGTGTCCTTCGACCACGCACCGCACAACTTC
GGCTTCCGTTTCTTCTATCTTCACTACAAGCTCAAGCACGAAGGACCTTTCAAGCGAAAGACCTGTAAGCA
GGAGCAAACTACAGAGATGACCAGCTGCCTCCTTCAAAATGTTTCTCCAGGGGATTATATAATTGAGCTGG
TGGATGACACTAACACAACAAGAAAAGTGATGCATTATGCCTTAAAGCCAGTGCACTCCCCGTGGGCCGGG
CCCATCAGAGCCGTGGCCATCACAGTGCCACTGGTAGTCATATCGGCATTCGCGACGCTCTTCACTGTGAT
GTGCCGCAAGAAGCAACAAGAAAATATATATTCACATTTAGATGAAGAGAGCTCTGAGTCTTCCACATACA
CTGCAGCACTCCCAAGAGAGAGGCTCCGGCCGCGGCCGAAGGTCTTTCTCTGCTATTCCAGTAAAGATGGC
CAGAATCACATGAATGTCGTCCAGTGTTTCGCCTACTTCCTCCAGGACTTCTGTGGCTGTGAGGTGGCTCT
GGACCTGTGGGAAGACTTCAGCCTCTGTAGAGAAGGGCAGAGAGAATGGGTCATCCAGAAGATCCACGAGT
CCCAGTTCATCATTGTGGTTTGTTCCAAAGGTATGAAGTACTTTGTGGACAAGAAGAACTACAAACACAAA
GGAGGTGGCCGAGGCTCGGGGAAAGGAGAGCTCTTCCTGGTGGCGGTGTCAGCCATTGCCGAAAAGCTCCG
CCAGGCCAAGCAGAGTTCGTCCGCGGCGCTCAGCAAGTTTATCGCCGTCTACTTTGATTATTCCTGCGAGG
GAGACGTCCCCGGTATCCTAGACCTGAGTACCAAGTACAGACTCATGGACAATCTTCCTCAGCTCTGTTCC
CACCTGCACTCCCGAGACCACGGCCTCCAGGAGCCGGGGCAGCACACGCGACAGGGCAGCAGAAGGAACTA
CTTCCGGAGCAAGTCAGGCCGGTCCCTATACGTCGCCATTTGCAACATGCACCAGTTTATTGACGAGGAGC
CCGACTGGTTCGAAAAGCAGTTCGTTCCCTTCCATCCTCCTCCACTGCGCTACCGGGAGCCAGTCTTGGAG
AAATTTGATTCGGGCTTGGTTTTAAATGATGTCATGTGCAAACCAGGGCCTGAGAGTGACTTCTGCCTAAA
GGTAGAGGCGGCTGTTCTTGGGGCAACCGGACCAGCCGACTCCCAGCACGAGAGTCAGCATGGGGGCCTGG
ACCAAGACGGGGAGGCCCGGCCTGCCCTTGACGGTAGCGCCGCCCTGCAACCCCTGCTGCACACGGTGAAA
GCCGGCAGCCCCTCGGACATGCCGCGGGACTCAGGCATCTATGACTCGTCTGTGCCCTCATCCGAGCTGTC
TCTGCCACTGATGGAAGGACTCTCGACGGACCAGACAGAAACGTCTTCCCTGACGGAGAGCGTGTCCTCCT
CTTCAGGCCTGGGTGAGGAGGAACCTCCTGCCCTTCCTTCCAAGCTCCTCTCTTCTGGGTCATGCAAAGCA
GATCTTGGTTGCCGCAGCTACACTGATGAACTCCACGCGGTCGCCCCTTTGTAACAAAACGAAAGAGTCTA
AGCATTGCCACTTTAAAAAAAAAAAAAAAAAAAAAAAAAAAAAAAA

FIGURE 18

```
MPRASASGVPALFVSGEQGVGPASRNSGLYNITFKYDNCTTYLNPVGKHVIADAQNITISQYACHDQVAVT
ILWSPGALGIEFLKGFRVILEELKSEGRQCQQLILKDPKQLNSSFKRTGMESQPFLNMKFETDYFVKVVPF
PSIKNESNYHPFFFRTRACDLLLQPDNLACKPFWKPRNLNISQHGSDMQVSFDHAPHGSDMQVSFDHAPHN
FGFRFFYLHYKLKHEGPFKRKTCKQEQTTEMTSCLLQNVSPGDYIIELVDDTNTTRKVMHYALKPVHSPWA
GPIRAVAITVPLVVISAFATLFTVMCRKKQQENIYSHLDEESSESSTYTAALPRERLRPRPKVFLCYSSKD
GQNHMNVVQCFAYFLQDFCGCEVALDLWEDFSLCREGQREWVIQKIHESQFIIVVCSKGMKYFVDKKNYKH
KGGGRGSGKGELFLVAVSAIAEKLRQAKQSSSAALSKFIAVYFDYSCEGDVPGILDLSTKYRLMDNLPQLC
SHLHSRDHGLQEPGQHTRQGSRRNYFRSKSGRSLYVAICNMHQFIDEEPDWFEKQFVPFHPPPLRYREPVL
EKFDSGLVLNDVMCKPGPESDFCLKVEAAVLGATGPADSQHESQHGGLDQDGEARPALDGSAALQPLLHTV
KAGSPSDMPRDSGIYDSSVPSSELSLPLMEGLSTDQTETSSLTESVSSSSGLGEEEPPALPSKLLSSGSCK
ADLGCRSYTDELHAVAPL
```

Transmembrane domain:                Amino acids 283-307

N-glycosylation sites:               Amino acids 31-34;38-41;56-59;
                                     113-116;147-150;182-185;266-269

Glycosaminoglycan attachment sites:  Amino acids 433-436;689-692 cAMP- and cGMP-dependent protein kinase phosphorylation:
                                     Amino acids 232-235

Tyrosine kinase phosphorylation sites:   Amino acids 312-319;416-424

N-myristoylation site:               Amino acids 19-24;375-380;428-433;
                                     429-434;432-437;517-522;574-579;
                                     652-657;707-712

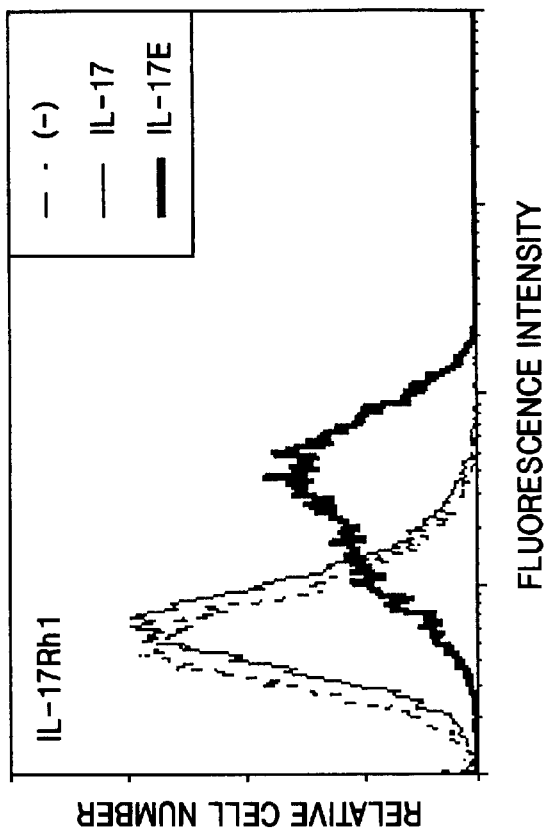
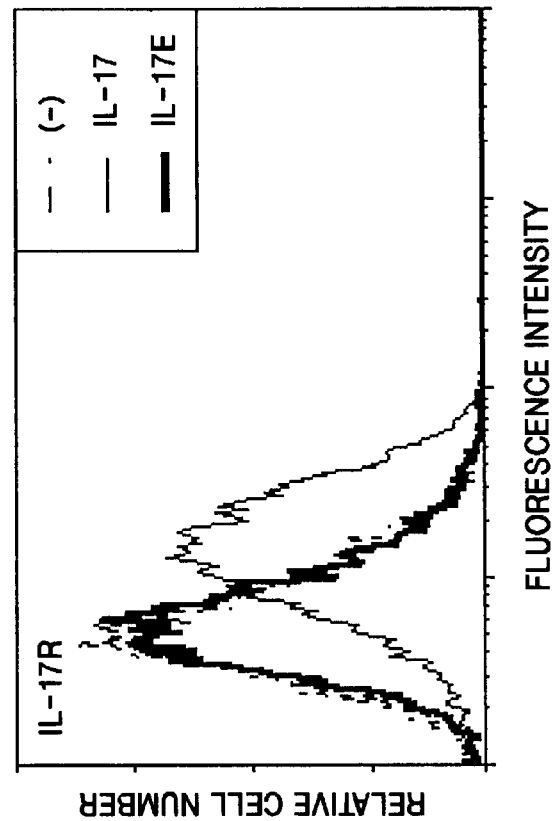
FIG. 32A

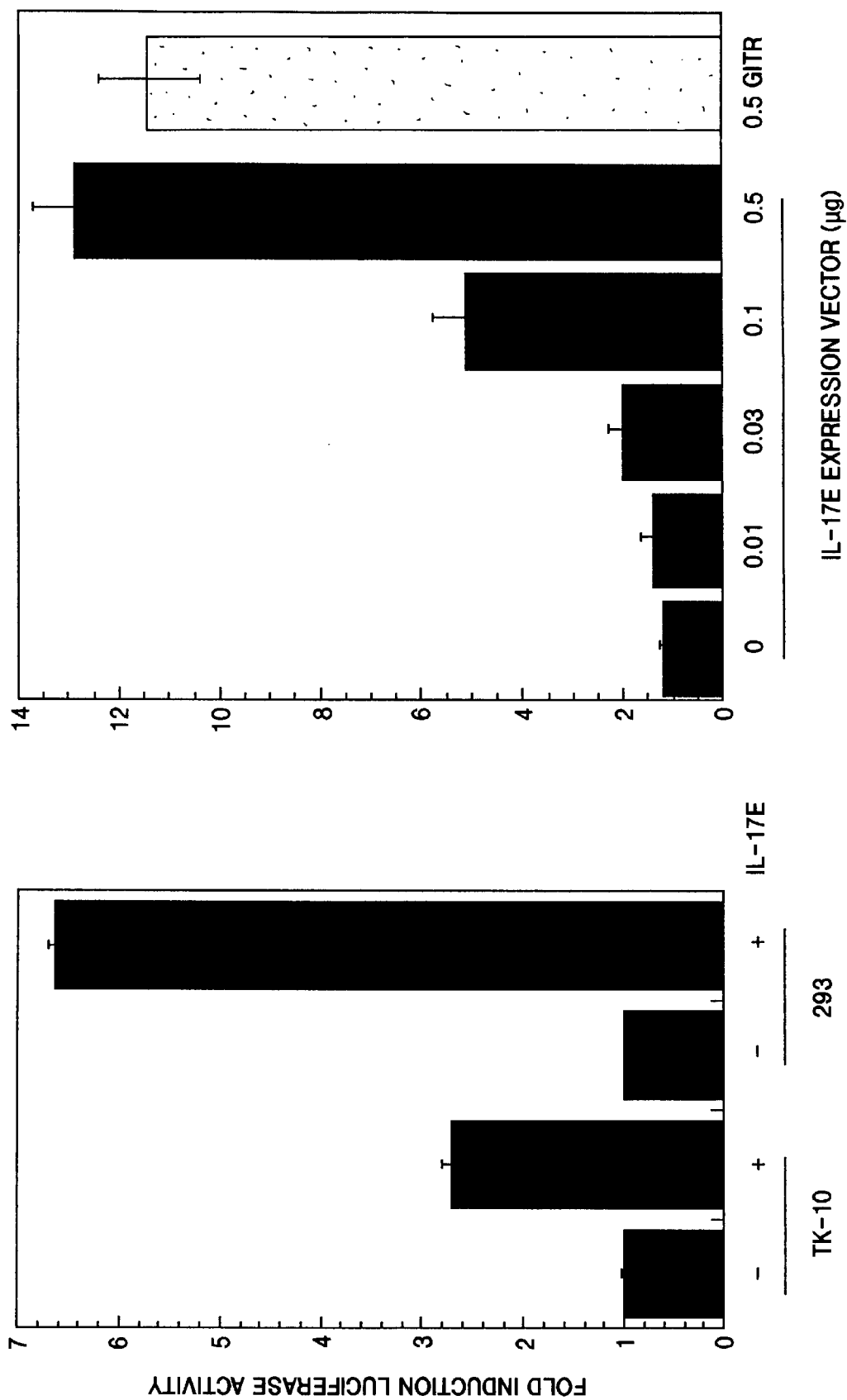

INHIBITION OF NITRIC OXIDE RELEASE DOES NOT BLOCK THE DETRIMENTAL
EFFECTS OF IL 17 ON MATRIX BREAKDOWN OR SYNTHESIS

SEQUENCE LISTING

<160> NUMBER OF SEQ ID NOS: 39

<210> SEQ ID NO 1
<211> LENGTH: 687
<212> TYPE: DNA
<213> ORGANISM: Homo Sapien

<400> SEQUENCE: 1
aggcgggcag cagctgcagg ctgaccttgc agcttggcgg aatggactgg          50
cctcacaacc tgctgtttct tcttaccatt tccatcttcc tggggctggg         100
ccagcccagg agccccaaaa gcaagaggaa ggggcaaggg cggcctgggc         150
ccctggcccc tggccctcac caggtgccac tggacctggt gtcacggatg         200
aaaccgtatg cccgcatgga ggagtatgag aggaacatcg aggagatggt         250
ggcccagctg aggaacagct cagagctggc ccagagaaag tgtgaggtca         300

```
acttgcagct gtggatgtcc aacaagagga gcctgtctcc ctggggctac            350
agcatcaacc acgacccag ccgtatcccc gtggacctgc cggaggcacg             400
gtgcctgtgt ctgggctgtg tgaacccctt caccatgcag gaggaccgca            450
gcatggtgag cgtgccggtg ttcagccagg ttcctgtgcg ccgccgcctc            500
tgcccgccac cgccccgcac agggccttgc cgccagcgcg cagtcatgga            550
gaccatcgct gtgggctgca cctgcatctt ctgaatcacc tggcccagaa            600
gccaggccag cagcccgaga ccatcctcct tgcacctttg tgccaagaaa            650
ggcctatgaa aagtaaacac tgactttga aagcaag                           687
```

<210> SEQ ID NO 2
<211> LENGTH: 180
<212> TYPE: PRT
<213> ORGANISM: Homo Sapien

<400> SEQUENCE: 2

```
Met Asp Trp Pro His Asn Leu Leu Phe Leu Leu Thr Ile Ser Ile
 1               5                  10                  15

Phe Leu Gly Leu Gly Gln Pro Arg Ser Pro Lys Ser Lys Arg Lys
            20                  25                  30

Gly Gln Gly Arg Pro Gly Pro Leu Ala Pro Gly Pro His Gln Val
        35                  40                  45

Pro Leu Asp Leu Val Ser Arg Met Lys Pro Tyr Ala Arg Met Glu
    50                  55                  60

Glu Tyr Glu Arg Asn Ile Glu Glu Met Val Ala Gln Leu Arg Asn
65                  70                  75

Ser Ser Glu Leu Ala Gln Arg Lys Cys Glu Val Asn Leu Gln Leu
            80                  85                  90

Trp Met Ser Asn Lys Arg Ser Leu Ser Pro Trp Gly Tyr Ser Ile
        95                 100                 105

Asn His Asp Pro Ser Arg Ile Pro Val Asp Leu Pro Glu Ala Arg
   110                 115                 120

Cys Leu Cys Leu Gly Cys Val Asn Pro Phe Thr Met Gln Glu Asp
   125                 130                 135

Arg Ser Met Val Ser Val Pro Val Phe Ser Gln Val Pro Val Arg
       140                 145                 150

Arg Arg Leu Cys Pro Pro Pro Arg Thr Gly Pro Cys Arg Gln
       155                 160                 165

Arg Ala Val Met Glu Thr Ile Ala Val Gly Cys Thr Cys Ile Phe
       170                 175                 180
```

<210> SEQ ID NO 3
<211> LENGTH: 1047
<212> TYPE: DNA
<213> ORGANISM: Homo Sapien

<400> SEQUENCE: 3

```
gccaggtgtg caggccgctc caagcccagc ctgccccgct gccgccacca             50
tgacgctcct ccccggcctc ctgtttctga cctggctgca cacatgcctg            100
gcccaccatg acccctccct caggggggcac ccccacagtc acggtacccc           150
acactgctac tcggctgagg aactgcccct cggccaggcc cccccacacc            200
tgctggctcg aggtgccaag tggggcagg ctttgcctgt agccctggtg             250
tccagcctgg aggcagcaag ccacaggggg aggcacgaga ggccctcagc            300
```

```
tacgacccag tgcccggtgc tgcggccgga ggaggtgttg gaggcagaca        350
cccaccagcg ctccatctca ccctggagat accgtgtgga cacggatgag        400
gaccgctatc cacagaagct ggccttcgcc gagtgcctgt gcagaggctg        450
tatcgatgca cggacgggcc gcagacagc tgcgctcaac tccgtgcggc         500
tgctccagag cctgctggtg ctgcgccgcc ggccctgctc ccgcgacggc        550
tcggggctcc ccacacctgg ggcctttgcc ttccacaccg agttcatcca        600
cgtccccgtc ggctgcacct gcgtgctgcc ccgttcagtg tgaccgccga        650
ggccgtgggg cccctagact ggacacgtgt gctccccaga gggcaccccc        700
tatttatgtg tatttattgt tatttatatg cctcccccaa cactaccctt        750
ggggtctggg cattccccgt gtctggagga cagccccca ctgttctcct         800 catctccagc ctcagtagtt gggggtagaa ggagctcagc acctcttcca        850
gcccttaaag ctgcagaaaa ggtgtcacac ggctgcctgt accttggctc        900
cctgtcctgc tcccggcttc ccttacccta tcactggcct caggcccgc         950 aggctgcctc ttcccaacct ccttggaagt acccctgttt cttaaacaat        1000
tatttaagtg tacgtgtatt attaaactga tgaacacatc cccaaaa          1047
```

<210> SEQ ID NO 4
<211> LENGTH: 197
<212> TYPE: PRT
<213> ORGANISM: Homo Sapien

<400> SEQUENCE: 4

```
Met Thr Leu Leu Pro Gly Leu Leu Phe Leu Thr Trp Leu His Thr
 1               5                  10                  15

Cys Leu Ala His His Asp Pro Ser Leu Arg Gly His Pro His Ser
                20                  25                  30

His Gly Thr Pro His Cys Tyr Ser Ala Glu Glu Leu Pro Leu Gly
                35                  40                  45

Gln Ala Pro Pro His Leu Leu Ala Arg Gly Ala Lys Trp Gly Gln
                50                  55                  60

Ala Leu Pro Val Ala Leu Val Ser Ser Leu Glu Ala Ala Ser His
                65                  70                  75

Arg Gly Arg His Glu Arg Pro Ser Ala Thr Thr Gln Cys Pro Val
                80                  85                  90

Leu Arg Pro Glu Glu Val Leu Glu Ala Asp Thr His Gln Arg Ser
                95                  100                 105

Ile Ser Pro Trp Arg Tyr Arg Val Asp Thr Asp Glu Asp Arg Tyr
               110                  115                 120

Pro Gln Lys Leu Ala Phe Ala Glu Cys Leu Cys Arg Gly Cys Ile
               125                  130                 135

Asp Ala Arg Thr Gly Arg Glu Thr Ala Ala Leu Asn Ser Val Arg
               140                  145                 150

Leu Leu Gln Ser Leu Leu Val Leu Arg Arg Pro Cys Ser Arg
               155                  160                 165

Asp Gly Ser Gly Leu Pro Thr Pro Gly Ala Phe Ala Phe His Thr
               170                  175                 180

Glu Phe Ile His Val Pro Val Gly Cys Thr Cys Val Leu Pro Arg
               185                  190                 195

Ser Val
```

<210> SEQ ID NO 5
<211> LENGTH: 1320
<212> TYPE: DNA
<213> ORGANISM: Homo Sapien

<400> SEQUENCE: 5

| | | |
|---|---|---|
| ggcttgctga aaataaaatc aggactccta acctgctcca gtcagcctgc | 50 |
| ttccacgagg cctgtcagtc agtgcccgac ttgtgactga gtgtgcagtg | 100 |
| cccagcatgt accaggtcag tgcagagggc tgcctgaggg ctgtgctgag | 150 |
| agggagagga gcagagatgc tgctgagggt ggagggaggc caagctgcca | 200 |
| ggtttggggc tgggggccaa gtggagtgag aaactgggat cccaggggga | 250 |
| gggtgcagat gagggagcga cccagattag gtgaggacag ttctctcatt | 300 |
| agccttttcc tacaggtggt tgcattcttg caatggtca tgggaaccca | 350 |
| cacctacagc cactggccca gctgctgccc cagcaaaggg caggacacct | 400 |
| ctgaggagct gctgaggtgg agcactgtgc ctgtgcctcc cctagagcct | 450 |
| gctaggccca accgccaccc agagtcctgt agggccagtg aagatggacc | 500 |
| cctcaacagc agggccatct cccctggag atatgagttg acagagact | 550 |
| tgaaccggct cccccaggac ctgtaccacg cccgttgcct gtgcccgcac | 600 |
| tgcgtcagcc tacagacagg ctcccacatg gaccccgggg caactcgga | 650 |
| gctgctctac cacaaccaga ctgtcttcta caggcggcca tgccatggcg | 700 |
| agaagggcac ccacaagggc tactgcctgg agcgcaggc gtaccgtgtt | 750 |
| tccttagctt gtgtgtgtgt gcggccccgt gtgatgggct agccggacct | 800 |
| gctggaggct ggtccctttt tgggaaacct ggagccaggt gtacaaccac | 850 |
| ttgccatgaa gggccaggat gcccagatgc ttggcccctg tgaagtgctg | 900 |
| tctggagcag caggatcccg ggacaggatg gggggctttg gggaaaacct | 950 |
| gcacttctgc acattttgaa aagagcagct gctgcttagg gccgccggaa | 1000 |
| gctggtgtcc tgtcattttc tctcaggaaa ggttttcaaa gttctgccca | 1050 |
| tttctggagg ccaccactcc tgtctcttcc tcttttccca tcccctgcta | 1100 |
| ccctggccca gcacaggcac tttctagata tttccccctt gctggagaag | 1150 |
| aaagagcccc tggttttatt tgtttgttta ctcatcactc agtgagcatc | 1200 |
| tactttgggt gcattctagt gtagttacta gtcttttgac atggatgatt | 1250 |
| ctgaggagga agctgttatt gaatgtatag agatttatcc aaataaatat | 1300 |
| ctttatttaa aaatgaaaaa | 1320 |

<210> SEQ ID NO 6
<211> LENGTH: 177
<212> TYPE: PRT
<213> ORGANISM: Homo Sapien

<400> SEQUENCE: 6

Met Arg Glu Arg Pro Arg Leu Gly Glu Asp Ser Ser Leu Ile Ser
 1               5                  10                  15

Leu Phe Leu Gln Val Val Ala Phe Leu Ala Met Val Met Gly Thr
                20                  25                  30

His Thr Tyr Ser His Trp Pro Ser Cys Cys Pro Ser Lys Gly Gln
                35                  40                  45

―continued

```
Asp Thr Ser Glu Glu Leu Leu Arg Trp Ser Thr Val Pro Val Pro
                 50                  55                  60

Pro Leu Glu Pro Ala Arg Pro Asn Arg His Pro Glu Ser Cys Arg
             65                  70                  75

Ala Ser Glu Asp Gly Pro Leu Asn Ser Arg Ala Ile Ser Pro Trp
             80                  85                  90

Arg Tyr Glu Leu Asp Arg Asp Leu Asn Arg Leu Pro Gln Asp Leu
             95                 100                 105

Tyr His Ala Arg Cys Leu Cys Pro His Cys Val Ser Leu Gln Thr
                110                 115                 120

Gly Ser His Met Asp Pro Arg Gly Asn Ser Glu Leu Leu Tyr His
                125                 130                 135

Asn Gln Thr Val Phe Tyr Arg Arg Pro Cys His Gly Glu Lys Gly
                140                 145                 150

Thr His Lys Gly Tyr Cys Leu Glu Arg Arg Leu Tyr Arg Val Ser
                155                 160                 165

Leu Ala Cys Val Cys Val Arg Pro Arg Val Met Gly
                170                 175
```

<210> SEQ ID NO 7
<211> LENGTH: 1754
<212> TYPE: DNA
<213> ORGANISM: Homo Sapien

<400> SEQUENCE: 7

```
atgctggtag ccggcttcct gctggcgctg ccgccgagct gggccgcggg        50
cgcccccagg gcgggcaggc gccccgcgcg gccgcggggc tgcgcggacc       100
ggccggagga gctactggag cagctgtacg ggcgcctggc ggccggcgtg       150
ctcagtgcct tccaccacac gctgcagctg ggccgcgtg agcaggcgcg        200
caacgcgagc tgcccggcag ggggcaggcc cggcgaccgc cgcttccggc       250
cgcccaccaa cctgcgcagc gtgtcgccct gggcctacag aatctcctac       300
gacccggcga ggtaccccag gtacctgcct gaagcctact gcctgtgccg       350
gggctgcctg accgggctgt cggcgagga ggacgtgcgc ttccgcagcg        400
ccctgtctca catgcccacc gtcgtcctgc gccgcacccc cgcctgcgcc       450
ggcggccgtt ccgtctacac cgaggcctac gtcaccatcc ccgtgggctg       500
cacctgcgtc cccgagccgg agaaggacgc agacagcatc aactccagca       550
tcgacaaaca gggcgccaag ctcctgctgg gccccaacga cgcgcccgct       600
ggccctgag gccggtcctg ccccgggagg tctccccggc ccgcatcccg        650
aggcgcccaa gctggagccg cctggagggc tcggtcggcg acctctgaag       700
agagtgcacc gagcaaacca gtgccggag caccagcgcc gcctttccat        750
ggagactcgt aagcagcttc atctgacacg ggcatcctg gcttgctttt        800
agctacaagc aagcagcgtg gctggaagct gatgggaaac gacccggcac       850
gggcatcctg tgtgcggccc gcatggaggg tttggaaaag ttcacggagg       900
ctccctgagg agcctctcag atcggctgct gcgggtgcag ggcgtgactc       950
accgctgggt gcttgccaaa gagatagggc gcatatgct tttaaagca       1000
atctaaaaat aataataagt atagcgacta tatacctact tttaaaatca      1050
actgttttga atagaggcag agctatttta tattatcaaa tgagagctac      1100
```

```
tctgttacat ttcttaacat ataaacatcg ttttttactt cttctggtag         1150
aattttttaa agcataattg gaatccttgg ataaattttg tagctggtac         1200
actctggcct gggtctctga attcagcctg tcaccgatgg ctgactgatg         1250
aaatggacac gtctcatctg acccactctt ccttccactg aaggtcttca         1300
cgggcctcca ggtggaccaa agggatgcac aggcggctcg catgccccag         1350
ggccagctaa gagttccaaa gatctcagat ttggttttag tcatgaatac         1400
ataaacagtc tcaaactcgc acaattttt ccccttttg aaagccactg           1450 gggccaattt gtggttaaga ggtggtgaga taagaagtgg aacgtgacat         1500
ctttgccagt tgtcagaaga atccaagcag gtattggctt agttgtaagg         1550
gctttaggat caggctgaat atgaggacaa agtgggccac gttagcatct         1600
gcagagatca atctggaggc ttctgtttct gcattctgcc acgagagcta         1650
ggtccttgat cttttctta gattgaaagt ctgtctctga acacaattat          1700
ttgtaaaagt tagtagttct tttttaaatc attaaaagag gcttgctgaa         1750
ggat                                                           1754
```

<210> SEQ ID NO 8
<211> LENGTH: 202
<212> TYPE: PRT
<213> ORGANISM: Homo Sapien

<400> SEQUENCE: 8

```
Met Leu Val Ala Gly Phe Leu Leu Ala Leu Pro Pro Ser Trp Ala
 1               5                  10                  15

Ala Gly Ala Pro Arg Ala Gly Arg Arg Pro Ala Arg Pro Arg Gly
                20                  25                  30

Cys Ala Asp Arg Pro Glu Glu Leu Leu Glu Gln Leu Tyr Gly Arg
                35                  40                  45

Leu Ala Ala Gly Val Leu Ser Ala Phe His His Thr Leu Gln Leu
                50                  55                  60

Gly Pro Arg Glu Gln Ala Arg Asn Ala Ser Cys Pro Ala Gly Gly
                65                  70                  75

Arg Pro Gly Asp Arg Arg Phe Arg Pro Pro Thr Asn Leu Arg Ser
                80                  85                  90

Val Ser Pro Trp Ala Tyr Arg Ile Ser Tyr Asp Pro Ala Arg Tyr
                95                 100                 105

Pro Arg Tyr Leu Pro Glu Ala Tyr Cys Leu Cys Arg Gly Cys Leu
               110                 115                 120

Thr Gly Leu Phe Gly Glu Glu Asp Val Arg Phe Arg Ser Ala Pro
               125                 130                 135

Val Tyr Met Pro Thr Val Val Leu Arg Arg Thr Pro Ala Cys Ala
               140                 145                 150

Gly Gly Arg Ser Val Tyr Thr Glu Ala Tyr Val Thr Ile Pro Val
               155                 160                 165

Gly Cys Thr Cys Val Pro Glu Pro Glu Lys Asp Ala Asp Ser Ile
               170                 175                 180

Asn Ser Ser Ile Asp Lys Gln Gly Ala Lys Leu Leu Leu Gly Pro
               185                 190                 195

Asn Asp Ala Pro Ala Gly Pro
               200
```

<210> SEQ ID NO 9
<211> LENGTH: 559
<212> TYPE: DNA
<213> ORGANISM: Homo Sapien

<400> SEQUENCE: 9

| | | | | |
|---|---|---|---|---|
| caactgcacc | tcggttctat | cgatagccac | cagcgcaaca | tgacagtgaa | 50 |
| gaccctgcat | ggcccagcca | tggtcaagta | cttgctgctg | tcgatattgg | 100 |
| ggcttgcctt | tctgagtgag | gcggcagctc | ggaaaatccc | caaagtagga | 150 |
| catactttt | tccaaaagcc | tgagagttgc | ccgcctgtgc | caggaggtag | 200 |
| tatgaagctt | gacattggca | tcatcaatga | aaaccagcgc | gtttccatgt | 250 |
| cacgtaacat | cgagagccgc | tccacctccc | cctggaatta | cactgtcact | 300 |
| tgggacccca | accggtaccc | ctcggaagtt | gtacaggccc | agtgtaggaa | 350 |
| cttgggctgc | atcaatgctc | aaggaaagga | agacatctcc | atgaattccg | 400 |
| ttcccatcca | gcaagagacc | ctggtcgtcc | ggaggaagca | ccaaggctgc | 450 |
| tctgtttctt | tccagttgga | gaaggtgctg | gtgactgttg | gctgcacctg | 500 |
| cgtcacccct | gtcatccacc | atgtgcagta | agaggtgcat | atccactcag | 550 |
| ctgaagaag | | | | | 559 |

<210> SEQ ID NO 10
<211> LENGTH: 163
<212> TYPE: PRT
<213> ORGANISM: Homo Sapien

<400> SEQUENCE: 10

Met Thr Val Lys Thr Leu His Gly Pro Ala Met Val Lys Tyr Leu
 1               5                  10                  15

Leu Leu Ser Ile Leu Gly Leu Ala Phe Leu Ser Glu Ala Ala Ala
                20                  25                  30

Arg Lys Ile Pro Lys Val Gly His Thr Phe Phe Gln Lys Pro Glu
                35                  40                  45

Ser Cys Pro Val Pro Gly Gly Ser Met Lys Leu Asp Ile Gly
                50                  55                  60

Ile Ile Asn Glu Asn Gln Arg Val Ser Met Ser Arg Asn Ile Glu
                65                  70                  75

Ser Arg Ser Thr Ser Pro Trp Asn Tyr Thr Val Thr Trp Asp Pro
                80                  85                  90

Asn Arg Tyr Pro Ser Glu Val Val Gln Ala Gln Cys Arg Asn Leu
                95                  100                 105

Gly Cys Ile Asn Ala Gln Gly Lys Glu Asp Ile Ser Met Asn Ser
                110                 115                 120

Val Pro Ile Gln Gln Glu Thr Leu Val Val Arg Arg Lys His Gln
                125                 130                 135

Gly Cys Ser Val Ser Phe Gln Leu Glu Lys Val Leu Val Thr Val
                140                 145                 150

Gly Cys Thr Cys Val Thr Pro Val Ile His His Val Gln
                155                 160

<210> SEQ ID NO 11
<211> LENGTH: 1515
<212> TYPE: DNA
<213> ORGANISM: Homo Sapien

```
<400> SEQUENCE: 11
ccggcgatgt cgctcgtgct gctaagcctg gccgcgctgt gcaggagcgc         50
cgtaccccga gagccgaccg ttcaatgtgg ctctgaaact gggccatctc        100
cagagtggat gctacaacat gatctaatcc ccggagactt gagggacctc        150
cgagtagaac ctgttacaac tagtgttgca acaggggact attcaatttt        200
gatgaatgta agctgggtac tccgggcaga tgccagcatc cgcttgttga        250
aggccaccaa gatttgtgtg acgggcaaaa gcaacttcca gtcctacagc        300
tgtgtgaggt gcaattacac agaggccttc cagactcaga ccagaccctc        350
tggtggtaaa tggacatttt cctacatcgg cttccctgta gagctgaaca        400
cagtctattt cattggggcc cataatattc ctaatgcaaa tatgaatgaa        450
gatggcccctt ccatgtctgt gaatttcacc tcaccaggct gcctagacca       500
cataatgaaa tataaaaaaa agtgtgtcaa ggccggaagc ctgtgggatc        550
cgaacatcac tgcttgtaag aagaatgagg agacagtaga agtgaacttc        600
acaaccactc ccctgggaaa cagatacatg gctcttatcc aacacagcac        650
tatcatcggg ttttctcagg tgtttgagcc acaccagaag aaacaaacgc        700
gagcttcagt ggtgattcca gtgactgggg atagtgaagg tgctacggtg        750
cagctgactc catattttcc tacttgtggc agcgactgca tccgacataa        800
aggaacagtt gtgctctgcc cacaaacagg cgtccctttc cctctggata        850
acaacaaaag caagccggga ggctggctgc ctctcctcct gctgtctctg        900
ctggtggcca tgggtgct ggtggcaggg atctatctaa tgtggaggca          950
cgaaaggatc aagaagactt ccttttctac caccacacta ctgcccccca       1000
ttaaggttct tgtggtttac ccatctgaaa tatgtttcca tcacacaatt       1050
tgttacttca ctgaatttct tcaaaaccat tgcagaagtg aggtcatcct       1100
tgaaaagtgg cagaaaaaga aaatagcaga atgggtccca gtgcagtggc       1150
ttgccactca aaagaaggca gcagacaaag tcgtcttcct tctttccaat       1200
gacgtcaaca gtgtgtgcga tggtacctgt ggcaagagcg agggcagtcc       1250
cagtgagaac tctcaagacc tcttcccccct tgcctttaac cttttctgca      1300
gtgatctaag aagccagatt catctgcaca aatacgtggt ggtctacttt       1350
agagagattg atacaaaaga cgattacaat gctctcagtg tctgccccaa       1400
gtaccacctc atgaaggatg ccactgcttt ctgtgcagaa cttctccatg       1450
tcaagcagca ggtgtcagca ggaaaaagat cacaagcctg ccacgatggc       1500
tgctgctcct tgtag                                             1515

<210> SEQ ID NO 12
<211> LENGTH: 502
<212> TYPE: PRT
<213> ORGANISM: Homo Sapien

<400> SEQUENCE: 12

Met Ser Leu Val Leu Leu Ser Leu Ala Ala Leu Cys Arg Ser Ala
 1               5                  10                  15

Val Pro Arg Glu Pro Thr Val Gln Cys Gly Ser Glu Thr Gly Pro
                20                  25                  30

Ser Pro Glu Trp Met Leu Gln His Asp Leu Ile Pro Gly Asp Leu
```

```
                35                  40                  45
Arg Asp Leu Arg Val Glu Pro Val Thr Thr Ser Val Ala Thr Gly
                50                  55                  60
Asp Tyr Ser Ile Leu Met Asn Val Ser Trp Val Leu Arg Ala Asp
                65                  70                  75
Ala Ser Ile Arg Leu Leu Lys Ala Thr Lys Ile Cys Val Thr Gly
                80                  85                  90
Lys Ser Asn Phe Gln Ser Tyr Ser Cys Val Arg Cys Asn Tyr Thr
                95                 100                 105
Glu Ala Phe Gln Thr Gln Thr Arg Pro Ser Gly Lys Trp Thr
               110                 115                 120
Phe Ser Tyr Ile Gly Phe Pro Val Glu Leu Asn Thr Val Tyr Phe
               125                 130                 135
Ile Gly Ala His Asn Ile Pro Asn Ala Asn Met Asn Glu Asp Gly
               140                 145                 150
Pro Ser Met Ser Val Asn Phe Thr Ser Pro Gly Cys Leu Asp His
               155                 160                 165
Ile Met Lys Tyr Lys Lys Cys Val Lys Ala Gly Ser Leu Trp
               170                 175                 180
Asp Pro Asn Ile Thr Ala Cys Lys Lys Asn Glu Glu Thr Val Glu
               185                 190                 195
Val Asn Phe Thr Thr Thr Pro Leu Gly Asn Arg Tyr Met Ala Leu
               200                 205                 210
Ile Gln His Ser Thr Ile Ile Gly Phe Ser Gln Val Phe Glu Pro
               215                 220                 225
His Gln Lys Lys Gln Thr Arg Ala Ser Val Val Ile Pro Val Thr
               230                 235                 240
Gly Asp Ser Glu Gly Ala Thr Val Gln Leu Thr Pro Tyr Phe Pro
               245                 250                 255
Thr Cys Gly Ser Asp Cys Ile Arg His Lys Gly Thr Val Val Leu
               260                 265                 270
Cys Pro Gln Thr Gly Val Pro Phe Pro Leu Asp Asn Asn Lys Ser
               275                 280                 285
Lys Pro Gly Gly Trp Leu Pro Leu Leu Leu Ser Leu Val
               290                 295                 300
Ala Thr Trp Val Leu Val Ala Gly Ile Tyr Leu Met Trp Arg His
               305                 310                 315
Glu Arg Ile Lys Lys Thr Ser Phe Ser Thr Thr Thr Leu Leu Pro
               320                 325                 330
Pro Ile Lys Val Leu Val Val Tyr Pro Ser Glu Ile Cys Phe His
               335                 340                 345
His Thr Ile Cys Tyr Phe Thr Glu Phe Leu Gln Asn His Cys Arg
               350                 355                 360
Ser Glu Val Ile Leu Glu Lys Trp Gln Lys Lys Ile Ala Glu
               365                 370                 375
Met Gly Pro Val Gln Trp Leu Ala Thr Gln Lys Lys Ala Ala Asp
               380                 385                 390
Lys Val Val Phe Leu Leu Ser Asn Asp Val Asn Ser Val Cys Asp
               395                 400                 405
Gly Thr Cys Gly Lys Ser Glu Gly Ser Pro Ser Glu Asn Ser Gln
               410                 415                 420
Asp Leu Phe Pro Leu Ala Phe Asn Leu Phe Cys Ser Asp Leu Arg
               425                 430                 435
```

```
Ser Gln Ile His Leu His Lys Tyr Val Val Tyr Phe Arg Glu
            440                 445                 450

Ile Asp Thr Lys Asp Asp Tyr Asn Ala Leu Ser Val Cys Pro Lys
            455                 460                 465

Tyr His Leu Met Lys Asp Ala Thr Ala Phe Cys Ala Glu Leu Leu
            470                 475                 480

His Val Lys Gln Gln Val Ser Ala Gly Lys Arg Ser Gln Ala Cys
            485                 490                 495

His Asp Gly Cys Cys Ser Leu
            500

<210> SEQ ID NO 13
<211> LENGTH: 2380
<212> TYPE: DNA
<213> ORGANISM: Homo Sapien

<400> SEQUENCE: 13
acactggcca aacaaaaacg aaagcactcc gtgctggaag taggaggaga              50
gtcaggactc ccaggacaga gagtgcacaa actacccagc acagccccct             100 ccgcccctc tggaggctga agagggattc cagcccctgc acccacaga              150 cacgggctga ctgggtgtc tgccccctt ggggggggc agcacagggc               200 ctcaggcctg ggtgccacct ggcacctaga agatgcctgt gccctggttc             250
ttgctgtcct tggcactggg ccgaagccca gtggtccttt ctctggagag             300
gcttgtgggg cctcaggacg ctacccactg ctctccgggc ctctcctgcc             350
gcctctggga cagtgacata ctctgcctgc ctggggacat cgtgcctgct             400
ccgggccccg tgctggcgcc tacgcacctg cagacagagc tggtgctgag             450
gtgccagaag gagaccgact gtgacctctg tctgcgtgtg gctgtccact             500
tggccgtgca tgggcactgg gaagagcctg aagatgagga aaagtttgga             550
ggagcagctg actcaggggt ggaggagcct aggaatgcct ctctccaggc             600
ccaagtcgtg ctctccttcc aggcctaccc tactgcccgc tgcgtcctgc             650
tggaggtgca agtgcctgct gcccttgtgc agtttggtca gtctgtgggc             700
tctgtggtat atgactgctt cgaggctgcc ctagggagtg aggtacgaat             750
ctggtcctat actcagccca ggtacgagaa ggaactcaac cacacacagc             800
agctgcctgc cctgccctgg ctcaacgtgt cagcagatgg tgacaacgtg             850
catctggttc tgaatgtctc tgaggagcag cacttcggcc tctccctgta             900
ctggaatcag gtccagggcc ccccaaaacc ccggtggcac aaaaacctga             950
ctggaccgca gatcattacc ttgaaccaca cagacctggt tccctgcctc            1000
tgtattcagg tgtggcctct ggaacctgac tccgttagga cgaacatctg            1050 cccttcagg gaggaccccc gcgcacacca gaacctctgg caagccgccc             1100
gactgcgact gctgacctg cagagctggc tgctggacgc accgtgctcg             1150
ctgcccgcag aagcggcact gtgctggcgg gctccgggtg gggacccctg            1200
ccagccactg gtcccaccgc tttcctggga gaacgtcact gtggacaagg            1250
ttctcgagtt cccattgctg aaaggccacc ctaacctctg tgttcaggtg            1300
aacagctcgg agaagctgca gctgcaggag tgcttgtggg ctgactccct            1350
ggggcctctc aaagacgatg tgctactgtt ggagacacga ggcccccagg            1400
```

-continued

```
acaacagatc cctctgtgcc ttggaaccca gtggctgtac ttcactaccc         1450
agcaaagcct ccacgagggc agctcgcctt ggagagtact tactacaaga         1500
cctgcagtca ggccagtgtc tgcagctatg ggacgatgac ttgggagcgc         1550
tatgggcctg ccccatggac aaatacatcc acaagcgctg ggccctcgtg         1600
tggctggcct gcctactctt tgccgctgcg ctttccctca tcctccttct         1650
caaaaaggat cacgcgaaag ggtggctgag gctcttgaaa caggacgtcc         1700
gctcgggggc ggccgccagg ggccgcgcgg ctctgctcct ctactcagcc         1750
gatgactcgg gtttcgagcg cctggtgggc gccctggcgt cggccctgtg         1800
ccagctgccg ctgcgcgtgg ccgtagacct gtggagccgt cgtgaactga         1850
gcgcgcaggg gcccgtggct tggtttcacg cgcagcggcg ccagaccctg         1900
caggagggcg cgtggtggt cttgctcttc tctcccggtg cggtggcgct          1950
gtgcagcgag tggctacagg atggggtgtc cgggcccggg gcgcacggcc         2000
cgcacgacgc cttccgcgcc tcgctcagct gcgtgctgcc cgacttcttg         2050
cagggccggg cgcccggcag ctacgtgggg gcctgcttcg acaggctgct         2100
ccacccggac gccgtacccg cccttttccg caccgtgccc gtcttcacac         2150
tgccctccca actgccagac ttcctggggg ccctgcagca gcctcgcgcc         2200
ccgcgttccg gcggctcca agagagagcg agcaagtgt cccgggccct           2250 tcagccagcc ctggatagct acttccatcc cccggggact cccgcgccgg         2300
gacgcggggt gggaccaggg gcgggacctg gggcggggga cgggacttaa         2350
ataaaggcag acgctgtttt tctaaaaaaa                               2380
```

<210> SEQ ID NO 14
<211> LENGTH: 705
<212> TYPE: PRT
<213> ORGANISM: Homo Sapien

<400> SEQUENCE: 14

```
Met Pro Val Pro Trp Phe Leu Leu Ser Leu Ala Leu Gly Arg Ser
 1               5                  10                  15

Pro Val Val Leu Ser Leu Glu Arg Leu Val Gly Pro Gln Asp Ala
                20                  25                  30

Thr His Cys Ser Pro Gly Leu Ser Cys Arg Leu Trp Asp Ser Asp
                35                  40                  45

Ile Leu Cys Leu Pro Gly Asp Ile Val Pro Ala Pro Gly Pro Val
                50                  55                  60

Leu Ala Pro Thr His Leu Gln Thr Glu Leu Val Leu Arg Cys Gln
                65                  70                  75

Lys Glu Thr Asp Cys Asp Leu Cys Leu Arg Val Ala Val His Leu
                80                  85                  90

Ala Val His Gly His Trp Glu Glu Pro Glu Asp Glu Glu Lys Phe
                95                 100                 105

Gly Gly Ala Ala Asp Ser Gly Val Glu Glu Pro Arg Asn Ala Ser
               110                 115                 120

Leu Gln Ala Gln Val Val Leu Ser Phe Gln Ala Tyr Pro Thr Ala
               125                 130                 135

Arg Cys Val Leu Leu Glu Val Gln Val Pro Ala Ala Leu Val Gln
               140                 145                 150
```

-continued

```
Phe Gly Gln Ser Val Gly Ser Val Val Tyr Asp Cys Phe Glu Ala
            155                 160                 165

Ala Leu Gly Ser Glu Val Arg Ile Trp Ser Tyr Thr Gln Pro Arg
            170                 175                 180

Tyr Glu Lys Glu Leu Asn His Thr Gln Leu Pro Ala Leu Pro
            185                 190                 195

Trp Leu Asn Val Ser Ala Asp Gly Asp Asn Val His Leu Val Leu
            200                 205                 210

Asn Val Ser Glu Glu Gln His Phe Gly Leu Ser Leu Tyr Trp Asn
            215                 220                 225

Gln Val Gln Gly Pro Pro Lys Pro Arg Trp His Lys Asn Leu Thr
            230                 235                 240

Gly Pro Gln Ile Ile Thr Leu Asn His Thr Asp Leu Val Pro Cys
            245                 250                 255

Leu Cys Ile Gln Val Trp Pro Leu Glu Pro Asp Ser Val Arg Thr
            260                 265                 270

Asn Ile Cys Pro Phe Arg Glu Asp Pro Arg Ala His Gln Asn Leu
            275                 280                 285

Trp Gln Ala Ala Arg Leu Arg Leu Leu Thr Leu Gln Ser Trp Leu
            290                 295                 300

Leu Asp Ala Pro Cys Ser Leu Pro Ala Glu Ala Ala Leu Cys Trp
            305                 310                 315

Arg Ala Pro Gly Gly Asp Pro Cys Gln Pro Leu Val Pro Pro Leu
            320                 325                 330

Ser Trp Glu Asn Val Thr Val Asp Lys Val Leu Glu Phe Pro Leu
            335                 340                 345

Leu Lys Gly His Pro Asn Leu Cys Val Gln Val Asn Ser Ser Glu
            350                 355                 360

Lys Leu Gln Leu Gln Glu Cys Leu Trp Ala Asp Ser Leu Gly Pro
            365                 370                 375

Leu Lys Asp Asp Val Leu Leu Leu Glu Thr Arg Gly Pro Gln Asp
            380                 385                 390

Asn Arg Ser Leu Cys Ala Leu Glu Pro Ser Gly Cys Thr Ser Leu
            395                 400                 405

Pro Ser Lys Ala Ser Thr Arg Ala Ala Arg Leu Gly Glu Tyr Leu
            410                 415                 420

Leu Gln Asp Leu Gln Ser Gly Gln Cys Leu Gln Leu Trp Asp Asp
            425                 430                 435

Asp Leu Gly Ala Leu Trp Ala Cys Pro Met Asp Lys Tyr Ile His
            440                 445                 450

Lys Arg Trp Ala Leu Val Trp Leu Ala Cys Leu Leu Phe Ala Ala
            455                 460                 465

Ala Leu Ser Leu Ile Leu Leu Leu Lys Lys Asp His Ala Lys Gly
            470                 475                 480

Trp Leu Arg Leu Leu Lys Gln Asp Val Arg Ser Gly Ala Ala Ala
            485                 490                 495

Arg Gly Arg Ala Ala Leu Leu Leu Tyr Ser Ala Asp Asp Ser Gly
            500                 505                 510

Phe Glu Arg Leu Val Gly Ala Leu Ala Ser Ala Leu Cys Gln Leu
            515                 520                 525

Pro Leu Arg Val Ala Val Asp Leu Trp Ser Arg Arg Glu Leu Ser
            530                 535                 540

Ala Gln Gly Pro Val Ala Trp Phe His Ala Gln Arg Arg Gln Thr
```

```
                545                 550                 555
Leu Gln Glu Gly Gly Val Val Leu Leu Phe Ser Pro Gly Ala
                560                 565                 570
Val Ala Leu Cys Ser Glu Trp Leu Gln Asp Gly Val Ser Gly Pro
                575                 580                 585
Gly Ala His Gly Pro His Asp Ala Phe Arg Ala Ser Leu Ser Cys
                590                 595                 600
Val Leu Pro Asp Phe Leu Gln Gly Arg Ala Pro Gly Ser Tyr Val
                605                 610                 615
Gly Ala Cys Phe Asp Arg Leu Leu His Pro Asp Ala Val Pro Ala
                620                 625                 630
Leu Phe Arg Thr Val Pro Val Phe Thr Leu Pro Ser Gln Leu Pro
                635                 640                 645
Asp Phe Leu Gly Ala Leu Gln Gln Pro Arg Ala Pro Arg Ser Gly
                650                 655                 660
Arg Leu Gln Glu Arg Ala Glu Gln Val Ser Arg Ala Leu Gln Pro
                665                 670                 675
Ala Leu Asp Ser Tyr Phe His Pro Pro Gly Thr Pro Ala Pro Gly
                680                 685                 690
Arg Gly Val Gly Pro Gly Ala Gly Pro Gly Ala Gly Asp Gly Thr
                695                 700                 705

<210> SEQ ID NO 15
<211> LENGTH: 2138
<212> TYPE: DNA
<213> ORGANISM: Homo Sapien

<400> SEQUENCE: 15
cgagggctcc tgctggtact gtgttcgctg ctgcacagca aggccctgcc          50
acccaccttc aggccatgca gccatgttcc gggagcccta attcacaga           100
agcccatggg gagctccaga ctggcagccc tgctcctgcc tctcctcctc          150
atagtcatcg acctctctga ctctgctggg attggctttc gccacctgcc          200
ccactggaac acccgctgtc ctctggcctc ccacacggat gacagtttca          250
ctggaagttc tgcctatatc ccttgccgca cctggtgggc cctcttctcc          300
acaaagcctt ggtgtgtgcg agtctggcac tgttcccgct gtttgtgcca          350
gcatctgctg tcaggtggct caggtcttca cgggggcctc ttccacctcc          400
tggtgcagaa atccaaaaag tcttccacat tcaagttcta taggagacac          450
aagatgccag cacctgctca gaggaagctg ctgcctcgtc gtcacctgtc          500
tgagaagagc catcacattt ccatcccctc cccagacatc tcccacaagg          550
gacttcgctc taaaggacc caaccttcgg atccagagac atgggaaagt           600
cttcccagat tggactcaca aaggcatgga ggacccgagt tctcctttga          650
tttgctgcct gaggcccggg ctattcgggt gaccatatct tcaggccctg          700
aggtcagcgt gcgtctttgt caccagtggg cactggagtg tgaagagctg          750
agcagtccct atgatgtcca gaaaattgtg tctgggggcc acactgtaga          800
gctgccttat gaattccttc tgccctgtct gtgcatagag gcatcctacc          850
tgcaagagga cactgtgagg cgcaaaaaat gtcccttcca gagctggcca          900
gaagcctatg gctcggactt ctggaagtca gtgcacttca ctgactacag          950
ccagcacact cagatggtca tggccctgac actccgctgc ccactgaagc          1000
```

-continued

```
tggaagctgc cctctgccag aggcacgact ggcatacccct ttgcaaagac        1050 ctcccgaatg ccacggctcg agagtcagat gggtggtatg ttttggagaa        1100
ggtggacctg cacccccagc tctgcttcaa gttctctttt ggaaacagca        1150
gccatgttga atgcccccac cagactgggt ctctcacatc ctggaatgta        1200
agcatggata cccaagccca gcagctgatt cttcacttct cctcaagaat        1250
gcatgccacc ttcagtgctg cctggagcct cccaggcttg ggcaggaca         1300 cttttggtgcc ccccgtgtac actgtcagcc aggcccgggg ctcaagccca       1350
gtgtcactag acctcatcat tcccttcctg aggccagggt gctgtgtcct        1400
ggtgtggcgg tcagatgtcc agtttgcctg gaagcacctc ttgtgtccag        1450
atgtctctta cagacacctg gggctcttga tcctggcact gctggccctc        1500
ctcaccctac tgggtgttgt tctggccctc acctgccggc ccccacagtc        1550
aggcccgggc ccagcgcggc cagtgctcct cctgcacgcg cggactcgg         1600 aggcgcagcg cgcctggtg ggagcgctgg ctgaactgct acgggcagcg         1650
ctgggcggcg ggcgcgacgt gatcgtggac ctgtgggagg ggaggcacgt        1700
ggcgcgcgtg ggcccgctgc cgtggctctg ggcggcgcgg acgcgcgtag        1750
cgcgggagca gggcactgtg ctgctgctgt ggagcggcgc cgaccttcgc        1800
ccggtcagcg gccccgaccc ccgcgccgcg ccctgctcg ccctgctcca         1850 cgctgccccg cgcccgctgc tgctgctcgc ttacttcagt cgcctctgcg        1900
ccaagggcga catccccccg ccgctgcgcg ccctgccgcg ctaccgcctg        1950
ctgcgcgacc tgccgcgtct gctgcgggcg ctggacgcgc ggcctttcgc       2000
agaggccacc agctggggcc gccttggggc gcggcagcgc aggcagagcc       2050
gcctagagct gtgcagccgg cttgaacgag aggccgcccg acttgcagac       2100
ctaggttgag cagagctcca ccgcagtccc gggtgtct                    2138
```

<210> SEQ ID NO 16
<211> LENGTH: 667
<212> TYPE: PRT
<213> ORGANISM: Homo Sapien

<400> SEQUENCE: 16

```
Met Gly Ser Ser Arg Leu Ala Ala Leu Leu Pro Leu Leu Leu
 1               5                  10                  15

Ile Val Ile Asp Leu Ser Asp Ser Ala Gly Ile Gly Phe Arg His
                20                  25                  30

Leu Pro His Trp Asn Thr Arg Cys Pro Leu Ala Ser His Thr Asp
                35                  40                  45

Asp Ser Phe Thr Gly Ser Ser Ala Tyr Ile Pro Cys Arg Thr Trp
                50                  55                  60

Trp Ala Leu Phe Ser Thr Lys Pro Trp Cys Val Arg Val Trp His
                65                  70                  75

Cys Ser Arg Cys Leu Cys Gln His Leu Leu Ser Gly Gly Ser Gly
                80                  85                  90

Leu Gln Arg Gly Leu Phe His Leu Val Gln Lys Ser Lys Lys
                95                  100                 105

Ser Ser Thr Phe Lys Phe Tyr Arg Arg His Lys Met Pro Ala Pro
                110                 115                 120
```

```
Ala Gln Arg Lys Leu Leu Pro Arg Arg His Leu Ser Glu Lys Ser
            125                 130                 135

His His Ile Ser Ile Pro Ser Pro Asp Ile Ser His Lys Gly Leu
            140                 145                 150

Arg Ser Lys Arg Thr Gln Pro Ser Asp Pro Glu Thr Trp Glu Ser
            155                 160                 165

Leu Pro Arg Leu Asp Ser Gln Arg His Gly Gly Pro Glu Phe Ser
            170                 175                 180

Phe Asp Leu Leu Pro Glu Ala Arg Ala Ile Arg Val Thr Ile Ser
            185                 190                 195

Ser Gly Pro Glu Val Ser Val Arg Leu Cys His Gln Trp Ala Leu
            200                 205                 210

Glu Cys Glu Glu Leu Ser Ser Pro Tyr Asp Val Gln Lys Ile Val
            215                 220                 225

Ser Gly Gly His Thr Val Glu Leu Pro Tyr Glu Phe Leu Leu Pro
            230                 235                 240

Cys Leu Cys Ile Glu Ala Ser Tyr Leu Gln Glu Asp Thr Val Arg
            245                 250                 255

Arg Lys Lys Cys Pro Phe Gln Ser Trp Pro Glu Ala Tyr Gly Ser
            260                 265                 270

Asp Phe Trp Lys Ser Val His Phe Thr Asp Tyr Ser Gln His Thr
            275                 280                 285

Gln Met Val Met Ala Leu Thr Leu Arg Cys Pro Leu Lys Leu Glu
            290                 295                 300

Ala Ala Leu Cys Gln Arg His Asp Trp His Thr Leu Cys Lys Asp
            305                 310                 315

Leu Pro Asn Ala Thr Ala Arg Glu Ser Asp Gly Trp Tyr Val Leu
            320                 325                 330

Glu Lys Val Asp Leu His Pro Gln Leu Cys Phe Lys Phe Ser Phe
            335                 340                 345

Gly Asn Ser Ser His Val Glu Cys Pro His Gln Thr Gly Ser Leu
            350                 355                 360

Thr Ser Trp Asn Val Ser Met Asp Thr Gln Ala Gln Leu Ile
            365                 370                 375

Leu His Phe Ser Ser Arg Met His Ala Thr Phe Ser Ala Ala Trp
            380                 385                 390

Ser Leu Pro Gly Leu Gly Gln Asp Thr Leu Val Pro Pro Val Tyr
            395                 400                 405

Thr Val Ser Gln Ala Arg Gly Ser Ser Pro Val Ser Leu Asp Leu
            410                 415                 420

Ile Ile Pro Phe Leu Arg Pro Gly Cys Cys Val Leu Val Trp Arg
            425                 430                 435

Ser Asp Val Gln Phe Ala Trp Lys His Leu Leu Cys Pro Asp Val
            440                 445                 450

Ser Tyr Arg His Leu Gly Leu Leu Ile Leu Ala Leu Leu Ala Leu
            455                 460                 465

Leu Thr Leu Leu Gly Val Val Leu Ala Leu Thr Cys Arg Arg Pro
            470                 475                 480

Gln Ser Gly Pro Gly Pro Ala Arg Pro Val Leu Leu Leu His Ala
            485                 490                 495

Ala Asp Ser Glu Ala Gln Arg Arg Leu Val Gly Ala Leu Ala Glu
            500                 505                 510

Leu Leu Arg Ala Ala Leu Gly Gly Gly Arg Asp Val Ile Val Asp
```

```
                        515                 520                 525
Leu Trp Glu Gly Arg His Val Ala Arg Val Gly Pro Leu Pro Trp
                530                 535                 540
Leu Trp Ala Ala Arg Thr Arg Val Ala Arg Glu Gln Gly Thr Val
                545                 550                 555
Leu Leu Leu Trp Ser Gly Ala Asp Leu Arg Pro Val Ser Gly Pro
                560                 565                 570
Asp Pro Arg Ala Ala Pro Leu Leu Ala Leu Leu His Ala Ala Pro
                575                 580                 585
Arg Pro Leu Leu Leu Leu Ala Tyr Phe Ser Arg Leu Cys Ala Lys
                590                 595                 600
Gly Asp Ile Pro Pro Leu Arg Ala Leu Pro Arg Tyr Arg Leu
                605                 610                 615
Leu Arg Asp Leu Pro Arg Leu Leu Arg Ala Leu Asp Ala Arg Pro
                620                 625                 630
Phe Ala Glu Ala Thr Ser Trp Gly Arg Leu Gly Ala Arg Gln Arg
                635                 640                 645
Arg Gln Ser Arg Leu Glu Leu Cys Ser Arg Leu Glu Arg Glu Ala
                650                 655                 660
Ala Arg Leu Ala Asp Leu Gly
                665

<210> SEQ ID NO 17
<211> LENGTH: 2319
<212> TYPE: DNA
<213> ORGANISM: Homo Sapien

<400> SEQUENCE: 17
gccaggccct atctccctgc caggaggccg agtggggga ggtcagacgg            50 ggcggttgga gggggaggga tgccacgcgc ttctgcctca ggtgttcctg           100
cgttgtttgt cagtggagag cagggagtgg ggccagccag cagaaacagt           150
gggctgtaca acatcacctt caaatatgac aattgtacca cctacttgaa           200
tccagtgggg aagcatgtga ttgctgacgc ccagaatatc accatcagcc           250
agtatgcttg ccatgaccaa gtggcagtca ccattctttg gtccccaggg           300
gccctcggca tcgaattcct gaaaggattt cgggtaatac tggaggagct           350
gaagtcggag ggaagacagt gccaacaact gattctaaag gatccgaagc           400
agctcaacag tagcttcaaa gaactggaa tggaatctca acctttcctg            450
aatatgaaat ttgaaacgga ttatttcgta aaggttgtcc ctttcccttc           500
cattaaaaac gaaagcaatt accacccttt cttctttaga acccgagcct           550
gtgacctgtt gttacagccg acaatctag cttgtaaacc cttctggaag            600
cctcggaacc tgaacatcag ccagcatggc tcggacatgc aggtgtcctt           650
cgaccacgca ccgcatggct cggacatgca ggtgtccttc gaccacgcac           700
cgcacaactt cggcttccgt ttcttctatc ttcactacaa gctcaagcac           750
gaaggacctt tcaagcgaaa gacctgtaag caggagcaaa ctacagagat           800
gaccagctgc ctccttcaaa atgtttctcc aggggattat ataattgagc           850
tggtggatga cactaacaca acaagaaaag tgatgcatta tgccttaaag           900
ccagtgcact ccccgtgggc cgggcccatc agagccgtgg ccatcacagt           950
gccactggta gtcatatcgg cattcgcgac gctcttcact gtgatgtgcc          1000
```

-continued

```
gcaagaagca acaagaaaat atatattcac atttagatga agagagctct      1050
gagtcttcca catacactgc agcactccca agagagaggc tccggccgcg      1100
gccgaaggtc tttctctgct attccagtaa agatggccag aatcacatga      1150
atgtcgtcca gtgtttcgcc tacttcctcc aggacttctg tggctgtgag      1200
gtggctctgg acctgtggga agacttcagc ctctgtagaa aagggcagag      1250
agaatgggtc atccagaaga tccacgagtc ccagttcatc attgtggttt      1300
gttccaaagg tatgaagtac tttgtggaca agaagaacta caaacacaaa      1350
ggaggtggcc gaggctcggg gaaaggagag ctcttcctgg tggcggtgtc      1400
agccattgcc gaaaagctcc gccaggccaa gcagagttcg tccgcggcgc      1450
tcagcaagtt tatcgccgtc tactttgatt attcctgcga gggagacgtc      1500
cccggtatcc tagacctgag taccaagtac agactcatgg acaatcttcc      1550
tcagctctgt tcccacctgc actcccgaga ccacggcctc caggagccgg      1600
ggcagcacac gcgacagggc agcagaagga actacttccg gagcaagtca      1650
ggccggtccc tatacgtcgc catttgcaac atgcaccagt ttattgacga      1700
ggagcccgac tggttcgaaa agcagttcgt tcccttccat cctcctccac      1750
tgcgctaccg ggagccagtc ttggagaaat ttgattcggg cttggtttta      1800
aatgatgtca tgtgcaaacc agggcctgag agtgacttct gcctaaaggt      1850
agaggcggct gttcttgggg caaccggacc agccgactcc cagcacgaga      1900
gtcagcatgg gggcctggac caagacgggg aggcccggcc tgcccttgac      1950
ggtagcgccg ccctgcaacc cctgctgcac acggtgaaag ccggcagccc      2000
ctcggacatg ccgcgggact caggcatcta tgactcgtct gtgccctcat      2050
ccgagctgtc tctgccactg atggaaggac tctcgacgga ccagacagaa      2100
acgtcttccc tgacggagag cgtgtcctcc tcttcaggcc tgggtgagga      2150
ggaacctcct gcccttcctt ccaagctcct ctcttctggg tcatgcaaag      2200
cagatcttgg ttgccgcagc tacactgatg aactccacgc ggtcgcccct      2250
ttgtaacaaa acgaaagagt ctaagcattg ccactttaaa aaaaaaaaa      2300
aaaaaaaaaa aaaaaaaa                                        2319
```

<210> SEQ ID NO 18
<211> LENGTH: 728
<212> TYPE: PRT
<213> ORGANISM: Homo Sapien

<400> SEQUENCE: 18

```
Met Pro Arg Ala Ser Ala Ser Gly Val Pro Ala Leu Phe Val Ser
 1               5                  10                  15

Gly Glu Gln Gly Val Gly Pro Ala Ser Arg Asn Ser Gly Leu Tyr
                20                  25                  30

Asn Ile Thr Phe Lys Tyr Asp Asn Cys Thr Thr Tyr Leu Asn Pro
                35                  40                  45

Val Gly Lys His Val Ile Ala Asp Ala Gln Asn Ile Thr Ile Ser
                50                  55                  60

Gln Tyr Ala Cys His Asp Gln Val Ala Val Thr Ile Leu Trp Ser
            65                      70                  75

Pro Gly Ala Leu Gly Ile Glu Phe Leu Lys Gly Phe Arg Val Ile
```

-continued

```
                    80                  85                  90
Leu Glu Glu Leu Lys Ser Glu Gly Arg Gln Cys Gln Gln Leu Ile
                    95                 100                 105
Leu Lys Asp Pro Lys Gln Leu Asn Ser Ser Phe Lys Arg Thr Gly
                   110                 115                 120
Met Glu Ser Gln Pro Phe Leu Asn Met Lys Phe Glu Thr Asp Tyr
                   125                 130                 135
Phe Val Lys Val Val Pro Phe Pro Ser Ile Lys Asn Glu Ser Asn
                   140                 145                 150
Tyr His Pro Phe Phe Phe Arg Thr Arg Ala Cys Asp Leu Leu Leu
                   155                 160                 165
Gln Pro Asp Asn Leu Ala Cys Lys Pro Phe Trp Lys Pro Arg Asn
                   170                 175                 180
Leu Asn Ile Ser Gln His Gly Ser Asp Met Gln Val Ser Phe Asp
                   185                 190                 195
His Ala Pro His Gly Ser Asp Met Gln Val Ser Phe Asp His Ala
                   200                 205                 210
Pro His Asn Phe Gly Phe Arg Phe Phe Tyr Leu His Tyr Lys Leu
                   215                 220                 225
Lys His Glu Gly Pro Phe Lys Arg Lys Thr Cys Lys Gln Glu Gln
                   230                 235                 240
Thr Thr Glu Met Thr Ser Cys Leu Leu Gln Asn Val Ser Pro Gly
                   245                 250                 255
Asp Tyr Ile Ile Glu Leu Val Asp Asp Thr Asn Thr Thr Arg Lys
                   260                 265                 270
Val Met His Tyr Ala Leu Lys Pro Val His Ser Pro Trp Ala Gly
                   275                 280                 285
Pro Ile Arg Ala Val Ala Ile Thr Val Pro Leu Val Val Ile Ser
                   290                 295                 300
Ala Phe Ala Thr Leu Phe Thr Val Met Cys Arg Lys Lys Gln Gln
                   305                 310                 315
Glu Asn Ile Tyr Ser His Leu Asp Glu Glu Ser Ser Glu Ser Ser
                   320                 325                 330
Thr Tyr Thr Ala Ala Leu Pro Arg Glu Arg Leu Arg Pro Arg Pro
                   335                 340                 345
Lys Val Phe Leu Cys Tyr Ser Ser Lys Asp Gly Gln Asn His Met
                   350                 355                 360
Asn Val Val Gln Cys Phe Ala Tyr Phe Leu Gln Asp Phe Cys Gly
                   365                 370                 375
Cys Glu Val Ala Leu Asp Leu Trp Glu Asp Phe Ser Leu Cys Arg
                   380                 385                 390
Glu Gly Gln Arg Glu Trp Val Ile Gln Lys Ile His Glu Ser Gln
                   395                 400                 405
Phe Ile Ile Val Val Cys Ser Lys Gly Met Lys Tyr Phe Val Asp
                   410                 415                 420
Lys Lys Asn Tyr Lys His Lys Gly Gly Arg Gly Ser Gly Lys
                   425                 430                 435
Gly Glu Leu Phe Leu Val Ala Val Ser Ala Ile Ala Glu Lys Leu
                   440                 445                 450
Arg Gln Ala Lys Gln Ser Ser Ala Ala Leu Ser Lys Phe Ile
                   455                 460                 465
Ala Val Tyr Phe Asp Tyr Ser Cys Glu Gly Asp Val Pro Gly Ile
                   470                 475                 480
```

```
Leu Asp Leu Ser Thr Lys Tyr Arg Leu Met Asp Asn Leu Pro Gln
            485                 490                 495

Leu Cys Ser His Leu His Ser Arg Asp His Gly Leu Gln Glu Pro
        500                 505                 510

Gly Gln His Thr Arg Gln Gly Ser Arg Asn Tyr Phe Arg Ser
    515                 520                 525

Lys Ser Gly Arg Ser Leu Tyr Val Ala Ile Cys Asn Met His Gln
            530                 535                 540

Phe Ile Asp Glu Glu Pro Asp Trp Phe Glu Lys Gln Phe Val Pro
            545                 550                 555

Phe His Pro Pro Pro Leu Arg Tyr Arg Glu Pro Val Leu Glu Lys
            560                 565                 570

Phe Asp Ser Gly Leu Val Leu Asn Asp Val Met Cys Lys Pro Gly
            575                 580                 585

Pro Glu Ser Asp Phe Cys Leu Lys Val Glu Ala Ala Val Leu Gly
            590                 595                 600

Ala Thr Gly Pro Ala Asp Ser Gln His Glu Ser Gln His Gly Gly
            605                 610                 615

Leu Asp Gln Asp Gly Glu Ala Arg Pro Ala Leu Asp Gly Ser Ala
            620                 625                 630

Ala Leu Gln Pro Leu Leu His Thr Val Lys Ala Gly Ser Pro Ser
            635                 640                 645

Asp Met Pro Arg Asp Ser Gly Ile Tyr Asp Ser Ser Val Pro Ser
            650                 655                 660

Ser Glu Leu Ser Leu Pro Leu Met Glu Gly Leu Ser Thr Asp Gln
            665                 670                 675

Thr Glu Thr Ser Ser Leu Thr Glu Ser Val Ser Ser Ser Ser Gly
            680                 685                 690

Leu Gly Glu Glu Glu Pro Pro Ala Leu Pro Ser Lys Leu Leu Ser
            695                 700                 705

Ser Gly Ser Cys Lys Ala Asp Leu Gly Cys Arg Ser Tyr Thr Asp
            710                 715                 720

Glu Leu His Ala Val Ala Pro Leu
            725

<210> SEQ ID NO 19
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 19
atccacagaa gctggccttc gccg                                    24

<210> SEQ ID NO 20
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 20
gggacgtgga tgaactcggt gtgg                                    24

<210> SEQ ID NO 21
<211> LENGTH: 40
```

```
<212> TYPE: DNA
<213> ORGANISM: Artificial Sequence
<220> FEATURE:
<223> OTHER INFORMATION: Synthetic Oligonucleotide Probe

<400> SEQUENCE: 21
tatccacaga agctggcctt cgccgagtgc ctgtgcagag                    40

<210> SEQ ID NO 22
<211> LENGTH: 27
<212> TYPE: DNA
<213> ORGANISM: Artificial Sequence
<220> FEATURE:
<223> OTHER INFORMATION: Synthetic Oligonucleotide Probe

<400> SEQUENCE: 22
gttgcattct tggcaatggt catggga                                  27

<210> SEQ ID NO 23
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 23
ggtccatgtg ggagcctgtc tgta                                     24

<210> SEQ ID NO 24
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 24
cagcagctcc tcagaggtgt cctgccctt gctggggcag cagct              45

<210> SEQ ID NO 25
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 25
gctcagtgcc ttccaccaca cgc                                      23

<210> SEQ ID NO 26
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 26
ctgcgtcctt ctccggctcg g                                        21

<210> SEQ ID NO 27
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 27
```

```
cgttccgtct acaccgaggc ctacgtcacc atccccgtgg gctgc          45
```

<210> SEQ ID NO 28
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 28

```
actccatatt ttcctacttg tggca                                25
```

<210> SEQ ID NO 29
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 29

```
cccaaagtga cctaagaac                                       19
```

<210> SEQ ID NO 30
<211> LENGTH: 27
<212> TYPE: DNA
<213> ORGANISM: Artificial Sequence
<220> FEATURE:
<223> OTHER INFORMATION: Synthetic Oligonucleotide Probe

<400> SEQUENCE: 30

```
tcactgaatt tcttcaaaac cattgca                              27
```

<210> SEQ ID NO 31
<211> LENGTH: 50
<212> TYPE: DNA
<213> ORGANISM: Artificial Sequence
<220> FEATURE:
<223> OTHER INFORMATION: Synthetic Oligonucleotide Probe

<400> SEQUENCE: 31

```
tgtggcagcg actgcatccg acataaagga acagttgtgc tctgcccaca     50
```

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 32

```
ccgacttctt gcagggccgg                                      20
```

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 33

```
gcagcacgca gctgagcgag                                      20
```

<210> SEQ ID NO 34
<211> LENGTH: 33
<212> TYPE: DNA
<213> ORGANISM: Artificial Sequence

```
<220> FEATURE:
<223> OTHER INFORMATION: Synthetic Oligonucleotide Probe

<400> SEQUENCE: 34
agcgagtggc tacaggatgg ggtgtccggg ccc                          33

<210> SEQ ID NO 35
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 35
cgttgtttgt cagtggagag caggg                                   25

<210> SEQ ID NO 36
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 36
caggaacacc tgaggcagaa gcg                                     23

<210> SEQ ID NO 37
<211> LENGTH: 40
<212> TYPE: DNA
<213> ORGANISM: Artificial Sequence
<220> FEATURE:
<223> OTHER INFORMATION: Synthetic Oligonucleotide Probe

<400> SEQUENCE: 37
ctatctccct gccaggaggc cggagtgggg gaggtcagac                   40

<210> SEQ ID NO 38
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 38
ctgtacctcg agggtgcaga g                                       21

<210> SEQ ID NO 39
<211> LENGTH: 58
<212> TYPE: DNA
<213> ORGANISM: Artificial Sequence
<220> FEATURE:
<223> OTHER INFORMATION: Synthetic Oligonucleotide Probe

<400> SEQUENCE: 39
cccaagcttg ggtcaatgat gatgatgatg atgatgatgc cacagggca         50 tgtagtcc                                                      58
```

IL-17 RELATED MAMMALIAN CYTOKINE POLYPEPTIDES (IL-17E)

This application is a continuing application (filed under 35 U.S.C. §120) which application claims priority to U.S. Provisional Application Nos.: 60/253,646, filed Nov. 28, 2000; 60/244,072, filed Oct. 26, 2000: 60/242,837, filed Oct. 24, 2000; 60/213,807, filed Jun. 22, 2000; 60/191,007, filed Mar. 21, 2000, now abandoned; 60/175,481, filed Jan. 11, 2000, now abandoned; 60/172,096, filed Dec. 23, 1999, now abandoned; 60/138,387, filed Jun. 9, 1999, now abandoned; 60/134,287, filed May 14, 1999, now abandoned; 60/13 1,022, filed Apr. 26, 1999, now abandoned; 60/130,232, filed Apr. 21, 1999, now abandoned; 60/113,621, filed Dec. 23, 1998, now abandoned; and 60/085,579, filed May 15, 1998, now abandoned; to which U.S. Provisional Applications claim priority under 35 U.S.C. §119; and to International PCT Application Nos. and U.S. patent application Ser. Nos.: PCT/US01/06520, filed Feb. 28, 2001; PCT/US00/34956, filed Dec. 20, 2000; Ser. No. 09/747,259, filed Dec. 20, 2000; PCT/US00/32678, filed Dec. 1, 2000; PCT/US00/30873, filed Nov. 10, 2000; PCT/US00/23328, filed Aug. 24, 2000; Ser. No. 09/644,848, filed Aug. 22, 2000; PCT/US00/15264, filed June 2, 2000; PCT/US00/07532, filed Mar. 21, 2000; PCT/US00/05841, filed Mar. 2, 2000; PCT/US00/05601, filed Mar. 1, 2000; PCT/US00/04341, filed Feb. 18, 2000; PCT/US99/31274, filed Dec. 30, 1999; Ser. No. 09/380,138, filed Aug. 25, 1999; Ser. No. 09/380,142, filed Aug. 25, 1999; PCT/US99/10733, filed May 14, 1999; Ser. No. 09/311,832, filed May 14, 1999; and PCT/US99/05028, filed Mar. 8, 1999; to which International PCT Applications and U.S. patent applications claim priority under 35 U.S.C. §120; the entire disclosures of which are hereby incorporated by reference in their entireties.

FIELD OF THE INVENTION

The present invention relates generally to the identification and isolation of novel DNA and to the recombinant production of novel polypeptides having sequence similarity to interleukin-17 and to interleukin-17 receptor protein, designated herein as "PRO" polypeptides.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents.

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Similarly to secreted proteins, membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native secreted proteins and native receptor or membrane-bound proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.*, 93:7108–7113 (1996); U.S. Pat. No. 5,536,637)].

In this regard, the present invention relates to identifying novel secreted polypeptides and receptors of the interleukin-17 (IL-17) family which have been shown to be related to immune-mediated and inflammatory disease. Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, etc.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

A central event in both humoral and cell mediated immune responses is the activation and clonal expansion of helper T cells. Helper T cell activation is initiated by the interaction of the T cell receptor (TCR)—CD3 complex with an antigen-MHC on the surface of an antigen presenting cell. This interaction mediates a cascade of biochemical events that induce the resting helper T cell to enter a cell cycle (the G0 to G1 transition) and results in the expression of a high affinity receptor for IL-2 and sometimes IL-4. The activated T cell progresses through the cycle proliferating and differentiating into memory cells or effector cells.

In addition to the signals mediated through the TCR, activation of T cells involves additional costimulation induced by cytokines released by the antigen presenting cell or through interactions with membrane bound molecules on the antigen presenting cell and the T cell. The cytokines IL-1 and IL-6 have been shown to provide a costimulatory signal. Also, the interaction between the B7 molecule expressed on the surface of an antigen presenting cell and CD28 and CTLA-4 molecules expressed on the T cell surface effect T cell activation. Activated T cells express an increased number of cellular adhesion molecules, such as ICAM-1, integrins, VLA-4, LFA-1, CD56, etc.

T-cell proliferation in a mixed lymphocyte culture or mixed lymphocyte reaction (MLR) is an established indication of the ability of a compound to stimulate the immune system. In many immune responses, inflammatory cells infiltrate the site of injury or infection. The migrating cells may be neutrophilic, eosinophilic, monocytic or lymphocytic as can be determined by histologic examination of the affected tissues. *Current Protocols in Immunology*, ed. John E. Coligan, 1994, John Wiley & Sons, Inc.

Immune related diseases could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

Interleukin-17 (IL-17) has been identified as a cellular ortholog of a protein encoded by the T lymphotropic Herpes virus Saimiri (HSV) [see, Rouvier et al., *J. Immunol.*, 150(12): 5445–5456 (19993); Yao et al., *J. Immunol.*, 122 (12):5483–5486 (1995) and Yao et al., *Immunity*, 3(6) :811–821 (1995)]. Subsequent characterization has shown that this protein is a potent cytokine that acts to induce proinflammatory responses in a wide variety of peripheral tissues. IL-17 is a homodimeric cytokine of about 32 kDa which is synthesized and secreted only by CD4$^+$ activated memory T cells (reviewed in Fossiez et al., *Int. Rev. Immunol.* 16: 541–551 [1998]).

Despite its restricted tissue distribution, IL-17 exhibits pleitropic biological activities on various types of cells. IL-17 has been found to stimulate the production of many cytokines. It induces the secretion of IL-6, IL-8, IL-12, leukemia inhibitory factor (LIF), prostaglandin E2, MCP-1 and G-CSF by adherent cells like fibroblasts, keratinocytes, epithelial and endothelial cells. IL-17 also has the ability to induce ICAM-1 surface expression, proliferation of T cells, and growth and differentiation of CD34$^+$ human progenitors into neutrophils. IL-17 has also been implicated in bone metabolism, and has been suggested to play an important role in pathological conditions characterized by the presence of activated T cells and TNF-α production such as rheumatoid arthritis and loosening of bone implants (Van Bezooijen et al.,*J. Bone Miner. Res.*, 14: 1513–1521 [1999]). Activated T cells of synovial tissue derived from rheumatoid arthritis patients were found to secrete higher amounts of IL-17 than those derived from normal individuals or osteoarthritis patients (Chabaud et al., *Arthritis Rheum.*, 42: 963–970 [1999]). It was suggested that this proinflammatory cytokine actively contributes to synovial inflammation in rheumatoid arthritis. Apart from its proinflammatory role, IL-17 seems to contribute to the pathology of rheumatoid arthritis by yet another mechanism. For example, IL-17 has been shown to induce the expression of osteoclast differentiation factor (ODF) mRNA in osteoblasts (Kotake et al., *J. Clin. Invest.*, 103: 1345–1352 [1999]). ODF stimulates differentiation of progenitor cells into osteoclasts, the cells involved in bone resorption. Since the level of IL-17 is significantly increased in synovial fluid of rheumatoid arthritis patients, it appears that IL-17 induced osteoclast formation plays a crucial role in bone resorption in rheumatoid arthritis. IL-17 is also believed to play a key role in certain other autoimmune disorders such as multiple sclerosis (Matusevicius et al., *Mult. Scler.*, 5: 101–104 [1999]). IL-17 has further been shown, by intracellular signalling, to stimulate $Ca^{2+}$ influx and a reduction in $[cAMP]_i$ in human macrophages (Jovanovic et al.,*J. Immunol.*, 160:3513 [1998]). Fibroblasts treated with IL-17 induce the activation of NF-κB, [Yao et al., *Immunity*, 3:811 (1995), Jovanovic et al., supra], while macrophages treated with it activate NF-κB and mitogen-activated protein kinases (Shalom-Barek et al., *J. Biol. Chem.*, 273:27467 [1998]).

Additionally, IL-17 also shares sequence similarity with mammalian cytokine-like factor 7 that is involved in bone and cartilage growth. Other proteins with which IL-17 polypeptides share sequence similarity are human embryo-derived interleulkin-related factor (EDIRF) and interleukin-20.

Consistent with IL-17's wide-range of effects, the cell surface receptor for IL-17 has been found to be widely expressed in many tissues and cell types (Yao et al., *Cytokine*, 9:794 [1997]). While the amino acid sequence of the human IL-17 receptor (IL-R) (866 amino acids) predicts a protein with a single transmembrane domain and a long, 525 amino acid intracellular domain, the receptor sequence is unique and is not similar to that of any of the receptors from the cytokine/growth factor receptor family. This coupled with the lack of similarity of IL-17 itself to other known proteins indicates that IL-17 and its receptor may be part of a novel family of signalling proteins and receptors. It has been demonstrated that IL-17 activity is mediated through binding to its unique cell surface receptor, wherein previous studies have shown that contacting T cells with a soluble form of the IL-17 receptor polypeptide inhibited T cell proliferation and IL-2 production induced by PHA, concanavalin A and anti-TCR monoclonal antibody (Yao et al., *J. Immunol.*, 155:5483–5486 [1995]). As such, there is significant interest in identifying and characterizing novel polypeptides having homology to the known cytokine receptors, specifically IL-17 receptors.

Recently, we have identified two new proteins termed IL-17B and IL-17C that are clearly related to IL-17, establishing that there exists a family of IL-17-like molecules (Li et al., *Proc. Natl. Acad. Sci. (USA)*, 97(2):773–778 [2000]). Interestingly, they do not appear to be ligands for IL-17 receptor, suggesting that there exists other molecules that serve as cognate receptors for these factors. Interest in this family of molecules has increased as it has become apparent that IL-17 may contribute to a number of important medical conditions related to immune function: including rheumatoid arthritis, immune mediated renal diseases, hepatobiliary diseases, inflammatory bowel disease, psoriasis, asthma, multiple sclerosis, atherosclerosis, promotion of tumor growth, or degenerative joint disease. Given the potential of IL-17 related molecules to occupy important roles in the control of immune function, there is an interest in the identification of other members of this family and the receptors that direct the actions of these molecules through particular target cell populations. In this respect, the present invention describes the cloning and characterization of novel proteins (designated herein as "PRO" polypeptides) that are similar in amino acid sequence to IL-17, and active variants thereof, as well as novel interleukin-receptor molecules which have been shown to interact with the novel IL-17 protein ligands.

SUMMARY OF THE INVENTION

A. Embodiments

The present invention concerns compositions and methods useful for the diagnosis and treatment of immune related disease in mammals, including humans. The present invention is based on the identification of proteins (including agonist and antagonist antibodies) which either stimulate or inhibit the immune response in mammals. Immune related diseases can be treated by suppressing or enhancing the immune response. Molecules that enhance the immune response stimulate or potentiate the immune response to an antigen. Molecules which stimulate the immune response can be used therapeutically where enhancement of the immune response would be beneficial. Alternatively, molecules that suppress the immune response attenuate or reduce the immune response to an antigen (e.g., neutralizing antibodies) can be used therapeutically where attenuation of the immune response would be beneficial (e.g., inflammation). Accordingly, the PRO polypeptides of the present invention and agonists and antagonists thereof are also useful to prepare medicines and medicaments for the treatment of immune-related and inflammatory diseases. In a specific aspect, such medicines and medicaments comprise a therapeutically effective amount of a PRO polypeptide, agonist or antagonist thereof with a pharmaceutically acceptable carrier. Preferably, the admixture is sterile.

In a further embodiment, the invention concerns a method of identifying agonists of or antagonists to a PRO polypeptide which comprises contacting the PRO polypeptide with a candidate molecule and monitoring a biological activity mediated by said PRO polypeptide. Preferably, the PRO polypeptide is a native sequence PRO polypeptide. In a specific aspect, the PRO agonist or antagonist is an anti-PRO antibody.

In another embodiment, the invention concerns a composition of matter comprising a PRO polypeptide or an agonist or antagonist antibody which binds the polypeptide in admixture with a carrier or excipient. In one aspect, the composition comprises a therapeutically effective amount of the polypeptide or antibody. In another aspect, when the composition comprises an immune stimulating molecule, the composition is useful for: (a) enhancing infiltration of inflammatory cells into a tissue of a mammal in need thereof, (b) stimulating or enhancing an immune response in a mammal in need thereof, (c) increasing the proliferation of T-lymphocytes in a mammal in need thereof in response to an antigen, (d) stimulating the activity of T-lymphocytes or (e) increasing the vascular permeability. In a further aspect, when the composition comprises an immune inhibiting molecule, the composition is useful for: (a) decreasing infiltration of inflammatory cells into a tissue of a mammal in need thereof, (b) inhibiting or reducing an immune response in a mammal in need thereof, (c) decreasing the activity of T-lymphocytes or (d) decreasing the proliferation of T-lymphocytes in a mammal in need thereof in response to an antigen. In another aspect, the composition comprises a further active ingredient, which may, for example, be a further antibody or a cytotoxic or chemotherapeutic agent. Preferably, the composition is sterile.

In another embodiment, the invention concerns a method of treating an immune related disorder in a mammal in need thereof, comprising administering to the mammal a therapeutically effective amount of a PRO polypeptide, an agonist thereof, or an antagonist thereto. In a preferred aspect, the immune related disorder is selected form the group consisting of: systemic lupus erythematosis, rheumatoid arthritis, osteoarthritis, juvenile chronic arthritis, spondyloarthropathies, systemic sclerosis, idiopathic inflammatory myopathies, Sjögren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious, autoimmune chronic active hepatitis, primary biliary cirrhosis, granulomatous hepatitis, and sclerosing cholangitis, inflammatory bowel disease, gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, transplantation associated diseases including graft rejection and graft-versus-host-disease.

In another embodiment, the invention provides an antibody which specifically binds to any of the above or below described polypeptides. Optionally, the antibody is a monoclonal antibody, humanized antibody, antibody fragment or single-chain antibody. In one aspect, the present invention concerns an isolated antibody which binds a PRO polypeptide. In another aspect, the antibody mimics the activity of a PRO polypeptide (an agonist antibody) or conversely the antibody inhibits or neutralizes the activity of a PRO polypeptide (an antagonist antibody). In another aspect, the antibody is a monoclonal antibody, which preferably has nonhuman complementarity determining region (CDR) residues and human framework region (FR) residues. The antibody may be labeled and may be immobilized on a solid support. In a further aspect, the antibody is an antibody fragment, a monoclonal antibody, a single-chain antibody, or an anti-idiotypic antibody.

In yet another embodiment, the present invention provides a composition comprising an anti-PRO antibody in admixture with a pharmaceutically acceptable carrier. In one aspect, the composition comprises a therapeutically effective amount of the antibody. Preferably, the composition is sterile. The composition may be administered in the form of a liquid pharmaceutical formulation, which may be preserved to achieve extended storage stability. Alternatively, the antibody is a monoclonal antibody, an antibody fragment, a humanized antibody, or a single-chain antibody.

In a further embodiment, the invention concerns an article of manufacture, comprising:
(a) a composition of matter comprising a PRO polypeptide or agonist, antagonist, or an antibody that specifically binds to said polypeptide thereof;
(b) a container containing said composition; and
(c) a label affixed to said container, or a package insert included in said container referring to the use of said PRO polypeptide or agonist or antagonist thereof in the treatment of an immune related disease. The composition may comprise a therapeutically effective amount of the PRO polypeptide or the agonist or antagonist thereof.

In yet another embodiment, the present invention concerns a method of diagnosing an immune related disease in a mammal, comprising detecting the level of expression of a gene encoding a PRO polypeptide (a) in a test sample of tissue cells obtained from the mammal, and (b) in a control sample of known normal tissue cells of the same cell type, wherein a higher or lower expression level in the test sample as compared to the control sample indicates the presence of immune related disease in the mammal from which the test tissue cells were obtained.

In another embodiment, the present invention concerns a method of diagnosing an immune disease in a mammal, comprising (a) contacting an anti-PRO antibody with a test sample of tissue cells obtained from the mammal, and (b) detecting the formation of a complex between the antibody and a PRO polypeptide, in the test sample; wherein the formation of said complex is indicative of the presence or absence of said disease. The detection may be qualitative or quantitative, and may be performed in comparison with monitoring the complex formation in a control sample of known normal tissue cells of the same cell type. A larger quantity of complexes formed in the test sample indicates the presence or absence of an immune disease in the mammal from which the test tissue cells were obtained. The antibody preferably carries a detectable label. Complex formation can be monitored, for example, by light microscopy, flow cytometry, fluorimetry, or other techniques known in the art. The test sample is usually obtained from an individual suspected of having a deficiency or abnormality of the immune system.

In another embodiment, the invention provides a method for determining the presence of a PRO polypeptide in a sample comprising exposing a test sample of cells suspected of containing the PRO polypeptide to an anti-PRO antibody and determining the binding of said antibody to said cell sample. In a specific aspect, the sample comprises a cell suspected of containing the PRO polypeptide and the antibody binds to the cell. The antibody is preferably detectably labeled and/or bound to a solid support.

In another embodiment, the present invention concerns an immune-related disease diagnostic kit, comprising an anti-PRO antibody and a carrier in suitable packaging. The kit preferably contains instructions for using the antibody to detect the presence of the PRO polypeptide. Preferably the carrier is pharmaceutically acceptable.

In another embodiment, the present invention concerns a diagnostic kit, containing an anti-PRO antibody in suitable packaging. The kit preferably contains instructions for using the antibody to detect the PRO polypeptide.

In another embodiment, the invention provides a method of diagnosing an immune-related disease in a mammal which comprises detecting the presence or absence or a PRO polypeptide in a test sample of tissue cells obtained from said mammal, wherein the presence or absence of the PRO polypeptide in said test sample is indicative of the presence of an immune-related disease in said mammal.

In another embodiment, the present invention concerns a method for identifying an agonist of a PRO polypeptide comprising:
(a) contacting cells and a test compound to be screened under conditions suitable for the induction of a cellular response normally induced by a PRO polypeptide; and (b) determining the induction of said cellular response to determine if the test compound is an effective agonist, wherein the induction of said cellular response is indicative of said test compound being an effective agonist.

In another embodiment, the invention concerns a method for identifying a compound capable of inhibiting the activity of a PRO polypeptide comprising contacting a candidate compound with a PRO polypeptide under conditions and for a time sufficient to allow these two components to interact and determining whether the activity of the PRO polypeptide is inhibited. In a specific aspect, either the candidate compound or the PRO polypeptide is immobilized on a solid support. In another aspect, the non-immobilized component carries a detectable label. In a preferred aspect, this method comprises the steps of:
(a) contacting cells and a test compound to be screened in the presence of a PRO polypeptide under conditions suitable for the induction of a cellular response normally induced by a PRO polypeptide; and (b) determining the induction of said cellular response to determine if the test compound is an effective antagonist.

In another embodiment, the invention provides a method for identifying a compound that inhibits the expression of a PRO polypeptide in cells that normally express the polypeptide, wherein the method comprises contacting the cells with a test compound and determining whether the expression of the PRO polypeptide is inhibited. In a preferred aspect, this method comprises the steps of:
(a) contacting cells and a test compound to be screened under conditions suitable for allowing expression of the PRO polypeptide; and (b) determining the inhibition of expression of said polypeptide.

In yet another embodiment, the present invention concerns a method for treating an immune-related disorder in a mammal that suffers therefrom comprising administering to the mammal a nucleic acid molecule that codes for either (a) a PRO polypeptide, (b) an agonist of a PRO polypeptide or (c) an antagonist of a PRO polypeptide, wherein said agonist or antagonist may be an anti-PRO antibody. In a preferred embodiment, the mammal is human. In another preferred embodiment, the nucleic acid is administered via ex vivo gene therapy. In a further preferred embodiment, the nucleic acid is comprised within a vector, more preferably an adenoviral, adeno-associated viral, lentiviral or retroviral vector.

In yet another aspect, the invention provides a recombinant viral particle comprising a viral vector consisting essentially of a promoter, nucleic acid encoding (a) a PRO polypeptide, (b) an agonist polypeptide of a PRO polypeptide, or (c) an antagonist polypeptide of a PRO polypeptide, and a signal sequence for cellular secretion of the polypeptide, wherein the viral vector is in association with viral structural proteins. Preferably, the signal sequence is from a mammal, such as from a native PRO polypeptide.

In a still further embodiment, the invention concerns an ex vivo producer cell comprising a nucleic acid construct that expresses retroviral structural proteins and also comprises a retroviral vector consisting essentially of a promoter, nucleic acid encoding (a) a PRO polypeptide, (b) an agonist polypeptide of a PRO polypeptide or (c) an antagonist polypeptide of a PRO polypeptide, and a signal sequence for cellular secretion of the polypeptide, wherein said producer cell packages the retroviral vector in association with the structural proteins to produce recombinant retroviral particles.

In a still further embodiment, the invention provides a method for enhancing the infiltration of inflammatory cells from the vasculature into a tissue of a mammal comprising administering to said mammal (a) a PRO polypeptide, (b) an agonist of a PRO polypeptide, or (c) an antagonist of a PRO polypeptide, wherein the infiltration of inflammatory cells from the vasculature in the mammal is enhanced.

In a still further embodiment, the invention provides a method for decreasing the infiltration of inflammatory cells from the vasculature into a tissue of a mammal comprising administering to said mammal (a) a PRO polypeptide, (b) an agonist of a PRO polypeptide, or (c) an antagonist of a PRO polypeptide, wherein the infiltration of inflammatory cells from the vasculature in the mammal is decreased.

In a still further embodiment, the invention provides a method of increasing the activity of T-lymphocytes in a mammal comprising administering to said mammal (a) a PRO polypeptide, (b) an agonist of a PRO polypeptide, or (c) an antagonist of a PRO polypeptide, wherein the activity of T-lymphocytes in the mammal is increased.

In a still further embodiment, the invention provides a method of decreasing the activity of T-lymphocytes in a mammal comprising administering to said mammal (a) a PRO polypeptide, (b) an agonist of a PRO polypeptide, or (c) an antagonist of a PRO polypeptide, wherein the activity of T-lymphocytes in the mammal is decreased.

In a still further embodiment, the invention provides a method of increasing the proliferation of T-lymphocytes in a mammal comprising administering to said mammal (a) a PRO polypeptide, (b) an agonist of a PRO polypeptide, or (c) an antagonist of a PRO polypeptide, wherein the proliferation of T-lymphocytes in the mammal is increased.

In a still further embodiment, the invention provides a method of decreasing the proliferation of T-lymphocytes in a mammal comprising administering to said mammal (a) a PRO polypeptide, (b) an agonist of a PRO polypeptide, or (c) an antagonist of a PRO polypeptide, wherein the proliferation of T-lymphocytes in the mammal is decreased.

In a still further embodiment, the invention provides a method of stimulating the proliferation of T-cells comprising contacting said T-cells with a PRO1031 or PRO10272 polypeptide or agonist thereof, wherein said T-cell proliferation is stimulated.

In a still further embodiment, the invention provides a method of decreasing the proliferation of T-lymphocytes comprising contacting said T-lymphocytes with an antagonist of a PRO1031 or PRO10272 polypeptide, wherein the proliferation of T-lymphocytes is decreased.

In a still further embodiment, the invention provides a method of enhancing the infiltration of inflammatory cells into a tissue of a mammal comprising administering an effective amount of a PRO1031 polypeptide or agonist thereof, wherein said infiltration is enhanced.

In a still further embodiment, the invention provides a method of decreasing the infiltration of inflammatory cells into a tissue of a mammal comprising administering an effective amount of an antagonist of a PRO1031 polypeptide, wherein said infiltration is decreased.

In yet another embodiment, the invention provides a method for inhibiting angiogenesis induced by a PRO1031 polypeptide or an agonist thereof in a mammal comprising administering a therapeutically effective amount of an anti-PRO1031 antibody to the mammal. Preferably, the mammal is a human, and more preferably the mammal has a tumor or a retinal disorder.

In yet another embodiment, the invention provides a method for stimulating angiogenesis induced by a PRO1031 polypeptide in a mammal comprising administering a therapeutically effective amount of a PRO1031 polypeptide or agonist thereof to the mammal. Preferably, the mammal is a human, and more preferably angiogenesis would promote tissue regeneration or wound healing.

In another embodiment, the invention provides a method for inhibiting angiogenesis in a mammal comprising administering a therapeutically effective amount of an antagonist of a PRO1031 polypeptide to the mammal, wherein said angiogenesis is inhibited.

In still a further embodiment, the invention concerns the use of a PRO1031, PRO1122, or PRO10272 polypeptide, or an agonist or antagonist thereof as hereinbefore described, or an anti-PRO1031, anti-PRO1122 or anti-PRO10272 antibody, for the preparation of a medicament useful in the treatment of a condition which is responsive to the PRO1031, PRO1122 or PRO10272 polypeptide or an agonist or antagonist thereof (e.g., anti-PRO1031, anti-PRO1122 or anti-PRO10272). In a particular aspect, the invention concerns the use of a PRO1031, PRO1122 or PRO10272 polypeptide, or an agonist or antagonist thereof in a method for treating a degenerative cartilaginous disorder.

In still a further embodiment, the invention relates to a method of treating a degenerative cartilaginous disorder in a mammal comprising administering a therapeutically effective amount of a PRO1031, PRO1122 or PRO10272 polypeptide, agonist, or antagonist thereof, to said mammal suffering from said disorder.

In still a further embodiment, the invention relates to a kit comprising a composition comprising a PRO1031, PRO1122 or PRO10272 polypeptide, or an agonist or antagonist thereof, in admixture with a pharmaceutically acceptable carrier; a container containing said composition; and a label affixed to said container, referring to the use of said composition, in the treatment of a degenerative cartilaginous disorder.

In a further embodiment, the invention relates to a method of detecting a polypeptide designated as A, B, or C in a sample suspected of containing an A, B, or C polypeptide, said method comprising contacting said sample with a polypeptide designated herein as D, E, or F and determining the formation of a A/D, B/D, C/E or C/F polypeptide conjugate in said sample, wherein the formation of said conjugate is indicative of the presence of an A, B, or C polypeptide in said sample and wherein A is a PRO1031 polypeptide (herein also designated IL-17B), B is a PRO10272 polypeptide (herein also designated IL-17E), C is a PRO20110 polypeptide (herein also designated IL-17F), D is a PRO5801 polypeptide (herein also designated IL-17RH1), E is a PRO1 polypeptide (herein known as IL-17R), and F is a PRO20040 polypeptide (herein also designated IL-17RH2). In one aspect of this embodiment, said sample comprises cells suspected of expressing said A, B, or C polypeptide.

In another aspect of this embodiment said D, E, or F polypeptide is labeled with a detectable label and said D, E, or F polypeptide is attached to a solid support.

In yet another embodiment, the invention relates to a method of detecting a polypeptide designated as D, E, or F in a sample suspected of containing an D, E, or F polypeptide, said method comprising contacting said sample with a polypeptide designated herein as A, B, or C and determining the formation of a A/D, B/D, C/E, or C/F polypeptide conjugate in said sample, wherein the formation of said conjugate is indicative of the presence of an A, B, or C polypeptide in said sample and wherein A is a PRO1031 polypeptide (herein also designated IL-17B), B is a PRO10272 polypeptide (herein also designated IL-17E), C is a PRO20110 polypeptide (herein also designated IL-17F), D is a PRO5801 polypeptide (herein also designated IL-17RH1), E is a PRO1 polypeptide (herein known as IL-17R), and F is a PRO20040 polypeptide (herein also designated IL-17RH2). In one aspect of this embodiment, said sample comprises cells suspected of expressing said D, E, or F polypeptide. In another aspect of this embodiment, said A, B, or C polypeptide is labeled with a detectable label and said A, B, or C polypeptide is attached to a solid support.

In still a further embodiment, the invention relates to a method of linking a bioactive molecule to a cell expressing a polypeptide designated as A, B, or C, said method comprising contacting said cell with a polypeptide designated as D, E, or F that is bound to said bioactive molecule and allowing said A, B, or C and said D, E, or F polypeptides to bind to one another, thereby linking said bioactive molecules to said cell, wherein A is a PRO1031 polypeptide (herein also designated IL-17B), B is a PRO10272 polypeptide (herein also designated IL-17E), C is a PRO20110 polypeptide (herein also designated IL-17F), D is a PRO5801 polypeptide (herein also designated IL-17RH1), E is a PRO1 polypeptide (herein known as IL-17R), and F is a PRO20040 polypeptide (herein also designated IL-17RH2). In one aspect of this embodiment, said bioactive molecule is a toxin, a radiolabel or an antibody. In another aspect of this embodiment, said bioactive molecule causes the death of said cell.

In a further embodiment, the invention relates to a method of lining a bioactive molecule to a cell expressing a polypeptide designated as D, E, or F, said method comprising contacting said cell with a polypeptide designated as A, B, or C that is bound to said bioactive molecule and allowing said A, B, or C and said D, E, or F polypeptides to bind to one another, thereby linking said bioactive molecules to said cell, wherein A is a PRO1031 polypeptide (herein also designated IL-17B), B is a PRO10272 polypeptide (herein also designated IL-17E), C is a PRO20110 polypeptide (herein also designated IL-17F), D is a PRO5801 polypeptide (herein also designated IL-17RH1), E is a PRO1 polypeptide (herein known as IL-17R), and F is a PRO20040 polypeptide (herein also designated IL-17RH2). In one aspect of this embodiment, said bioactive molecule is a toxin, a radiolabel or an antibody. In another aspect of this embodiment, said bioactive molecule causes the death of said cell.

In still another embodiment, the invention relates to a method of modulating at least one biological activity of a cell expressing a polypeptide designated as A, B, or C, said method comprising contacting said cell with a polypeptide designated as D, E, or F or an anti-A, anti-B, or anti-C polypeptide antibody, whereby said D, E, or F polypeptide or anti-A, anti-B, or anti-C polypeptide antibody binds to said A, B, or C polypeptide, thereby modulating at least one biological activity of said cell, wherein A is a PRO1031 polypeptide (herein also designated IL-17B), B is a PRO10272 polypeptide (herein also designated IL-17E), C is a PRO20110 polypeptide (herein also designated IL-17F), D is a PRO5801 polypeptide (herein also designated IL-17RH1), E is a PRO1 polypeptide (herein known as IL-17R), and F is a PRO20040 polypeptide (herein also designated IL-17RH2). In one aspect of this embodiment, said cell is killed.

In yet a further embodiment, the invention relates to a method of modulating at least one biological activity of a cell expressing a polypeptide designated as D, E, or F, said method comprising contacting said cell with a polypeptide designated as A, B, or C or an anti-D, anti-E, or anti-F polypeptide antibody, whereby said A, B, or C polypeptide or anti-D, anti-E, or anti-F polypeptide antibody binds to said D, E, or F polypeptide, thereby modulating at least one biological activity of said cell, wherein A is a PRO1031 polypeptide (herein also designated IL-17B), B is a PRO10272 polypeptide (herein also designated IL-17E), C is a PRO20110 polypeptide (herein also designated IL-17F), D is a PRO5801 polypeptide (herein also designated IL-17RH1), E is a PRO1 polypeptide (herein known as IL-17R), and F is a PRO20040 polypeptide (herein also designated IL-17RH2). In one aspect of this embodiment, said cell is killed.

B. Additional Embodiments

In other embodiments of the present invention, the invention provides an isolated nucleic acid molecule comprising a nucleotide sequence that encodes a PRO polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO polypeptide cDNA as disclosed herein, the coding sequence of a PRO polypeptide lacking the signal peptide as disclosed herein, the coding sequence of an extracellular domain of a transmembrane PRO polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect of the present invention provides an isolated nucleic acid molecule comprising a nucleotide sequence encoding a PRO polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO polypeptides are contemplated.

Another embodiment is directed to fragments of a PRO polypeptide coding sequence, or the complement thereof, that may find use as, for example, hybridization probes, for encoding fragments of a PRO polypeptide that may optionally encode a polypeptide comprising a binding site for an anti-PRO antibody or as antisense oligonucleotide probes. Such nucleic acid fragments are usually at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 200 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of a PRO polypeptide-encoding nucleotide sequence may be determined in a routine manner by aligning the PRO polypeptide-encoding nucleotide sequence with other known nucleotide sequences using any of a number of well known sequence alignment programs and determining which PRO polypeptide-encoding nucleotide sequence fragment(s) are novel. All of such PRO polypeptide-encoding nucleotide sequences are contemplated herein. Also contemplated are the PRO polypeptide fragments encoded by these nucleotide molecule fragments, preferably those PRO polypeptide fragments that comprise a binding site for an anti-PRO antibody.

In another embodiment, the invention provides an isolated PRO polypeptide encoded by any of the isolated nucleic acid sequences hereinabove identified.

In a certain aspect, the invention concerns an isolated PRO polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In a further aspect, the invention concerns an isolated PRO polypeptide comprising an amino acid sequence scoring at least about 80% positives, alternatively at least about 81% positives, alternatively at least about 82% positives, alternatively at least about 83% positives, alternatively at least about 84% positives, alternatively at least about 85% positives, alternatively at least about 86% positives, alternatively at least about 87% positives, alternatively at least about 88% positives, alternatively at least about 89% positives, alternatively at least about 90% positives, alternatively at least about 91% positives, alternatively at least about 92% positives, alternatively at least about 93% positives, alternatively at least about 94% positives, alternatively at least about 95% positives, alternatively at least about 96% positives, alternatively at least about 97% positives, alternatively at least about 98% positives and alternatively at least about 99% positives when compared with the amino acid sequence of a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a specific aspect, the invention provides an isolated PRO polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

Another aspect of the invention provides an isolated PRO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

In yet another embodiment, the invention concerns agonists and antagonists of a native PRO polypeptide as defined herein. In a particular embodiment, the agonist or antagonist is an anti-PRO antibody or a small molecule.

In a further embodiment, the invention concerns a method of identifying agonists or antagonists to a PRO polypeptide which comprise contacting the PRO polypeptide with a candidate molecule and monitoring a biological activity mediated by said PRO polypeptide. Preferably, the PRO polypeptide is a native PRO polypeptide.

In a still further embodiment, the invention concerns a composition of matter comprising a PRO polypeptide, or an agonist or antagonist of a PRO polypeptide as herein described, or an anti-PRO antibody, in combination with a carrier. Optionally, the carrier is a pharmaceutically acceptable carrier.

Another embodiment of the present invention is directed to the use of a PRO polypeptide, or an agonist or antagonist thereof as hereinbefore described, or an anti-PRO antibody, for the preparation of a medicament useful in the treatment of a condition which is responsive to the PRO polypeptide, an agonist or antagonist thereof or an anti-PRO antibody.

In additional embodiments of the present invention, the invention provides vectors comprising DNA encoding any of the herein described polypeptides. Host cell comprising any such vector are also provided. By way of example, the host cells may be CHO cells, E. coli, yeast, or Baculovirus-infected insect cells. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In yet another embodiment, the invention provides an antibody which specifically binds to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences or as antisense probes, wherein those probes may be derived from any of the above or below described nucleotide sequences.

BRIEF DESCRIPTION OF THE DRAWINGS

FIG. 1 shows a nucleotide sequence (SEQ ID NO:1) of a native sequence PRO1031 cDNA, wherein SEQ ID NO:1 is a clone designated herein as "DNA59294-1381-1".

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence PRO1122 cDNA, wherein SEQ ID NO:3 is a clone designated herein as "DNA62377-1381-1".

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence PRO10272 cDNA, wherein SEQ ID NO:5 is a clone designated herein as "DNA147531-2821".

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a native sequence PRO21175 cDNA, wherein SEQ ID NO:7 is a clone designated herein as "DNA173894-2947".

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a native sequence PRO20110 cDNA, wherein SEQ ID NO:9 is a clone designated herein as "DNA166819".

FIG. 10 shows the amino acid sequence (SEQ ID NO:10) derived from the coding sequence of SEQ ID NO:9 shown in FIG. 9.

FIG. 11 shows a nucleotide sequence (SEQ ID NO:11) of a native sequence PRO5801 cDNA, wherein SEQ ID NO:11 is a clone designated herein as "DNA115291-2681".

FIG. 12 shows the amino acid sequence (SEQ ID NO:12) derived from the coding sequence of SEQ ID NO:11 shown in FIG. 11.

FIG. 13 shows a nucleotide sequence (SEQ ID NO:13) of a native sequence PRO20040 cDNA, wherein SEQ ID NO:13 is a clone designated herein as "DNA164625-2890".

FIG. 14 shows the amino acid sequence (SEQ ID NO:14) derived from the coding sequence of SEQ ID NO:13 shown in FIG. 13.

FIG. 15 shows a nucleotide sequence (SEQ ID NO:15) of a native sequence PRO9877 cDNA, wherein SEQ ID NO:15 is a clone designated herein as "DNA119502-2789".

FIG. 16 shows the amino acid sequence (SEQ ID NO:16) derived from the coding sequence of SEQ ID NO:15 shown in FIG. 15.

FIG. 17 shows a nucleotide sequence (SEQ ID NO:17) of a native sequence PRO20026 cDNA, wherein SEQ ID NO:17 is a clone designated herein as "DNA154095-2998".

FIG. 18 shows the amino acid sequence (SEQ ID NO:18) derived from the coding sequence of SEQ ID NO:17 shown in FIG. 17.

Figure 19:
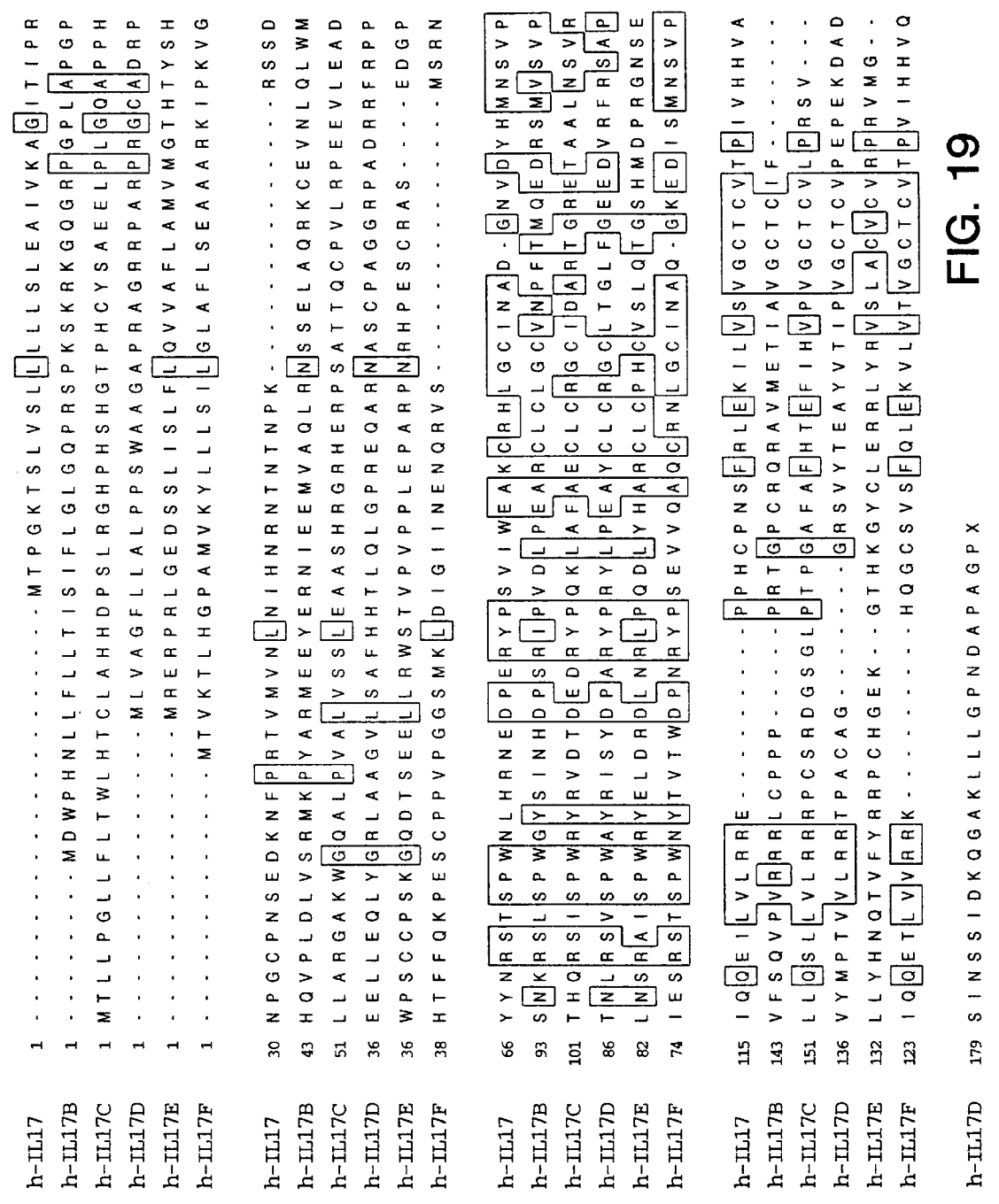

FIG. 19 shows the alignment of the human IL-17 family members: h-IL17 [SEQ ID NO:40]; h-IL17B [PRO1031; SEQ ID NO:2]; h-IL17C [PRO1122; SEQ ID NO:4]; h-IL17D [PRO21175; SEQ ID NO:8]; h-ILE [PRO10272; SEQ ID NO:6]; and h-IL17F [PRO20110; SEQ ID NO:10].

FIG. 30 shows the alignment of the human IL-17 family members (h-IL17; h-IL17B; h-IL17C; and h-ILE). The predicted signal sequences are underlined. Conserved cysteines are indicated by bullet, and potential N-linked glycosylation sites are boxed.

FIG. 31 shows mRNA expression of IL-17RH1 receptor (PRO5801).

FIG. 32 shows IL-17E (PRO10272) ligand binding to IL-17RH1 receptor (PRO5801). FIG. 32A shows a comparison of IL-17 and IL-17E (PRO10272) ligand binding to IL-17R receptor (herein designated PRO1) and IL-17RH1 receptor (PRO5801). 293 cells were transiently co-transfected with expression vectors for green fluorescent protein (GCP) and IL-17R or IL-17RH1 receptors as indicated. Cells were incubated with IL-17-Fc or IL-17E-Fc protein as indicated and binding was revealed with PE conjugated anti-human Fc antibody. FACS curves show PE staining within the co-transfected GFP positive cell population.

FIG. 33 shows the induction of NF-κB by IL-17E (PRO10272). FIG. 33 (part A) shows the results of transiently transfecting human 293 and TK-10 cells with the NF-κB responsive luciferase reporter pGL3.ELAM.tk and expression vector for IL-17E as indicated. Luciferase activity was determined as indicated in EXAMPLE 22. FIG. 33 (part B) depicts titration of NF-κB induction by IL-17E. Human 293 cells were transfected with the NF-κB responsive luciferase reporter pGL3.ELAM.tk and the indicated expression vector for IL-17E as indicated.

FIG. 36 (part A.) shows human foreskin fibroblast (HFF) cells cultured with control Fc fusion protein, IL-17, IL-17B.Fc or IL-17C.Fc at 100 ng/ml for 18 hours and the conditioned media were assayed for IL-6 as described in EXAMPLE 28. FIG. 36 (part B.) shows the human leukemic cell line, THP-1, which was treated with the same cytokines (100 ng/ml) as above under the same conditions wherein the supernatants were assayed for the level of TNF-α release. Results are expressed as the mean +/− SE of triplicate determinations from one representative experiment.

In FIG. 37 (part A.), THP-1 cells were incubated with 100 ng/ml (2.2 nM) of IL-17B.Fc or IL-17C.Fc for 0.5 to 32 hours, the conditioned media harvested, and the TNF-α concentration quantitated as described in EXAMPLE 28. In FIG. 37 (part B.), THP-1 cells were treated with the IL-17B.Fc and IL-17C.Fc at a concentration range from 0 to 120 nM for 18 hours and the TNF-α release determined.

FIG. 41 part C. shows proteoglycan synthesis as determined by incorporation of $^{35}$S-sulphate into the tissue.

FIG. 46A. demonstrates inhibition of matrix synthesis. Human articular cartilage was treated with various concentrations of IL-17E and matrix synthesis was determined by measuring incorporation of $^{35}$S-sulfate as described in EXAMPLE 30. FIG. 46B. demonstrates the effect of IL-17E on inducing nitric oxide production. Human articular cartilage was treated with various concentrations of IL-17E and nitric oxide production was measured as described in EXAMPLE 30. FIG. 46C. demonstrates the effect of IL-17E on inducing IL-6 production in human articular cartilage. Human articular cartilage was treated with various concentrations of IL-17E, and production of IL-6 was measured by an ELISA assay as described in EXAMPLE 28.

DETAILED DESCRIPTION OF THE PREFERRED EMBODIMENTS

I. Definitions

Figure 20:
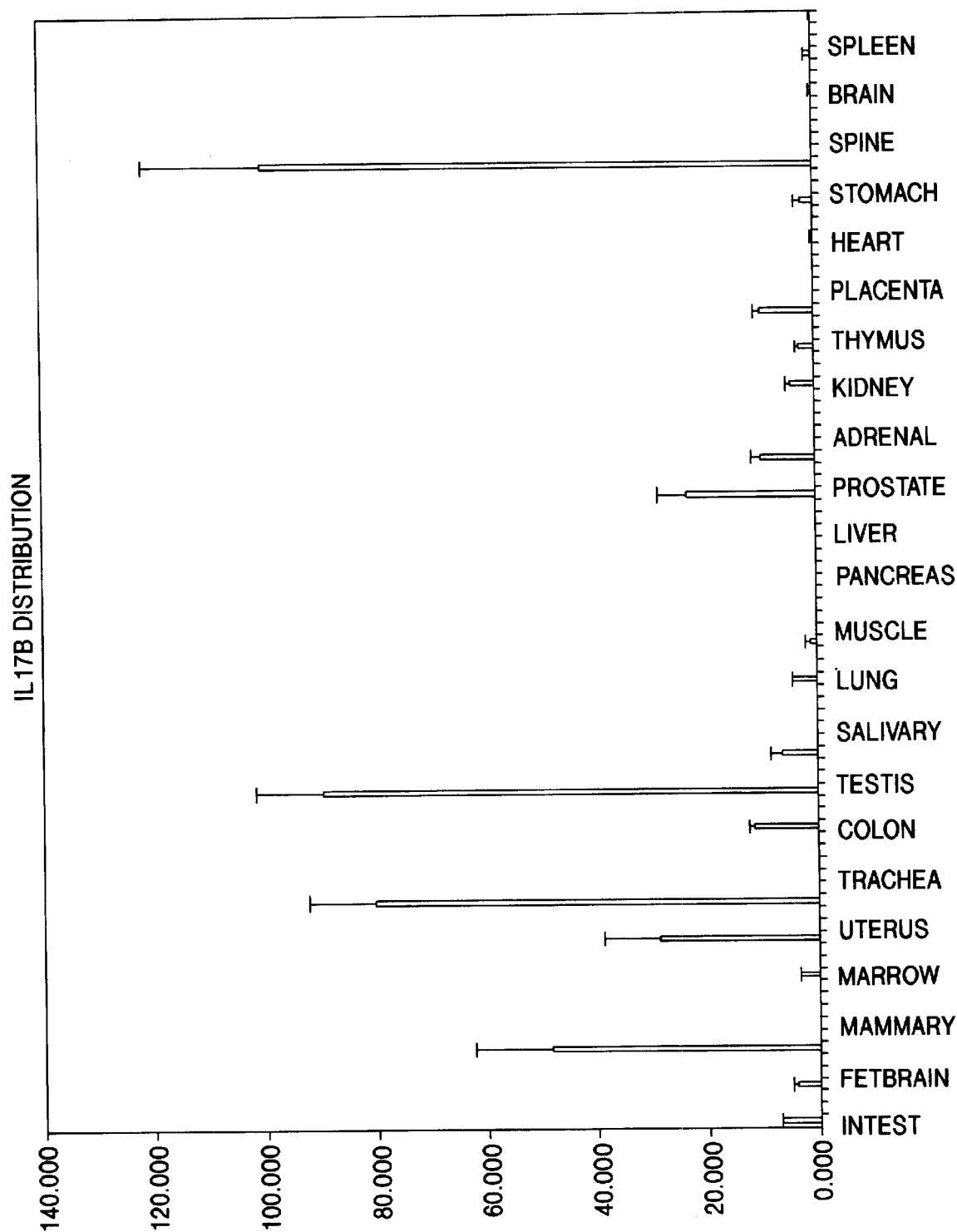
FIG. 20 shows the relative tissue expression distribution of the IL-17B ligand (PRO1031).
Figure 21:
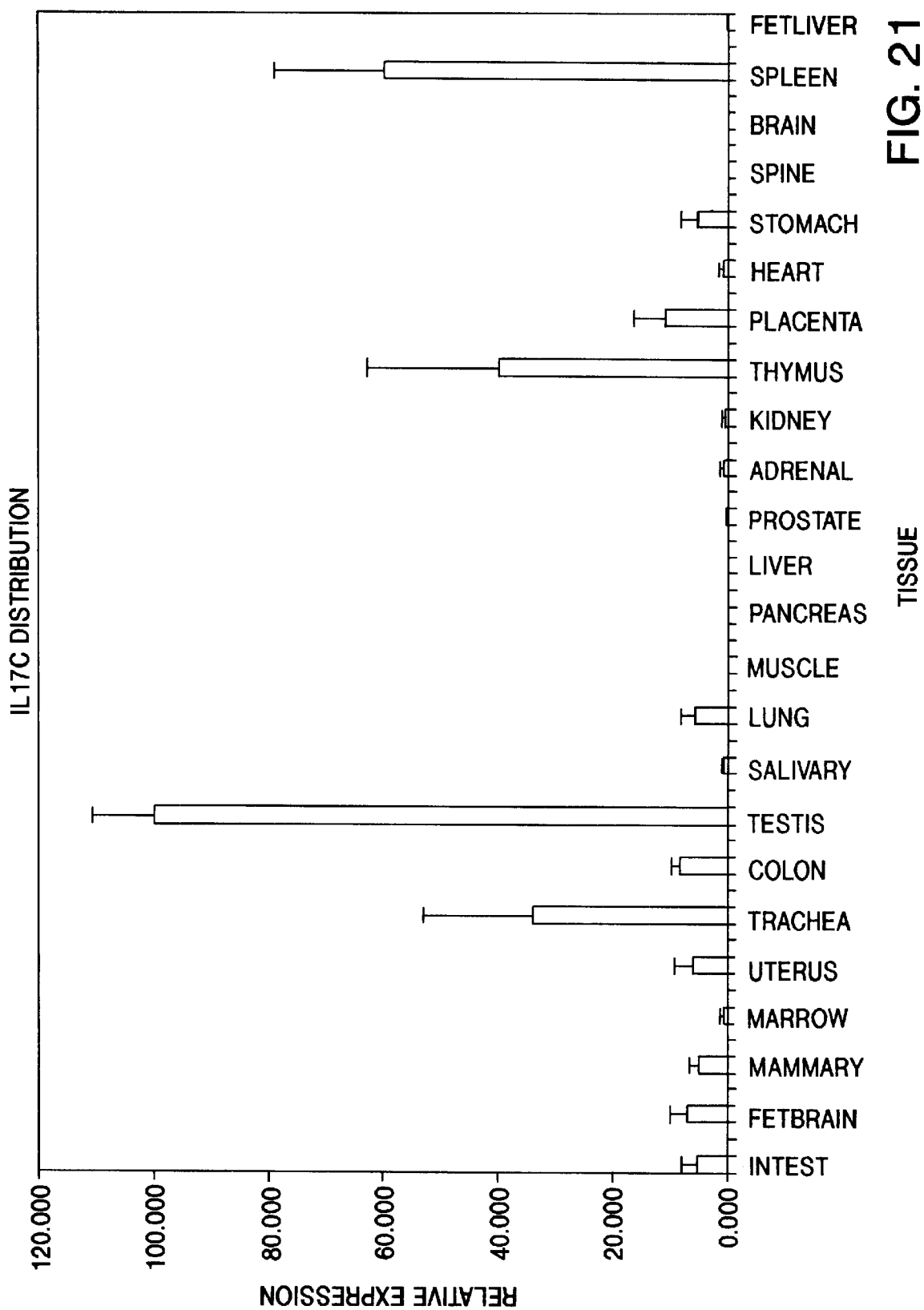
FIG. 21 shows the relative tissue expression distribution of the IL-17C ligand (PRO1122).
Figure 22:
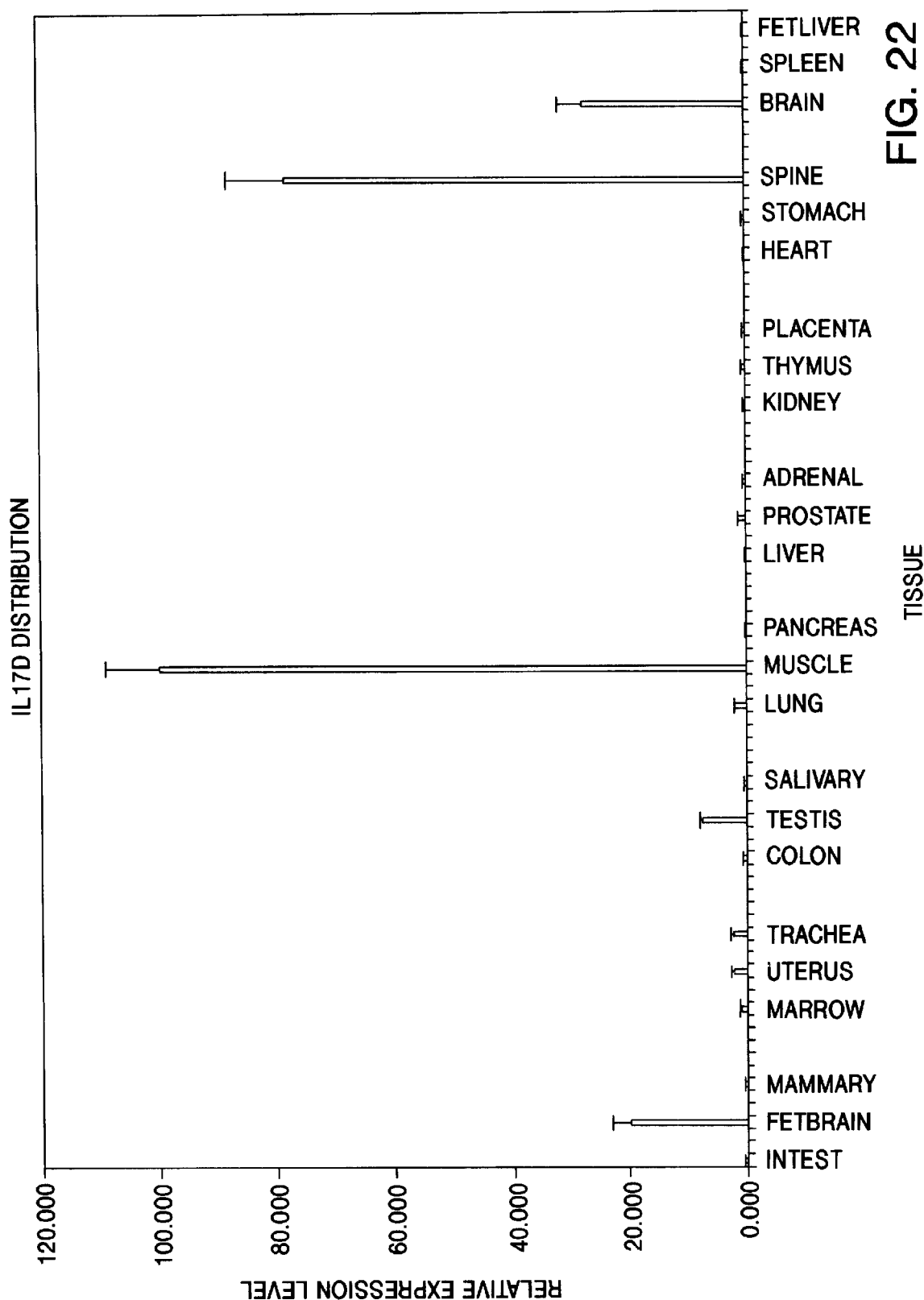
FIG. 22 shows the relative tissue expression distribution of the IL-17D ligand (PRO21175).

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO polypeptides described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO polypeptide" also includes variants of the PRO/number polypeptides disclosed herein.

A "native sequence PRO polypeptide" comprises a polypeptide having the same amino acid sequence as the corresponding PRO polypeptide derived from nature. Such native sequence PRO polypeptides can be isolated from nature or can be produced by recombinant or synthetic means. The term "native sequence PRO polypeptide" specifically encompasses naturally-occurring truncated or secreted forms of the specific PRO polypeptide (e.g., an extracellular domain sequence), naturally-occurring variant forms (e.g., alternatively spliced forms) and naturally-occurring allelic variants of the polypeptide. In various embodiments of the invention, the native sequence PRO polypeptides disclosed herein are mature or full-length native sequence polypeptides comprising the full-length amino acids sequences shown in the accompanying figures. Start and stop codons are shown in bold font and underlined in the figures. However, while the PRO polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO polypeptides.

The PRO polypeptide "extracellular domain" or "ECD" refers to a form of the PRO polypeptide which is essentially free of the transmembrane and cytoplasmic domains. Ordinarily, a PRO polypeptide ECD will have less than 1% of such transmembrane and/or cytoplasmic domains and preferably, will have less than 0.5% of such domains. It will be understood that any transmembrane domains identified for the PRO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various PRO polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., Prot. Eng., 10:1–6 (1997) and von Heinje et al., Nucl. Acids. Res., 14:4683–4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO polypeptide variant" means an active PRO polypeptide as defined above or below having at least about 80% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Such PRO polypeptide variants include, for instance, PRO polypeptides wherein one or more amino acid residues are added, or deleted, at the – or C-terminus of the full-length native amino acid sequence. Ordinarily, a PRO polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other specifically defined fragment of a full-length PRO polypeptide sequence as disclosed herein. Ordinarily, PRO variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the PRO polypeptide sequences identified herein is defined as the percentage of amino acid residues in a candidate sequence that are identical with the amino acid residues in the specific PRO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X", "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

Percent amino acid sequence identity may also be determined using the sequence comparison program NCBI-BLAST2 (Altschul et al., *Nucleic Acids Res.* 25:3389–3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO variant polynucleotide" or "PRO variant nucleic acid sequence" means a nucleic acid molecule which encodes an active PRO polypeptide as defined below and which has at least about 80% nucleic acid sequence identity with a nucleotide acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Ordinarily, a PRO variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal sequence, as disclosed herein or any other fragment of a full-length PRO polypeptide sequence as disclosed herein. Variants do not encompass the native nucleotide sequence.

Ordinarily, PRO variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to PRO-encoding nucleic acid sequences identified herein is defined as the percentage of nucleotides in a candidate sequence that are identical with the nucleotides in the PRO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i. e., the sequence against which the PRO polypeptide-encoding nucleic acid molecule of interest is being compared which may be a variant PRO polynucleotide) as determined by WU-BLAST-2 by (b) the total number of nucleotides of the PRO polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

Percent nucleic acid sequence identity may also be determined using the sequence comparison program NCBI-BLAST2 (Altschul et al., *Nucleic Acids Res.* 25:3389–3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand= all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO variant polynucleotides are nucleic acid molecules that encode an active PRO polypeptide and which are capable of hybridizing, preferably under stringent hybridization and wash conditions, to nucleotide sequences encoding a full-length PRO polypeptide as disclosed herein. PRO variant polypeptides may be those that are encoded by a PRO variant polynucleotide.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO polypeptide natural environment will not be present. Ordinarily, however, isolated polypeptide will be prepared by at least one purification step.

An "isolated" PRO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO monoclonal antibodies (including agonist, antagonist, and neutralizing antibodies), anti-PRO antibody compositions with polyepitopic specificity, single chain anti-PRO antibodies, and fragments of anti-PRO antibodies (see below). The term "monoclonal antibody" as used herein refers to an antibody obtained from a population of substantially homogeneous antibodies, i. e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficol/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and %SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising a PRO polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The term "antagonist" is used in the broadest sense, and includes any molecule that partially or fully blocks, inhibits, or neutralizes a biological activity of a native PRO polypeptide disclosed herein. In a similar manner, the term "agonist" is used in the broadest sense and includes any molecule that mimics a biological activity of a native PRO polypeptide disclosed herein. Suitable agonist or antagonist molecules specifically include agonist or antagonist antibodies or antibody fragments, fragments or amino acid sequence variants of native PRO polypeptides, peptides, antisense oligonucleotides, small organic molecules, etc. Methods for identifying agonists or antagonists of a PRO polypeptide may comprise contacting a PRO polypeptide with a candidate agonist or antagonist molecule and measuring a detectable change in one or more biological activities normally associated with the PRO polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.*, 8(10) :1057–1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$–$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444–6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

The term "modulate" means to affect (e.g., either upregulate, downregulate or otherwise control) the level of a signaling pathway. Cellular processes under the control of signal transduction include, but are not limited to, transcription of specific genes, normal cellular functions, such as metabolism, proliferation, differentiation, adhesion, apoptosis and survival, as well as abnormal processes, such as transformation, blocking of differentiation and metastasis.

"Active" or "activity" for the purposes herein refers to form(s) of a PRO polypeptide which retain a biological and/or an immunological activity of native or naturally-occurring PRO polypeptides, wherein "biological" activity refers to a biological function (either inhibitory or stimulatory) caused by a native or naturally-occurring PRO polypeptide other than the ability to induce the production of an antibody against an antigenic epitope possessed by a native or naturally-occurring PRO polypeptide and an "immunological" activity refers to the ability to induce the production of an antibody against an antigenic epitope possessed by a native or naturally-occurring PRO polypeptide. One preferred biological activity includes inducing activation of NF-κB and stimulation of the production of the proinflammatory chemokine IL-8. Another preferred biological activity includes stimulation of peripheral blood mononuclear cells or CD4⁺ cells. Another preferred biological activity includes stimulation of the proliferation of T-lymphocytes. Another preferred biological activity includes, for example, the release of TNF-α from THP1 cells. An alternative activity is the reduction in IL-1a induced NO (nitric oxide) production from articular cartilage. Another activity includes an enhancement of matrix synthesis in articular cartilage. Alternatively, another activity includes promoting breakdown of articular cartilage matrix as well as inhibiting matrix synthesis. Another preferred biological activity includes modulating the level of the interleukin-17 signalling pathway during mild to severe stages of inflammatory bowel disease or during stroke.

An "immunological" activity refers only to the ability to induce the production of an antibody against an antigenic epitope possessed by a native or naturally-occurring PRO polypeptide.

"Degenerative cartilagenous disorder" describes a host of disorders that is characterized principally by the destruction of the cartilage matrix. Additional pathologies includes nitric oxide production, and elevated proteoglycan breakdown. Exemplary disorders encompassed within this definition, include, for example, arthritis (e.g., osteoarthritis, rheumatoid arthritis, psoriatic arthritis).

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease.

Included within this term are immune-mediated inflammatory diseases, non-immune-mediated inflammatory diseases, infectious diseases, immunodeficiency diseases, neoplasia, etc.

The term "T cell mediated disease" means a disease in which T cells directly or indirectly mediate or otherwise contribute to a morbidity in a mammal. The T cell mediated disease may be associated with cell mediated effects, lymphokine mediated effects, etc., and even effects associated with B cells if the B cells are stimulated, for example, by the lymphokines secreted by T cells.

Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections and parasitic infections.

The term "effective amount" is a concentration or amount of a PRO polypeptide and/or agonist/antagonist which results in achieving a particular stated purpose. An "effective amount" of a PRO polypeptide or agonist or antagonist thereof may be determined empirically. Furthermore, a "therapeutically effective amount" is a concentration or amount of a PRO polypeptide and/or agonist/antagonist which is effective for achieving a stated therapeutic effect. This amount may also be determined empirically.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhône-Poulenc Rorer, Antony, France), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce GI arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al., (W B Saunders: Philadelphia, 1995), especially p. 13.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-10, IL-11, IL-12, or IL-17; a tumor necrosis factor such as TNF-α or TNF-β; and other polypeptide factors including leukemia inhibitory factor (LIF) and kit ligand (KL). As used herein, the term cytokine includes proteins from natural sources or from recombinant cell culture and biologically active equivalents of the native sequence cytokines.

TABLE 1

```
/*
 *
 * C-C increased from 12 to 15
 * Z is average of EQ
 * B is average of ND
 * match with stop is __M; stop-stop = 0; J (joker) match = 0
 */
#define __M      -8          /* value of a match with a stop */
int        __day[26][26] = {
/*   A B C D E F G H I J K L M N O P Q R S T U V W X Y Z */
/* A */ { 2, 0, -2, 0, 0, -4, 1, -1, -1, 0, -1, -2, -1, 0, __M, 1, 0, -2, 1, 1, 0, 0, -6, 0, -3, 0},
/* B */ { 0, 3, -4, 3, 2, -5, 0, 1, -2, 0, 0, -3, -2, 2, __M, -1, 1, 0, 0, 0, 0, -2, -5, 0, -3, 1},
/* C */ {-2, -4, 15, -5, -5, -4, -3, -3, -2, 0, -5, -6, -5, -4, __M, -3, -5, -4, 0, -2, 0, -2, -8, 0, 0, -5},
/* D */ { 0, 3, -5, 4, 3, -6, 1, 1, -2, 0, 0, -4, -3, 2, __M, -1, 2, -1, 0, 0, 0, -2, -7, 0, -4, 2},
/* E */ { 0, 2, -5, 3, 4, -5, 0, 1, -2, 0, 0, -3, -2, 1, __M, -1, 2, -1, 0, 0, 0, -2, -7, 0, -4, 3},
/* F */ {-4, -5, -4, -6, -5, 9, -5, -2, 1, 0, -5, 2, 0, -4, __M, -5, -5, -4, -3, -3, 0, -1, 0, 0, 7, -5},
/* G */ { 1, 0, -3, 1, 0, -5, 5, -2, -3, 0, -2, -4, -3, 0, __M, -1, -1, -3, 1, 0, 0, -1, -7, 0, -5, 0},
/* H */ {-1, 1, -3, 1, 1, -2, -2, 6, -2, 0, 0, -2, -2, 2, __M, 0, 3, 2, -1, -1, 0, -2, -3, 0, 0, 2},
/* I */ {-1, -2, -2, -2, -2, 1, -3, -2, 5, 0, -2, 2, 2, -2, __M, -2, -2, -2, -1, 0, 0, 4, -5, 0, -1, -2},
/* J */ { 0, 0, 0, 0, 0, 0, 0, 0, 0, 0, 0, 0, 0, 0, __M, 0, 0, 0, 0, 0, 0, 0, 0, 0, 0, 0},
/* K */ {-1, 0, -5, 0, 0, -5, -2, 0, -2, 0, 5, -3, 0, 1, __M, -1, 1, 3, 0, 0, 0, -2, -3, 0, -4, 0},
/* L */ {-2, -3, -6, -4, -3, 2, -4, -2, 2, 0, -3, 6, 4, -3, __M, -3, -2, -3, -3, -1, 0, 2, -2, 0, -1, -2}
/* M */ {-1, -2, -5, -3, -2, 0, -3, -2, 2, 0, 0, 4, 6, -2, __M, -2, -1, 0, -2, -1, 0, 2, -4, 0, -2, -1},
/* N */ { 0, 2, -4, 2, 1, -4, 0, 2, -2, 0, 1, -3, -2, 2, __M, -1, 1, 0, 1, 0, 0, -2, -4, 0, -2, 1},
/* O */ {__M,__M,__M,__M,__M,__M,__M,__M,__M,__M,__M,__M,__M,__M, 0,__M,__M,__M,__M,__M,__M,__M,__M,__M,__M,__M,},
/* P */ { 1, -1, -3, -1, -1, -5, -1, 0, -2, 0, -1, -3, -2, -1, __M, 6, 0, 0, 1, 0, 0, -1, -6, 0, -5, 0},
/* Q */ { 0, 1, -5, 2, 2, -5, -1, 3, -2, 0, 1, -2, -1, 1, __M, 0, 4, 1, -1, -1, 0, -2, -5, 0, -4, 3},
/* R */ {-2, 0, -4, -1, -1, -4, -3, 2, -2, 0, 3, -3, 0, 0, __M, 0, 1, 6, 0, -1, 0, -2, 2, 0, -4, 0},
/* S */ { 1, 0, 0, 0, 0, -3, 1, -1, -1, 0, 0, -3, -2, 1, __M, 1, -1, 0, 2, 1, 0, -1, -2, 0, -3, 0},
/* T */ { 1, 0, -2, 0, 0, -3, 0, -1, 0, 0, 0, -1, -1, 0, __M, 0, -1, -1, 1, 3, 0, 0, -5, 0, -3, 0},
/* U */ { 0, 0, 0, 0, 0, 0, 0, 0, 0, 0, 0, 0, 0, 0, __M, 0, 0, 0, 0, 0, 0, 0, 0, 0, 0, 0},
/* V */ { 0, -2, -2, -2, -2, -1, -1, -2, 4, 0, -2, 2, 2, -2, __M, -1, -2, -2, -1, 0, 0, 4, -6, 0, -2, -2},
/* W */ {-6, -5, -8, -7, -7, 0, -7, -3, -5, 0, -3, -2, -4, -4, __M, -6, -5, 2, -2, -5, 0, -6, 17, 0, 0, -6},
/* X */ { 0, 0, 0, 0, 0, 0, 0, 0, 0, 0, 0, 0, 0, 0, __M, 0, 0, 0, 0, 0, 0, 0, 0, 0, 0, 0},
/* Y */ {-3, -3, 0, -4, -4, 7, -5, 0, -1, 0, -4, -1, -2, -2, __M, -5, -4, -4, -3, -3, 0, -2, 0, 0, 10, -4},
/* Z */ { 0, 1, -5, 2, 3, -5, 0, 2, -2, 0, 0, -2, -1, 1, __M, 0, 3, 0, 0, 0, 0, -2, -6, 0, -4, 4},
};
/*
 */
#include <stdio.h>
#include <ctype.h>
#define MAXJMP    16      /* max jumps in a diag */
#define MAXGAP    24      /* don't continue to penalize gaps larger than this */
#define JMPS      1024    /* max jmps in an path */
#define MX        4       /* save if there's at least MX-1 bases since last jmp */
#define DMAT      3       /* value of matching bases */
#define DMIS      0       /* penalty for mismatched bases */
#define DINS0     8       /* penalty for a gap */
#define DINS1     1       /* penalty per base */
#define PINS0     8       /* penalty for a gap */
#define PINS1     4       /* penalty per residue */
struct jmp {
    short           n[MAXJMP];    /* size of jmp (neg for dely) */
    unsigned short  x[MAXJMP];    /* base no. of jmp in seq x */
                                  /* limits seq to 2^16 -1 */
};
struct diag {
    int             score;        /* score at last jmp */
    long            offset;       /* offset of prev block */
    short           ijmp;         /* current jmp index */
    struct jmp      jp;           /* list of jmps */
};
struct path {
    int             spc;          /* number of leading spaces */
    short           n[JMPS];      /* size of jmp (gap) */
    int             x[JMPS];      /* loc of jmp (last elem before gap) */
};
char     *ofile;                  /* output file name */
char     *namex[2];               /* seq names: getseqs() */
char     *prog;                   /* prog name for err msgs */
char     *seqx[2];                /* seqs: getseqs() */
int      dmax;                    /* best diag: nw() */
int      dmax0;                   /* final diag */
int      dna;                     /* set if dna: main() */
int      endgaps;                 /* set if penalizing end gaps */
int      gapx, gapy;              /* total gaps in seqs */
int      len0, len1;              /* seq lens */
int      ngapx, ngapy;            /* total size of gaps */
int      smax;                    /* max score: nw() */
```

TABLE 1-continued

```
int        *xbm;                    /* bitmap for matching */
long       offset;                  /* current offset in jmp file */
struct diag *dx;                    /* holds diagonals */
struct path pp[2];                  /* holds path for seqs */
char       *calloc(), *malloc(), *index(), *strcpy();
char       *getseq(), *g_calloc();
/* Needleman-Wunsch alignment program
*
* usage: progs file1 file2
* where file1 and file2 are two dna or two protein sequences.
* The sequences can be in upper- or lower-case an may contain ambiguity
* Any lines beginning with ';', '>' or '<' are ignored
* Max file length is 65535 (limited by unsigned short x in the jmp struct)
* A sequence with 1/3 or more of its elements ACGTU is assumed to be DNA
* Output is in the file "align.out"
*
* The program may create a tmp file in /tmp to hold info about traceback.
* Original version developed under BSD 4.3 on a vax 8650
*/
#include "nw.h"
#include "day.h"
static  _dbval[26] = {
        1,14,2,13,0,0,4,11,0,0,12,0,3,15,0,0,0,5,6,8,8,7,9,0,10,0
};
static  _pbval[26] = {
        1, 2|(1< <('D'-'A'))|(1< <('N'-'A')), 4, 8, 16, 32, 64,
        128, 256, 0xFFFFFFFF, 1< <10, 1< <11, 1< <12, 1< <13, 1< <14,
        1< <15, 1< <16, 1< <17, 1< <18, 1< <19, 1< <20, 1< <21, 1< <22,
        1< <23, 1< <24, 1< <25|(1< <('E'-'A'))|(1< <('Q'-'A'))
};
main(ac, av)                                                                        main
        int    ac;
        char   *av[];
{
        prog = av[0];
        if(ac != 3) {
                fprintf(stderr, "usage: %s file1 file2\n", prog);
                fprintf(stderr, "where file1 and file2 are two dna or two protein sequences.\n");
                fprintf(stderr, "The sequences can be in upper- or lower-case\n");
                fprintf(stderr, "Any lines beginning with ';' or '<' are ignored\n");
                fprintf(stderr, "Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;
        endgaps = 0;            /* 1 to penalize endgaps */
        ofile = "align.out";    /* output file */
        nw();                   /* fill in the matrix, get the possible jmps */
        readjmps();             /* get the actual jmps */
        print();                /* print stats, alignment */
        cleanup(0);             /* unlink any tmp files */
}
/* do the alignment, return best score: main()
* dna: values in Fitch and Smith, PNAS, 80, 1382–1386, 1983
* pro: PAM 250 values
* When scores are equal, we prefer mismatches to any gap, prefer
* a new gap to extending an ongoing gap, and prefer a gap in seqx
* to a gap in seq y.
*/
nw()                                                                                nw
{
        char   *px, *py;        /* seqs and ptrs */
        int    *ndely, *dely;   /* keep track of dely */
        int    ndelx, delx;     /* keep track of delx */
        int    *tmp;            /* for swapping row0, row1 */
        int    mis;             /* score for each type */
        int    ins0, ins1;      /* insertion penalties */
        register id;            /* diagonal index */
        register ij;            /* jmp index */
        register *col0, *col1;  /* score for curr, last row */
        register xx, yy;        /* index into seqs */
        dx = (struct diag *)g_calloc("to get diags", len0+len1+1, sizeof(struct diag));
        ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
```

TABLE 1-continued

```
ins0 = (dna)? DINS0 : PINS0;
ins1 = (dna)? DINS1 : PINS1;
smax = -10000;
if (endgaps) {
    for (col0[0] = dely[0] = -ins0, yy = 1; yy <= len1; yy++) {
        col0[yy] = dely[yy] = col0[yy-1] - ins1;
        ndely[yy] = yy;
    }
    col0[0] = 0;      /* Waterman Bull Math Biol 84 */
}
else
    for (yy= 1; yy <= len1; yy++)
        dely[yy] = -ins0;
/* fill in match matrix
 */
for (px = seqx[0], xx = 1; xx <= len0; px++, xx++) {
    /* initialize first entry in col
     */
    if (endgaps) {
        if (xx == 1)
            col1[0] = delx = -(ins0+ins1);
        else
            col1[0] = delx = col0[0]-ins1;
        ndelx = xx;
    }
    else {
        col1[0] = 0;
        delx = -ins0;
        ndelx = 0;
    }
                                                                        ...nw
    for (py = seqx[1], yy = 1; yy <= len1; py++, yy++) {
        mis = col0[yy-1];
        if (dna)
            mis + = (xbm[*px-'A']&xbm[*py-'A'])? DMAT : DMIS;
        else
            mis += _day[*px-'A'][*py-'A'];
        /* update penalty for del in x seq;
         * favor new del over ongong del
         * ignore MAXGAP if weighting endgaps
         */
        if (endgaps || ndely[yy] < MAXGAP) {
            if (col0[yy] - ins0 >= dely[yy]) {
                dely[yy] = col0[yy] - (ins0+ins1);
                ndely[yy] = 1;
            } else {
                dely[yy] -= ins1;
                ndely[yy]++;
            }
        } else {
            if (col0[yy] - (ins0+ins1) >= dely[yy]) {
                dely[yy] = col0[yy] - (ins0+ins1);
                ndely[yy] = 1;
            } else
                ndely[yy]++;
        }
        /* update penalty for del in y seq;
         * favor new del over ongong del
         */
        if (endgaps || ndelx < MAXGAP) {
            if(col1[yy-1] - ins0 >= delx) {
                delx = col1[yy-1] - (ins0+ins1);
                ndelx = 1;
            } else {
                delx -= ins1;
                ndelx++;
            }
        } else {
            if (col1[yy-1] - (ins0+ins1) >= delx) {
                delx = col1[yy-1] - (ins0+ins1);
                ndelx = 1;
            } else
                ndelx++;
        }
        /* pick the maximum score; we're favoring
         * mis over any del and delx over dely
         */
        id = xx - yy + len1 - 1;
                                                                        ...nw
```

TABLE 1-continued

```
            if (mis >= delx && mis >= dely[yy])
                col1[yy] = mis;
            else if (delx >= dely[yy]) {
                col1[yy] = delx;
                ij = dx[id].ijmp;
                if (dx[id].jp.n[0] && (!dna || (ndelx >= MAXJMP
                    && xx > dx[id].jp.x[ij]+MX) || mis > dx[id].score+DINS0)) {
                    dx[id].ijmp++;
                    if (++ij >= MAXJMP) {
                        writejmps(id);
                        ij = dx[id].ijmp = 0;
                        dx[id].offset = offset;
                        offset += sizeof(struct jmp) + sizeof(offset);
                    }
                }
                dx[id].jp.n[ij] = ndelx;
                dx[id].jp.x[ij] = xx;
                dx[id].score = delx;
            }
            else {
                col1[yy] = dely[yy];
                ij = dx[id].ijmp;
if (dx[id].jp.n[0] && (!dna || (ndely[yy] >= MAXJMP
                    && xx > dx[id].jp.x[ij]+MX) || mis > dx[id].score+DINS0)) {
                    dx[id].ijmp++;
                    if (++ij >= MAXJMP) {
                        writejmps(id);
                        ij = dx[id].ijmp = 0;
                        dx[id].offset = offset;
                        offset += sizeof(struct jmp) + sizeof(offset);
                    }
                }
                dx[id].jp.n[ij] =-ndely[yy];
                dx[id].jp.x[ij] = xx;
                dx[id].score = dely[yy];
            }
            if (xx == len0 && yy < len1) {
                /* last col
                 */
                if (endgaps)
                    col1[yy] -= ins0+ins1*(len1-yy);
                if(col1[yy] > smax) {
                    smax = col1[yy];
                    dmax = id;
                }
            }
        }
        if (endgaps && xx < len0)
            col1[yy-1] -= ins0+ins1*(len0-xx);
        if (col1[yy-1] > smax) {
            smax = col1[yy-1];
            dmax = id;
        }
        tmp = col0; col0 = col1; col1 = tmp;
    }
    (void) free((char *)ndely);
    (void) free((char *)dely);
    (void) free((char *)col0);
    (void) free((char *)col1);
}
/*
 *
 * print() -- only routine visible outside this module
 *
 * static:
 * getmat() -- trace back best path, count matches: print()
 * pr_align() -- print alignment of described in array p[]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() - -put a line of stars: dumpblock()
 * stripname() -- strip any path and prefix from a seqname
 */
#include "nw.h"
#define SPC         3
#define P_LINE      256     /* maximum output line */
#define P_SPC       3       /* space between name or num and seq */
extern      _day[26][26];
int         olen;           /* set output line length */
```

TABLE 1-continued

```
FILE       *fx;              /* output file */
print()                                                                          print
{
    int     lx, ly, firstgap, lastgap;    /* overlap */
    if ((fx = fopen(ofile, "w")) == 0) {
        fprintf(stderr, "%s: can't write %s\n", prog, ofile);
        cleanup(1);
    }
    fprintf(fx, "<first sequence: %s (length = %d)\n", namex[0], len0);
    fprintf(fx, "<second sequence: %s (length = %d)\n", namex[1], len1);
    olen = 60;
    lx = len0;
    ly = len1;
    firstgap = lastgap = 0;
    if (dmax < len1 - 1) {          /* leading gap in x */
        pp[0].spc = firstgap = len1 - dmax - 1;
        ly -= pp[0].spc;
    }
    else if (dmax > len1 - 1) {     /* leading gap in y */
        pp[1].spc = firstgap = dmax - (len1 - 1);
        lx -= pp[1].spc;
    }
    if (dmax0 < len0 - 1) {         /* trailing gap in x */
        lastgap = len0 - dmax0 -1;
        lx -= lastgap;
    }
    else if (dmax0 > len0 - 1) {    /* trailing gap in y */
        lastgap = dmax0 - (len0 - 1);
        ly -= lastgap;
    }
    getmat(lx, ly, firstgap, lastgap);
    pr_align();
}
/*
* trace back the best path, count matches
*/
static
getmat(lx, ly, firstgap, lastgap)                                                getmat
    int     lx, ly;              /* "core" (minus endgaps) */
    int     firstgap, lastgap;   /* leading trailing overlap */
{
    int             nm, i0, i1, siz0, siz1;
    char            outx[32];
    double          pct;
    register        n0, n1;
    register char   *p0, *p1;
    /* get total matches, score
     */
    i0 = i1 = siz0 = siz1 = 0;
    p0 = seqx[0] + pp[1].spc;
    p1 = seqx[1] + pp[0].spc;
    n0 = pp[1].spc + 1;
    n1 = pp[0].spc + 1;
    nm = 0;
    while ( *p0 && *p1 ) {
        if (siz0) {
            p1++;
            n1++;
            siz0--;
        }
        else if (siz1) {
            p0++;
            n0++;
            siz1--;
        }
        else {
            if (xbm[*p0-'A']&xbm[*p1-'A'])
                nm++;
            if (n0++ == pp[0].x[i0])
                siz0 = pp[0].n[i0++];
            if (n1++ == pp[1].x[i1])
                siz1 = pp[1].n[i1++];
            p0++;
            p1++;
        }
    }
    /* pct homology:
     * if penalizing endgaps, base is the shorter seq
     * else, knock off overhangs and take shorter core
```

TABLE 1-continued

```
      */
      if (endgaps)
            lx = (len0 < len1)? len0 : len1;
      else
            lx = (lx < ly)? lx : ly;
      pct = 100.*(double)nm/(double)lx;
      fprintf(fx, "\n");
      fprintf(fx, "<%d match%s in an overlap of %d: %.2f percent similarity\n",
            nm, (nm == 1)? "" : "es", lx, pct);
      fprintf(fx, "<gaps in first sequence: %d", gapx);                                              ...getmat
      if (gapx) {
            (void) sprintf(outx, "(%d %s%s)",
                  ngapx, (dna)? "base": "residue", (ngapx == 1)? "":"s");
            fprintf(fx, "% s", outx);
      fprintf(fx, ", gaps in second sequence: %d", gapy);
      if (gapy) {
            (void) sprintf(outx, "(%d %s%s)",
                  ngapy, (dna)? "base":"residue", (ngapy == 1)? "":"s");
            fprintf(fx, "%s", outx);
      }
      if (dna)
            fprintf(fx,
            "\n<score: %d (match = %d, mismatch = %d, gap penalty = %d + %d per base)\n",
            smax, DMAT, DMIS, DINS0, DINS1);
      else
            fprintf(fx,
            "\n<score: %d (Dayhoff PAM 250 matrix, gap penalty = %d + %d per residue)\n",
            smax, PINS0, PINS1);
      if (endgaps)
            fprintf(fx,
            "<endgaps penalized. left endgap: %d %s%s, right endgap: %d %s%s\n",
            firstgap, (dna)? "base" : "residue", (firstgap == 1)? "" : "s",
            lastgap, (dna)? "base" : "residue", (lastgap == 1)? "" : "s");
      else
            fprintf(fx, "<endgaps not penalized\n");
}
static       nm;                  /* matches in core -- for checking */
static       lmax;                /* lengths of stripped file names */
static       ij[2];               /* jmp index for a path */
static       nc[2];               /* number at start of current line */
static       ni[2];               /* current elem number -- for gapping */
static       siz[2];
static char  *ps[2];              /* ptr to current element */
static char  *po[2];              /* ptr to next output char slot */
static char  out[2][P_LINE];      /* output line */
static char  star[P_LINE];        /* set by stars() */
/*
* print alignment of described in struct path pp[]
*/
static
pr_align()                                                                                          pr_align
{
      int    nn;          /* char count */
      int    more;
      register i;
      for (i = 0, lmax = 0; i < 2++) {
            nn = stripname(namex[i]);
            if (nn > lmax)
                  lmax = nn;
            nc[i] = 1;
            ni[i] = 1;
            siz[i] = ij[i] = 0;
            ps[i] = seqx[i];
            po[i] = out[i];
      }
      for (nn = nm = 0, more = 1; more;) {                                                          ...pr_align
            for (i = more = 0; i < 2; i++) {
                  /*
                  * do we have more of this sequence?
                  */
                  if (!*ps[i])
                        continue;
                  more++;
                  if (pp[i].spc) {          /* leading space */
                        *po[i]++ = ' ';
                        pp[i].spc--;
                  }
                  else if (siz[i]) {        /* in a gap */
                        *po[i]++ = '-';
```

TABLE 1-continued

```
                siz[i]--;
            }
            else {              /* we're putting a seq element
                                 */
                *po[i] = *ps[i];
                if (islower(*ps[i]))
                    *ps[i] = toupper(*ps[i]);
                po[i]++;
                ps[i]++;
                /*
                 * are we at next gap for this seq?
                 */
                if (ni[i] == pp[i].x[ij[i]]) {
                    /*
                     * we need to merge all gaps
                     * at this location
                     */
                    siz[i] == pp[i].n[ij[i]++];
                    while (ni[i] == pp[i].x[ij[i]])
                        siz[i] += pp[i].n[ij[i]++];
                }
                ni[i]++;
            }
        }
        if (++nn == olen || !more && nn) {
            dumpblock();
            for (i = 0; i < 2; i++)
                po[i] = out[i];
            nn = 0;
        }
    }
}
/*
 * dump a block of lines, including numbers, stars: pr_align()
 */
static
dumpblock()                                                                         dumpblock
{
    register i;
    for(i = 0; i < 2; i++)
        *po[i]-- = '\0';
                                                                                    ...dumpblock
    (void) putc('\n', fx);
    for (i = 0; i < 2; i++) {
        if (*out[i] && (*out[i] != ' ' || *(po[i]) != ' ')) {
            if (i == 0)
                nums(i);
            if (i == 0 && *out[1])
                stars();
            putline(i);
            if (i == 0 && *out[1])
                fprintf(fx, star);
            if (i == 1)
                nums(i);
        }
    }
}
/*
 * put out a number line: dumpblock()
 */
static
nums(ix)                                                                            nums
    int    ix;      /* index in out[] holding seq line */
{
    char         nline[P_LINE];
    register     i, j;
    register char *pn, *px, *py;
    for(pn = nline, i = 0; i < lmax+P_SPC; i++, pn++)
        *pn = ' ';
    for (i = nc[ix], py = out[ix]; *py; py++, pn++) {
        if (*py == ' ' || *py == '-')
            *pn = ' ';
        else {
            if (i%10 == 0 || (i == 1 && nc[ix] != 1)) {
                j = (i < 0)? -i : i;
                for (px = pn; j; j /= 10, px--)
                    *px = j%10 + '0';
                if (i < 0)
                    *px = '-';
```

TABLE 1-continued

```
                    }
                    else
                            *pn = ' ';
                    i++;
            }
    }
    *pn = '\0';
    nc[ix] = i;
    for (pn = nline; *pn; pn++)
            (void) putc(*pn, fx);
    (void) putc('\n', fx);
}
/*
 * put out a line (name, [num], seq. [num]): dumpblock()
 */
static
putline(ix)                                                                             putline
        int     ix;
{
        int             i;
        register char   *px;
        for (px = namex[ix], i = 0; *px && *px != ':'; px++, i++)
                (void) putc(*px, fx);
        for (;i < lmax+P_SPC; i++)
                (void) putc(' ', fx);
        /* these count from 1:                                                          ...putline
         * ni[] is current element (from 1)
         * nc[] is number at start of current line
         */
        for (px = out[ix]; *px; px++)
                (void) putc(*px&0x7F, fx);
        (void) putc('\n', fx);
}
/*
 * put a line of stars (seqs always in out[0], out[1]): dumpblock()
 */
static
stars()                                                                                 stars
{
        int             i;
        register char   *p0, *p1, cx, *px;
        if    (!*out[0] || (*out[0] == ' ' && *(p0[0]) == ' ') ||
               !*out[1] || (*out[1] == ' ' && *(po[1]) == ' '))
                return;
        px = star;
        for (i = lmax+P_SPC; i; i--)
                *px++ = ' ';
        for (p0 = out[0], p1 = out[1]; *p0 && *p1; p0++, p1++) {
                if (isalpha(*p0) && isalpha(*p1)) {
                        if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
/*
 * strip path or prefix from pn, return len: pr_align()
 */
static
stripname(pn)                                                                           stripname
        char    *pn;            /* file name (may be path) */
{
        register char           *px, *py;
        py = 0;
        for (px = pn; *px; px++)
                if (*px == '/')
                        py = px + 1;
        if (py)
```

TABLE 1-continued

```
            (void) strcpy(pn, py);
            return(strlen(pn));
}
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
#include "nw.h"
#include <sys/file.h>
char    *jname = "/tmp/homgXXXXXX";     /* tmp file for jmps */
FILE    *fj;
int     cleanup();                       /* cleanup tmp file */
long    lseek();
/*
 * remove any tmp file if we blow
 */
cleanup(i)                                                                          cleanup
        int     i;
{
        if (fj)
                (void) unlink(jname);
        exit(i);
}
/*
 * read, return ptr to seq, set dna, len, maxlen
 * skip lines starting with ';', '<', or '>'
 * seq in upper or lower case
 */
char   *
getseq(file, len)                                                                   getseq
        char    *file;          /* file name */
        int     *len;           /* seq len */
{
        char                    line[1024], *pseq;
        register char           *px, *py;
        int                     natgc, tlen;
        FILE                    *fp;
        if ((fp = fopen(file, "r")) == 0) {
            fprintf(stderr, "%s: can't read %s\n", prog, file);
            exit(1);
        }
        tlen = natgc = 0;
        while (fgets(line, 1024, fp)) {
            if (*line == ';' || *line == '<' || *line == '>')
                    continue;
            for (px = line; *px != '\n'; px++)
                if (isupper(*px) || islower(*px))
                    tlen++;
        }
        if ((pseq = malloc((unsigned)(tlen+6))) == 0) {
            fprintf(stderr, "%s: malloc() failed to get %d bytes for %s\n", prog, tlen+6, file);
            exit(1);
        }
        pseq[0] = pseq[1] = pseq[2] = pseq[3] = '\0';
                                                                                    ...getseq
        py = pseq + 4;
        *len = tlen;
        rewind(fp);
        while (fgets(line, 1024, fp)) {
            if (*line == ';' || *line == '<' || *line == '>')
                    continue;
            for (px = line; *px != '\n'; px++) {
                if (isupper(*px))
                    *py++ = *px;
                else if (islower(*px))
                    *py++ = toupper(*px);
                if (index("ATGCU", *(py-1)))
                    natgc++;
            }
        }
        *py++ = '\0';
        *py = '\0';
        (void) fclose(fp);
        dna = natgc > (tlen/3);
        return(pseq+4);
}
```

TABLE 1-continued

```
char   *
g_calloc(msg, nx, sz)                                                                      g_calloc
    char    *msg;          /* program, calling routine */
    int     nx, sz;        /* number and size of elements */
{
    char            *px, *calloc();
    if ((px = calloc((unsigned)nx, (unsigned)sz)) == 0) {
        if (*msg) {
            fprintf(stderr, "%s: g_calloc() failed %s (n= %d, sz= %d)\n", prog, msg, nx, sz);
            exit(1);
        }
    }
    return(px);
}
/*
* get final jmps from dx[] or tmp file, set pp[], reset dmax: main()
*/
readjmps()                                                                                 readjmps
{
    int         fd = -1;
    int         siz, i0, i1;
    register i, j, xx;
    if (fj) {
        (void) fclose(fj);
        if ((fd = open(jname, O_RDONLY, 0)) < 0) {
            fprintf(stderr, "%s: can't open() %s\n", prog, jname);
            cleanup(1);
        }
    }
    for (i = i0 = i1 = 0, dmax0 = dmax, xx = len0; ;i++) {
        while (1) {
            for (j = dx[dmax].ijmp; j >= 0 && dx[dmax].jp.x[j] >= xx; j--)
                ;
                                                                                           ...readjmps
            if (j < 0 && dx[dmax].offset && fj) {
                (void) lseek(fd, dx[dmax].offset, 0);
                (void) read(fd, (char *)&dx[dmax].jp, sizeof(struct jmp));
                (void) read(fd, (char *)&dx[dmax].offset, sizeof(dx[dmax].offset));
                dx[dmax].ijmp = MAXJMP-1;
            }
            else
                break;
        }
        if (i >= JMPS) {
            fprintf(stderr, "%s: too many gaps in alignment\n", prog);
            cleanup(1);
        }
        if (j >= 0) {
            siz = dx[dmax].jp.n[j];
            xx = dx[dmax].jp.x[j];
            dmax += siz;
            if (siz < 0) {           /* gap in second seq */
                pp[1].n[i1] = -siz;
                xx += siz;
                /* id = xx - yy + len1 - 1
                */
                pp[1].x[i1] = xx - dmax + len1 - 1;
                gapy++;
                ngapy -= siz;
/* ignore MAXGAP when doing endgaps */
                siz = (-siz < MAXGAP || endgaps)? -siz : MAXGAP;
                i1++;
            }
            else if (siz > 0) {      /* gap in first seq */
                pp[0].n[i0] = siz;
                pp[0].x[i0] = xx;
                gapx++;
                ngapx += siz;
/* ignore MAXGAP when doing endgaps */
                siz = (siz < MAXGAP || endgaps)? siz : MAXGAP;
                i0++;
            }
        }
        else
            break;
    }
    /* reverse the order of jmps
    */
    for (j = 0, i0--; j < i0; j++, i0--) {
```

TABLE 1-continued

```
            i = pp[0].n[j]; pp[0].n[j] = pp[0].n[i0]; pp[0].n[i0] = i;
            i = pp[0].x[j]; pp[0].x[j] = pp[0].x[i0]; pp[0].x[i0] = i;
        }
        for (j = 0, i1--; j < i1; j++, i1--) {
            i = pp[1].n[j]; pp[1].n[j] = pp[1].n[i1]; pp[1].n[i1] = i;
            i = pp[1].x[j]; pp[1].x[j] = pp[1].x[i1]; pp[1].x[i1] = i;
        }
        if (fd >= 0)
            (void) close(fd);
        if (fj) {
            (void) unlink(jname);
            fj = 0;
            offset = 0;
        }
    }
}
/*
* write a filled jmp struct offset of the prev one (if any): nw()
*/
writejmps(ix)                                                                                         writejmps
    int    ix;
{
    char    *mktemp();
    if (!fj) {
        if (mktemp(jname) < 0) {
            fprintf(stderr, "%s: can't mktemp() %s\n", prog, jname);
            cleanup(1);
        }
        if ((fj = fopen(jname, "w")) == 0) {
            fprintf(stderr, "%s: can't write %s\n", prog, jname);
            exit(1);
        }
    }
    (void) fwrite((char *)&dx[ix].jp, sizeof(struct jmp), 1, fj);
    (void) fwrite((char *)&dx[ix].offset, sizeof(dx[ix].offset), 1, fj);
}
```

TABLE 2

```
PRO                       XXXXXXXXXXXXXXX  (Length = 15 amino acids)
Comparison Protein        XXXXXYYYYYYY     (Length = 12 amino acids)
```

% amino acid sequence identity =

(the number of identically matching amino acid residues between the two
polypeptide sequences as determined by ALIGN-2) divided by (the total num-
ber of amino acid residues of the PRO polypeptide) = 5 divided by 15
= 33.3%

TABLE 3

```
PRO                       XXXXXXXXXX        (Length = 10 amino acids)
Comparison Protein        XXXXXYYYYYYZZYZ   (Length = 15 amino acids)
```

% amino acid sequence identity =

(the number of identically matching amino acid residues between the two
polypeptide sequences as determined by ALIGN-2) divided by (the total num-
ber of amino acid residues of the PRO polypeptide) = 5 divided by 10 = 50%

TABLE 4

```
PRO-DNA                   NNNNNNNNNNNNNN    (Length = 14 nucleotides)
Comparison DNA            NNNNNNLLLLLLLLLL  (Length = 16 nucleotides)
```

% nucleic acid sequence identity =

(the number of identically matching nucleotides between the two nucleic acid
sequences as determined by ALIGN-2) divided by (the total number of nucle-
otides of the PRO-DNA nucleic acid sequence) = 6 divided by 14 = 42.9%

TABLE 5

```
PRO-DNA            NNNNNNNNNNNN   (Length = 12 nucleotides)
Comparison DNA     NNNNLLLVV      (Length = 9 nucleotides)
```

% nucleic acid sequence identity =

(the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-length PRO Polypeptides

The present invention provides newly identified and isolated nucleotide sequences encoding polypeptides referred to in the present application as PRO polypeptides. In particular, cDNAs encoding various PRO polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO polypeptides and encoding nucleic acids described herein, Applicants have identified what is believed to be the reading frame best identifiable with the sequence information available at the time.

B. PRO Polypeptide Variants

In addition to the full-length native sequence PRO polypeptides described herein, it is contemplated that PRO variants can be prepared. PRO variants can be prepared by introducing appropriate nucleotide changes into the PRO DNA, and/or by synthesis of the desired PRO polypeptide. Those skilled in the art will appreciate that amino acid changes may alter post-translational processes of the PRO, such as changing the number or position of glycosylation sites or altering the membrane anchoring characteristics.

Variations in the native full-length sequence PRO or in various domains of the PRO described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO that results in a change in the amino acid sequence of the PRO as compared with the native sequence PRO. Optionally the variation is by substitution of at least one amino acid with any other amino acid in one or more of the domains of the PRO. Guidance in determining which amino acid residue may be inserted, substituted or deleted without adversely affecting the desired activity may be found by comparing the sequence of the PRO with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO polypeptide.

PRO fragments may be prepared by any of a number of conventional techniques. Desired peptide fragments may be chemically synthesized. An alternative approach involves generating PRO fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO polypeptide fragments share at least one biological and/or immunological activity with the native PRO polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |

TABLE 6-continued

| Original Residue | Exemplary Substitutions | Preferred Substitutions |
|---|---|---|
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis (Wells et al., *Gene,* 34:315 [1985]), restriction selection mutagenesis (Wells et al., *Philos. Trans. R. Soc. London SerA,* 317:415 [1986]) or other known techniques can be performed on the cloned DNA to produce the PRO variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, *Science,* 244: 1081–1085 [1989]). Alanine is also typically preferred because it is the most common amino acid. Further, it is frequently found in both buried and exposed positions (Creighton, *The Proteins,* (W.H. Freeman & Co., N.Y.); Chothia, *J. Mol. Biol.,* 150:1 [1976]). If alanine substitution does not yield adequate amounts of variant, an isoteric amino acid can be used.

C. Modifications of PRO

Covalent modifications of PRO are included within the scope of this invention. One type of covalent modification includes reacting targeted amino acid residues of a PRO polypeptide with an organic derivatizing agent that is capable of reacting with selected side chains or the – or C-terminal residues of the PRO. Derivatization with bifunctional agents is useful, for instance, for crosslinking PRO to a water-insoluble support matrix or surface for use in the method for purifying anti-PRO antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties,* W.H. Freeman & Co., San Francisco, pp. 79–86 (1983)], acetylation of the N-terminal amine, and amidation of any C-terminal carboxyl group.

Another type of covalent modification of the PRO polypeptide included within the scope of this invention comprises altering the native glycosylation pattern of the polypeptide. "Altering the native glycosylation pattern" is intended for purposes herein to mean deleting one or more carbohydrate moieties found in native sequence PRO (either by removing the underlying glycosylation site or by deleting the glycosylation by chemical and/or enzymatic means), and/or adding one or more glycosylation sites that are not present in the native sequence PRO. In addition, the phrase includes qualitative changes in the glycosylation of the native proteins, involving a change in the nature and proportions of the various carbohydrate moieties present.

Addition of glycosylation sites to the PRO polypeptide may be accomplished by altering the amino acid sequence. The alteration may be made, for example, by the addition of, or substitution by, one or more serine or threonine residues to the native sequence PRO (for O-linked glycosylation sites). The PRO amino acid sequence may optionally be altered through changes at the DNA level, particularly by mutating the DNA encoding the PRO polypeptide at preselected bases such that codons are generated that will translate into the desired amino acids.

Another means of increasing the number of carbohydrate moieties on the PRO polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.,* pp. 259–306 (1981).

Removal of carbohydrate moieties present on the PRO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Another type of covalent modification of PRO comprises linking the PRO polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO of the present invention may also be modified in a way to form a chimeric molecule comprising PRO fused to another, heterologous polypeptide or amino acid sequence.

In one embodiment, such a chimeric molecule comprises a fusion of the PRO with a tag polypeptide which provides an epitope to which an anti-tag antibody can selectively bind. The epitope tag is generally placed at the amino- or carboxyl-terminus of the PRO. The presence of such epitope-tagged forms of the PRO can be detected using an antibody against the tag polypeptide. Also, provision of the epitope tag enables the PRO to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.,* 8:2159–2165 (1988)]; the c-myc tag and the 8F9, 3C7, 6E10, G4, B7 and 9E10 antibodies thereto [Evan et al., *Molecular and Cellular Biology,* 5:3610–3616 (1985)]; and the Herpes Simplex virus glycoprotein D (gD) tag and its antibody [Paborsky et al., *Protein Engineering,* 3(6):547–553 (1990)]. Other tag polypeptides include the Flag-peptide [Hopp et al., *Bio Technology,* 6:1204–1210 (1988)]; the KT3 epitope peptide [Martin et al., *Science,* 255:192–194 (1992)]; an α-tubulin epitope peptide [Skinner et al., *J. Biol. Chem.,* 266:15163–15166 (1991)]; and the T7 gene 10 protein peptide tag [Lutz-Freyermuth et al., *Proc. Natl. Acad. Sci. USA,* 87:6393–6397 (1990)].

In an alternative embodiment, the chimeric molecule may comprise a fusion of the PRO with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

In yet a further embodiment, the PRO polypeptides of the present invention may also be modified in a way to form a chimeric molecule comprising a PRO polypeptide fused to a leucine zipper. Various leucine zipper polypeptides have been described in the art. See, e.g., Landschulz et al., *Science,* 240:1759 (1988); WO 94/10308; Hoppe et al., *FEBS Letters,* 344:1991 (1994); Maniatis et al., *Nature,* 341:24 (1989). It is believed that use of a leucine zipper fused to a PRO polypeptide may be desirable to assist in dimerizing or trimerizing soluble PRO polypeptide in solution. Those skilled in the art will appreciate that the leucine zipper may be fused at either the – or C-terminal end of the PRO molecule.

D. Preparation of PRO

The description below relates primarily to production of PRO by culturing cells transformed or transfected with a vector containing PRO nucleic acid. It is, of course, contemplated that alternative methods, which are well known in the art, may be employed to prepare PRO. For instance, the PRO sequence, or portions thereof, may be produced by direct peptide synthesis using solid-phase techniques [see, e.g., Stewart et al., *Solid-Phase Peptide Synthesis,* W.H. Freeman Co., San Francisco, Calif. (1969); Merrifield, *J. Am. Chem. Soc.,* 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO may be chemically synthesized separately and combined using chemical or enzymatic methods to produce the full-length PRO.

1. Isolation of DNA Encoding PRO

DNA encoding PRO may be obtained from a cDNA library prepared from tissue believed to possess the PRO mRNA and to express it at a detectable level. Accordingly, human PRO DNA can be conveniently obtained from a cDNA library prepared from human tissue, such as described in the Examples. The PRO-encoding gene may also be obtained from a genomic library or by known synthetic procedures (e.g., automated nucleic acid synthesis).

Libraries can be screened with probes (such as antibodies to the PRO or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach,* M. Butler, ed. (IRL Press, 1991) and Sambrook et al., supra.

Methods of eukaryotic cell transfection and prokaryotic cell transformation are known to the ordinarily skilled artisan, for example, CaCl$_2$, CaPO$_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published Jun. 29, 1989. For mammalian cells without such cell walls, the calcium phosphate precipitation method of Graham and van der Eb, *Virology*, 52:456–457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO-encoding vectors. *Saccharomyces cerevisiae* is a commonly used lower eukaryotic host microorganism. Others include *Schizosaccharomyces pombe* [Beach and Nurse, *Nature*, 290: 140 (1981); EP 139,383 published May 2, 1985]; Kluyveromyces hosts (U.S. Pat. No. 4,943,529; Fleer et al., *Bio/Technology*, 9:968–975 [1991]) such as, e.g., *K. lactis* (MW98-8C, CBS683, CBS4574; Louvencourt et al., *J. Bacteriol.*, 154(2):737–742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 [1990]), *K. thermotolerans*, and *K. marxianus*; *yarrowia* (EP 402,226); *Pichia pastoris* (EP 183,070; Sreekrishna et al., *J. Basic Microbiol.*, 28:265–278 [1988]); Candida; *Trichoderma reesia* (EP 244,234); *Neurospora crassa* (Case et al., *Proc. Natl. Acad. Sci. USA*, 76:5259–5263 [1979]); Schwanniomyces such as *Schwanniomyces occidentalis* (EP 394,538 published Oct. 31, 1990); and filamentous fungi such as, e.g., Neurospora, Penicillium, Tolypocladium (WO 91/00357 published Jan. 10, 1991), and Aspergillus hosts such as *A. nidulans* (Ballance et al., *Biochem. Biophys. Res. Commun.*, 112:284–289 [1983]; Tilburn et al., *Gene*, 26:205–221 [1983]; Yelton et al., *Proc. Natl. Acad. Sci. USA*, 81:1470–1474 [1984]) and *A. niger* (Kelly and Hynes, *EMBO J.*, 4:475–479 [1985]). Methylotropic yeasts are suitable herein and include, but are not limited to, yeast capable of growth on methanol selected from the genera consisting of Hansenula, Candida, Kloeckera, Pichia, Saccharomyces, Torulopsis, and Rhodotorula. A list of specific species that are exemplary of this class of yeasts may be found in C. Anthony, *The Biochemistry of Methylotrophs*, 269 (1982).

Suitable host cells for the expression of glycosylated PRO are derived from multicellular organisms. Examples of invertebrate cells include insect cells such as Drosophila S2 and Spodoptera Sf9 or Spodoptera High 5 cells, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 [1980]); mouse sertoli cells (TM4, Mather, *Biol. Reprod.*, 23:243–251 [1980]); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010, 182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10: 157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the PRO-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21–25 (1983)]. Promoters for use in bacterial systems also will contain a Shine-Dalgarno (S.D.) sequence operably linked to the DNA encoding PRO.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the PRO coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO.

Still other methods, vectors, and host cells suitable for adaptation to the synthesis of PRO in recombinant vertebrate cell culture are described in Gething et al., *Nature,* 293:620–625 (1981); Mantei et al., *Nature,* 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA,* 77:5201–5205 [1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO polypeptide or against a synthetic peptide based on the DNA sequences provided herein or against exogenous sequence fused to PRO DNA and encoding a specific antibody epitope.

5. Purification of Polypeptide

Forms of PRO may be recovered from culture medium or from host cell lysates. If membrane-bound, it can be released from the membrane using a suitable detergent solution (e.g., Triton-X 100) or by enzymatic cleavage. Cells employed in expression of PRO can be disrupted by various physical or chemical means, such as freeze-thaw cycling, sonication, mechanical disruption, or cell lysing agents.

It may be desired to purify PRO from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular PRO produced.

E. Uses for PRO

Nucleotide sequences (or their complement) encoding PRO have various applications in the art of molecular biology, including uses as hybridization probes, in chromosome and gene mapping and in the generation of anti-sense RNA and DNA. PRO nucleic acid will also be useful for the preparation of PRO polypeptides by the recombinant techniques described herein.

The full-length native sequence PRO gene, or portions thereof, may be used as hybridization probes for a cDNA library to isolate the full-length PRO cDNA or to isolate still other cDNAs (for instance, those encoding naturally-occurring variants of PRO or PRO from other species) which have a desired sequence identity to the native PRO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO. By way of example, a screening method will comprise isolating the coding region of the PRO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO nucleic acids include antisense or sense oligonucleotides comprising a singe-stranded nucleic acid sequence (either RNA or DNA) capable of binding to target PRO mRNA (sense) or PRO DNA (antisense) sequences. Antisense or sense oligonucleotides, according to the present invention, comprise a fragment of the coding region of PRO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, [1988]) and van der Krol et al. (*Bio Techniques*, 6:958, [1988]).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO coding sequences.

Nucleotide sequences encoding a PRO can also be used to construct hybridization probes for mapping the gene which encodes that PRO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO encode a protein which binds to another protein (example, where the PRO is a receptor), the PRO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO can be used to isolate correlative ligand(s). Screening assays can be designed to find lead compounds that mimic the biological activity of a native PRO or a receptor for PRO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO can be used to clone genomic DNA encoding PRO in accordance with established techniques and the genomic sequences used to generate transgenic animals that contain cells which express DNA encoding PRO. Methods for generating transgenic animals, particularly animals such as mice or rats, have become conventional in the art and are described, for example, in U.S. Pat. Nos. 4,736,866 and 4,870,009. Typically, particular cells would be targeted for PRO transgene incorporation with tissue-specific enhancers. Transgenic animals that include a copy of a transgene encoding PRO introduced into the germ line of the animal at an embryonic stage can be used to examine the effect of increased expression of DNA encoding PRO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO can be used to construct a PRO "knock out" animal which has a defective or altered gene encoding PRO as a result of homologous recombination between the endogenous gene encoding PRO and altered genomic DNA encoding PRO introduced into an embryonic stem cell of the animal. For example, cDNA encoding PRO can be used to clone genomic DNA encoding PRO in accordance with established techniques. A portion of the genomic DNA encoding PRO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see, e.g., Li et al., *Cell,* 69:915 (1992)]. The selected cells are then injected into a blastocyst of an animal (e.g., a mouse or rat) to form aggregation chimeras [see, e.g., Bradley, in *Teratocarcinomas and Embryonic Stem Cells: A Practical Approach,* E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knock-out animals can be characterized for instance, for their ability to defend against certain pathological conditions and for their development of pathological conditions due to absence of the PRO polypeptide.

Nucleic acid encoding the PRO polypeptides may also be used in gene therapy. In gene therapy applications, genes are introduced into cells in order to achieve in viva synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA,* 83:4143–4146 [1986]). The oligonucleotides can be modified to enhance their uptake, e.g., by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology*, 11: 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.*, 262: 4429–4432 (1987); and Wagner et al., *Proc. Natl. Acad. Sci. USA*, 87: 3410–3414 (1990). For review of gene marking and gene therapy protocols see Anderson et al., *Science*, 256: 808–813 (1992).

The PRO polypeptides described herein may also be employed as molecular weight markers for protein electrophoresis purposes and the isolated nucleic acid sequences may be used for recombinantly expressing those markers.

The nucleic acid molecules encoding the PRO polypeptides or fragments thereof described herein are useful for chromosome identification. In this regard, there exists an ongoing need to identify new chromosome markers, since relatively few chromosome marking reagents, based upon actual sequence data are presently available. Each PRO nucleic acid molecule of the present invention can be used as a chromosome marker.

The PRO polypeptides and nucleic acid molecules of the present invention may also be used diagnostically for tissue typing, wherein the PRO polypeptides of the present invention may be differentially expressed in one tissue as compared to another, preferably in a diseased tissue as compared to a normal tissue of the same tissue type. PRO nucleic acid molecules will find use for generating probes for PCR, Northern analysis, Southern analysis and Western analysis.

The PRO polypeptides described herein may also be employed as therapeutic agents. The PRO polypeptides of the present invention can be formulated according to known methods to prepare pharmaceutically useful compositions, whereby the PRO product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g., injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In *Toxicokinetics and New Drug Development*, Yacobi et al., Eds., Pergamon Press, New York 1989, pp. 42–96.

When in vivo administration of a PRO polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO polypeptide is desired in a formulation with release characteristics suitable for the treatment of any disease or disorder requiring administration of the PRO polypeptide, microencapsulation of the PRO polypeptide is contemplated. Microencapsulation of recombinant proteins for sustained release has been successfully performed with human growth hormone (rhGH), interferon-(rhIFN-), interleukin-2, and MN rgp120. Johnson et al., *Nat. Med.*, 2:795–799 (1996); Yasuda, *Biomed. Ther.*, 27:1221–1223 (1993); Hora et al., *Bio/Technology*, 8:755–758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439–462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1–41.

This invention encompasses methods of screening compounds to identify those that mimic the PRO polypeptide (agonists) or prevent the effect of the PRO polypeptide (antagonists). Screening assays for antagonist drug candidates are designed to identify compounds that bind or complex with the PRO polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO polypeptide and drying. Alternatively, an immobilized antibody, e.g., a monoclonal antibody, specific for the PRO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature* (London), 340:245–246 [1989]); Chien et al., *Proc. Natl. Acad. Sci. USA*, 88:9578–9582 [1991]) as disclosed by Chevray and Nathans, *Proc. Natl. Acad. Sci. USA*, 89:5789–5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO polypeptide may be added to a cell along with the compound to be screened for a particular activity and the ability of the compound to inhibit the activity of interest in the presence of the PRO polypeptide indicates that the compound is an antagonist to the PRO polypeptide. Alternatively, antagonists may be detected by combining the PRO polypeptide and a potential antagonist with membrane-bound PRO polypeptide receptors or recombinant receptors under appropriate conditions for a competitive inhibition assay. The PRO polypeptide can be labeled, such as by radioactivity, such that the number of PRO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the PRO polypeptide and a cDNA library created from this RNA is divided into pools and used to transfect COS cells or other cells that are not responsive to the PRO polypeptide. Transfected cells that are grown on glass slides are exposed to labeled PRO polypeptide. The PRO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO polypeptide in the presence of the candidate compound. The ability of the compound to enhance or block this interaction could then be measured.

More specific examples of potential antagonists include an oligonucleotide that binds to the fusions of immunoglobulin with PRO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO polypeptide that recognizes the receptor but imparts no effect, thereby competitively inhibiting the action of the PRO polypeptide.

Another potential PRO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241:456 (1988); Dervan et al., *Science*, 251:1360 (1991)), thereby preventing transcription and the production of the PRO polypeptide. The antisense RNA oligonucleotide hybridizes to the mRNA in vivo and blocks translation of the mRNA molecule into the PRO polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO polypeptide, thereby blocking the normal biological activity of the PRO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469–471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Diagnostic and therapeutic uses of the herein disclosed molecules may also be based upon the positive functional assay hits disclosed and described below F. Tissue Distribution The location of tissues expressing the PRO can be identified by determining mRNA expression in various human tissues. The location of such genes provides information about which tissues are most likely to be affected by the stimulating and inhibiting activities of the PRO polypeptides. The location of a gene in a specific tissue also provides sample tissue for the activity blocking assays discussed below.

As noted before, gene expression in various tissues may be measured by conventional Southern blotting, Northern blotting to quantitate the transcription of mRNA (Thomas, *Proc. Natl. Acad. Sci. USA*, 77:5201–5205 [1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence of a PRO polypeptide or against a synthetic peptide based on the DNA sequences encoding the PRO polypeptide or against an exogenous sequence fused to a DNA encoding a PRO polypeptide and encoding a specific antibody epitope. General techniques for generating antibodies, and special protocols for Northern blotting and in situ hybridization are provided below.

G. Antibody Binding Studies

The activity of the PRO polypeptides can be further verified by antibody binding studies, in which the ability of anti-PRO antibodies to inhibit the effect of the PRO polypeptides, respectively, on tissue cells is tested. Exemplary antibodies include polyclonal, monoclonal, humanized, bispecific, and heteroconjugate antibodies, the preparation of which will be described hereinbelow.

Antibody binding studies may be carried out in any known assay method, such as competitive binding assays, direct and indirect sandwich assays, and immunoprecipitation assays. Zola, *Monoclonal Antibodies: A Manual of Techniques*, pp.147–158 (CRC Press, Inc., 1987).

Competitive binding assays rely on the ability of a labeled standard to compete with the test sample analyte for binding with a limited amount of antibody. The amount of target protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme. For immunohistochemistry, the tissue sample may be fresh or frozen or may be embedded in paraffin and fixed with a preservative such as formalin, for example.

H. Cell-based Assays

Cell-based assays and animal models for immune related diseases can be used to further understand the relationship between the genes and polypeptides identified herein and the development and pathogenesis of immune related disease.

In a different approach, cells of a cell type known to be involved in a particular immune related disease are transfected with the cDNAs described herein, and the ability of these cDNAs to stimulate or inhibit immune function is analyzed. Suitable cells can be transfected with the desired gene, and monitored for immune function activity. Such transfected cell lines can then be used to test the ability of poly- or monoclonal antibodies or antibody compositions to inhibit or stimulate immune function, for example to modulate T-cell proliferation or inflammatory cell infiltration. Cells transfected with the coding sequences of the genes identified herein can further be used to identify drug candidates for the treatment of immune related diseases.

In addition, primary cultures derived from transgenic animals (as described below) can be used in the cell-based assays herein, although stable cell lines are preferred. Techniques to derive continuous cell lines from transgenic animals are well known in the art (see, e.g., Small et al., *Mol. Cell. Biol.*, 5: 642–648 [1985]).

One suitable cell based assay is the mixed lymphocyte reaction (MLR). *Current Protocols in Immunology*, unit 3.12; edited by J E Coligan, A M Kruisbeek, D H Marglies, E M Shevach, W Strober, National Institutes of Health, Published by John Wiley & Sons, Inc. In this assay, the ability of a test compound to stimulate or inhibit the proliferation of activated T cells is assayed. A suspension of responder T cells is cultured with allogeneic stimulator cells and the proliferation of T cells is measured by uptake of tritiated thymidine. This assay is a general measure of T cell reactivity. Since the majority of T cells respond to and produce IL-2 upon activation, differences in responsiveness in this assay in part reflect differences in IL-2 production by the responding cells. The MLR results can be verified by a standard lymphokine (IL-2) detection assay. *Current Protocols in Immunology*, above, 3.15, 6.3.

A proliferative T cell response in an MLR assay may be due to direct mitogenic properties of an assayed molecule or to external antigen induced activation. Additional verification of the T cell stimulatory activity of the PRO polypeptides can be obtained by a costimulation assay. T cell activation requires an antigen specific signal mediated through the T-cell receptor (TCR) and a costimulatory signal mediated through a second ligand binding interaction, for example, the B7 (CD80, CD86)/CD28 binding interaction. CD28 crosslinking increases lymphokine secretion by activated T cells. T cell activation has both negative and positive controls through the binding of ligands which have a negative or positive effect. CD28 and CTLA-4 are related glycoproteins in the Ig superfamily which bind to B7. CD28 binding to B7 has a positive costimulation effect of T cell activation; conversely, CTLA-4 binding to B7 has a negative T cell deactivating effect. Chambers, C. A. and Allison, J. P., *Curr. Opin. Immunol.*, (1997) 9:396. Schwartz, R. H., *Cell* (1992) 71:1065; Linsley, P. S. and Ledbetter, J. A., *Annu. Rev. Immunol.* (1993) 11:191; June, C. H. et al., *Immunol. Today* (1994) 15:321; Jenkins, M. K., *Immunity* (1994) 1:405. In a costimulation assay, the PRO polypeptides are assayed for T cell costimulatory or inhibitory activity.

PRO polypeptides, as well as other compounds of the invention, which are stimulators (costimulators) of T cell proliferation and agonists, e.g., agonist antibodies, thereto as determined by MLR and costimulation assays, for example, are useful in treating immune related diseases characterized by poor, suboptimal or inadequate immune function. These diseases are treated by stimulating the proliferation and activation of T cells (and T cell mediated immunity) and enhancing the immune response in a mammal through administration of a stimulatory compound, such as the stimulating PRO polypeptides. The stimulating polypeptide may, for example, be a PRO polypeptide or an agonist antibody thereof.

Direct use of a stimulating compound as in the invention has been validated in experiments with 4-1BB glycoprotein, a member of the tumor necrosis factor receptor family, which binds to a ligand (4-1BBL) expressed on primed T cells and signals T cell activation and growth. Alderson, M. E. et al., *J. Immunol.* 24:2219 (1994).

The use of an agonist stimulating compound has also been validated experimentally. Activation of 4-1BB by treatment with an agonist anti-4-1BB antibody enhances eradication of tumors. Hellstrom, I. and Hellstrom, K. E., *Crit. Rev. Immunol.*, 18:1 (1998). Immunoadjuvant therapy for treatment of tumors, described in more detail below, is another example of the use of the stimulating compounds of the invention. An immune stimulating or enhancing effect can also be achieved by antagonizing or blocking the activity of a PRO which has been found to be inhibiting in the MLR assay. Negating the inhibitory activity of the compound produces a net stimulatory effect. Suitable antagonists/blocking compounds are antibodies or fragments thereof which recognize and bind to the inhibitory protein, thereby blocking the effective interaction of the protein with its receptor and inhibiting signaling through the receptor. This effect has been validated in experiments using anti-CTLA-4 antibodies which enhance T cell proliferation, presumably by removal of the inhibitory signal caused by CTLA-4 binding. Walunas, T. L. et al., *Immunity*, 1:405 (1994).

Alternatively, an immune stimulating or enhancing effect can also be achieved by administration of a PRO polypeptide which has vascular permeability enhancing properties.

Enhanced vacuolar permeability would be beneficial to disorders which can be attenuated by local infiltration of immune cells (e.g., monocytes, eosinophils, PMNs) and inflammation.

On the other hand, PRO polypeptides, as well as other compounds of the invention, which are direct inhibitors of T cell proliferation/activation, lymphokine secretion, and/or vascular permeability can be directly used to suppress the immune response. These compounds are useful to reduce the degree of the immune response and to treat immune related diseases characterized by a hyperactive, superoptimal, or autoimmune response. This use of the compounds of the invention has been validated by the experiments described above in which CTLA-4 binding to receptor B7 deactivates T cells. The direct inhibitory compounds of the invention function in an analogous manner. The use of compound which suppress vascular permeability would be expected to reduce inflammation. Such uses would be beneficial in treating conditions associated with excessive inflammation.

Alternatively, compounds, e.g., antibodies, which bind to stimulating PRO polypeptides and block the stimulating effect of these molecules produce a net inhibitory effect and can be used to suppress the T cell mediated immune response by inhibiting T cell proliferation/activation and/or lymphokine secretion. Blocking the stimulating effect of the polypeptides suppresses the immune response of the mammal. This use has been validated in experiments using an anti-IL2 antibody. In these experiments, the antibody binds to IL2 and blocks binding of IL2 to its receptor thereby achieving a T cell inhibitory effect.

I. Animal Models

The results of the cell based in vitro assays can be further verified using in vivo animal models and assays for T-cell function. A variety of well known animal models can be used to further understand the role of the genes identified herein in the development and pathogenesis of immune related disease, and to test the efficacy of candidate therapeutic agents, including antibodies, and other antagonists of the native polypeptides, including small molecule antagonists. The in vivo nature of such models makes them predictive of responses in human patients. Animal models of immune related diseases include both non-recombinant and recombinant (transgenic) animals. Non-recombinant animal models include, for example, rodent, e.g., murine models. Such models can be generated by introducing cells into syngeneic mice using standard techniques, e.g., subcutaneous injection, tail vein injection, spleen implantation, intraperitoneal implantation, implantation under the renal capsule, etc.

Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in *Current Protocols in Immunology*, above, unit 4.3.

An animal model for skin allograft rejection is a means of testing the ability of T cells to mediate in vivo tissue destruction and a measure of their role in transplant rejection. The most common and accepted models use murine tail-skin grafts. Repeated experiments have shown that skin allograft rejection is mediated by T cells, helper T cells and killer-effector T cells, and not antibodies. Auchincloss, H. Jr. and Sachs, D. H., *Fundamental Immunology*, 2nd ed., W. E. Paul ed., Raven Press, NY, 889–992 (1989). A suitable procedure is described in detail in *Current Protocols in Immunology*, above, unit 4.4. Other transplant rejection models which can be used to test the compounds of the invention are the allogeneic heart transplant models described by Tanabe, M. et al., *Transplantation*, 58:23 (1994) and Tinubu, S. A. et al., *J. Immunol.*, 4330–4338 (1994).

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in *Current Protocols in Immunology*, above, unit 4.5.

EAE is a T cell mediated autoimmune disease characterized by T cell and mononuclear cell inflammation and subsequent demyelination of axons in the central nervous system. EAE is generally considered to be a relevant animal model for MS in humans. Bolton, C., *Multiple Sclerosis*, 1:143 (1995). Both acute and relapsing-remitting models have been developed. The compounds of the invention can be tested for T cell stimulatory or inhibitory activity against immune mediated demyelinating disease using the protocol described in *Current Protocols in Immunology*, above, units 15.1 and 15.2. See also the models for myelin disease in which oligodendrocytes or Schwann cells are grafted into the central nervous system as described in Duncan, I. D. et al., *Molec. Med. Today*, 554–561 (1997).

Contact hypersensitivity is a simple delayed type hypersensitivity in vivo assay of cell mediated immune function. In this procedure, cutaneous exposure to exogenous haptens which gives rise to a delayed type hypersensitivity reaction which is measured and quantitated. Contact sensitivity involves an initial sensitizing phase followed by an elicitation phase. The elicitation phase occurs when the T lymphocytes encounter an antigen to which they have had previous contact. Swelling and inflammation occur, making this an excellent model of human allergic contact dermatitis. A suitable procedure is described in detail in *Current Protocols in Immunology*, Eds. J. E. Cologan, A. M. Kruisbeek, D. H. Margulies, E. M. Shevach and W. Strober, John Wiley & Sons, Inc., unit 4.2 (1994). I also Grabbe, S. and Schwarz, T, *Immun. Today*, 19 (1): 37–44 (1998).

An animal model for arthritis is collagen-induced arthritis. This model shares clinical, histological and immunological characteristics of human autoimmune rheumatoid arthritis and is an acceptable model for human autoimmune arthritis. Mouse and rat models are characterized by synovitis, erosion of cartilage and subchondral bone. The compounds of the invention can be tested for activity against autoimmune arthritis using the protocols described in *Current Protocols in Immunology*, above, units 15.5. See also the model using a monoclonal antibody to CD18 and VLA-4 integrins described in Issekutz, A. C. et al., *Immunology*, 88:569 (1996).

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test the compounds of the invention for activity and effectiveness in the treatment of asthma are described by Wolyniec, W. W. et al., *Am. J. Respir. Cell Mol. Biol.,* 18:777 (1998) and the references cited therein.

Additionally, the compounds of the invention can be tested on animal models for psoriasis like diseases. Evidence suggests a T cell pathogenesis for psoriasis. The compounds of the invention can be tested in the scid/scid mouse model described by Schon, M. P. et al., *Nat. Med.,* 3:183 (1997), in which the mice demonstrate histopathologic skin lesions resembling psoriasis. Another suitable model is the human skin/scid mouse chimera prepared as described by Nickoloff, B. J. et al., *Am. J. Path.,* 146:580 (1995).

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g., baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA,* 82, 6148–615 [1985]); gene targeting in embryonic stem cells (Thompson et al., *Cell,* 56, 313–321 [1989]); electroporation of embryos (Lo, *Mol. Cel. Biol.,* 3, 1803–1814 [1983]); sperm-mediated gene transfer (Lavitrano et al., *Cell,* 57, 717–73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA,* 89, 6232–636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry.

The animals may be further examined for signs of immune disease pathology, for example by histological examination to determine infiltration of immune cells into specific tissues. Blocking experiments can also be performed in which the transgenic animals are treated with the compounds of the invention to determine the extent of the T cell proliferation stimulation or inhibition of the compounds. In these experiments, blocking antibodies which bind to the PRO polypeptide, prepared as described above, are administered to the animal and the effect on immune function is determined.

Alternatively, "knock out" animals can be constructed which have a defective or altered gene encoding a polypeptide identified herein, as a result of homologous recombination between the endogenous gene encoding the polypeptide and altered genomic DNA encoding the same polypeptide introduced into an embryonic cell of the animal. For example, cDNA encoding a particular polypeptide can be used to clone genomic DNA encoding that polypeptide in accordance with established techniques. A portion of the genomic DNA encoding a particular polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach,* E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the polypeptide.

J. Immuno adjuvant Therapy

In one embodiment, the immunostimulating compounds of the invention can be used in immunoadjuvant therapy for the treatment of tumors (cancer). It is now well established that T cells recognize human tumor specific antigens. One group of tumor antigens, encoded by the MAGE, BAGE and GAGE families of genes, are silent in all adult normal tissues, but are expressed in significant amounts in tumors, such as melanomas, lung tumors, head and neck tumors, and bladder carcinomas. DeSmet, C. et al., *Proc. Natl. Acad. Sci. USA,* 93:7149 (1996). It has been shown that costimulation of T cells induces tumor regression and an antitumor response both in vitro and in vivo. Melero, I. et al., *Nature Medicine.* 3:682 (1997); Kwon, E. D. et al., *Proc. Natl. Acad. Sci. USA,* 94: 8099 (1997); Lynch, D. H. et al., *Nature Medicine,* 3:625 (1997); Finn, O. J. and Lotze, M. T., *J. Immunol.,* 21:114 (1998). The stimulatory compounds of the invention can be administered as adjuvants, alone or together with a growth regulating agent, cytotoxic agent or chemotherapeutic agent, to stimulate T cell proliferation/activation and an antitumor response to tumor antigens. The growth regulating, cytotoxic, or chemotherapeutic agent may be administered in conventional amounts using known administration regimes. Immunostimulating activity by the compounds of the invention allows reduced amounts of the growth regulating, cytotoxic, or chemotherapeutic agents thereby potentially lowering the toxicity to the patient.

K. Screening Assays for Drug Candidates

Screening assays for drug candidates are designed to identify compounds that bind to or complex with the polypeptides encoded by the genes identified herein or a biologically active fragment thereof, or otherwise interfere with the interaction of the encoded polypeptides with other cellular proteins. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly) peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art. All assays are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment, the polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the polypeptide and drying. Alternatively, an immobilized antibody, e.g., a monoclonal antibody, specific for the polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labelled antibody specifically binding the immobilized complex.

If the candidate compound interacts with but does not bind to a particular protein encoded by a gene identified herein, its interaction with that protein can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, *Nature (London)*, 340, 245–246 (1989); Chien et al., *Proc. Natl. Acad. Sci. USA*, 88, 9578–9582 (1991)] as disclosed by Chevray and Nathans, *Proc. Natl. Acad. Sci. USA*, 89, 5789–5793 (1991). Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

In order to find compounds that interfere with the interaction of a gene identified herein and other intra- or extracellular components can be tested, a reaction mixture is usually prepared containing the product of the gene and the intra- or extracellular component under conditions and for a time allowing for the interaction and binding of the two products. To test the ability of a test compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described above. The formation of a complex in the control reaction(s) but not in the reaction mixture containing the test compound indicates that the test compound interferes with the interaction of the test compound and its reaction partner.

L. Compositions and Methods for the Treatment of Immune Related Diseases

The compositions useful in the treatment of immune related diseases include, without limitation, proteins, antibodies, small organic molecules, peptides, phosphopeptides, antisense and ribozyme molecules, triple helix molecules, etc. that inhibit or stimulate immune function, for example, T cell proliferation/activation, lymphokine release, or immune cell infiltration.

For example, antisense RNA and RNA molecules act to directly block the translation of mRNA by hybridizing to targeted mRNA and preventing protein translation. When antisense DNA is used, oligodeoxyribonucleotides derived from the translation initiation site, e.g., between about −10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4, 469–471 (1994), and PCT publication No. WO 97/33551 (published Sep. 18, 1997).

Nucleic acid molecules in triple helix formation used to inhibit transcription should be single-stranded and composed of deoxynucleotides. The base composition of these oligonucleotides is designed such that it promotes triple helix formation via Hoogsteen base pairing rules, which generally require sizeable stretches of purines or pyrimidines on one strand of a duplex. For further details see, e.g., PCT publication No. WO 97/33551, supra.

These molecules can be identified by any or any combination of the screening assays discussed above and/or by any other screening techniques well known for those skilled in the art.

M. Anti-PRO Antibodies

The present invention further provides anti-PRO antibodies. Exemplary antibodies include polyclonal, monoclonal, humanized, bispecific, and heteroconjugate antibodies.

1. Polyclonal Antibodies

The anti-PRO antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications,* Marcel Dekker, Inc., New York, (1987) pp. 51–63].

The culture medium in which the hybridoma cells are cultured can then be assayed for the presence of monoclonal antibodies directed against PRO. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al., and Boerner et al., are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., *Bio/Technology*, 10, 779–783 (1992); Lonberg et al., *Nature*, 368: 856–859 (1994); Morrison, *Nature*, 368: 812–13 (1994); Fishwild et al., *Nature Biotechnology*, 14: 845–51 (1996); Neuberger, *Nature Biotechnology*, 14: 826 (1996); Lonberg and Huszar, *Intern. Rev. Immunol.*, 13: 65–93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

4. Bispecific Antibodies

Bispecific antibodies are monoclonal, preferably human or humanized, antibodies that have binding specificities for at least two different antigens. In the present case, one of the binding specificities is for the PRO, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies can be prepared as full length antibodies or antibody fragments (e.g., F(ab')2 bispecific antibodies). Techniques for generating bispecific antibodies from antibody fragments have been described in the literature. For example, bispecific antibodies can be prepared can be prepared using chemical linkage. Brennan et al., *Science*, 229:81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217–225 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., *J. Immunol.*, 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA.* 90:6444–6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See, Gruber et al., *J. Immunol.*, 152:5368 (1994).

Antibodies with more than two valencies are contemplated. For example, trispecific antibodies can be prepared. Tutt et al., *J. Immunol.* 147:60 (1991).

Exemplary bispecific antibodies may bind to two different epitopes on a given PRO polypeptide herein. Alternatively, an anti-PRO polypeptide arm may be combined with an arm which binds to a triggering molecule on a leukocyte such as a T-cell receptor molecule (e.g., CD2, CD3, CD28, or B7), or Fc receptors for IgG (FcgR), such as FcgRI (CD64), FcgRII (CD32) and FcgRIII (CD16) so as to focus cellular defense mechanisms to the cell expressing the particular PRO polypeptide. Bispecific antibodies may also be used to localize cytotoxic agents to cells which express a particular PRO polypeptide. These antibodies possess a PRO-binding arm and an arm which binds a cytotoxic agent or a radionuclide chelator, such as EOTUBE, DPTA, DOTA, or TETA. Another bispecific antibody of interest binds the PRO polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191–1195 (1992) and Shopes, *J. Immunol.*, 148: 2918–2922 (1992). Homodimeric antibodies with enhanced anti-tumor activity may also be prepared using heterobifunctional cross-linkers as described in Wolff et al., *Cancer Research*, 53: 2560–2565 (1993). Alternatively, an antibody can be engineered that has dual Fc regions and may thereby have enhanced complement lysis and ADCC capabilities. See Stevenson et al., *Anti-cancer Drug Design*, 3: 219–230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 23:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA,* 82:3688 (1985); Hwang et al., *Proc. Natl Acad. Sci. USA,* 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.,* 257: 286–288 (1982) via a disulfide-interchange reaction. A chemotherapeutic agent (such as Doxorubicin) is optionally contained within the liposome. See Gabizon et al., *J. National Cancer Inst.,* 81(19):1484 (1989).

9. Uses for anti-PRO Antibodies

The anti-PRO antibodies of the invention have various utilities. For example, anti-PRO antibodies may be used in diagnostic assays for PRO, e.g., detecting its expression (and in some cases, differential expression) in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques,* CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

Anti-PRO antibodies also are useful for the affinity purification of PRO from recombinant cell culture or natural sources. In this process, the antibodies against PRO are immobilized on a suitable support, such a Sephadex resin or filter paper, using methods well known in the art. The immobilized antibody then is contacted with a sample containing the PRO to be purified, and thereafter the support is washed with a suitable solvent that will remove substantially all the material in the sample except the PRO, which is bound to the immobilized antibody. Finally, the support is washed with another suitable solvent that will release the PRO from the antibody.

The following examples are offered for illustrative purposes only, and are not intended to limit the scope of the present invention in any way.

All patent and literature references cited in the present specification are hereby incorporated by reference in their entirety.

N. Pharmaceutical Compositions

The active PRO molecules of the invention (e.g., PRO polypeptides, anti-PRO antibodies, and/or variants of each) as well as other molecules identified by the screening assays disclosed above, can be administered for the treatment of immune related diseases, in the form of pharmaceutical compositions. Therapeutic formulations of the active PRO molecule, preferably a polypeptide or antibody of the invention, are prepared for storage by mixing the active molecule having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Compounds identified by the screening assays disclosed herein can be formulated in an analogous manner, using standard techniques well known in the art.

Lipofections or liposomes can also be used to deliver the PRO molecule into cells. Where antibody fragments are used, the smallest inhibitory fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g., Marasco et al., *Proc. Natl. Acad. Sci. USA.* 90:7889–7893 [1993]).

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active PRO molecules may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations or the PRO molecules may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

O. Methods of Treatment

It is contemplated that the polypeptides, antibodies and other active compounds of the present invention may be used to treat various immune related diseases and conditions, such as T cell mediated diseases, including those characterized by infiltration of inflammatory cells into a tissue, stimulation of T-cell proliferation, inhibition of T-cell proliferation, increased or decreased vascular permeability or the inhibition thereof.

Exemplary conditions or disorders to be treated with the polypeptides, antibodies and other compounds of the invention, include, but are not limited to systemic lupus erythematosis, rheumatoid arthritis, juvenile chronic arthritis, osteoarthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, transplantation associated diseases including graft rejection and graft-versus-host-disease.

In systemic lupus erythematosus, the central mediator of disease is the production of auto-reactive antibodies to self proteins/tissues and the subsequent generation of immune-mediated inflammation. Antibodies either directly or indirectly mediate tissue injury. Though T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid if infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, interstitial pneumonitis with pulmonary fibrosis, keratoconjunctivitis sicca, and rheumatoid nodules.

Juvenile chronic arthritis is a chronic idiopathic inflammatory disease which begins often at less than 16 years of age. Its phenotype has some similarities to RA; some patients which are rheumatoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing spondylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the $CD8^+$ T lymphocyte, a cell which targets antigen presented by class I MHC molecules. CD8+ T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of anti-nuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjögren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including biliary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet cells; this destruction is mediated by auto-antibodies and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including multiple sclerosis; idiopathic demyelinating polyneuropathy or Guillain-Barré syndrome; and chronic inflammatory demyelinating polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+ T lymphocytes are the predominant cell type at lesions. The mechanism of oligodendrocyte cell death and subsequent demyelination is not known but is likely T lymphocyte driven.

Inflammatory and fibrotic lung disease, including eosinophilic pneumonia; idiopathic pulmonary fibrosis, and hypersensitivity pneumonitis may involve a disregulated immune-inflammatory response. Inhibition of that response would be of therapeutic benefit.

Autoimmune or immune-mediated skin disease including bullous skin diseases, erythema multiforme, and contact dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils.

Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including graft rejection and graft-versus-host-disease (GVHD) are T lymphocyte-dependent; inhibition of T lymphocyte function is ameliorative.

Other diseases in which intervention of the immune and/or inflammatory response have benefit are infectious disease including but not limited to viral infection (including but not limited to AIDS, hepatitis A, B, C, D, E and herpes) bacterial infection, fungal infections, and protozoal and parasitic infections (molecules (or derivatives/agonists) which stimulate the MLR can be utilized therapeutically to enhance the immune response to infectious agents), diseases of immunodeficiency (molecules/derivatives/agonists) which stimulate the MLR can be utilized therapeutically to enhance the immune response for conditions of inherited, acquired, infectious induced (as in HIV infection), or iatrogenic (i.e., as from chemotherapy) immunodeficiency, and neoplasia.

It has been demonstrated that some human cancer patients develop an antibody and/or T lymphocyte response to antigens on neoplastic cells. It has also been shown in animal models of neoplasia that enhancement of the immune response can result in rejection or regression of that particular neoplasm. Molecules that enhance the T lymphocyte response in the MLR have utility in vivo in enhancing the immune response against neoplasia. Molecules which enhance the T lymphocyte proliferative response in the MLR (or small molecule agonists or antibodies that affected the same receptor in an agonistic fashion) can be used therapeutically to treat cancer. Molecules that inhibit the lymphocyte response in the MLR also function in vivo during neoplasia to suppress the immune response to a neoplasm; such molecules can either be expressed by the neoplastic cells themselves or their expression can be induced by the neoplasm in other cells. Antagonism of such inhibitory molecules (either with antibody, small molecule antagonists or other means) enhances immune-mediated tumor rejection.

Additionally, inhibition of molecules with proinflammatory properties may have therapeutic benefit in reperfusion injury; stroke; myocardial infarction; atherosclerosis; acute lung injury; hemorrhagic shock; burn; sepsis/septic shock; acute tubular necrosis; endometriosis; degenerative joint disease and pancreatitis. The compounds of the present invention, e.g., polypeptides or antibodies, are administered to a mammal, preferably a human, in accord with known methods, such as intravenous administration as a bolus or by continuous infusion over a period of time, by intramuscular, intraperitoneal, intracerebral spinal, subcutaneous, intra-articular, intra synovial, intrathecal, oral, topical, or inhalation (intranasal, intrapulmonary) routes. Intravenous or inhaled administration of polypeptides and antibodies is preferred. In immunoadjuvant therapy, other therapeutic regimens, such administration of an anti-cancer agent, may be combined with the administration of the proteins, antibodies or compounds of the instant invention. For example, the patient to be treated with a the immunoadjuvant of the invention may also receive an anti-cancer agent (chemotherapeutic agent) or radiation therapy. Preparation and dosing schedules for such chemotherapeutic agents may be used according to manufacturers' instructions or as determined empirically by the skilled practitioner. Preparation and dosing schedules for such chemotherapy are also described in *Chemotherapy Service*, Ed., M. C. Perry, Williams & Wilkins, Baltimore, Md. (1992). The chemotherapeutic agent may precede, or follow administration of the immunoadjuvant or may be given simultaneously therewith. Additionally, an anti-oestrogen compound such as tamoxifen or an anti-progesterone such as onapristone (see, EP 616812) may be given in dosages known for such molecules.

It may be desirable to also administer antibodies against other immune disease associated or tumor associated antigens, such as antibodies which bind to CD20, CD11a, CD18, ErbB2, EGFR, ErbB3, ErbB4, or vascular endothelial factor (VEGF). Alternatively, or in addition, two or more antibodies binding the same or two or more different antigens disclosed herein may be coadministered to the patient. Sometimes, it may be beneficial to also administer one or more cytokines to the patient. In one embodiment, the PRO polypeptides are coadministered with a growth inhibitory agent. For example, the growth inhibitory agent may be administered first, followed by a PRO polypeptide. However, simultaneous administration or administration first is also contemplated. Suitable dosages for the growth inhibitory agent are those presently used and may be lowered due to the combined action (synergy) of the growth inhibitory agent and the PRO polypeptide. For the treatment or reduction in the severity of immune related disease, the appropriate dosage of an a compound of the invention will depend on the type of disease to be treated, as defined above, the severity and course of the disease, whether the agent is administered for preventive or therapeutic purposes, previous therapy, the patient's clinical history and response to the compound, and the discretion of the attending physician. The compound is suitably administered to the patient at one time or over a series of treatments.

For example, depending on the type and severity of the disease, about 1 mg/kg to 15 mg/kg (e.g., 0.1–20 mg/kg) of polypeptide or antibody is an initial candidate dosage for administration to the patient, whether, for example, by one or more separate administrations, or by continuous infusion. A typical daily dosage might range from about 1 mg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

P. Articles of Manufacture

In another embodiment of the invention, an article of manufacture containing materials (e.g., comprising a PRO molecule) useful for the diagnosis or treatment of the disorders described above is provided. The article of manufacture comprises a container and an instruction. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually a polypeptide or an antibody of the invention. An instruction or label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

Q. Diagnosis and Prognosis of Immune Related Disease

Cell surface proteins, such as proteins which are overexpressed in certain immune related diseases, are excellent targets for drug candidates or disease treatment. The same proteins along with secreted proteins encoded by the genes amplified in immune related disease states find additional use in the diagnosis and prognosis of these diseases. For example, antibodies directed against the protein products of genes amplified in multiple sclerosis, rheumatoid arthritis, inflammatory bowel disorder, or another immune related disease, can be used as diagnostics or prognostics.

For example, antibodies, including antibody fragments, can be used to qualitatively or quantitatively detect the expression of proteins encoded by amplified or overexpressed genes ("marker gene products"). The antibody preferably is equipped with a detectable, e.g., fluorescent label, and binding can be monitored by light microscopy, flow cytometry, fluorimetry, or other techniques known in the art. These techniques are particularly suitable, if the overexpressed gene encodes a cell surface protein Such binding assays are performed essentially as described above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Isolation of cDNA Clones Encoding Human PRO1031

The extracellular domain (ECD) sequences (including the secretion signal, if any) of from about 950 known secreted proteins from the Swiss-Prot public protein database were used to search expressed sequence tag (EST) databases. The EST databases included public EST databases (e.g., GenBank, Merck/Wash U.) and a proprietary EST DNA database (LIFESEQ®, Incyte Pharmaceuticals, Palo Alto, Calif.). The search was performed using the computer program BLAST or BLAST2 (Altshul et al., *Methods in Enzymology*, 266:460–480 (1996)) as a comparison of the ECD protein sequences to a 6 frame translation of the EST sequence. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

An initial virtual sequence fragment (consensus assembly) was assembled relative to other EST sequences using phrap. The initial consensus DNA sequence was extended using repeated cycles of BLAST and phrap to extend the consensus sequence as far as possible using the sources of EST sequences discussed above. The results of this consensus assembly is referred to as DNA47332.

One sequence comprising the consensus assembly, W74558 (clone 344649) was further examined. The sequence was obtained from the IMAGE consortium and analyzed. Lennon et al., *Genomics,* 33: 151 (1996). DNA sequencing gave the full-length DNA sequence for PRO1031 [herein designated as DNA59294-1381] (SEQ ID NO:1) and the derived PRO1031 protein sequence (UNQ516)(SEQ ID NO:2).

The entire nucleotide sequence of DNA59294-1381 is shown in FIG. 1 (SEQ ID NO:1). Clone DNA59294-1381 contains a single open reading frame with an apparent translational initiation site at nucleotide positions 42–44 and ending at the stop codon at nucleotide positions 582–584 (FIG. 1; SEQ ID NO:1). The predicted polypeptide precursor is 180 amino acids long (FIG. 2; SEQ ID NO:2). The full-length PRO1031 (UNQ516) protein shown in FIG. 2 (SEQ ID NO:2) has an estimated molecular weight of about 20,437 daltons and a pI of about 9.58. Clone DNA59294-1381 has been deposited with the ATCC, and has been assigned deposit number 209866. In the event of any sequencing irregularities or errors with the sequences provided herein, it is understood that the deposited clone contains the correct sequence for DNA59624-1381 (SEQ ID NO:1). Furthermore, the sequences provided herein are the result of known sequencing techniques.

Analysis of the amino acid sequence of the full-length PRO1031 polypeptide (UNQ516)(SEQ ID NO:2) suggests that it is a novel interleukin-17 homolog, herein designated as IL-17B.

Further analysis of the amino acid sequence of SEQ ID NO:2 reveals that the putative signal peptide is at about amino acids 1–20 of SEQ ID NO:2. An N-glycosylation site is at about amino acids 75–78 of SEQ ID NO:2. A region having sequence identity with IL-17 is at about amino acids 96–180. The corresponding nucleotides can be routinely determined given the sequences provided herein.

Example 2

Isolation of cDNA clones Encoding Human PRO1122

An expressed sequence tag (EST) DNA database (LIFESEQ®, Incyte Pharmaceuticals, Palo Alto, Calif.) was searched and an EST was identified. The EST was Incyte 1347523 also called DNA49665. Based on DNA49665, oligonucleotides were synthesized: 1) to identify by PCR a cDNA library that contained the sequence of interest, and 2) for use as probes to isolated a clone of the full-length coding sequence for the PRO1122. [e.g., Sambrook et al., *Molecular Cloning: A Laboratory Manual* (New York: Cold Spring Harbor Laboratory Press, 1989); Dieffenbach et al., *PCR Primer: A Laboratory Manual* (Cold Spring Harbor Laboratory Press, 1995)].

Forward and reverse PCR primers generally range from 20 to 30 nucleotides and are often designed to give a PCR product of about 100–1000 bp in length. The probes sequences are typically 40–55 bp in length. In some cases, additional oligonucleotides are synthesized when the consensus sequence is greater than about 1–1.5 kpb. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

PCR primers (forward, reverse and hybridization) were synthesized:

```
forward PCR primer:
5'-ATCCACAGAAGCTGGCCTTCGCCG-3'                    (SEQ ID NO:19)

reverse PCR primer:
5'-GGGACGTGGATGAACTCGGTGTGG-3'                    (SEQ ID NO:20)

hybridization probe:
5'-TATCCACAGAAGCTGGCCTTCGCCGAGTGCCTGTGCAGAG 3'    (SEQ ID NO:21).
```

In order to screen several libraries for a source of a full-length clone, DNA from the libraries was screened by PCR amplification with the PCR primer pair identified above. A positive library was then used to isolate clones encoding the PRO1122 gene using the probe oligonucleotide and one of the PCR primers.

RNA for construction of the cDNA libraries was isolated from human fetal kidney tissue. The cDNA libraries used to isolate the cDNA clones were constructed using standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 235: 1278–1280 (1991)) in the unique XhoI and NotI sites.

DNA sequencing of the clones isolated as described above gave the full-length DNA sequence for PRO1122 [herein designated as DNA62377-1381-1](SEQ ID NO:3) and the derived protein PRO1122 sequence (UNQ561)(SEQ ID NO:4).

The entire nucleotide sequence of DNA62377-1381-1 (SEQ ID NO:3) is shown in FIG. 3 (SEQ ID NO:3). Clone DNA62377-1381-1 (SEQ ID NO:3) contains a single open reading frame with an apparent translational initiation site at nucleotide positions 50–52 and ending at the stop codon at nucleotide positions 641–643 of SEQ ID NO:3 (FIG. 3). The predicted polypeptide precursor is 197 amino acids long (FIG. 4; SEQ ID NO:4). The full-length PRO1122 protein shown in FIG. 4 (UNQ561)(SEQ ID NO:4) has an estimated molecular weight of about 21765 daltons and a pI of about 8.53. Clone DNA62377-1381-1 has been deposited with the ATCC on Dec. 22, 1998 and has been assigned deposit number 203552. It is understood that in the event or a sequencing irregularity or error in the sequences provided herein, the correct sequence is the sequence deposited. Furthermore, all sequences provided herein are the result of known sequencing techniques.

Analysis of the amino acid sequence of the isolated full-length PRO1122 (UNQ561) suggests that it possesses similarity with IL-17, thereby indicating that PRO1122 (UNQ561) may be a novel cytokine and is herein designated IL-17C. FIG. 4 (SEQ ID NO:4) also shows the approximate locations of the signal peptide, leucine zipper pattern, and a region having sequence identity with IL-17.

Example 3

Isolation of cDNA clones Encoding Human PRO10272

The extracellular domain (ECD) sequences (including the secretion signal sequence, if any) from about 950 known secreted proteins from the Swiss-Prot public database were used to search genomic DNA sequences from GenBank. The search was performed using the computer program BLAST or BLAST2 [Altschul et al., *Methods in Enzymology*, 266:460–480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap as described above. This consensus sequence is herein designated DNA146646. In some cases, the consensus sequence derives from an intermediate consensus DNA sequence which was extended using repeated cycles of BLAST and phrap to extend that intermediate consensus sequence as far as possible using the sources of EST sequences discussed above.

Based on the DNA146646 consensus sequence, oligonucleotides were synthesized: 1) to identify by PCR a cDNA library that contained the sequence of interest, and 2) for use as probes to isolate a clone of the full-length coding sequence for PRO10272. Forward and reverse PCR primers generally range from 20 to 30 nucleotides and are often designed to give a PCR product of about 100–1000 bp in length. The probe sequences are typically 40–55 bp in length. In some cases, additional oligonucleotides are synthesized when the consensus sequence is greater than about 1–1.5 kbp. In order to screen several libraries for a full-length clone, DNA from the libraries was screened by PCR amplification, as per Ausubel et al., *Current Protocols in Molecular Biology*, supra, with the PCR primer pair. A positive library was then used to isolate clones encoding the gene of interest using the probe oligonucleotide and one of the primer pairs. PCR primers (forward and reverse) were synthesized:

```
forward PCR primer:
5'-GTTGCATTCTTGGCAATGGTCATGGGA-3'      (SEQ ID NO:22)

reverse PCR primer:
5'-GGTCCATGTGGGAGCCTGTCTGTA-3'         (SEQ ID NO:23)
```

Additionally, a synthetic oligonucleotide hybridization probe was constructed from the consensus DNA 146646 sequence which had the following nucleotide sequence:

```
hybridization probe
5'-CAGCAGCTCCTCAGAGGTGTCCTGCCCTTTGCTGGGGCAGCAGCT-3'    (SEQ ID NO:24)
```

RNA for construction of the cDNA libraries was isolated from human testis tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or PRKD; pRK5B is a precursor of pRK5D that does not contain the SfiI site; see, Holmes et al., *Science,* 253:1278–1280 (1991)) in the unique XhoI and NotI sites.

DNA sequencing of the clones isolated as described above gave the full-length DNA sequence for a full-length PRO10272 polypeptide (designated herein as DNA147531-2821 [FIG. 5, SEQ ID NO:5]) and the derived protein sequence for that PRO10272 polypeptide.

The full length clone identified above contained a single open reading frame with an apparent translational initiation site at nucleotide positions 259–261 and a stop signal at nucleotide positions 790–792 (FIG. 5, SEQ ID NO:5). The predicted polypeptide precursor is 177 amino acids long, has a calculated molecular weight of approximately 20,330 daltons and an estimated pI of approximately 8.78. Analysis of the full-length PRO10272 sequence shown in FIG. 6 (SEQ ID NO:6) evidences the presence of a variety of important polypeptide domains as shown in FIG. 6, wherein the locations given for those important polypeptide domains are approximate as described above. Clone DNA147531-2821 has been deposited with ATCC on Jan. 11, 2000 and is assigned ATCC deposit no. PTA-1185.

Analysis of the amino acid sequence of the isolated full-length PRO10272 suggests that it possesses similarity with IL-17 and various homologs of it, thereby indicating that PRO10272 may be a novel cytokine and is herein designated IL-17E. Specifically, an analysis of the Dayhoff database (version 35.45 SwissProt 35), using the ALIGN-2 sequence alignment analysis of the full-length sequence shown in FIG. 6 (SEQ ID NO:6), evidenced sequence identity between the PRO10272 amino acid sequence and the following Dayhoff sequences:

P_Y22197, P_W85620, AF18469_1, P_Y41762, P_Y28235, P_W97350, P_Y22198, P_Y28236, P_W28514, P_W13651.

Example 4

Isolation of cDNA Clones Encoding a Human PRO21175

An expressed sequence tag (EST) DNA database from Merck/Washington University was searched and an EST was identified which showed homology to Interleukin-17.

A pool of 50 different human cDNA libraries from various tissues was used in cloning. The cDNA libraries used to isolate the cDNA clones encoding human PRO21175 were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253: 1278–1280 (1991)) in the unique XhoI and NotI.

Oligonucleotides probes based upon the above described EST sequence were then synthesized: 1) to identify by PCR a cDNA library that contained the sequence of interest, and 2) for use as probes to isolate a clone of the full-length coding sequence for PRO21175. Forward and reverse PCR primers generally range from 20 to 30 nucleotides and are often designed to give a PCR product of about 100–1000 bp in length. The probe sequences are typically 40–55 bp in length. In order to screen several libraries for a full-length clone, DNA from the libraries was screened by PCR amplification, as per Ausubel et al., *Current Protocols in Molecular Biology,* supra, with the PCR primer pair. A positive library was then used to isolate clones encoding the gene of interest using the probe oligonucleotide and one of the primer pairs.

The oligonucleotide probes employed were as follows:

```
forward PCR primer
5'-GCTCAGTGCCTTCCACCACACGC-3'                          (SEQ ID NO:25)

reverse PCR primer
5'-CTGCGTCCTTCTCCGGCTCGG-3'                            (SEQ ID NO:26)

hybridization probe
5' CGTTCCGTCTACACCGAGGCCTACGTCACCATCCCCGTGGGCTGC-3'    (SEQ ID NO:27)
```

A full length clone was identified that contained a single open reading frame with an apparent translational initiation site at nucleotide positions 1–3 and a stop signal at nucleotide positions 607–609 (FIG. 7, SEQ ID NO:7). The predicted polypeptide precursor is 202 amino acids long, has a calculated molecular weight of approximately 21,879 daltons and an estimated pI of approximately 9.3. Analysis of the full-length PRO21175 sequence shown in FIG. 8 (SEQ ID NO:8) evidences the presence of a variety of important polypeptide domains as shown in FIG. 8, wherein the locations given for those important polypeptide domains are approximate as described above. Chromosome mapping evidences that the PRO21175-encoding nucleic acid maps to 13q11 in humans. Clone DNA173894-2947 has been deposited with ATCC on June 20, 2000 and is assigned ATCC deposit no. PTA-2108.

Analysis of the amino acid sequence of the isolated full-length PRO21175 suggests that it possesses similarity with IL-17, thereby indicating that PRO21175 may be a novel cytoline and is herein designated IL-17D. Specifically, an analysis of the protein database (version 35.45 SwissProt 35), using the ALIGN-2 sequence alignment analysis of the full-length sequence shown in FIG. 8 (SEQ ID NO:8), evidenced sequence identity between the PRO21175 amino acid sequence and the following sequence: AF152099_1.

PCR primers (forward and reverse) were synthesized:

```
forward PCR primer 1
5'-ACTCCATATTTTCCTACTTGTGGCA-3'      (SEQ ID NO:28)

forward PCR primer 2
5'-CCCAAAGTGACCTAAGAAC-3'            (SEQ ID NO:29)

reverse PCR primer
5'-TCACTGAATTTCTTCAAAACCATTGCA-3'    (SEQ ID NO:30)
```

Additionally, a synthetic oligonucleotide hybridization probe was constructed from the consensus DNA105850 sequence which had the following nucleotide sequence

```
hybridization probe
5'-TGTGGCAGCGACTGCATCCGACATAAAGGAACAGTTGTGCTCTGCCCACA-3'   (SEQ ID NO:31)
```

Example 5

Isolation of cDNA Clones Encoding a Human PRO5801

The extracellular domain (ECD) sequences (including the secretion signal sequence, if any) from about 950 known secreted proteins from the Swiss-Prot public database were used to search EST databases. The EST databases included (1) public EST databases (e.g., GenBank) and (2) a proprietary EST database (LIFESEQ®, Incyte Pharmaceuticals, Palo Alto, Calif.). The search was performed using the computer program BLAST or BLAST2 [Altschul et al., *Methods in Enzymology*, 266:460–480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash).

A consensus DNA sequence was assembled relative to other EST sequences using phrap as described above. This consensus sequence is herein designated DNA105850. In some cases, the consensus sequence derives from an intermediate consensus DNA sequence which was extended using repeated cycles of BLAST and phrap to extend that intermediate consensus sequence as far as possible using the sources of EST sequences discussed above.

Based on the DNA105850 consensus sequence, oligonucleotides were synthesized: 1) to identify by PCR a cDNA library that contained the sequence of interest, and 2) for use as probes to isolate a clone of the full-length coding sequence for PRO5801. Forward and reverse PCR primers generally range from 20 to 30 nucleotides and are often designed to give a PCR product of about 100–1000 bp in length. The probe sequences are typically 40–55 bp in length. In some cases, additional oligonucleotides are synthesized when the consensus sequence is greater than about 1–1.5 kbp. In order to screen several libraries for a full-length clone, DNA from the libraries was screened by PCR amplification, as per Ausubel et al., *Current Protocols in Molecular Biology*, supra, with the PCR primer pair. A positive library was then used to isolate clones encoding the gene of interest using the probe oligonucleotide and one of the primer pairs.

RNA for construction of the cDNA libraries was isolated from human fetal liver tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278–1280 (1991)) in the unique XhoI and NotI sites.

DNA sequencing of the clones isolated as described above gave the full-length DNA sequence for a full-length PRO5801 polypeptide (designated herein as DNA115291-2681 [FIG. 11, SEQ ID NO:11]) and the derived protein sequence for that PRO5801 polypeptide.

The full length clone identified above contained a single open reading frame with an apparent translational initiation site at nucleotide positions 7–9 and a stop signal at nucleotide positions 1513–1515 (FIG. 12, SEQ ID NO:12). The predicted polypeptide precursor is 502 amino acids long, has a calculated molecular weight of approximately 55,884 daltons and an estimated pI of approximately 8.52. Analysis of the full-length PRO5801 sequence shown in FIG. 12 (SEQ ID NO:12) evidences the presence of a variety of important polypeptide domains as shown in FIG. 12, wherein the locations given for those important polypeptide domains are approximate as described above. Clone DNA115291-2681 has been deposited with ATCC on Jun. 8, 1999 and is assigned ATCC deposit no. PTA-202.

An analysis of the Dayhoff database shows that PRO5801 has sequence similarity to an IL-17 receptor protein and PRO5801 is also designated herein as IL-17RH1 as described in Example 22 of the present application. Specifically, an analysis of the Dayhoff database (version 35.45 SwissProt 35), using the ALIGN-2 sequence alignment analysis of the full-length sequence shown in FIG. 12 (SEQ ID NO:12), evidenced sequence identity between the PRO5801 amino acid sequence and the following Dayhoff sequences:

HSU58917_1, P_W92409, P_W61272, P_W04185, P_W61271, P_WO4184, P_W92408, GEN13979, MMU31993_1 and YSO2_CAEEL.

Example 6

Isolation of cDNA Clones Encoding a Human PRO20040

An expressed sequence tag (EST) DNA database (Merck/ Washington University) was searched and an EST was identified which showed homology to Interleukin 17 receptor.

RNA for construction of cDNA libraries was then isolated from a pool of 50 different human cDNA libraries. The cDNA libraries used to isolate the cDNA clones encoding human PRO20040 were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278–1280 (1991)) in the unique XhoI and NotI.

Oligonucleotides probes based upon the above described EST sequence were then synthesized: 1) to identify by PCR a cDNA library that contained the sequence of interest, and 2) for use as probes to isolate a clone of the full-length coding sequence for PRO20040. Forward and reverse PCR primers generally range from 20 to 30 nucleotides and are often designed to give a PCR product of about 100–1000 bp in length. The probe sequences are typically 40–55 bp in length. In order to screen several libraries for a full-length clone, DNA from the libraries was screened by PCR amplification, as per Ausubel et al., *Current Protocols in Molecular Biology*, supra, with the PCR primer pair. A positive library was then used to isolate clones encoding the gene of interest using the probe oligonucleotide and one of the primer pairs.

The oligonucleotide probes employed were as follows:

```
forward PCR primer
                                       (SEQ ID NO:32)
5'-CCGACTTCTTGCAGGGCCGG-3' reverse PCR primer
                                       (SEQ ID NO:33)
5'-GCAGCACGCAGCTGAGCGAG-3' hybridization probe
                                       (SEQ ID NO:34)
5'-AGCGAGTGGCTACAGGATGGGGTGTCCGGGCCC-3'
```

A full length clone was identified that contained a single open reading frame with an apparent translational initiation site at nucleotide positions 233–235 and a stop signal at nucleotide positions 2348–2350 (FIG. 13, SEQ ID NO:13). The predicted polypeptide precursor is 705 amino acids long, has a calculated molecular weight of approximately 76,898 daltons and an estimated pI of approximately 6.08 Analysis of the full-length PRO20040 sequence shown in FIG. 14 (SEQ ID NO:14) evidences the presence of a variety of important polypeptide domains as shown in FIG. 14, wherein the locations given for those important polypeptide domains are approximate as described above. Clone DNA164625-2890 has been deposited with ATCC on Mar. 21, 2000 and is assigned ATCC deposit no. PTA-1535.

An analysis of the Dayhoff database shows that PRO20040 has sequence similarity to an IL-17 receptor protein and PRO20040 is also designated herein as IL-17RH2 as described in Example 20 of the present application. Specifically, an analysis of the Dayhoff database (version 35.45 SwissProt 35), using the ALIGN-2 sequence alignment analysis of the full-length sequence shown in FIG. 14 (SEQ ID NO:14), evidenced sequence identity between the PRO20040 amino acid sequence and the following Dayhoff sequences: HSU58917_1.

Example 7

Isolation of cDNA Clones Encoding a Human PRO9877

DNA119502-2789 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the LIFESEQ® database, designated herein as CLU42993. This EST cluster sequence was then compared to a variety of expressed sequence tag (EST) databases which included public EST databases (e.g.,GenBank) and a proprietary EST DNA database (LIFESEQ® Incyte Pharmaceuticals, Palo Alto, Calif.) to identify existing homologies. The homology search was performed using the computer program BLAST or BLAST2 (Altshul et al., *Methods in Enzymology*, 266:460–480 (1996)). Those comparisons resulting in a BLAST score of 70 (or in some cases, 90) or greater that did not encode known proteins were clustered and assembled into a consensus DNA sequence with the program "phrap" (Phil Green, University of Washington, Seattle, Wash.). The consensus sequence obtained therefrom is herein designated DNAFROM.

In light of an observed sequence homology between the DNAFROM sequence and an EST sequence encompassed within clone no. 700536 from the LIFESEQ® database, clone no. 700536 was purchased and the cDNA insert was obtained and sequenced. It was found herein that that cDNA insert encoded a full-length protein. The sequence of this cDNA insert is shown in FIG. 15 and is herein designated as DNA119502-2789.

Clone DNA119502-2789 contains a single open reading frame with an apparent translational initiation site at nucleotide positions 106–108 and ending at the stop codon at nucleotide positions 2107–2109 (FIG. 15; SEQ ID NO:15). The predicted polypeptide precursor is 667 amino acids long (FIG. 16). The full-length PRO9877 protein shown in FIG. 16 has an estimated molecular weight of about 74,810 daltons and a pI of about 9.55. Analysis of the full-length PRO9877 sequence shown in FIG. 16 (SEQ ID NO:16) evidences the presence of a variety of important polypeptide domains as shown in FIG. 16, wherein the locations given for those important polypeptide domains are approximate as described above. Clone DNA119502-2789 has been deposited with ATCC on Dec. 22, 1999 and is assigned ATCC deposit no. PTA-1082.

An analysis of the Dayhoff database shows that PRO9877 has sequence similarity to an IL-17 receptor protein and PRO9877 is also designated herein as IL-17RH3. Specifically, an analysis of the Dayhoff database (version 35.45 SwissProt 35), using the ALIGN-2 sequence alignment analysis of the full-length sequence shown in FIG. 16 (SEQ ID NO:16), evidenced sequence identity between the PRO9877 amino acid sequence and the following Dayhoff sequences:

> P_W61272, HSU58917_1, P_W04185, P_W92409, GEN13979, P_W04184, P_W92408, MMU31993_1, P_W61271, and AF090114_1.

PCR primers (forward and reverse) were synthesized:

```
forward PCR primer:
5'-CGTTGTTTGTCAGTGGAGAGCAGGG-3'      (SEQ ID NO:35)

reverse PCR primer
5'-CAGGAACACCTGAGGCAGAAGCG-3'        (SEQ ID NO:36)
```

Additionally, a synthetic oligonucleotide hybridization probe was constructed from the consensus DNA149870 sequence which had the following nucleotide sequence

```
hybridization probe
5'-CTATCTCCCTGCCAGGAGGCCGGAGTGGGGGAGGTCAGAC-3'  (SEQ ID NO:37)
```

Example 8

Isolation of cDNA Clones Encoding a Human PRO20026

The extracellular domain (ECD) sequences (including the secretion signal sequence, if any) from about 950 known secreted proteins from the Swiss-Prot public database were used to search EST databases. The EST databases included a proprietary EST database (LIFESEQ®, Incyte Pharmaceuticals, Palo Alto, Calif.). The search was performed using the computer program BLAST or BLAST2 [Altschul et al., *Methods in Enzymology*, 266:460–480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap as described above. This consensus sequence is herein designated DNA149870. In some cases, the DNA149870 consensus sequence derives from an intermediate consensus DNA sequence which was extended using repeated cycles of BLAST and phrap to extend that intermediate consensus sequence as far as possible using the sources of EST sequences discussed above.

Based on the DNA149870 consensus sequence, flip cloning was performed. Oligonucleotides were synthesized: 1) to identify by PCR a cDNA library that contained the sequence of interest, and 2) for use as probes to isolate a clone of the full-length coding sequence for PRO20026. Forward and reverse PCR primers generally range from 20 to 30 nucleotides and are often designed to give a PCR product of about 100–1000 bp in length. The probe sequences are typically 40–55 bp in length. In some cases, additional oligonucleotides are synthesized when the consensus sequence is greater than about 1–1.5kbp. In order to screen several libraries for a full-length clone, DNA from the libraries was screened by Flip PCR amplification, as per Schanke et al., *BioTechniques*, 16:414–416 (1994), with the PCR primer pair. A positive library was then used to isolate clones encoding the gene of interest using the probe oligonucleotide and one of the primer pairs.

RNA for construction of the cDNA libraries was isolated from human tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278–1280 (1991)) in the unique XhoI and NotI sites.

DNA sequencing of the clones isolated as described above gave the full-length DNA sequence for a full-length PRO20026 polypeptide (designated herein as DNA154095-2998 [FIG. 17, SEQ ID NO:17]) and the derived protein sequence for that PRO20026 polypeptide.

The full length clone identified above contained a single open reading frame with an apparent translational initiation site at nucleotide positions 70–72 and a stop signal at nucleotide positions 2254–2256 (FIG. 17, SEQ ID NO:17). The predicted polypeptide precursor is 728 amino acids long, has a calculated molecular weight of approximately 81,310 daltons and an estimated pI of approximately 6.84. Analysis of the full-length PRO20026 sequence shown in FIG. 18 (SEQ ID NO:18) evidences the presence of a variety of important polypeptide domains as shown in FIG. 18, wherein the locations given for those important polypeptide domains are approximate as described above. Clone DNA154095-2998 has been deposited with ATCC on Oct. 10, 2000 and is assigned ATCC Deposit No. PTA-2591.

An analysis of the Dayhoff database shows that PRO20026 has sequence similarity to an IL-17 receptor protein and PRO2006 is also designated herein as IL-17RH4. Specifically, an analysis of the Dayhoff database (version 35.45 SwissProt 35), using the ALIGN-2 sequence alignment analysis of the full-length sequence shown in FIG. 18 (SEQ ID NO:18), evidenced sequence identity between the PRO20026 amino acid sequence and the following Dayhoff sequences:

> T42695, P_W04185, P_W92409, P_W61272, NM_014339_1, HSU58917_1, MMU31993_1, GEN13979, P_W04184, P_W61271.

Example 9

Use of PRO as a Hybridization Probe

The following method describes use of a nucleotide sequence encoding PRO as a hybridization probe.

DNA comprising the coding sequence of full-length or mature PRO as disclosed herein is employed as a probe to screen for homologous DNAs (such as those encoding naturally-occurring variants of PRO) in human tissue cDNA libraries or human tissue genomic libraries.

Hybridization and washing of filters containing either library DNAs is performed under the following high stringency conditions. Hybridization of radiolabeled PRO-derived probe to the filters is performed in a solution of 50% formamide, 5×SSC, 0.1% SDS, 0.1% sodium pyrophosphate, 50 mM sodium phosphate, pH CD3 complex with an antigen-MHC on the surface of an antigen presenting cell. This interaction mediates a 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO can then be identified using standard techniques known in the art.

Example 10

In situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, *Cell Vision*, 1:169–176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A[$^{33}$-P] UTP-labeled antisense riboprobe was generated from a PCR product and hybridized at 55° C. overnight. The slides were dipped in Kodak NTB2 nuclear track emulsion and exposed for 4 weeks.

$^{33}$P-riboprobe Synthesis 6.0 µl (125 mCi) of $^{33}$P-UTP (Amersham BF 1002, SA<2000 Ci/mmol) were speed vac dried. To each tube containing dried $^{33}$P-UTP, the following ingredients were added:

2.0 µl 5×transcription buffer
1.0 µl DTT (100 mM)
2.0 µl NTP mix (2.5 mM: 10 µl; each of 10 mM GTP, CTP & ATP+10 µl H$_2$O)
1.0 µl UTP (50 µM)
1.0 µl Rnasin
1.0 µl DNA template (1 µg)
1.0 µl H$_2$O
1.0 µl RNA polymerase (for PCR products T3=AS, T7=S, usually)

The tubes were incubated at 37° C. for one hour. 1.0 µl RQ1 DNase were added, followed by incubation at 37° C. for 15 minutes. 90 µl TE (10 mM Tris pH 7.6/1 mM EDTA pH 8.0) were added, and the mixture was pipetted onto DE81 paper. The remaining solution was loaded in a Microcon-50 ultrafiltration unit, and spun using program 10 (6 minutes). The filtration unit was inverted over a second tube and spun using program 2 (3 minutes). After the final recovery spin, 100 µl TE were added. 1 µl of the final product was pipetted on DE81 paper and counted in 6 ml of Biofluor II.

The probe was run on a TBE/urea gel. 1–3 µl of the probe or 5 µl of RNA Mrk III were added to 3 µl of loading buffer. After heating on a 95° C. heat block for three minutes, the gel was immediately placed on ice. The wells of gel were flushed, the sample loaded, and run at 180–250 volts for 45 minutes. The gel was wrapped in saran wrap and exposed to XAR film with an intensifying screen in –70° C. freezer one hour to overnight.

$^{33}$P-hybridization

A. Pretreatment of Frozen Sections

The slides were removed from the freezer, placed on aluminum trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+975 ml SQ H$_2$O). After deproteination in 0.5 µg/ml proteinase K for 10 minutes at 37° C. (12.5 µl of 10 mg/ml stock in 250 ml prewarmed RNase-free RNase buffer), the sections were washed in 0.5×SSC for 10 minutes at room temperature. The sections were dehydrated in 70%, 95%, 100% ethanol, 2 minutes each.

B. Pretreatment of Paraffin-embedded Sections

The slides were deparaffinized, placed in SQ H$_2$O, and rinsed twice in 2×SSC at room temperature, for 5 minutes each time. The sections were deproteinated in 20 µg/ml proteinase K (500 µl of 10 mg/ml in 250 ml RNase-free RNase buffer; 37° C., 15 minutes)—human embryo, or 8×proteinase K (100 µl in 250 ml RNase buffer, 37° C., 30 minutes)—formalin tissues. Subsequent rinsing in 0.5×SSC and dehydration were performed as described above.

C. Prehybridization

The slides were laid out in a plastic box lined with Box buffer (4×SSC, 50% formamide)—saturated filter paper. The tissue was covered with 50 µl of hybridization buffer (3.75 g Dextran Sulfate+6 ml SQ H$_2$O), vortexed and heated in the microwave for 2 minutes with the cap loosened. After cooling on ice, 18.75 ml formamide, 3.75 ml 20×SSC and 9 ml SQ H$_2$O were added, the tissue was vortexed well, and incubated at 42° C. for 1–4 hours.

D. Hybridization 1.0×10$^6$ cpm probe and 1.0 µl tRNA (50 mg/ml stock) per slide were heated at 95° C. for 3 minutes. The slides were cooled on ice, and 48 µl hybridization buffer were added per slide. After vortexing, 50 µl $^{33}$P mix were added to 50 µl prehybridization on slide. The slides were incubated overnight at 55° C.

E. Washes

Washing was done 2×10 minutes with 2×SSC, EDTA at room temperature (400 ml 20×SSC+16 ml 0.25M EDTA, V$_f$=4L), followed by RNaseA treatment at 37° C. for 30 minutes (500 µl of 10 mg/ml in 250 ml RNase buffer=20 µg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, V$_f$=4L).

F. Oligonucleotides

In situ analysis was performed on DNA59294-1381 disclosed herein. The oligonucleotides employed for this analysis were derived from the nucleotide sequences disclosed herein and generally range from about 40 to 55 nucleotides in length.

G. Results

In situ analysis was performed on DNA59294-1381 as disclosed herein. The results from this analysis is as follows.

DNA59294-1381 (PRO1031)

The expression of this IL17 homolog was evaluated in a panel consisting of normal adult and fetal tissues and tissues with inflammation, predominantly chronic lymphocytic inflammation. This panel is designed to specifically evaluate the expression pattern in immune mediated inflammatory disease of novel proteins that modulate T lymphocyte function (stimulatory or inhibitory). This protein when expressed as an Ig-fusion protein was immunostimulatory in a dose dependent fashion in the human mixed lymphocyte reaction (MLR); it caused a 285% and 147% increase above the baseline stimulation index when utilized at two different concentrations (1.0% and 0.1% of a 560 nM stock) [see EXAMPLE 25 below]. Summary: expression was restricted to muscle, certain types of smooth muscle in the adult and in skeletal and smooth muscle in the human fetus. Expression in adult human was in smooth muscle of tubular organs evaluated including colon and gall bladder. There was no expression in the smooth muscle of vessels or bronchi. No adult human skeletal muscle was evaluated. In fetal tissues there was moderate to high diffuse expression in skeletal muscle, in the axial skeleton and limbs. There was weak expression in the smooth muscle of the intestinal wall but no expression in cardiac muscle. Adult human tissues with expression include: Colon: there was low level diffuse expression in the smooth muscle (tunica muscularis) in 5 specimens with chronic inflammatory bowel disease; Gall bladder: there was weak to low level expression in the smooth muscle of the gall bladder; Fetal human tissues with expression: there was moderate diffuse expression in skeletal muscle and weak to low expression in smooth muscle, there was no expression in fetal heart or any other fetal organ including liver, spleen, CNS, kidney, gut, lung; Human tissues with no expression: lung with chronic granulomatous inflammation and chronic bronchitis (5 patients), peripheral nerve, prostate, heart, placenta, liver (disease multi block), brain (cerebrum and cerebellum), tonsil (reactive hyperplasia), peripheral lymph node, thymus.

Example 11

Expression of PRO in E. coli

This example illustrates preparation of an un glycosylated form of PRO polypeptides by recombinant expression in E. coli.

The DNA sequence encoding a PRO polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyHis leader (including the first six STII codons, polyHis sequence, and enterokinase cleavage site), the PRO polypeptide coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO protein can then be purified using a metal chelating column under conditions that allow tight binding of the protein.

PRO polypeptides may be expressed in E. coli in a poly-His tagged form, using the following procedure. The DNA encoding a PRO polypeptide is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an E. coli host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3–5 is reached. Cultures are then diluted 50–100 fold into CRAP media (prepared by mixing 3.57 g $(NH_4)_2SO_4$, 0.71 g sodium citrate•$2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20–30 hours at 30° C. with shaking. Samples are removed to verify expression by SDS-PAGE analysis, and the bulk culture is centrifuged to pellet the cells. Cell pellets are frozen until purification and refolding.

E. coli paste from 0.5 to 1 L fermentations (6–10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentrifuge for 30 min. The supernatant is diluted with 3–5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 μm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12–36 hours. The refolding reaction is quenched by the addition of TFA to a final concentration of 0.4% (pH of approximately 3). Before further purification of the protein, the solution is filtered through a 0.22 micron filter and acetonitrile is added to 2–10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Many of the PRO polypeptides disclosed herein were successfully expressed as described above.

Example 12

Expression of PRO in Mammalian Cells

This example illustrates preparation of a potentially glycosylated form of PRO polypeptides by recombinant expression in mammalian cells.

The vector, pRK5 (see EP 307,247, published Mar. 15, 1989), is employed as the expression vector. Optionally, the PRO DNA is ligated into pRK5 with selected restriction enzymes to allow insertion of the PRO DNA using ligation methods such as described in Sambrook et al., supra. The resulting vector is called pRK5-PRO.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO DNA is mixed with about 1 μg DNA encoding the VA RNA gene [Thimmappaya et al., Cell, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 Ci/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of the PRO polypeptide. The cultures containing transfected cells may undergo further incubation (in serum free medium) and the medium is tested in selected bioassays.

In an alternative technique, PRO may be introduced into 293 cells transiently using the dextran sulfate method described by Somparyrac et al., Proc. Natl. Acad. Sci. 12:7575 (1981). 293 cells are grown to maximal density in a spinner flask and 700 μg pRK5-PRO DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing the expressed PRO polypeptide can then be concentrated and purified by any selected method, such as dialysis and/or column chromatography.

In another embodiment, PRO polypeptides can be expressed in CHO cells. The pRK5-PRO can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of the PRO polypeptide, the culture medium may be replaced with serum free medium. Preferably, the cultures are incubated for about 6 days, and then the conditioned medium is harvested. The medium containing the expressed PRO polypeptide can then be concentrated and purified by any selected method.

Epitope-tagged PRO may also be expressed in host CHO cells. The PRO may be subcloned out of the pRK5 vector. The subclone insert can undergo PCR to fuse in frame with a selected epitope tag such as a poly-His tag into a Baculovirus expression vector. The poly-His tagged PRO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO can then be concentrated and purified by any selected method, such as by $Ni^{2+}$-chelate affinity chromatography.

PRO polypeptides may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g., extracellular domains) of the respective proteins are fused to an IgG1 constant region sequence containing the hinge, CH2 and CH2 domains, and/or as a poly-His tagged form.

Following PCR amplification, the respective DNAs are subcloned in a CHO expression vector using standard techniques as described in Ausubel et al., Current Protocols of Molecular Biology, Unit 3.16, John Wiley and Sons (1997). CHO expression vectors are constructed to have compatible restriction sites 5' and 3' of the DNA of interest to allow the convenient shuttling of cDNA's. The vector used in expression in CHO cells is as described in Lucas et al., Nucl. Acids Res., 24:9 (1774–1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Qiagen), Dosper® or Fugene® (Boehringer Mannheim). The cells are grown as described in Lucas et al., supra. Approximately $3 \times 10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1–2 days, the cells are transferred into a 250 mL spinner filled with 150 mL selective growth medium and incubated at 37° C. After another 2–3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number pH i.e. determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4–5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Many of the PRO polypeptides disclosed herein were successfully expressed as described above.

Example 13

Expression of PRO in Yeast

The following method describes recombinant expression of PRO polypeptides in yeast.

First, yeast expression vectors are constructed for intracellular production or secretion of PRO from the ADH2/GAPDH promoter. DNA encoding the PRO polypeptide and the promoter is inserted into suitable restriction enzyme sites in the selected plasmid to direct intracellular expression of the PRO polypeptide. For secretion, DNA encoding PRO can be cloned into the selected plasmid, together with DNA encoding the ADH2/GAPDH promoter, a native PRO signal peptide or other mammalian signal peptide, or, for example, a yeast alpha-factor or invertase secretory signal/leader sequence, and linker sequences (if needed) for expression of PRO.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO polypeptides can subsequently be isolated and purified by removing the yeast cells from the fermentation medium by centrifugation and then concentrating the medium using selected cartridge filters. The concentrate containing the PRO polypeptide may further be purified using selected column chromatography resins.

Many of the PRO polypeptides disclosed herein were successfully expressed as described above.

Example 14

Expression of PRO in Baculovirus-infected Insect Cells

The following method describes recombinant expression of PRO polypeptides in Baculovirus-infected insect cells.

The sequence coding for PRO is fused upstream of an epitope tag contained within a Baculovirus expression vector. Such epitope tags include poly-His tags and immunoglobulin tags (like Fc regions of IgG). A variety of plasmids may be employed, including plasmids derived from commercially available plasmids such as pVL1393 (Novagen). Briefly, the sequence encoding PRO or the desired portion of the coding sequence of PRO such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-His tagged PRO can then be purified, for example, by Ni$^{2+}$-chelate affinity chromatography as follows. Extracts are prepared from recombinant virus-infected Sf9 cells as described by Rupert et al., *Nature,* 362:175–179 (1993). Briefly, Sf9 cells are washed, resuspended in sonication buffer (25 mL Hepes, pH 7.9; 12.5 mM MgCl$_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A Ni$^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline A$_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching A$_{280}$ baseline again, the column is developed with a 0 to 500 mM Imidazole gradient in the secondary wash buffer. One mL fractions are collected and analyzed by SDS-PAGE and silver staining or Western blot with Ni$^{2+}$-NTA-conjugated to alkaline phosphatase (Qiagen). Fractions containing the eluted His$_{10}$-tagged PRO are pooled and dialyzed against loading buffer.

Alternatively, purification of the IgG tagged (or Fc tagged) PRO can be performed using known chromatography techniques, including for instance, Protein A or protein G column chromatography.

Many of the PRO polypeptides disclosed herein were successfully expressed as described above.

Example 15

Preparation of Antibodies that Bind PRO

This example illustrates preparation of monoclonal antibodies which can specifically bind PRO.

Techniques for producing the monoclonal antibodies are known in the art and are described, for instance, in Goding, supra. Immunogens that may be employed include purified PRO polypeptides, fusion proteins containing PRO polypeptides, and cells expressing recombinant PRO polypeptides on the cell surface. Selection of the immunogen can be made by the skilled artisan without undue experimentation.

Mice, such as BALB/c, are immunized with the PRO immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO antibodies.

After a suitable antibody titer has been detected, the animals "positive" for antibodies can be injected with a final intravenous injection of PRO. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO. Determination of "positive" hybridoma cells secreting the desired monoclonal antibodies against PRO is within the skill in the art.

The positive hybridoma cells can be injected intraperitoneally into syngeneic BALB/c mice to produce ascites containing the anti-PRO monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 16

Purification of PRO Polypeptides Using Specific Antibodies

Native or recombinant PRO polypeptides may be purified by a variety of standard techniques in the art of protein purification. For example, pro-PRO polypeptide, mature PRO polypeptide, or pre-PRO polypeptide is purified by immunoaffinity chromatography using antibodies specific for the PRO polypeptide of interest. In general, an immunoaffinity column is constructed by covalently coupling the anti-PRO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO polypeptide by preparing a fraction from cells containing PRO polypeptide in a soluble form. This preparation is derived by solubilization of the whole cell or of a subcellular fraction obtained via differential centrifugation by the addition of detergent or by other methods well known in the art. Alternatively, soluble PRO polypeptide containing a signal sequence may be secreted in useful quantity into the medium in which the cells are grown.

A soluble PRO polypeptide-containing preparation is passed over the immunoaffinity column, and the column is washed under conditions that allow the preferential absorbance of PRO polypeptide (e.g., high ionic strength buffers in the presence of detergent). Then, the column is eluted under conditions that disrupt antibody/PRO polypeptide binding (e.g., a low pH buffer such as approximately pH 2–3, or a high concentration of a chaotrope such as urea or thiocyanate ion), and PRO polypeptide is collected.

Example 17

Drug Screening

This invention is particularly useful for screening compounds by using PRO polypeptides or binding fragment thereof in any of a variety of drug screening techniques. The PRO polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO polypeptide or fragment. Drugs are screened against such transformed cells in competitive binding assays. Such cells, either in viable or fixed form, can be used for standard binding assays. One may measure, for example, the formation of complexes between PRO polypeptide or a fragment and the agent being tested. Alternatively, one can examine the diminution in complex formation between the PRO polypeptide and its target cell or target receptors caused by the agent being tested.

Thus, the present invention provides methods of screening for drugs or any other agents which can affect a PRO polypeptide-associated disease or disorder. These methods comprise contacting such an agent with an PRO polypeptide or fragment thereof and assaying (i) for the presence of a complex between the agent and the PRO polypeptide or fragment, or (ii) for the presence of a complex between the PRO polypeptide or fragment and the cell, by methods well known in the art. In such competitive binding assays, the PRO polypeptide or fragment is typically labeled. After suitable incubation, free PRO polypeptide or fragment is separated from that present in bound form, and the amount of free or uncomplexed label is a measure of the ability of the particular agent to bind to PRO polypeptide or to interfere with the PRO polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO polypeptide, the peptide test compounds are reacted with PRO polypeptide and washed. Bound PRO polypeptide is detected by methods well known in the art. Purified PRO polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO polypeptide specifically compete with a test compound for binding to PRO polypeptide or fragments thereof. In this manner, the antibodies can be used to detect the presence of any peptide which shares one or more antigenic determinants with PRO polypeptide.

Example 18

Rational Drug Design

The goal of rational drug design is to produce structural analogs of biologically active polypeptide of interest (i.e., a PRO polypeptide) or of small molecules with which they interact, e.g., agonists, antagonists, or inhibitors. Any of these examples can be used to fashion drugs which are more active or stable forms of the PRO polypeptide or which enhance or interfere with the function of the PRO polypeptide in vivo (cf., Hodgson, *Bio/Technology*, 9: 19–21 (1991)).

In one approach, the three-dimensional structure of the PRO polypeptide, or of an PRO polypeptide-inhibitor complex, is determined by x-ray crystallography, by computer modeling or, most typically, by a combination of the two approaches. Both the shape and charges of the PRO polypeptide must be ascertained to elucidate the structure and to determine active site(s) of the molecule. Less often, useful information regarding the structure of the PRO polypeptide may be gained by modeling based on the structure of homologous proteins. In both cases, relevant structural information is used to design analogous PRO polypeptide-like molecules or to identify efficient inhibitors. Useful examples of rational drug design may include molecules which have improved activity or stability as shown by Braxton and Wells, *Biochemistry*, 31:7796–7801 (1992) or which act as inhibitors, agonists, or antagonists of native peptides as shown by Athauda et al., *J. Biochem.*, 113:742–746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO polypeptide may be made available to perform such analytical studies as X-ray crystallography. In addition, knowledge of the PRO polypeptide amino acid sequence provided herein will provide guidance to those employing computer modeling techniques in place of or in addition to x-ray crystallography.

Example 19

Differential Tissue Expression Distribution

Oligonucleotide probes were constructed from the PRO1031, PRO1122, PRO21175, PRO10272, PRO20110, PRO5801, PRO20040, PRO9877, and PRO20026 polypeptide-encoding nucleotide sequences shown in the accompanying figures for use in quantitative PCR amplification reactions. The oligonucleotide probes were chosen so as to give an approximately 200–600 base pair amplified fragment from the 3' end of its associated template in a standard PCR reaction. The oligonucleotide probes were employed in standard quantitative PCR amplification reactions with cDNA libraries isolated from different human adult and/or fetal tissue sources and analyzed by agarose gel electrophoresis so as to obtain a quantitative determination of the level of expression of the polypeptide-encoding nucleic acids in the various tissues tested. Knowledge of the expression pattern or the differential expression of the polypeptide-encoding nucleic acid in various different human tissue types provides a diagnostic marker useful for tissue typing, with or without other tissue-specific markers, for determining the primary tissue source of a metastatic tumor, and the like. These assays provided the following results:

| DNA Molecule | Tissues w/ Significant Expression | Tissues w/o Significant Expression |
| --- | --- | --- |
| DNA59294-1381 | highly expressed in mammary gland, trachea, testis and spine | weakly expressed in intestine, bone marrow, lung, kidney and thymus; no expression in pancreas, liver, brain or spleen |
| DNA62377-1381-1 | strongly expressed in testis, spleen, thymus, and trachea | weakly expressed in intestine, fetal brain, mammary, uterus, colon, lung, placenta and stomach; no expression in muscle, pancreas, liver, spine, brain and fetal liver |
| DNA173894-2974 | highly expressed in muscle, spine and brain | not expressed in intestine, mammary gland, marrow, uterus, trachea, colon, salivary gland, lung, pancreas, liver, prostate, adrenal, kidney, thymus, placenta, heart, stomach and spleen |
| DNA147531-2821 | expressed at low levels in brain, kidney, lung, prostate, testis, spinal chord, adrenal gland and trachea | no expression in heart, liver, colon, marrow, intestine, spleen, muscle, stomach, uterus, placenta, thymus, muscle, uterus, placenta, pancreas, salivary gland, and mammary gland |
| DNA166819 | highly expressed in testis, kidney thymus, and stomach | not expressed in intestine, mammary gland, marrow, uterus, trachea, colon, salivary gland, lung, muscle, pancreas, liver, prostate, adrenal gland, placenta Heart, spine, brain, and spleen |
| DNA115291-2681 | highly expressed in the kidney; significant expression in liver and peripheral organs such as colon, small intestine, prostate, testis, pancreas and uterus | not expressed in heart, bone marrow, spleen and placenta |
| DNA164625-2890 | highly expressed in prostate; expressed in kidney, spine, placenta, liver, lung, colon, spleen, uterus, dendrocyte and hippocampus, intestine, mammary gland, bone marrow, testis, muscle, stomach and thymus | weakly expressed in heart, cartilage, colon tumor, substantia nigra and and macrophage; it is not expressed in lymphoblasts |
| DNA119502-2789 | strongly expressed in mammary gland, placenta and prostate; expressed in intestine, colon, lung, kidney, thymus, stomach, spine and spleen | not expressed in muscle, liver, and heart; weakly expressed in marrow, uterus, testis and brain |
| DNA154095-2998 | strongly expressed in fetal brain; significant expression in uterus and testis; expressed in prostate, esophagus and esophagial tumors, normal stomach and stomach tumor, kidney but expressed higher in kidney tumor, lung tumor, and rectal tumor | negligible expression in mammary gland, bone marrow, trachea, colon, lung, muscle, pancreas, liver, adrenal gland, thymus, placenta, heart, brain and spleen, rectum; not expressed in liver tumor |

Example 20

Identification of Receptor/Ligand Interactions—
Overview of Screening Assay of PRO Polypeptides
for Identification of Receptor/Ligand Interactions In this assay, various PRO polypeptides are tested for ability to bind to a panel of potential receptor or ligand molecules for the purpose of identifying receptor/ligand interactions. The identification of a ligand for a known receptor, a receptor for a known ligand or a novel receptor/ligand pair is useful for a variety of indications including, for example, targeting bioactive molecules (linked to the ligand or receptor) to a cell known to express the receptor or ligand, use of the receptor or ligand as a reagent to detect the presence of the ligand or receptor in a composition suspected of containing the same, wherein the composition may comprise cells suspected of expressing the ligand or receptor, modulating the growth of or another biological or immunological activity of a cell known to express or respond to the receptor or ligand, modulating the immune response of cells or toward cells that express the receptor or ligand, allowing the preparation of agonists, antagonists and/or antibodies directed against the receptor or ligand which will modulate the growth of or a biological or immunological activity of a cell expressing the receptor or ligand, and various other indications which will be readily apparent to the ordinarily skilled artisan.

In general, the assay is performed as follows. A PRO polypeptide of the present invention suspected of being a ligand for a receptor is expressed as a fusion protein containing the Fc domain of human IgG (an immunoadhesin). Receptor-ligand binding is detected by allowing interaction of the immunoadhesin polypeptide with cells (e.g. Cos cells) expressing candidate PRO polypeptide receptors and visualization of bound immunoadhesin with fluorescent reagents directed toward the Fc fusion domain and examination by microscope. Cells expressing candidate receptors are produced by transient transfection, in parallel, of defined subsets of a library of cDNA expression vectors encoding PRO polypeptides that may function as receptor molecules. Cells are then incubated for 1 hour in the presence of the PRO polypeptide immunoadhesin being tested for possible receptor binding. The cells are then washed and fixed with paraformaldehyde. The cells are then incubated with fluorescent conjugated antibody directed against the Fc portion of the PRO polypeptide immunoadhesin (e.g. FITC conjugated goat anti-human-Fc antibody). The cells are then washed again and examined by microscope. A positive interaction is judged by the presence of fluorescent labeling of cells transfected with cDNA encoding a particular PRO polypeptide receptor or pool of receptors and an absence of similar fluorescent labeling of similarly prepared cells that have been transfected with other cDNA or pools of cDNA. If a defined pool of cDNA expression vectors is judged to be positive for interaction with a PRO polypeptide immunoadhesin, the individual cDNA species that comprise the pool are tested individually (the pool is "broken down") to determine the specific cDNA that encodes a receptor able to interact with the PRO polypeptide immunoadhesin.

In another embodiment of this assay, an epitope-tagged potential ligand PRO polypeptide (e.g., 8 histidine "His" tag) is allowed to interact with a panel of potential receptor PRO polypeptide molecules that have been expressed as fusions with the Fc domain of human IgG (immunoadhesins). Following a 1 hour co-incubation with the epitope tagged PRO polypeptide, the candidate receptors are each immunoprecipitated with protein A beads and the beads are washed. Potential ligand interaction is determined by Western blot analysis of the immunoprecipitated complexes with antibody directed towards the epitope tag. An interaction is judged to occur if a band of the anticipated molecular weight of the epitope tagged protein is observed in the Western blot analysis with a candidate receptor, but is not observed to occur with the other members of the panel of potential receptors.

Using the above described assays, the following receptor/ligand interactions have been herein identified:

(1) PRO1031 (designated herein as human IL-17B ligand) binds to PRO5801 (designated herein as human IL-17RH1 receptor).

(2) PRO10272 (designated herein as human IL-17E ligand) binds to PRO5801 (designated herein as human IL-17RH1 receptor).

(3) PRO20110 (designated herein as human IL-17F ligand) binds to the human IL-17 receptor (IL-17R) [(Yao et al., *Cytokine*. 9(11):794–800 (1997); also herein designated as PRO1] and to PRO20040 (designated herein as human IL-17RH2 receptor).

(4) PRO1031 (IL-17B ligand) and PRO1122 (IL-17C ligand) do not bind to the human IL-17 receptor (Li et al., *Proc. Natl. Acad. Sci. (USA)*, 97(2):773–778 (2000)).

Example 21

Human IL-17 Receptor (IL-17R: designated PRO1) Binding with Novel Ligands IL-17B (Designated PRO1031) and IL-17C (Designated PRO1122)

A. Cloning of the ECD of Human IL-17 Receptor (Designated IL-17R; designated herein as PRO1)

The ECD of human IL-17 receptor (IL-17R) [Yao et al., *Cytokine* 9(11):794–800 (1997)] was in order to study the ligand/receptor interactions of the novel IL-17 homolog polypeptides IL-17B and IL-17C. Two oligonucleotide primers were designed at the 5' and 3' ends of the human IL-17R ECD based on the published sequence. [Yao et al., *Cytokine*, 9:794 (1997)]. The two probes had the following sequences:

The above primers were used in PCR reactions to amplify the full-length cDNA from a human testis cDNA library with Pfu Turbo DNA polymerase (Promega). A C-terminal His tag was introduced by PCR through the addition of nucleotides encoding eight histidines to the 3' end primer. The PCR product was then subcloned into an expression plasmid vector pRK5B. Sequence analysis confirmed that the insert contains a DNA fragment encoding the extracellular domain (1–320 amino acids) of the published hIL-17 receptor.

B. Immunoprecipitation of the IL-17R ECD

The differential activity of IL-17 when compared to IL-17B (PRO1031 ;SEQ ID NO:2) and IL-17C (PRO1122; SEQ ID NO:4) (see Examples 28 through 30 of the present application) suggested that they might bind and activate different cell surface receptors. In order to test whether IL-17B (PRO1031) or IL-17C (PRO1122) directly bind to the receptor, an expression plasmid containing the IL-17R (PRO1) (C-terminal His-tagged) was transfected into 293 cells using SuperFect transfection reagent (Qiagen). Metabolic labeling of 293 cells was performed 16 hours after transfection using 50 mCi/mil [$^{35}$S]-Cys/Met mixture for 6 hours. Conditioned medium was collected and concentrated (Centricon-10, Amicon). To examine the expression of the IL-17R ECD, Ni-NTA beads (Qiagen) were used to affinity precipitate the His-tagged IL-17R ECD from the conditioned medium.

The conditioned medium was diluted in RIPA buffer (1% NP40, 0.5% sodium deoxycholate, 0.1% SDS in PBS) and was incubated with IL-17 and the Fc fusion proteins overnight at 4° C. Protein A-agarose beads (Pierce) were added to precipitate the Fc fusion proteins. The precipitates were washed three times to precipitate the Fc fusion proteins. The precipitates were washed three times in RIPA buffer, denatured in SDS sample buffer, and electrophoresed on NuPAGE 4–12% Bis-Tris gels (Novex). For IL-17 immunoprecipitation, anti-IL-17 antibody (R&D Systems) was added. In a competitive binding experiment, immunoprecipitation of IL-17R ECD by IL-17 is performed in the presence of a 5-fold molar excess of IL-17B.His, IL-17C.His and control his tagged protein.

Figures 29A, 29B:
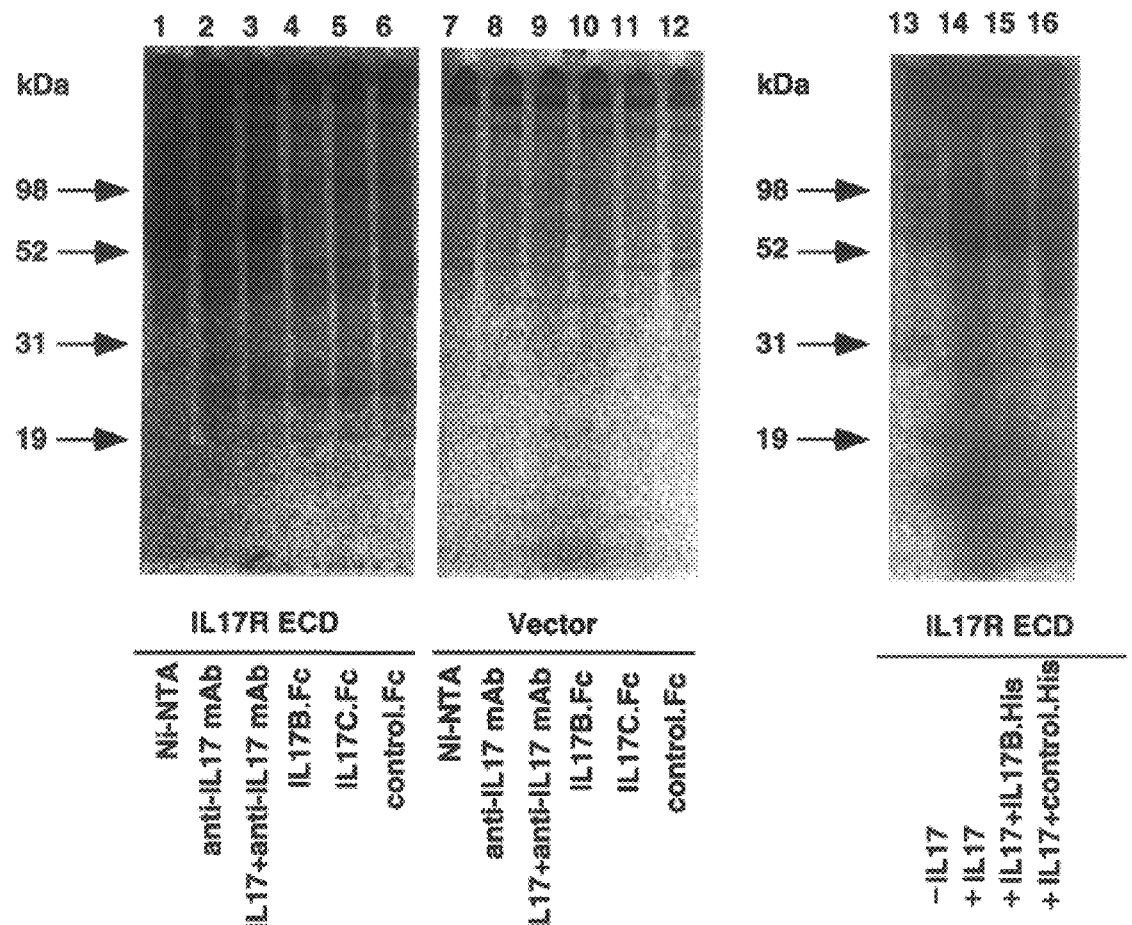
FIG. 29 shows immunoprecipitation of IL-17R extracellular domain (ECD) with IL-17, IL-17B (PRO1031) and IL-17C (PRO1122). His-tagged IL-17R ECD was expressed in 293 cells and metabolically labeled with $^{35}$S as described in EXAMPLE 21. The supernatant was recovered and Ni-NTA beads were used to affinity precipitate the His-tagged IL-17R ECD in the supernatant (lane 1). In part A., IL-17, IL-17B.Fc and IL-17C.Fc, or control Fe fusion proteins were incubated with the supernatant and protein-A-agarose beads were added to precipitate the Fc fusion proteins. For the IL-17 immunoprecipitation reaction, anti-IL17 antibodies were included. Part B. shows the results of a competitive binding experiment, wherein immunoprecipitation of IL-17R ECD by IL-17 was performed in the presence of a five-fold excess of IL-17B.His and control His-tagged proteins. Precipitates in both part A. and B. were analyzed by electrophoresis on NuPAGE (4–12% Bis-Tris) gels. Molecular weight markers are indicated on the left of each panel.

The IL-17R ECD migrated as a 60 kDa band when purified via its histidine tag (FIG. 29A.), lane 1). Furthermore, the IL-17R ECD also precipitated in combination with IL-17 (lane 3). However, both IL-17B and IL-17C failed to compete for the binding of IL-17 for the labeled IL-17 receptor ECD (FIG. 29B.), lane 15 and 16).

Example 22

Novel Human IL-17 Receptor (IL-17RH1) (Designated PRO5801) Binding with Human IL-17 and Novel Ligands IL-17B (Designated PRO1031), IL-17C (Designated PRO1122, and IL-17E (Designated PRO10272): Induction of NF-κB Activity and IL-8 Production by IL-17E A. Isolation of IL-17E (PRO10272) and Construction of Expression Vectors IL-17E (DNA147531-2821; SEQ ID NO:5) and IL-17RH1 (DNA115291-2681; SEQ ID NO:11) cDNA clones were isolated from a human cDNA library and sequenced in their entirety as described in EXAMPLE 3 and

```
primer 1:  5'-CTG TAC CTC GAG GGT GCA GAG-3'                                                   (SEQ ID NO:38)

primer 2:  5'-CCC AAG CTT GGG TCA ATG ATG ATG ATG ATG ATG ATG ATG CCA CAG GGG CAT GTA GTC      (SEQ ID NO:39)
           C-3'
```

EXAMPLE 5, respectively. Fc fusion proteins (immunoadhesions) were prepared by fusion of the entire open reading frames of IL-17, IL-17B (PRO1031), IL-17C (PRO1122), and IL-17E (PRO10272) in frame with the Fc region of human IgG1 in the eukaryotic expression vector pRK5tkNEO and the baculovirus vector pHIF, a derivative of pVL1393 purchased from Pharmingen. Fusion proteins were transiently expressed in human 293 cells or Sf9 insect cells and purified over a Protein A column. The extracellular domain of the IL-17RH1 receptor (PRO5801) was also expressed as a C-terminal 8×His-tag fusion in baculovirus and purified by nickel affinity column. IL-17E (PRO10272) was also expressed as a 8×His-tag fusion in E. coli and was purified and refolded. The identities of the purified proteins were verified by N-terminal sequence analysis.

B. Western Blot, Northern Blot and Taqman™ Analysis

Western blot analysis of binding of IL-17E (PRO10272) to IL-17RH1 (PRO5801) was performed essentially as described by Xie et al., Cytokine, 11(10):729–735 (1999) and Xie et al., J. Biol. Chem., 275(40): 31335–31339 (2000). For Northern blot analysis, multiple tissue Northern blots (Clontech) were probed with a $^{32}$P-labeled probe of random primed IL-17RH1 cDNA according to manufacturer's recommendations and exposed to X-omat (Kodak) for 72 hours. For quantitative PCR analysis (Taqman™), total mRNA from human tissues (50 ng) was analyzed as recommended (Perkin Elmer) with primers based on the coding sequence of IL-17RH1.

C. FACS Analysis

Human 293 cells were transiently co-transfected with expression vectors for green fluorescent protein (GFP), and IL-17RH1 (PRO5801) or IL-17R (designated PRO1 ) as indicated. After 24 hours, cells were incubated with Fc tagged ligand as indicated and binding was revealed with PE conjugated anti-human Fc antibody. FACS curves show PE staining within the co-transfected GFP positive cell population. (FIG. 32A)

D. NF-κB, and IL-8 Assays and Western Blot Analysis

Luciferase reporter assays were conducted essentially as described by Gurney et al., Curr Biol., 9(4):215–218 (1999). Briefly, 293 or TK-10 cells (2×10$^5$) were transfected by Effectine (Qiagen) transfection with 0.5 μg of the firefly luciferase reporter plasmid pGL3-ELAM.tk and 0.05 μg of the Renilla luciferase reporter plasmid as internal transfection control as well as IL-17E expression plasmid (0. 1 μg) and carrier plasmid pRK5D to maintain constant DNA between transfections. After 24 hours cells were harvested and luciferase activity assayed as recommended (Pharmacia). IL-8 ELISA were performed according to manufacturer's instructions R&D) Systems). (FIG. 33)

E. Results and Discussion

Figure 30:
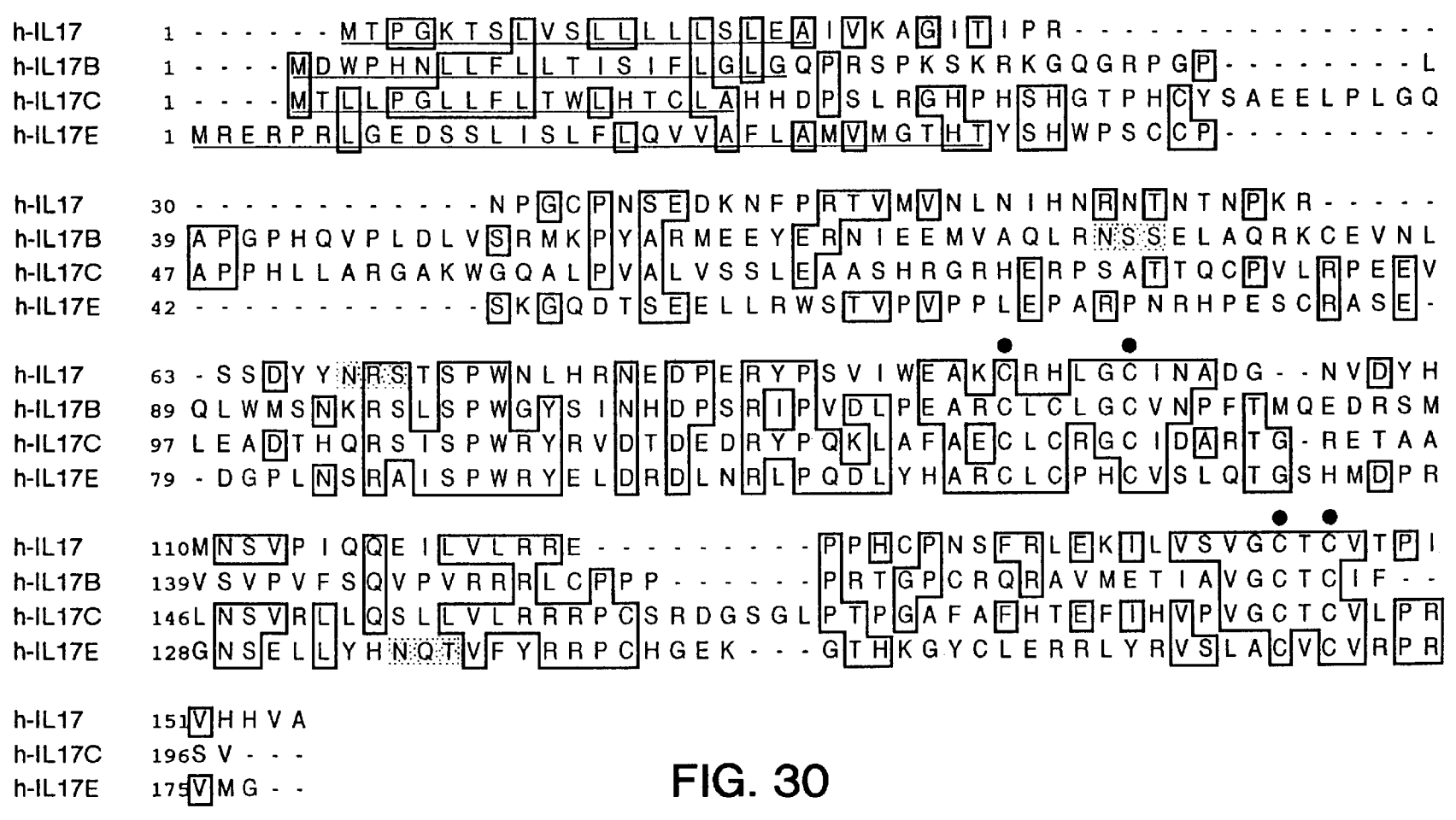

As described supra, novel members of IL-17 family have been identified and characterized, designated herein as IL-17B (PRO1031), IL-17C (PRO1122), IL-17D (PRO21175), and IL-17E (PRO10272). Four members of the IL-17 family: IL-17, IL-17B, IL-17C and IL-17E share greatest similarity in the C-terminal portion of the molecule with 20–30% amino acid sequence identity and strict conservation of four cysteines. Additional cysteines that may be functionally conserved are present with differences in position. In contrast, there is little conservation apparent in the N-terminal 80 residues. The alignment of the IL-17 family members [IL-17 (SEQ ID NO:40); IL-17B (PRO1031; SEQ ID NO:2); IL-17C (PRO1122, SEQ ID NO:4); and IL-17E (PRO10272, SEQ ID NO:6)] is demonstrated in FIG. 30. The predicted signal sequences are underlined. Conserved cysteines are indicated by bullet, and potential N-linked glycosylation sites are boxed.

Figure 23:
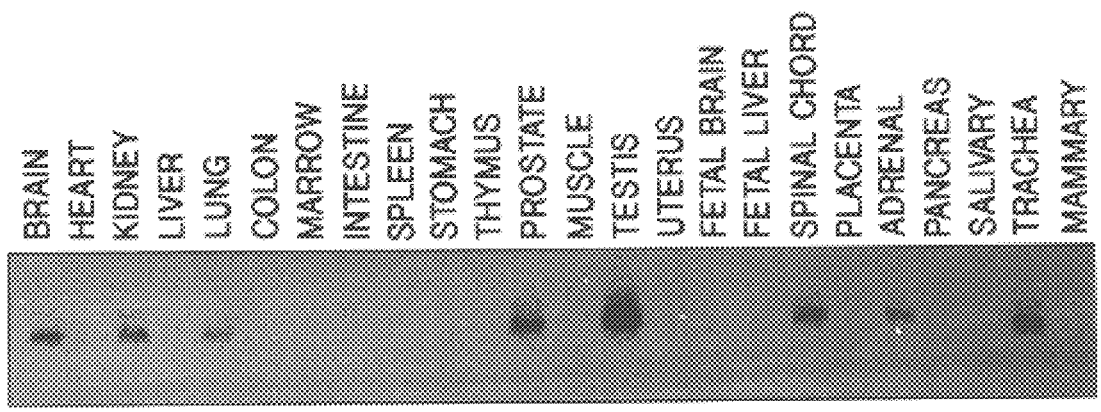
FIG. 23 shows mRNA expression of IL-17E (PRO10272) by RT-PCR analysis. RNA from the indicated tissues was subjected to RT-PCR with primers that were designed to amplify the entire coding sequence of IL-17E. The PCR product was resolved by agarose gel electrophoresis, transferred to nylon membrane and probed with a $^{32}$P-labeled IL-17E cDNA probe.
Figure 24:
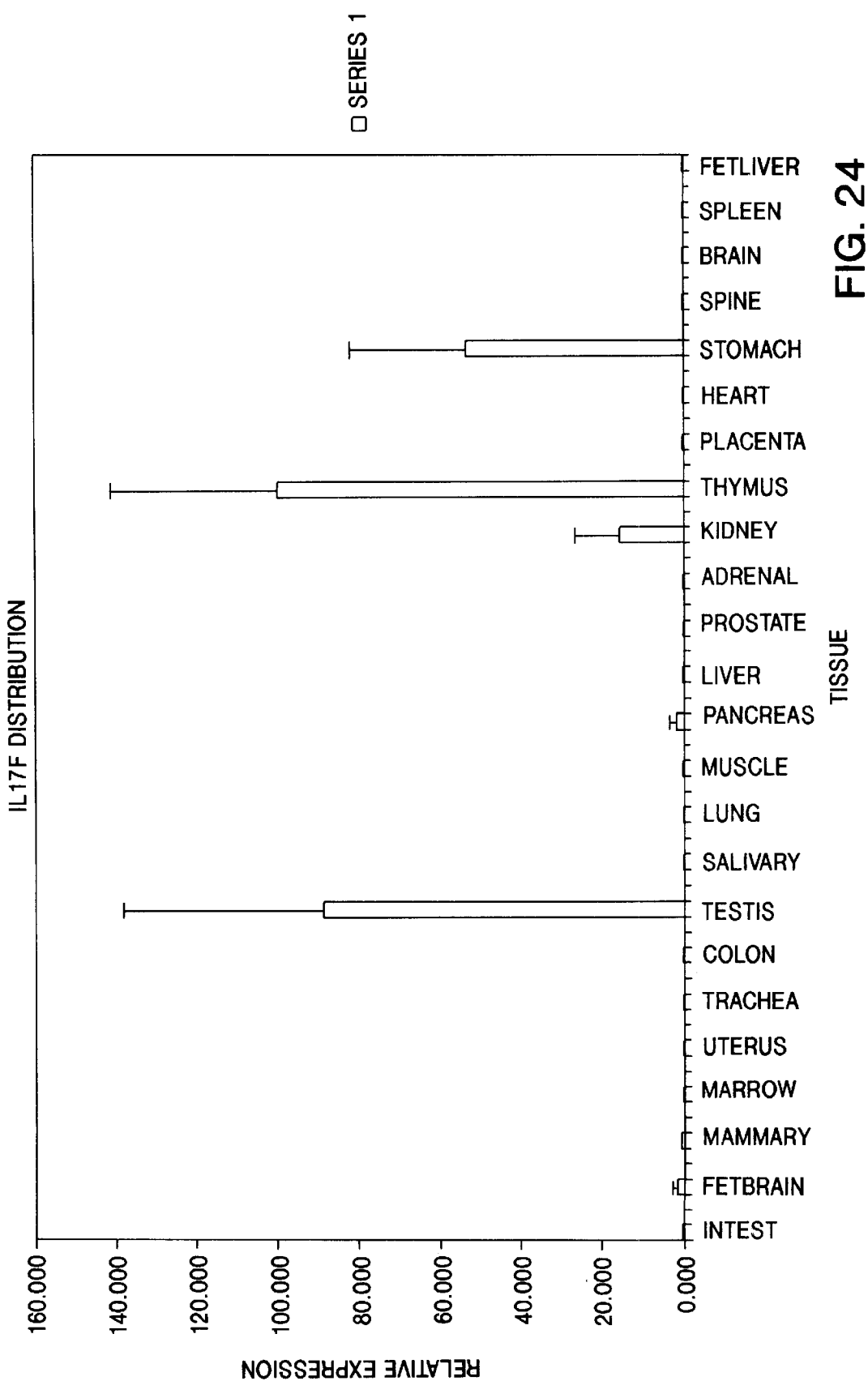
FIG. 24 shows the relative tissue expression distribution of the IL-17F ligand (PRO20110).
Figure 25:
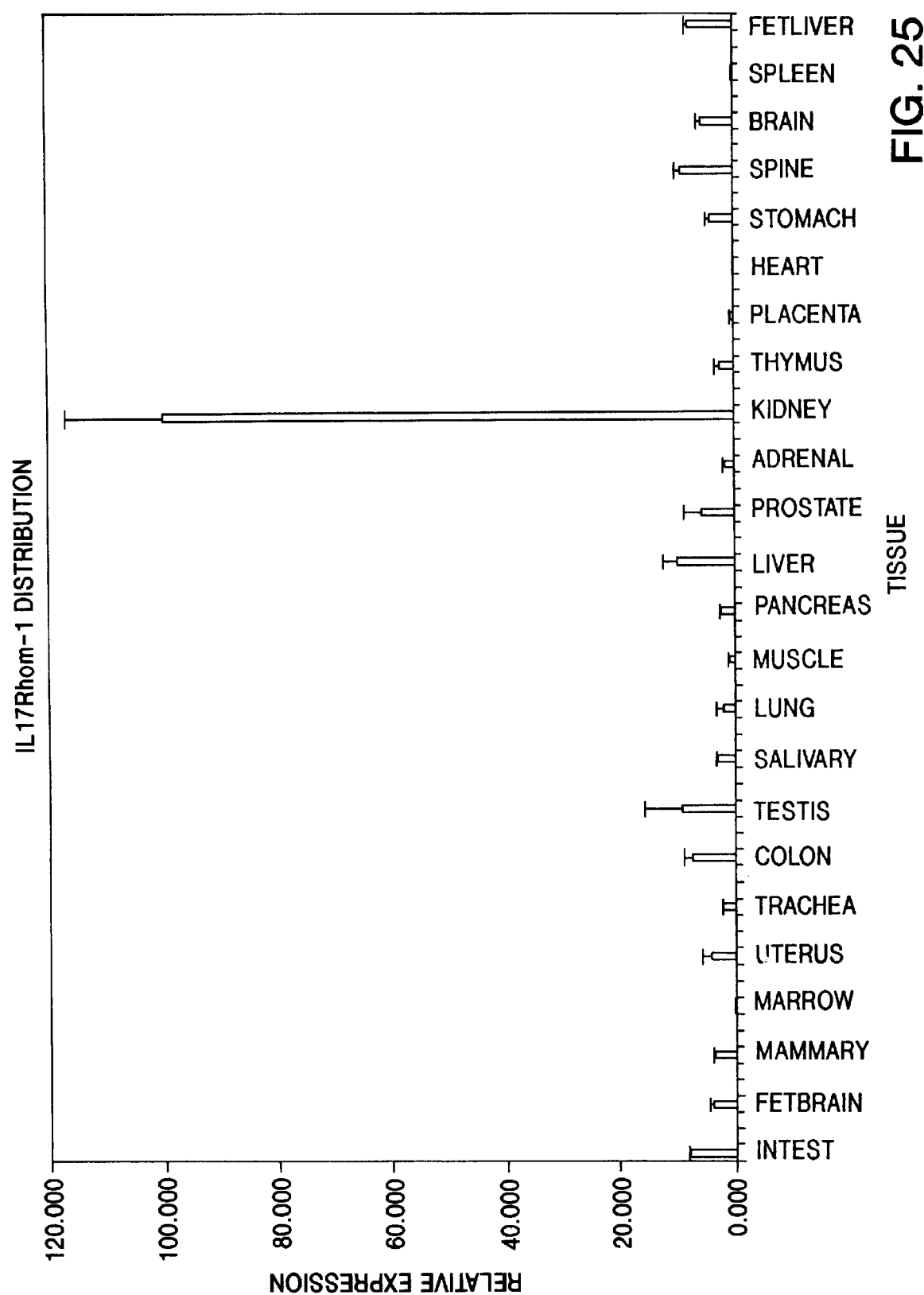
FIG. 25 shows the relative tissue expression distribution of the IL-17RH1 receptor (PRO5801).
Figure 26:
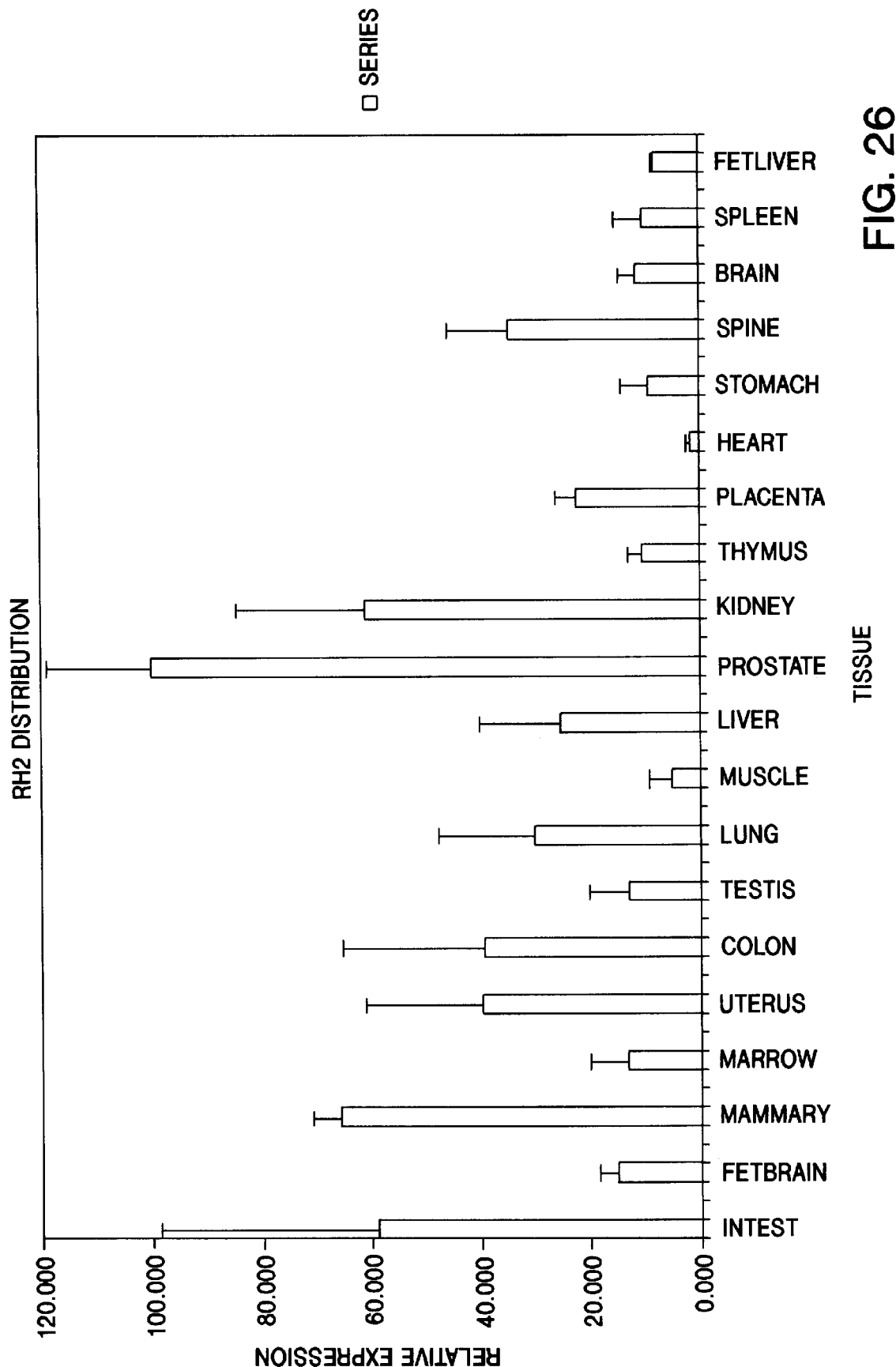
FIG. 26 shows the relative tissue expression distribution of the IL-17RH2 receptor (PRO20040).
Figure 27:
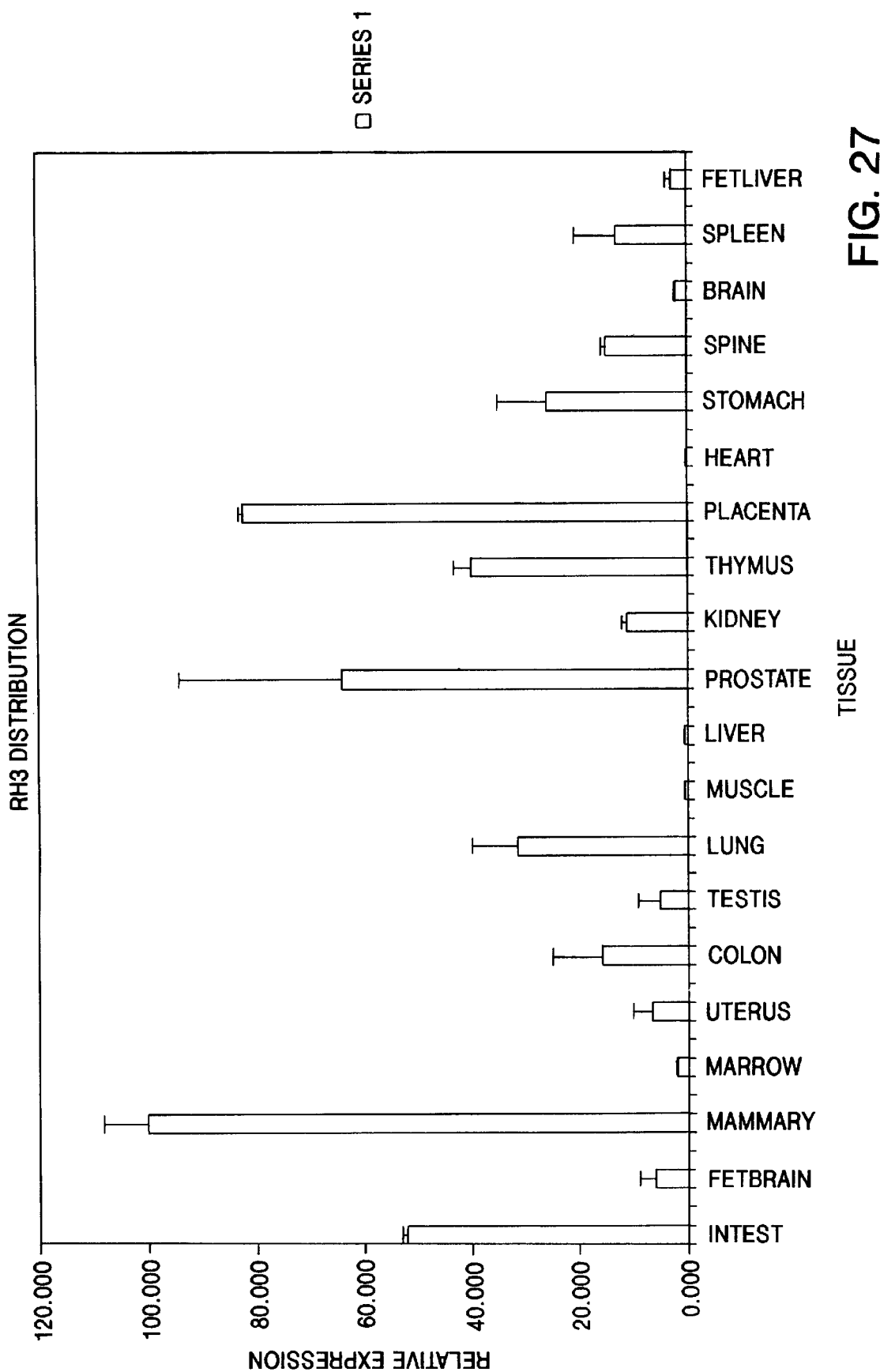
FIG. 27 shows the relative tissue expression distribution of the IL-17RH3 receptor (PRO09877).
Figure 28:
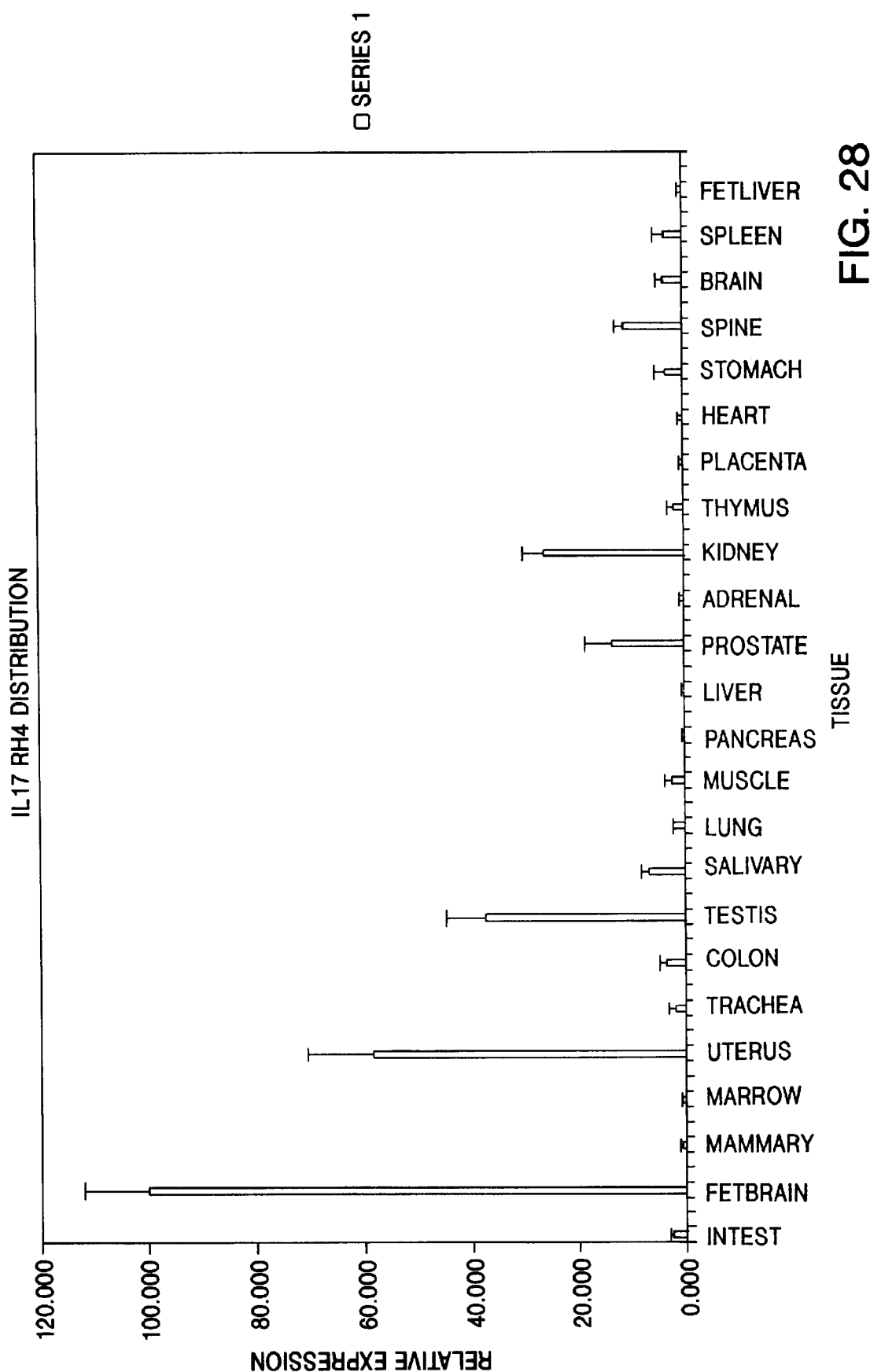
FIG. 28 shows the relative tissue expression distribution of the IL-17RH4 receptor (PRO20026).

IL-17E mRNA was not detected by Northern blot analysis. However, IL-17E was detected at very low levels in several tissues including brain, kidney, lung, prostate, testis, spinal chord, adrenal gland and trachea by RT-PCR using primers designed to distinguish spliced mRNA from genomic DNA. The results of RT-PCR analysis of IL-17E (PRO10272) expression is shown in FIG. 23. As described above, RNA from the indicated tissues was subjected to RT-PCR with primers that were designed to amplify the entire coding sequence of IL-17E. The PCR product was resolved by agarose gel electrophoresis, transferred to nylon membrane and probed with a $^{32}$P labeled IL-17E cDNA probe.

Figure 31A:
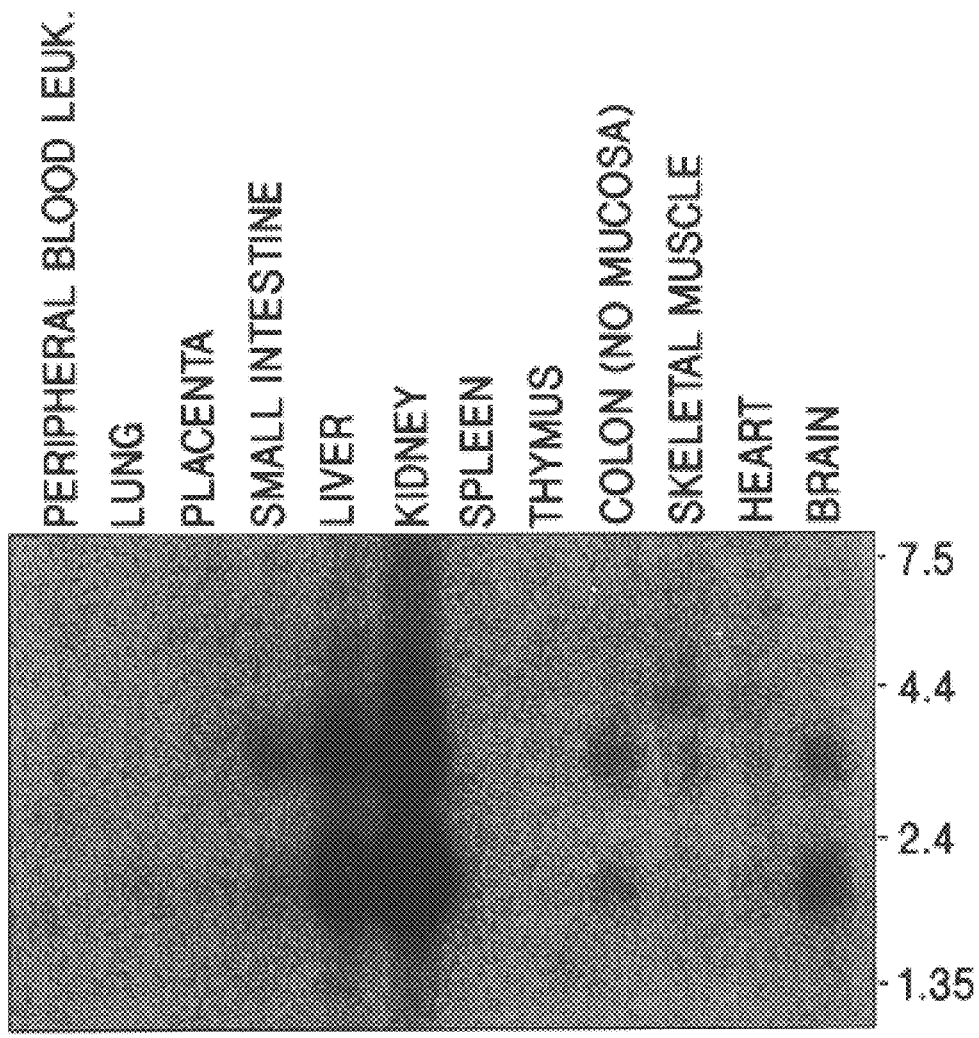
FIG. 31A shows Northern blot analysis of IL-17RH1 receptor in selected tissues.
Figure 31B:
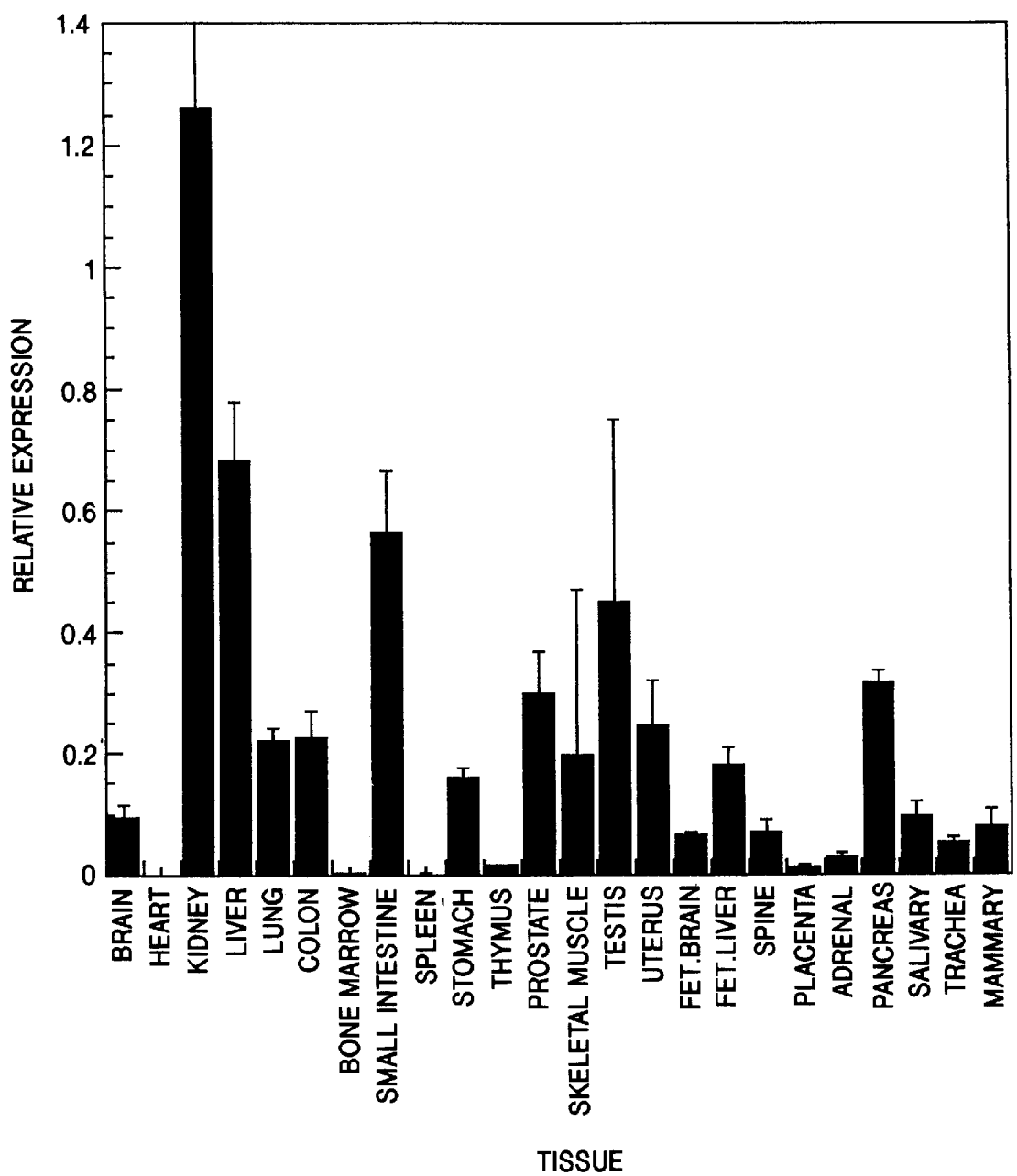
FIG. 31B shows the quantitative PCR analysis of IL-17RH1 mRNA expression in selected tissues.

Applicants have demonstrated that IL-17B (PRO1031) and IL-17C (PRO1122) do not bind to the human IL-17 receptor (designated herein PRO1) (see EXAMPLE 21). A novel IL-17 receptor (designated herein as IL-17RH1; PRO5801) has been herein identified and characterized. IL-17RH1 (DNA115291-2681; SEQ ID NO:11) cDNA clones were isolated from a human cDNA library and sequenced in their entirety as described in EXAMPLE 5. IL-17RH1 mRNA expression was examined by Northern blot analysis as shown in FIG. 31A and quantitative PCR as shown in FIG. 31B. Highest levels of expression of IL-17RH1 (PRO5801) were observed in kidney, with significant expression also observed in liver, and other peripheral organs such as colon, small intestine, prostate, testis, pancreas and uterus.

Figure 32B:
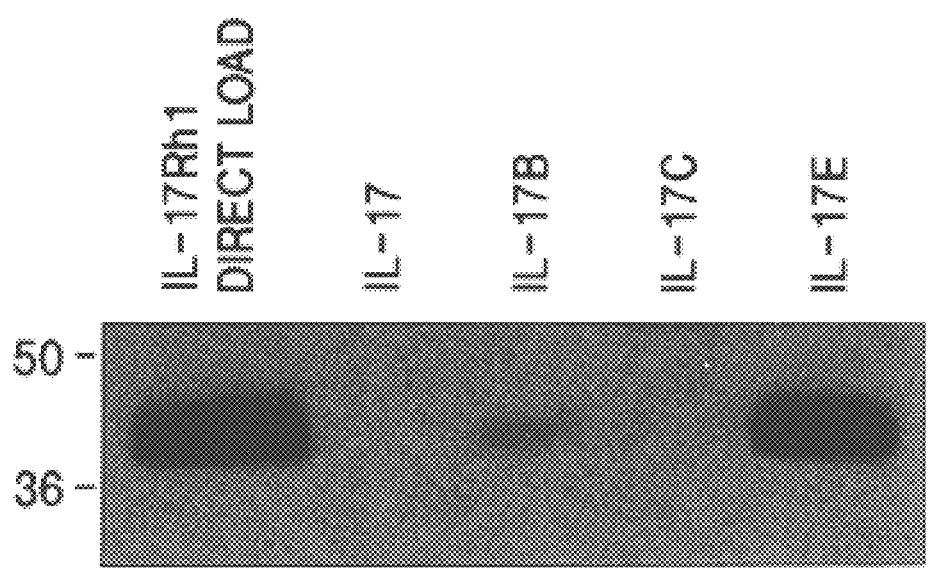
In FIG. 32B, His-epitope tagged IL-17RH1 receptor extracellular domain was incubated with ligand-Fc fusion protein for members of the human IL-17 family depicted as follows: lane 1, IL-17RH1-His direct load; lane 2, IL-17; lane 3, IL-17B (PRO1031); lane 4, IL-17C (PRO1122); and lane 5, IL-17E (PRO10272). Ligand immunoadhesins were immunoprecipitated with Protein A beads and bound IL-17RH1 receptor was analyzed by Western Blot analysis with antibody to the His-epitope tag. The positions of molecular weight markers (kDa) are indicated on the left.

Binding studies were conducted to determine whether this new molecule (designated IL-17RH1; PRO5801) serves as a receptor for other members of IL-17 family. Human 293 kidney cells transfected with an expression vector for IL-17RH1 were shown to bind to IL-17E-Fc fusion protein (immunoadhesin), but do not show significant binding of human IL-17 (as shown in FIG. 32A). IL-17E immunoadhesin binding to IL-17RH1 expressing cells could be completely inhibited by competition with His epitope tagged IL-17E. In comparison, cells transfected with expression vector for IL-17R bind IL-17 immunoadhesin but not IL-17E. To examine whether there was direct interaction with members of the IL-17 family, ligand binding studies were conducted with epitope tagged extracellular domain of the IL-17RH1 receptor. As shown in FIG. 32B, this novel receptor exhibits strong binding of IL-17E-Fc, and weak binding to IL-17B-Fc but does not bind IL-17-Fc or IL-17C-Fc.

Figure 34:
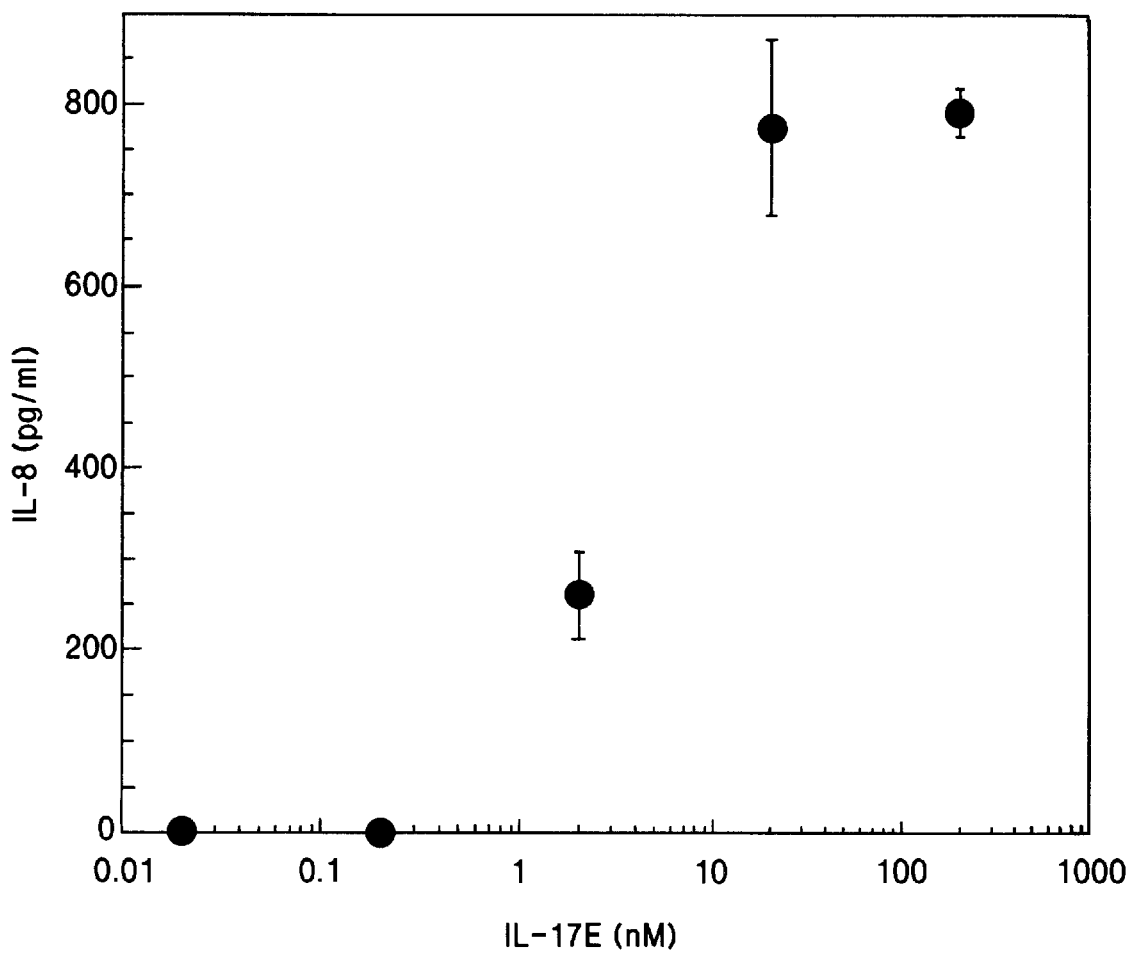
FIG. 34 shows the effect of IL-17E (PRO10272) on IL-8 production. Human TK-10 kidney derived cells lines were incubated by Elisa. Shown is the level of IL-8 measured minus the level of IL-8 production observed in the absence of cytokine addition. The experiments were repeated several times with similar results.

IL-17 has been observed to induce NF-κB activity (Jovanovic et al., supra). A study was done to determine whether IL-17E (PRO10272) would also induce activation of a NF-κB responsive luciferase reporter gene in two human renal cell carcinoma cell lines, 293 and TK-10 cells (both of these cell lines were found to express endogenous IL-17RH1 mRNA). The results of these studies are shown in FIG. 33A. Transfection of expression vector for IL-17E markedly induced luciferase activity. The luciferase activity was induced in a dose dependent manner, and was of similar magnitude to that observed by the overexpression of the TNF receptor superfamily member GITR (see FIG. 33B), previously shown to be a potent inducer of NF-κB activity (Gurney et al., supra). NF-κB is thought to mediate a proinflammatory signal, suggesting that IL-17E may have proinflammatory action. To examine this possibility, the production of IL-8, a proinflammatory chemokine induced by IL-17, was examined. As shown in FIG. 34, IL-17E (PRO10272) induced activation of IL-8 in TK-10 cells.

In summary, IL-17RH1 (PRO5801) is the second receptor identified which binds to members of the IL-17 family. The IL-17 receptor family is quite unrelated to other proteins. However, comparison of the two receptors does reveal conservation of many cysteines within the extracellular domain, suggesting they share similar structure. There are conserved elements within the intracellular domain as well, suggesting that these receptors likely engage similar intracellular machinery. This is supported by the observation that like IL-17, IL-17E signals activation of NK-κB. The regions of conservation within the intracellular domain do not bear obvious similarity to other receptor families known to activate NF-κB, the IL1/Toll and TNF receptor families.

IL-17E induces production of IL-8, a proinflammatory molecule that has also been observed to be induced by IL-17, suggesting the biological activities of these two cytokines may be similar. The IL-17 receptor has a very broad expression pattern, in contrast to the somewhat more restricted mRNA expression pattern of IL-17RH1 (PRO5801) (see FIG. 31). If these molecules mediate generally analogous proinflammatory responses, a key consideration in understanding the function of the different members of the expanding IL-17 cytokine family will be the expression patterns and regulation of the cognate receptors.

FIGS. 25 through 28 show the relative tissue expression distribution for the novel IL-17 receptor homologs identified herein as IL-17RH1 (PRO5801; SEQ ID NO:12), IL-17RH2 (PRO20040; SEQ ID NO:14), IL-17RH3 (PRO9877; SEQ ID NO:16) and IL-17RH4 (PRO20026; SEQ ID NO:18), respectively.

Figure 35:
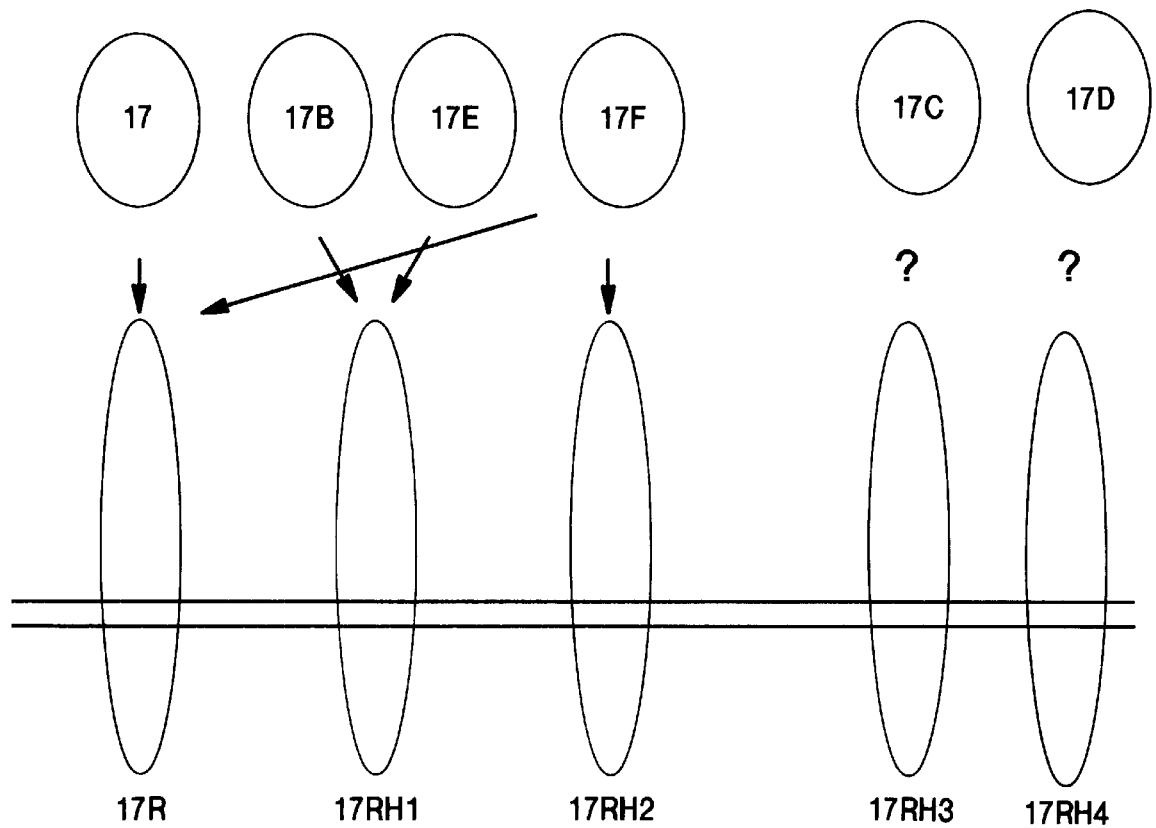
FIG. 35 depicts the IL-17 family of cytokines and the complex pattern of overlapping receptor-ligand specificities. From left to right, FIG. 35 demonstrates that IL-17 ligand binds to the IL-17 receptor (IL-17R; herein designated PRO1); IL-17B ligand (PRO1031) binds to the IL-17RH1 receptor (PRO5801); IL-17E ligand (PRO10272) binds to the IL-17RH1 receptor (PRO5801); IL-17F ligand (PRO20110) binds to both the IL-17 receptor (IL-17R, herein designated PRO1) as well as to the IL-17RH2 receptor (PRO20040); IL-17C ligand (PRO1122) and IL-17D ligand (PRO21175) do not interact with IL-17R, IL-17RH1 or IL-17RH2 receptors.

In summary, FIG. 35 depicts the IL-17 family of cytokines complex pattern of overlapping receptor-ligand specificities. As shown, ligands IL-17C and IL-17D appear to have specificity for a different interleukin-17 receptor other than IL-17R, IL-17RH1 or IL-17RH2. In addition, FIGS. 20 through 28 and FIG. 31 demonstrate the relative tissue expression distribution for the novel IL-17 homologs and IL-17 receptors identified herein.

Example 23

Induction of c-fos in Endothelial Cells (ASSAY #34)

This assay is designed to determine whether PRO polypeptides show the ability to induce c-fos in endothelial cells. PRO polypeptides testing positive in this assay would be expected to be useful for the therapeutic treatment of conditions or disorders where angiogenesis would be beneficial including, for example, wound healing, and the like (as would agonists of these PRO polypeptides). Antagonists of the PRO polypeptides testing positive in this assay would be expected to be useful for the therapeutic treatment of cancerous tumors.

Human venous umbilical vein endothelial cells (HUVEC, Cell Systems) in growth media (50% Ham's F12 w/o GHT: low glucose, and 50% DMEM without glycine: with $NaHCO_3$, 1% glutamine, 10 mM HEPES, 10% FBS, 10 ng/nl bFGF) are plated on 96-well microtiter plates at a cell density of $1 \times 10^4$ cells/well. The day after plating, the cells are starved by removing the growth media and treating the cells with 100 μl/well test samples and controls (positive control: growth media; negative control: 10 mM HEPES, 140 mM NaCl, 4% (w/v) mannitol, pH 6.8). The cells are incubated for 30 minutes at 37° C., in 5% $CO_2$. The samples are removed, and the first part of the bDNA kit protocol (Chiron Diagnostics, cat. #6005-037) is followed, where each capitalized reagent/buffer listed below is available from the kit.

Briefly, the amounts of the TM Lysis Buffer and Probes needed for the tests are calculated based on information provided by the manufacturer. The appropriate amounts of thawed Probes are added to the TM Lysis Buffer. The Capture Hybridization Buffer is warmed to room temperature. The bDNA strips are set up in the metal strip holders, and 100 μl of Capture Hybridization Buffer are added to each b-DNA well needed, followed by incubation for at least 30 minutes. The test plates with the cells are removed from the incubator, and the media are gently removed using the vacuum manifold. 100 μl of Lysis Hybridization Buffer with Probes are quickly pipetted into each well of the microtiter plates. The plates are then incubated at 55° C. for 15 minutes. Upon removal from the incubator, the plates are placed on the vortex mixer with the microtiter adapter head and vortex on the #2 setting for one minute. 80 μl of the lysate are removed and added to the bDNA wells containing the Capture Hybridization Buffer, and pipetted up and down to mix. The plates are incubated at 53° C. for at least 16 hours.

On the next day, the second part of the bDNA kit protocol is followed. Specifically, the plates are removed from the incubator and placed on the bench to cool for 10 minutes. The volumes of additions needed are calculated based upon information provided by the manufacturer. An Amplifier Working Solution is prepared by making a 1:100 dilution of the Amplifier Concentrate (20 fm/μl) in AL Hybridization Buffer. The hybridization mixture is removed from the plates and washed twice with Wash A. 50 μl of Amplifier Working Solution are added to each well and the wells are incubated at 53° C. for 30 minutes. The plates are then removed from the incubator and allowed to cool for 10 minutes. The Label Probe Working Solution is prepared by making a 1:100 dilution of Label Concentrate (40 pmoles/μl) in AL Hybridization Buffer. After the 10-minute cool-down period, the amplifier hybridization mixture is removed and the plates are washed twice with Wash A. 50 μl of Label Probe Working Solution are added to each well and the wells are incubated at 53° C. for 15 minutes. After cooling for 10 minutes, the Substrate is warmed to room temperature. Upon addition of 3 μl of Substrate Enhancer to each ml of Substrate needed for the assay, the plates are allowed to cool for 10 minutes, the label hybridization mixture is removed, and the plates are washed twice with Wash A and three times with Wash D. 50 μl of the Substrate Solution with Enhancer are added to each well. The plates are incubated for 30 minutes at 37° C. and RLU is read in an appropriate luminometer.

The replicates are averaged and the coefficient of variation is determined. The measure of activity of the fold increase over the negative control (HEPES buffer described above) value is indicated by chemiluminescence units (RLU). Samples that show an at least two-fold value over the negative control value are considered positive.

PRO1031 assayed "positive" as shown below:

| ASSAY #1 | | |
| --- | --- | --- |
| Negative control | = | 1.0 RLU |
| Positive control | = | 10.96 RLU |
| PRO1031 at 0.056 nM | = | 2.22 RLU |
| ASSAY #2 | | |
| Negative control | = | 1.0 RLU |
| Positive control | = | 10.96 RLU |
| PRO1031 at 0.56 nM | = | 2.01 RLU |

Example 24

Skin Vascular Permeability Assay (ASSAY #64)

This assay shows that certain PRO polypeptides stimulate an immune response and induce inflammation by inducing mononuclear cell, eosinophil and PMN infiltration at the site of injection of the animal. This skin vascular permeability assay is conducted as follows. Hairless guinea pigs weighing 350 grams or more are anesthetized with ketamine (75–80 mg/Kg) and 5 mg/Kg Xylazine intramuscularly (IM). A sample of purified PRO polypeptide or a conditioned media test sample is injected intradermally onto the backs of the test animals with 100 μL per injection site. It is possible to have about 10–30, preferably about 16–24, injection sites per animal. One mL of Evans blue dye (1% in physiologic buffered saline) is injected intracardially. Blemishes at the injection sites are then measured (mm diameter) at 1 hr, 6 hrs and 24 hrs post injection. Animals were sacrificed at 6 hrs after injection. Each skin injection site is biopsied and fixed in paraformaldehyde. The skins are then prepared for histopathalogic evaluation. Each site is evaluated for inflammatory cell infiltration into the skin. Sites with visible inflammatory cell inflammation are scored as positive. Inflammatory cells may be neutrophilic, eosinophilic, monocytic or lymphocytic.

At least a minimal perivascular infiltrate at the injection site is scored as positive, no infiltrate at the site of injection is scored as negative. PRO1031 gave positive results at time interval 24 hours in this assay.

Example 25

Stimulatory Activity in Mixed Lymphocyte Reaction (MLR) (ASSAY #24)

This example shows that the polypeptides of the invention are active as stimulators of the proliferation of T-lymphocytes. Compounds which stimulate proliferation of lymphocytes are useful therapeutically where enhancement of an immune response is beneficial. A therapeutic agent may also take the form of antagonists of the PRO polypeptides of the invention, for example, murine-human chimeric, humanized or human antibodies against the polypeptide, which would be expected to inhibit T-lymphocyte proliferation.

The basic protocol for this assay is described in *Current Protocols in Immunology*, unit 3.12; edited by J. E. Coligan, A. M. Kruisbeek, D. H. Marglies, E. M. Shevach, W. Strober, National Institutes of Health, Published by John Wiley & Sons, Inc.

More specifically, in one assay variant, peripheral blood mononuclear cells (PBMC) are isolated from mammalian individuals, for example a human volunteer, by leukopheresis (one donor will supply stimulator PBMCs, the other donor will supply responder PBMCs). If desired, the cells are frozen in fetal bovine serum and DMSO after isolation. Frozen cells may be thawed overnight in assay media (37° C., 5% $CO_2$ )and then washed and resuspended to $3\times10^6$ cells/nl of assay media (RPMI; 10% fetal bovine serum, 1% penicillin/streptomycin, 1% glutamine, 1% HEPES, 1% non-essential amino acids, 1% pyruvate). The stimulator PBMCs are prepared by irradiating the cells (about 3000 Rads). The assay is prepared by plating in triplicate wells a mixture of: 100:1 of test sample diluted to 1% or to 0.1%; 50:1 of irradiated stimulator cells and 50:1 of responder PBMC cells. 100 microliters of cell culture media or 100 microliter of CD4-IgG is used as the control. The wells are then incubated at 37° C., 5% $CO_2$ for 4 days. On day 5 and each well is pulsed with tritiated thymidine (1.0 mCi/well; Amersham). After 6 hours the cells are washed 3 times and then the uptake of the label is evaluated.

In another variant of this assay, PBMCs are isolated from the spleens of BALB/c mice and C57B6 mice. The cells are teased from freshly harvested spleens in assay media (RPMI; 10% fetal bovine serum, 1% penicillin/streptomycin, 1% glutamine, 1% HEPES, 1% non-essential amino acids, 1% pyruvate) and the PBMCs are isolated by overlaying these cells over Lympholyte M (Organon Teknika), centrifuging at 2000 rpm for 20 minutes, collecting and washing the mononuclear cell layer in assay media and resuspending the cells to $1\times10^7$ cells/ml of assay media. The assay is then conducted as described above. Positive increases over control are considered positive with increases of greater than or equal to 180% being preferred. However, any value greater than control indicates a stimulatory effect for the test protein. The results of this assay for compounds of the invention are shown below:

| PRO | PRO Concentration | Percent Increase Over Control |
|---|---|---|
| PRO10272 | 0.84 nM | 201.5 |

Example 26

Stimulation of Peripheral Blood Mononuclear Cells (PBMCs) or CD4+ cells with anti CD3 and PRO Protein (ASSAY #99)

This assay shows that one or more of the PRO polypeptides are active as enhancers of the stimulation of PBMCs or CD4+ cells. CD4+ cells are enriched by negative selection using MACs beads after LSM separation. The ability of the PRO polypeptide to replace anti-CD28 is examined to determine the stimulatory effect.

Anti-CD3 and anti-CD28 are known to stimulate PBMCs. The basic protocol for the isolation of PBMCs used in this assay is described in *Current Protocols in Immunology*, unit 3.1.2; edited by J. E. Coligan, A. M. Kruisbeek, D. H. Marglies, E. M. Shevach, W. Strober, National Institutes of Health, Published by John Wiley & Sons, Inc. (1993).

More specifically, in one assay variant, peripheral blood mononuclear cells (PBMC) are isolated from mammalian individuals, for example a human volunteer, by leukopheresis. If desired, the cells are enriched for CD4+ cells, then frozen in 90% fetal bovine serum and 10% DMSO after isolation. Frozen cells may be thawed overnight in assay media (37° C., 5% $CO_2$) and then washed and resuspended to $0.5\times10^6$ cells/ml of assay media (RPMI; 10% fetal bovine serum, 1% penicillin/streptomycin, 1% glutamine, 1% HEPES, 1% non-essential amino acids, 1% pyruvate).

The assay is prepared by plating in triplicate wells a mixture of: 200 μl of cells after the overnight coat of anti-CD3 and PRO protein.

50 μl of anti-CD3 (50 ng/ml, Amac 0178) and 50 μl of 1% of the PRO protein are coated on a 96 well plate in PBS 4° C. overnight. 50 μl Hu-IgG is used as the control in place of the PRO protein. The wells are then incubated at 37° C., 5% $CO_2$ for about 3 days. On day 4, each well is pulsed with tritiated thymidine (1.0 mC/well; Amersham). After 6 hours the cells are harvested and then the uptake of the label is evaluated.

A result which indicates a stimulatory effect (i.e., $^3$[H]-thymidine incorporation) greater than 200% of the control is considered to be positive stimulatory result.

In another variant of this assay, PBMCs or CD4+ splenocytes are isolated from the spleens of BALB/c mice. The cells are teased from freshly harvested spleens in assay media (RPMI; 10% fetal bovine serum, 1% penicillin/streptomycin, 1% glutamine, 1% HEPES, 1% non-essential amino acids, 1% pyruvate) and the PBMCs are isolated by overlaying these cells over Lympholyte M (Organon Teknika), centrifuging at 2000 rpm for 20 minutes, collecting and washing the mononuclear cell layer in assay media. CD4+ cells are enriched by negative selection using beads, washed in media and resuspended the cells to $1 \times 10^7$ cells/ml of assay media. The assay is then conducted as described above. Results are shown below:

| PRO concentration | stimulation (+)/inhibition (−) |
|---|---|
| PRO1031 5.6 nM | (+) 285% above baseline stimulation index |
| PRO1031 0.56 nM | (+) 147% above baseline stimulation index |

Example 27

Generating IL-17B and IL-17C Fc/His Fusion Proteins

The coding sequences of IL17B and IL17C were amplified by PCR and subcloned into the EcoRI and SmaI sites of pBPH.His.c to generate a C-terminal GHHHHHHHH tag or the EcoRI and Stu sites of pBPH.IgG to generate a C-terminal fusion with the Fc region of human IgG1. Vectors pBPH.His.c and pBPH.IgG are derivatives of the baculovirus expression vector pVL1393 (Pharmingen). A control Fc or His-tagged protein was constructed in a similar way be C-terminally linking pancreatitis-associated protein (175 amino acid) to the Fc portion of the human IgG1 or a his-8 tag.

The fusion proteins were expressed in High 5 cells using the manufacturer's recommended procedure (Invitrogen). In brief, the DNA constructs were co-transfected with BaculoGold Baculovirus DNA (Pharmingen) in a 7:1 ratio into adherent Sf9 cells. Cells were incubated at 28° C. for 4 days and the supernatant was harvested. The transfection supernatant was amplified and was subject to affinity purification by either protein A-Sepharose beads (Pharmacia) for Fc fusion proteins or Ni-NTA agarose beads (QIAGEN) for His-tagged proteins.

To examine the protein expression, SDS-PAGE analysis was performed on the affinity purified recombinant proteins under non-reducing and reducing conditions, followed by silver staining.

Example 28

Induction of IL-6 and TNF-α release by IL-17B (PRO1031), IL-17C (PRO1122)and IL-17E (PRO10272

Using the procedure outlined in Yao et al., *J. Immunol.* 155: 5483 (1995) for IL-6 release, human foreskin fibroblast cells (ATCC CRL-2091) were cultured in MEM media (10% FBS) with the test cytokine. After incubation for 18 hours at 37° C. and 5% $CO_2$, conditioned media were assayed for IL-6 using an ELISA kit (R&D Systems). For TNF-α secretion, human leukemia monocytic THP-1 cells were cultured in RPMI media (10% FBS) with test cytokine. After incubation for 18 hour at 37° C. and 5% $CO_2$, conditioned media were quantitated for TNF-α using and ELISA assay kit (R&D Systems).

Figure 36A:
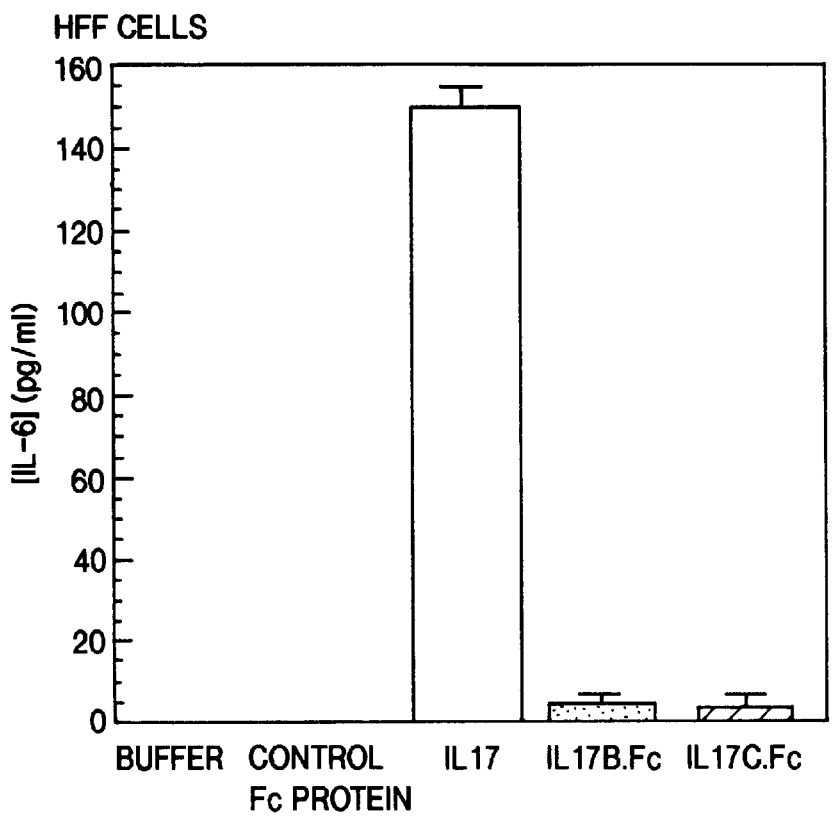
FIG. 36 depicts bar graphs representing the biological activities of IL-17, IL-17B (PRO1031), and IL-17C (PRO1122).

Human foreskin fibroblast cells (ATCC) were separately cultured in MEM media (10% FBS) in the presence of IL-17B (PRO1031), and IL-17C (PRO1122). After incubation for 18 hours at 37° C. and 5% $CO_2$, conditioned media were assayed for IL-6 using an ELISA kit (R&D Systems). In contrast to the high level of IL-6 induced by IL-17, both IL-17B (PRO1031) and IL17C (PRO1122) failed to stimulate IL-6 secretion in fibroblast cells (as shown in FIG. 36A).

Figure 36B:
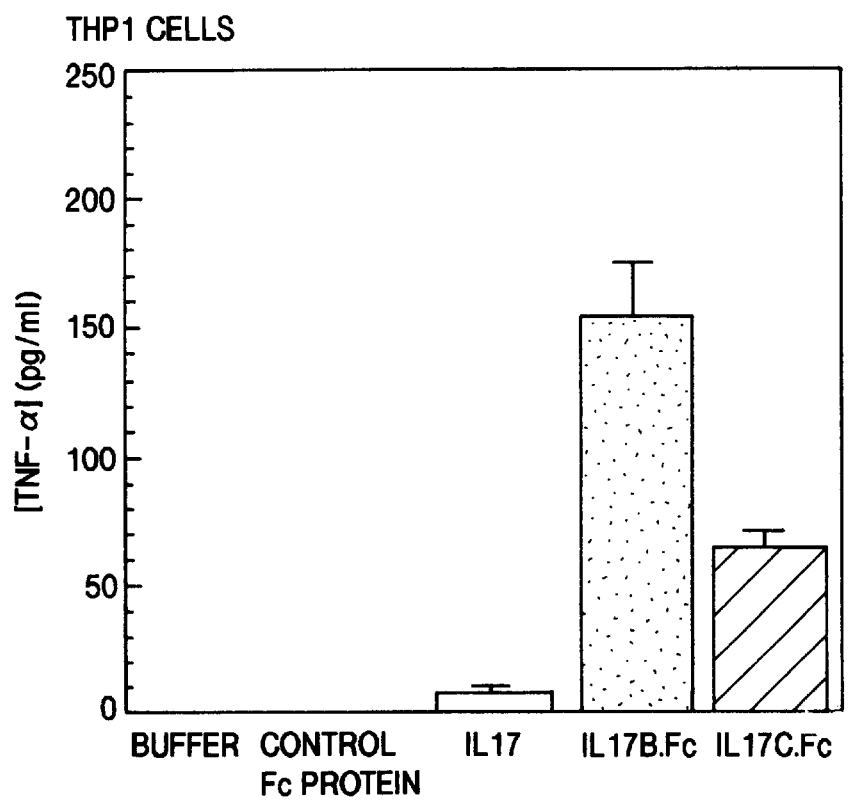

Using the procedure outlined in Yao et al., *Cytokine,* 9: 794 (1997), a human leukemic monocytic cell line, THP-1, was used to assay for the stimulation of TNF-α release by IL-17, IL-17B (PRO1031) and IL-17C (PRO1031) by culturing in RPMI media (10% FBS). After incubation for 18 hour at 37° C. and 5% $CO_2$, conditioned media were quantitated for TNF-α using an ELISA assay kit (R&D Systems). While IL-17 induced only a low level of TNF-α in THP-1 cells, both IL-17B and IL-17C (as Fc fusion proteins) stimulated TNF-α production in THP-1 cells (as shown in FIG. 36B). A control Fc fusion protein had no effect.

Figure 37A:
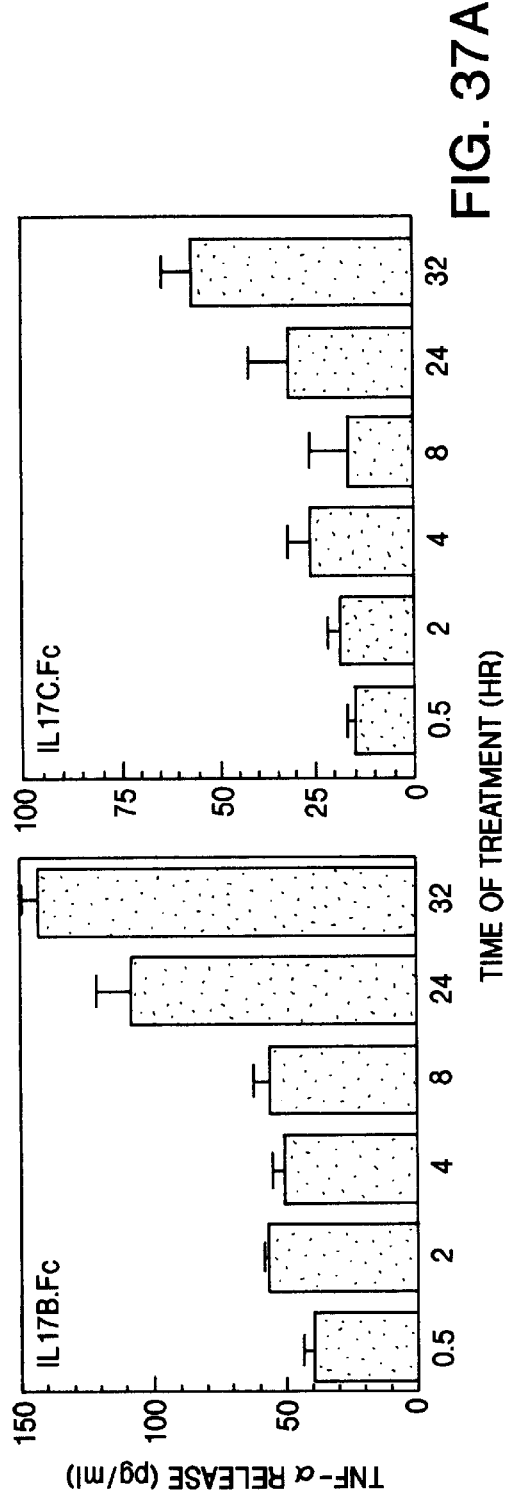
FIG. 37 shows a time course representing the dependence of IL-17B (PRO1031) and IL-17C (PRO1122) activated TNF-α release from THP-1 cells.
Figure 37B:
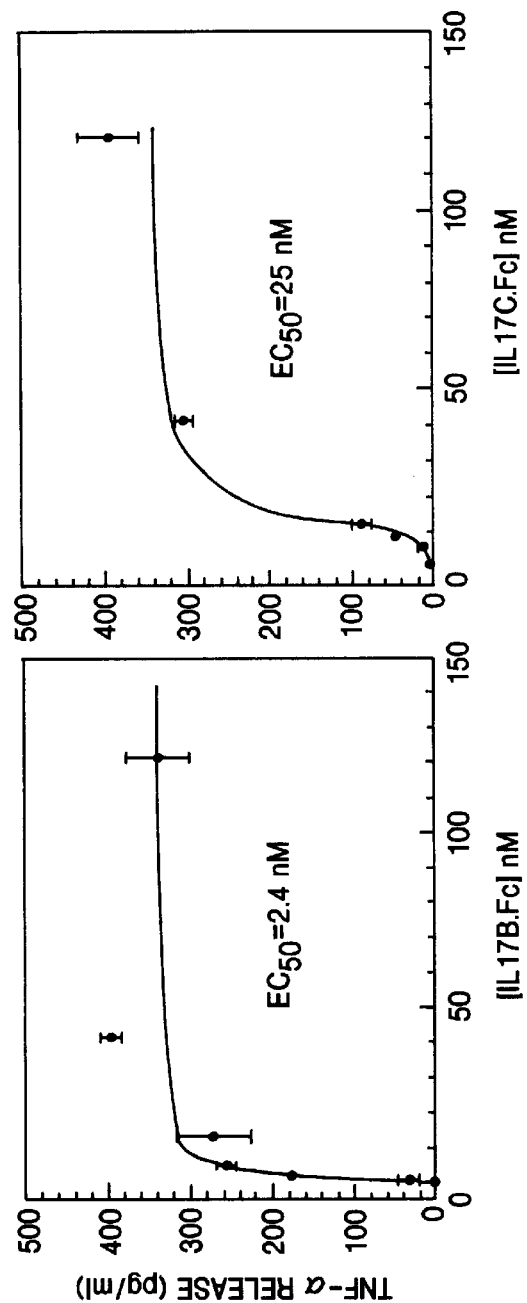

In order to further characterize the stimulation of TNF-α release by IL-17B and IL-17C, the time course and concentration dependence of the response were assayed in THP-1 cells. FIG. 37 illustrates that IL-17B and IL-17C stimulate the release of TNF-α in a time- and concentration-dependent manner. The EC50 for IL-17B stimulation is 2.4 nM, while the EC50 for IL-17C is 25 nM.

While the IL-17B and IL-17C preparations used in these experiments contained undetectable level of endotoxin (less than 1 EU/ml), additional control experiments were performed to confirm that the TNF-α release from THP-1 cells was real and not artifactual. The IL-17B and IL-17C activities were unaffected by polymyxin B treatment and were abolished by heat treatment, further supporting the notion that the proteins themselves were responsible for the activities and not any contaminating endotoxin.

Figure 46A:
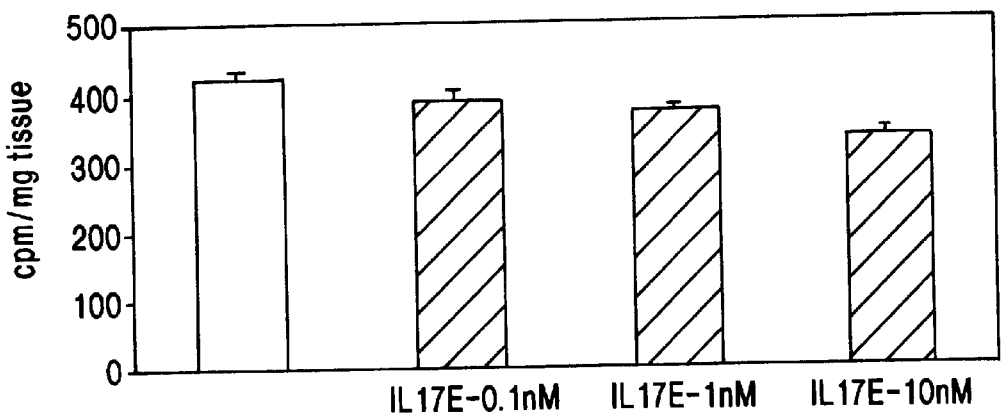
FIGS. 46A–46C shows the effect of IL-17E (PRO10272) on human articular cartilage.
Figure 46B:
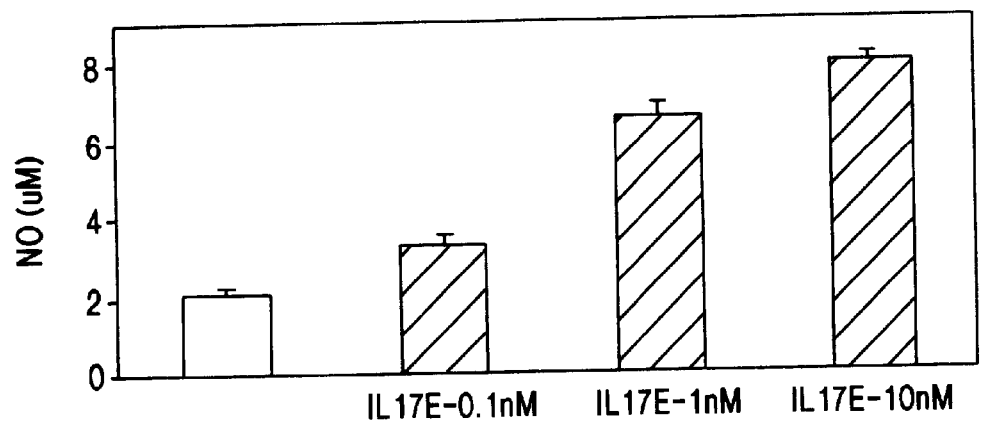
Figure 46C:
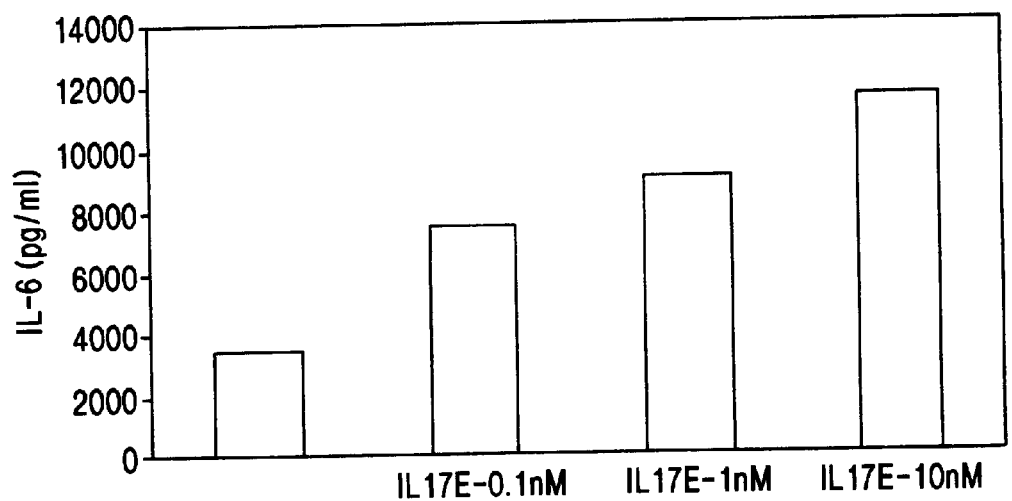

Preparations of IL-17E were used to study the effect on IL-6 production in human articular cartilage. Human articular cartilage was removed from human patients during surgery for joint replacement and cartilage explants were prepared as described in EXAMPLE 30 below. As shown in FIG. 46C, IL-17E was observed to induce IL-6 production in human articular cartilage. Human articular cartilage from diseased joints was cultured in media alone (−) or in combination with IL-17E at 0.1 nM, 1 nM or 10 nM concentrations and matrix synthesis was determined by an ELISA kit (R&D Systems) as described above. In contrast to the both IL-17B (PRO1031) and IL17C (PRO1122) which failed to stimulate IL-6 secretion in fibroblast cells (shown in FIG. 36A), IL-17E induced the production of IL-6, thereby exhibiting biological effects similar to IL-17 with respect to IL-6 release. IL-17 at 10 nM induced the production of IL-6 in human articular cartilage at comparable elevated levels (not shown).

Example 29

Fluorescence-activated Cell Sorter (FACS) Analysis of Binding to THP-1 Cells by IL-17, IL-17B and IL-17C Fusion Proteins THP-1 cells ($5 \times 10^5$) were pre-incubated in PBS containing 5% horse serum at 4° C. for 30 minutes to block non-specific binding. IL-17, IL-17B.Fc, IL-17C.Fc, or control Fc (1 mg each) were added and incubated with the THP-1 cells in a volume of 0.25 ml on ice for 1 hour. For the IL-17 binding experiment, primary anti hIL-17 antibody (1:100 dilution) and secondary goat anti-mouse antibody conjugated to FITC (Jackson Immunology Lab, 1:100 dilution) were added sequentially with 30–60 minutes incubation and extensive washes before each addition. For the Fc fusion proteins, the cells were stained with FITC conjugated goat anti-human IgG (Fc specific, Jackson Immunology Lab, 1:100 dilution). After thorough washes, a minimum of 5,000 cells were analyzed using a FACScan (Becton Dickinson).

Figure 38A:
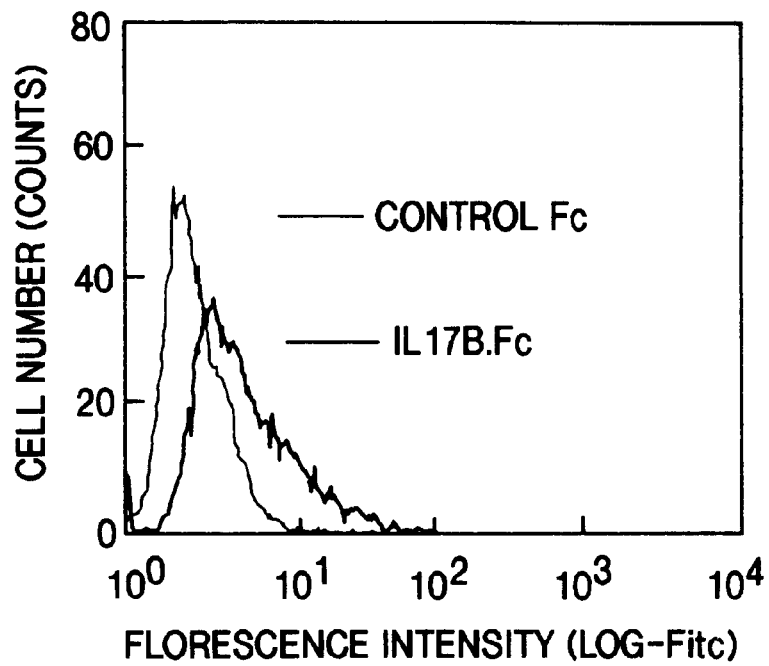
FIG. 38 shows FACS analysis of the binding of IL-17B.Fc and IL-17C.Fc to THP-1 cells as described in EXAMPLE 29. THP-1 cells were incubated with IL-17B.Fc (FIG. 38 partA.) or IL-17C.Fc (FIG. 38 partB.) or control Fc fusion proteins in PBS (5% horse serum) and followed by addition of FITC conjugated anti-Fc secondary antibodies.
Figure 38B:
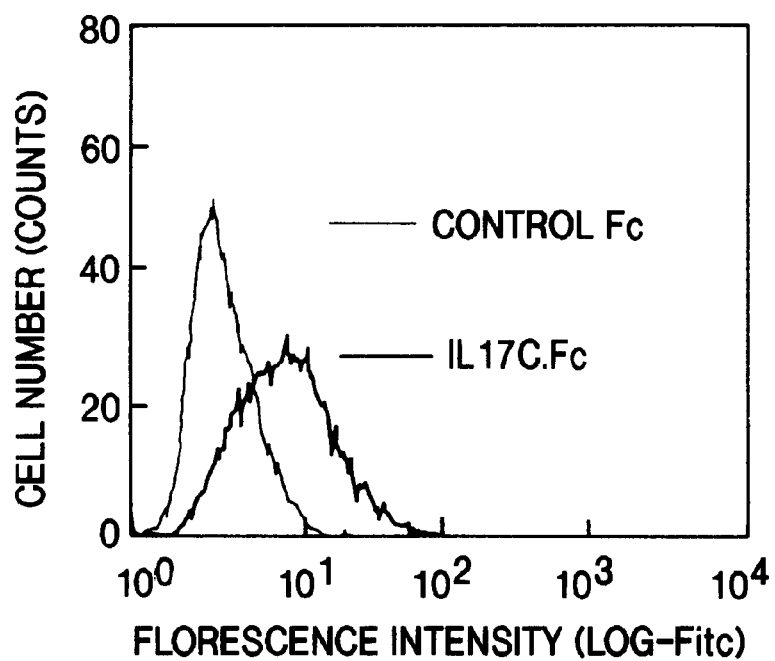

The resulting of the above procedure was that both IL-17B and IL-17C Fc fusion proteins displayed binding to THP-1 cells compared with a control Fc fusion protein (as shown in FIG. 38).

Example 30

Articular Cartilage Explant Assay For IL-17, IL-17C, and IL-17E

A. Introduction

As mentioned previously, IL-17 is likely to play a role in the initiation or maintenance of the proinflammatory response. IL-17 is a cytokine expressed by $CD4^+$ Th cells and induces the secretion of proinflammatory and hematopoietic cytokines (e.g., IL-1b, TNF-α, IL-6, IL-8, GM-CSF) in a number of cell types including synoviocytes and macrophages [Aarvak et al., *J. Immunol.*, 162:1246–1251 (1999); Fossiez et al., *J. Exp. Med.*, 183: 2593–2603 (1996); Jovanovic et al., *J. Immunol.*, 160:3513–3521 (1998)]. In the presence of IL-17, fibroblasts sustain the proliferation of $CD34^+$ hematopoietic progenitors and induce their preferential maturation into neutrophils. As a result, I1-17 may constitute an early initiator of the T cell-dependent inflammatory reaction and be part of the cytokine network which bridges the immune system to hematopoiesis.

Expression of IL-17 has been found in the synovium of patients with rheumatoid arthritis, psoriatic arthritis, or osteoarthritis, but not in normal joint tissues. IL-17 can synergize with the monocyte-derived, proinflammatory cytokines IL-1b or TNF-α to induce IL-6 and GM-CSF. By acting directly on synoviocytes, IL-17 could enhance secretion of proinflammatory cytokines in vivo and thus exacerbate joint inflammation and destruction.

While the role of IL-17 in inflammation has been studied by a number of investigators, the direct effects of IL-17 on articular cartilage have not been well-characterized. To further understand the possible role of IL-17, Applicants have tested the effects of IL-17 on cartilage matrix metabolism. In light of the known catabolic effects of nitric oxide (NO) on cartilage, and the existence of high levels of NO in arthritic joints, NO production was also measured. In addition, studies with two other novel IL-17 homologs IL-17C (PRO1122) and IL-17E (PRO10272) were undertaken to determine if similar physiological effects could be seen.

B. Methods

Articular Cartilage Explants Used in Studies with IL-17, IL-17C and IL-17E

In studies using test proteins IL-17 and/or IL-17C, the metacarpophalangeal joint of a 4–6 month old female pigs was aseptically dissected, and articular cartilage is removed by free-hand slicing in a careful manner so as to avoid the underlying bone. Similarly in studies with both IL-17 and IL-17E, human articular cartilage explants were removed from human patients during surgery for joint replacement. The cartilage from either source was treated similarly for the assays as described below. The cartilage was minced and cultured in bulk for at least 24 hours in a humidified atmosphere of 95% air 5% $CO_2$ in serum free (SF) media (DME/F121:1) with 0.1% BSA and antibiotics. After washing three times, approximately 80 mg of articular cartilage was aliquoted into micronics tubes and incubated for at least 24 hours in the above SF media. IL-17 35 and IL-17C test proteins were then added at 1% either alone or in combination with IL-1α (10 ng/ml) in studies with porcine cartilage. For IL-17 and IL-17E studies, human articular cartilage was treated with various concentrations of IL-17 and IL-17E (0.1 nM, 1 nM and 10 nM, respectively). Control (−) tubes contained media only. Media was harvested and changed at various timepoints (0, 24, 48, 72 hours) and assayed for proteoglycan content using the 1,9-dimethylmethylene blue (DMB) colorimetric assay described in Farndale and Buttle, *Biochem. Biophys. Acta*, 883:173–177 (1985). After labeling (overnight) with $^{35}$S-sulfur, the tubes were weighed to determine the amount of tissue. Following an overnight digestion, the amount of proteoglycan remaining in the tissue as well as proteoglycan synthesis ($^{35}$S-incorporation) is determined.

Measurement of NO Production: The assay is based on the principle that 2,3-diaminonapthalene (DAN) reacts with nitrite under acidic conditions to form 1-(H)-naphthotriazole, a flourescent product. As NO is quickly metabolized into nitrite (NO2-1) and nitrate (NO3-1), detection of nitrite, is one means of detecting (albeit undercounting) the actual NO produced. 10 mL of DAN (0.05 mg/mL in 0.62 M HCl) is added to 100 mL of sample (cell culture supernatant), mixed, and incubated at room temperature for 10–20 minutes. Reaction is terminated with 5 mL of 2.8N NaOH. Formation of 2,3-diaminonaphthotriazole was measured using a Cytoflor flourescent plate reader with excitation at 360 nm and emission read at 450 nm. For optimal measurement of flourescent intensity, black plates with clear bottoms were used.

C. Results and Discussion

Figure 39:
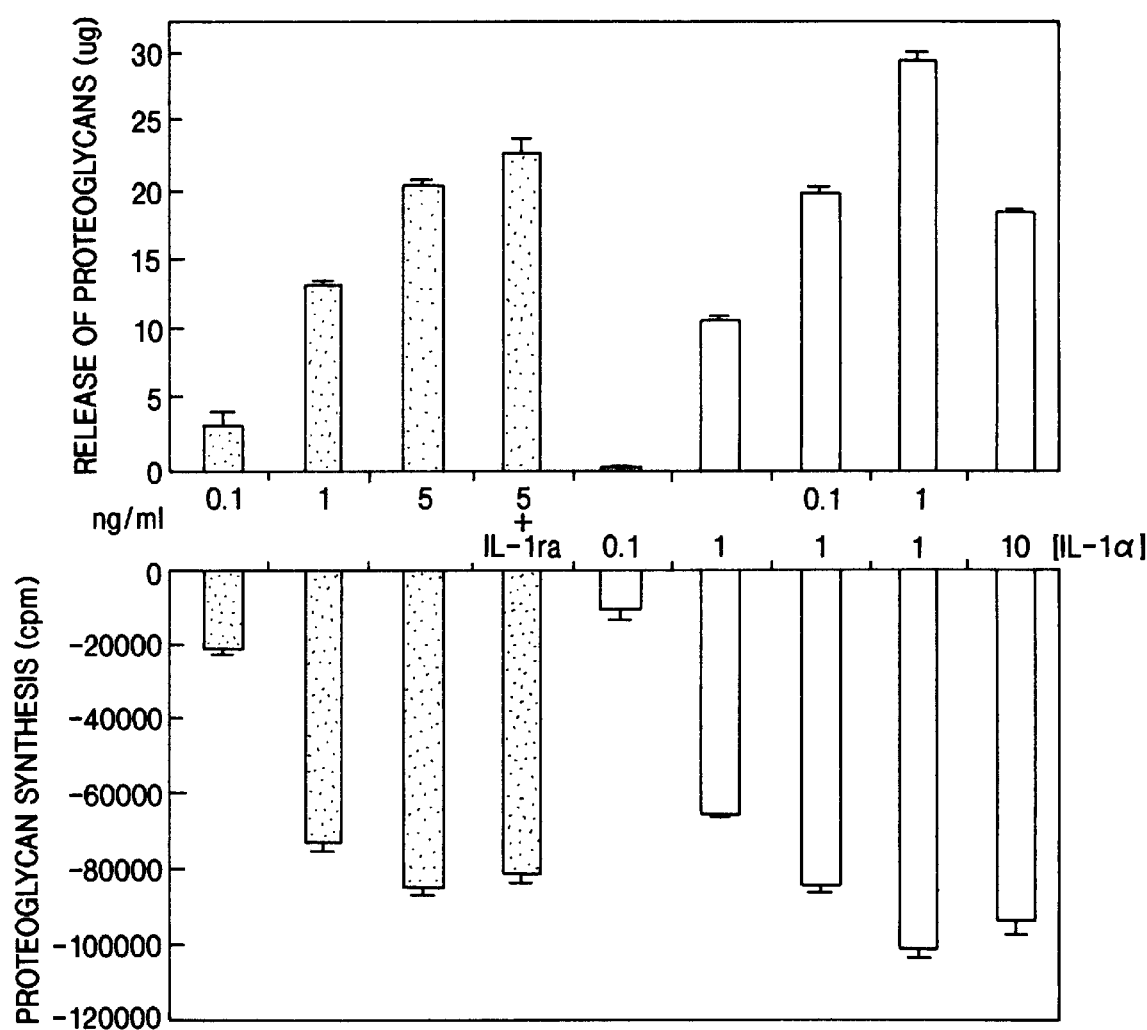
FIG. 39 shows the effect of IL-17 on articular cartilage. Cartilage explants were cultured with the indicated concentration of IL-17 alone (solid) or in the presence of IL-1α at the indicated concentration (hatched) or IL-1ra (IL-1 receptor antagonist, R & D Systems, 1 μg/ml, for 72 hours). Release of proteoglycans (PG) into the media (top panel) indicates matrix breakdown. Matrix synthesis was determined by incorporation of $^{35}$S-sulfate into the tissue (bottom panel).
Figure 40:
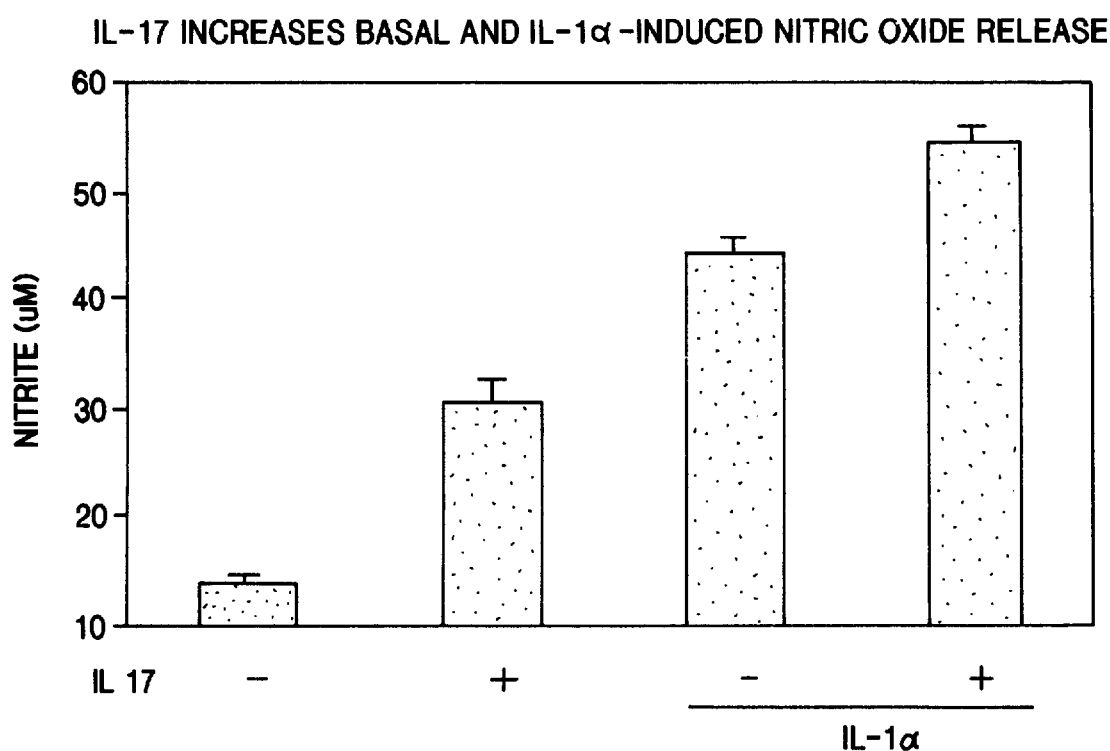
FIG. 40 shows the effect of IL-17 on the release of nitric oxide. Explants were treated with IL-17 (10 ng/ml) alone (left columns) or in the presence of IL-1α (10 ng/ml) (right columns). After 48 hours, media was assayed for nitrite concentration.
Figure 41A:
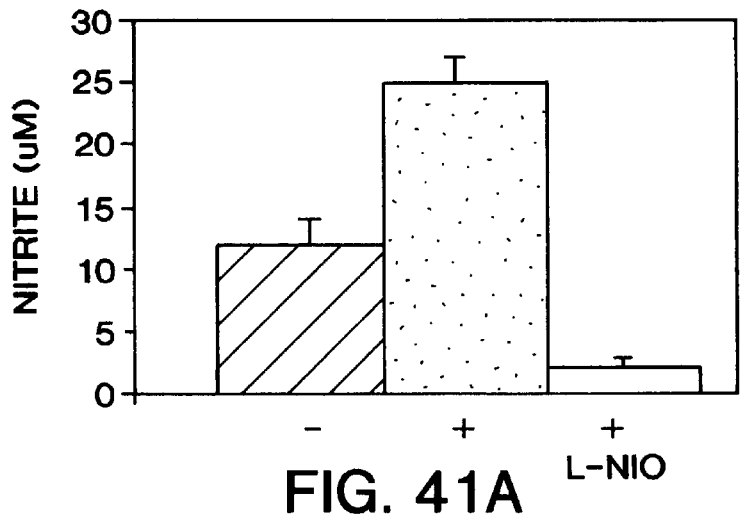
FIG. 41 shows the effect of nitric oxide (NO) on IL-17 induced changes in matrix metabolism. Explants were treated with IL-17 (5 ng/ml) alone (+) or with an irreversible inhibitor of nitric oxide synthase, NOS (L-NIO, Caymen Chemical, 0.5 mM). After 72 hours of treatment, media was assayed for nitrite (FIG. 41 part A.) and proteoglycans (Pgs) (FIG. 41 part B.).
Figure 41B:
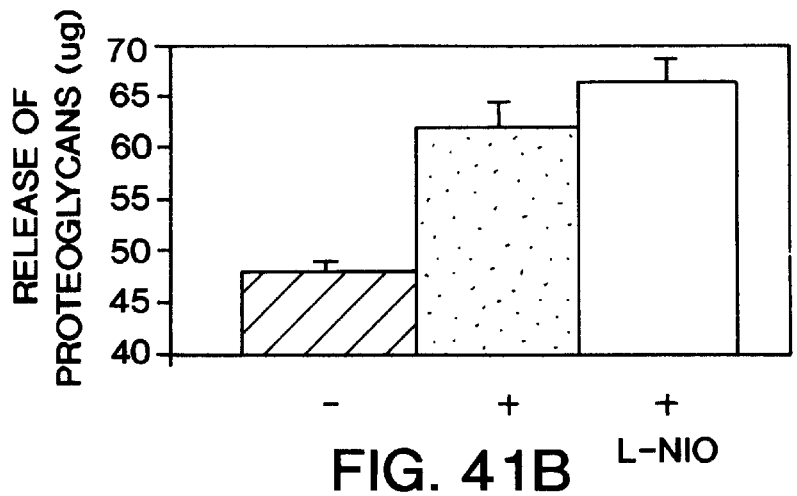
Figure 41C:
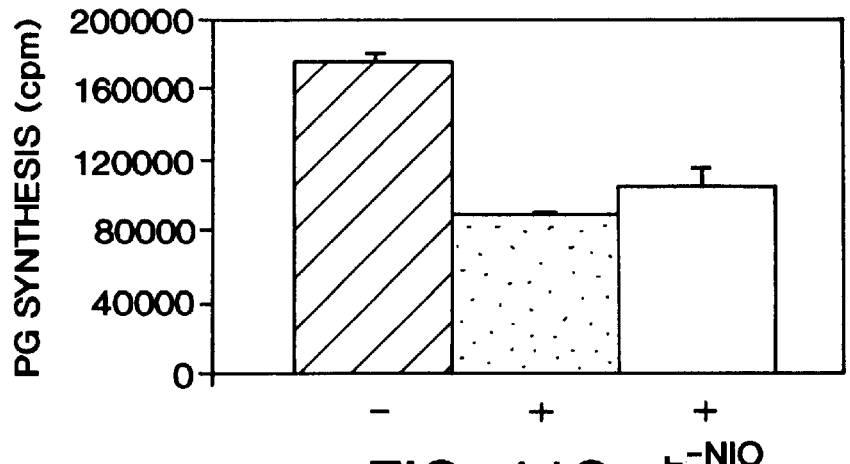
Figure 42:
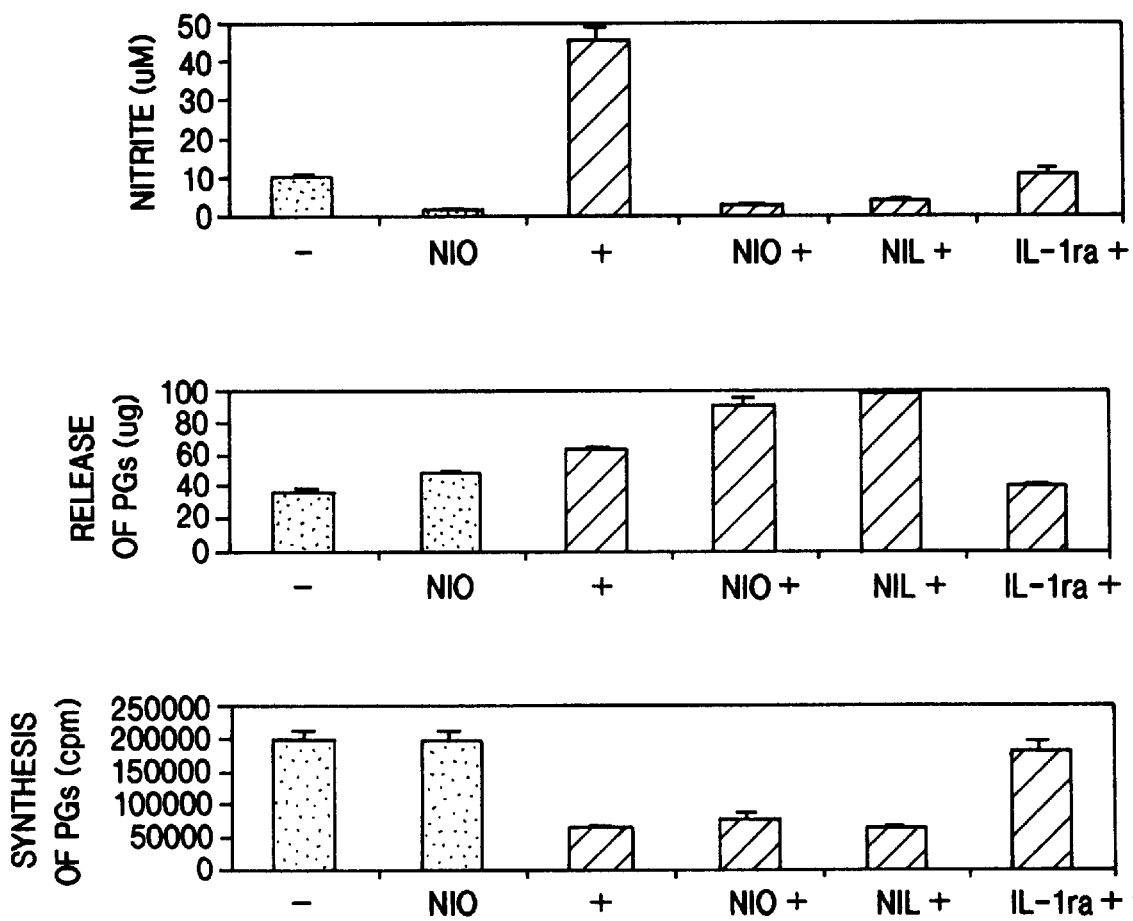
FIG. 42 shows the effect of the inhibition of nitric oxide (NO) on IL-17 induced changes in proteoglycan (PG) metabolism. Articular cartilage explants were treated with IL-1α (5 ng/ml) alone (+) or with inhibitors of NOS (L-NIO or L-NIL) (NIL, reversible NOS inhibitor, Caymen Chemical) or IL-1ra (IL-1 receptor antagonist, R & D Systems, 1 μg/ml). After 72 hours of treatment, media was assayed for nitrite concentration and amount of proteoglycans. Matrix synthesis was determined by incorporation of $^{35}$S-sulphate into the tissue.
Figure 43:
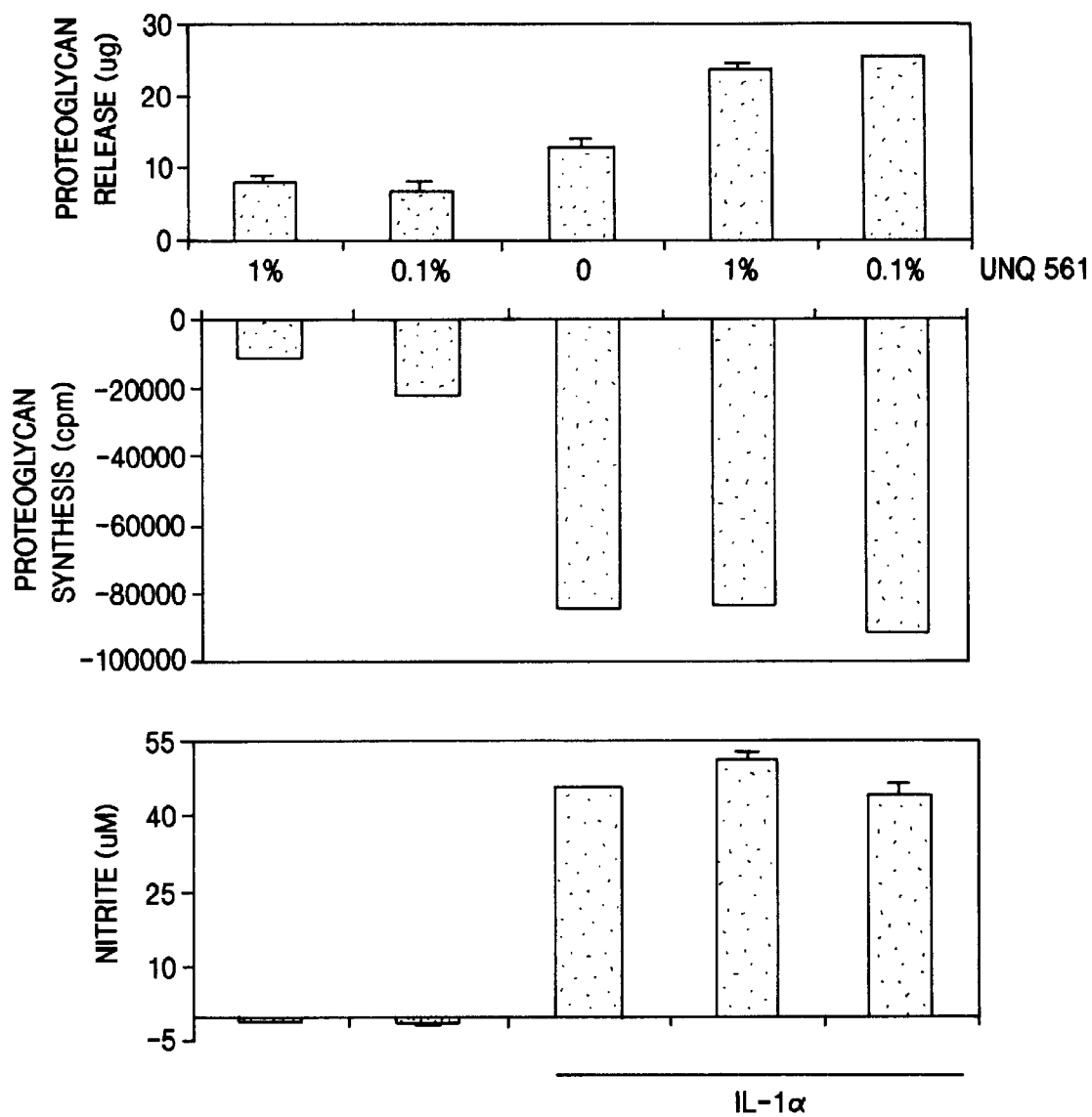
FIG. 43 shows the effect of IL-17C (PRO1122) on articular cartilage. Explants were treated with IL-17C at 1% or 0.1% in the absence (leftmost 3 columns) or presence (rightmost 3 columns) of IL-1α(+) (10 ng/ml. Proteoglycan (PG) release and synthesis are shown as amount above control.

IL-17 was observed to both increase the release of and decrease the synthesis of proteoglycans in both human and female pig articular cartilage explants (porcine extracts results are shown in FIG. 39). Moreover, this effect was additive to the effect observed from IL-1a. The effects of IL-17 are not mediated by the production of nitric oxide, nor does inhibition of nitric oxide release augment matrix breakdown (see FIGS. 40 to 42). IL-17C (PRO1122)was also observed to increase matrix breakdown and inhibit matrix synthesis in female pig articular cartilage explants (FIG. 43). Thus, expression of PRO1 122 is likely to be associated with degenerative cartilagenous disorders.

In addition, the effect of IL-17 and IL-17E (PRO10272) on human articular cartilage explants was studied wherein both IL-17 and IL-17E were observed to inhibit matrix synthesis in human cartilage at various concentrations. Human articular cartilage from diseased joints was cultured in media alone (−) or in combination with either IL-17 or IL-17E at 0.1 nM, 1 nM or 10 nM concentrations, respectively, and matrix synthesis determined by measuring $^{35}$S-sulfate uptake as described above (see FIG. 46A. for results with IL-17E) Likewise, the effects of IL-17 and IL-17E on nitric oxide production were studied. Human articular cartilage was cultured in media alone (−) or in combination with either IL-17 or IL-17E at 0.1 nM, 1 nM or 10 nM concentrations and the production of nitric oxide measured as described in Part B. Methods. (Measurement of NO production). FIG. 46B, demonstrates the effect of IL-17E on nitric acid production wherein various concentration of IL-17E induces nitric oxide production in comparison to the controls (−). IL-17 gave comparable increased levels over the controls (not shown). Thus, expression of PRO10272 is also likely to be associated with degenerative cartilagenous disorders.

In conclusion, IL-17, IL-17C and IL-17E likely contribute to loss of articular cartilage in arthritic joints, and thus inhibition of its activity might limit inflammation and cartilage destruction. IL-1a and IL-17 have similar yet distinct activities, due to their use of different receptors and overlapping downstream signaling mechanisms.

Given the findings of the potent catabolic effects of IL-17 on articular cartilage explants and the homology of IL-17E (PRO10272) and IL-17C (PRO1122) to IL-17, antagonists to any or all of these proteins may be useful for the treatment of inflammatory conditions and cartilage defects such as arthritis.

Finally, it is well known that growth factors can have biphasic effects and that diseased tissue can respond differently than normal tissue to a given factor in vivo. For these reasons, antagonists or agonists (e.g., the proteins themselves) of IL-17E (PRO10272), IL-17C (PRO1122), or IL-17, may be useful for the treatment of inflammatory conditions and joint disorders such as arthritis.

Example 31

Figure 44:
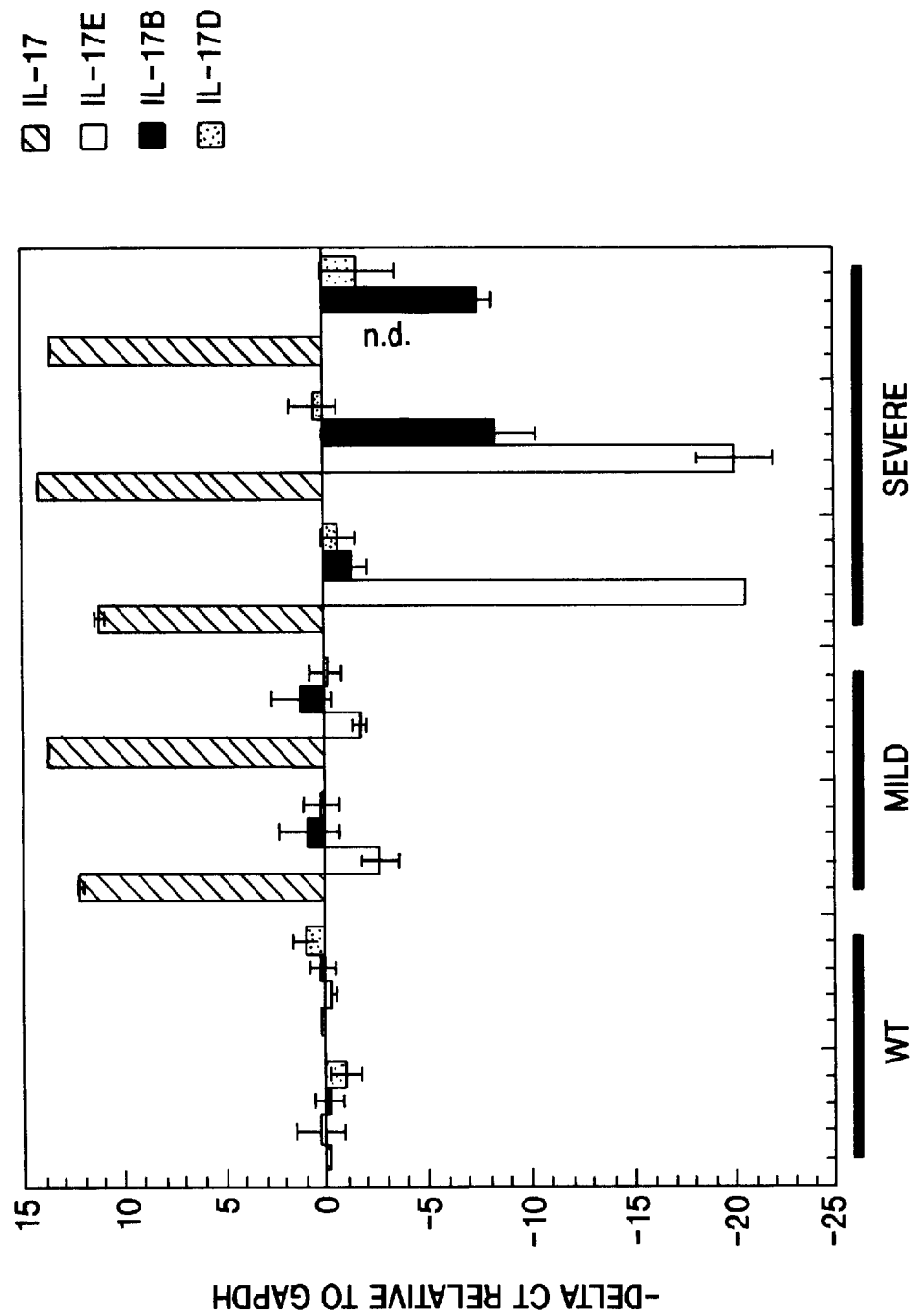
FIG. 44 shows the relative expression of the human IL-17 family in the mouse model of inflammatory bowel disease [IBD] as demonstrated by -delta Ct values relative to GAPDH. IL-17 shows enhanced expression in this mouse model during mild and severe stages of inflammatory bowel disease. In contrast, IL-17E (PRO10272) demonstrates a marked decrease in expression during severe stages of IBD, whereas IL-17B (PRO1031) demonstrates a moderate decrease in expression in severe IBD.

Inflammatory Bowel Disease (IBD): Expression of IL-17 Family in Mouse Model of IBD Mice deficient in the cytokine receptor CRF2-4/IL-10Rb develop spontaneous and progressive colitis that resembles the human condition of inflammatory bowel disease (IBD). This phenotype has been previously reported (Spencer et al., *J. Exp. Med.,* 187:571–578 [1998]). To examine the role of expression of IL-17 family members in this model of IBD, colons were harvested from normal (wild type "WT") mice and from CRF2-4 deficient mice. Colons from CRF2-4 deficient mice were sub-categorized into specimens exhibiting mild IBD and specimens exhibiting more advanced severe IBD. RNA was isolated from the colon samples and the relative expression of IL-17 family members was determined by quantitative PCR (Taqman™). FIG. 44 demonstrates the relative expression of IL-17, IL-17E (DNA147531-2821), IL-17B (DNA59294-1381-1), and IL-17D (DNA173894-2947) represented by -delta CT relative to GAPDH. The expression of IL-17E markedly decreases in more advanced severe IBD compared to expression levels in normal (wild type "WT") mice. In contrast, increased expression values of IL-17 were observed in mild to severe IBD. Thus, IL-17E may serve as a marker for this inflammatory condition.

Example 32

IL-17D Expression in Mouse Model of Stroke

Figure 45:
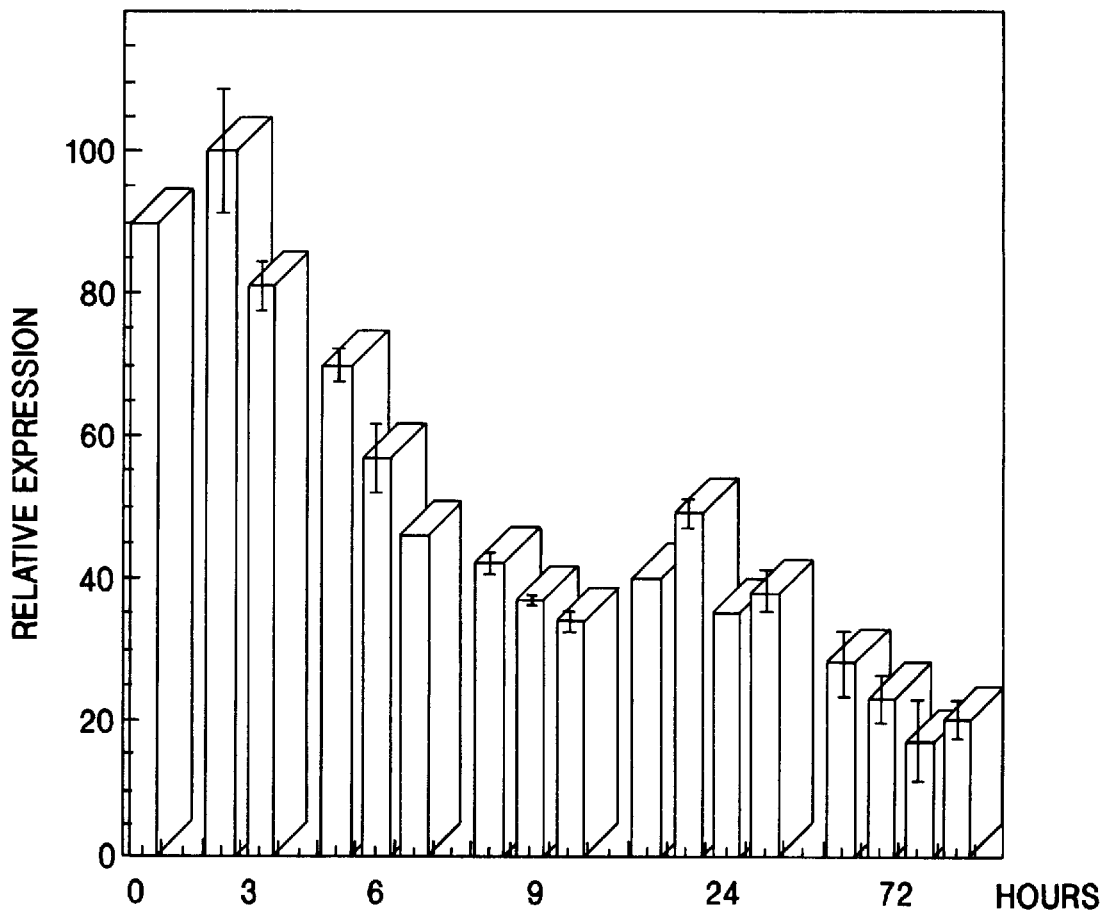
FIG. 45 shows a time course study which measures the relative expression of IL-17D (PRO21175) in a mouse model of stroke over the first 72 hours. IL-17D expression in the brain dramatically decreases from the time stroke is induced to the endpoint of 72 hours.

IL-17D (DNA173894-2947) expression was examined in a murine experimental model of stroke. The right common carotid artery (RCCA) of C57B1/6 male mice was isolated via a midline incision. A loose tie was placed around the vessel. The middle cerebral artery (MCA) was visualized by forming a cranial window in the skull at the level of the rhinal fissure. At the appointed time, the MCA and the RCCA were occluded for a 45 minute ischemic period with 11-0 suture and 6-0 suture, respectively. Following this ischemic insult, the RCCA and MCA sutures were untied to allow reperfusion of the MCA territory. The relative expression of IL-17D was determined by quantitative PCR (Taqman™) using RNA isolated from ischemic cortex at five time points following reperfusion (3, 6, 12, 24 and 72 hours) and compared with the expression of IL-17D observed in RNA isolated from control non-ischemic tissue. FIG. 45 depicts the results of this study. As shown, IL-17D expression decreases rapidly following stroke when examined over the five illustrated time points.

Example 33

Microarray Analysis to Detect Overexpression of PRO Polypeptides in Cancerous Tumors Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

The methodology of hybridization of nucleic acids and microarray technology is well known in the art. In the present example, the specific preparation of nucleic acids for hybridization and probes, slides, and hybridization conditions are all detailed in U.S. Provisional Patent Application Serial No. 60/193,767, filed on Mar. 31, 2000 and which is herein incorporated by reference.

In the present example, cancerous tumors derived from various human tissues were studied for PRO polypeptide-encoding gene expression relative to non-cancerous human tissue in an attempt to identify those PRO polypeptides which are overexpressed in cancerous tumors. Two sets of experimental data were generated. In one set, cancerous human colon tumor tissue and matched non-cancerous human colon tumor tissue from the same patient ("matched colon control") were obtained and analyzed for PRO polypeptide expression using the above described microarray technology. In the second set of data, cancerous human tumor tissue from any of a variety of different human tumors was obtained and compared to a "universal" epithelial control sample which was prepared by pooling non-cancerous human tissues of epithelial origin, including liver, kidney, and lung. mRNA isolated from the pooled tissues represents a mixture of expressed gene products from these different tissues. Microarray hybridization experiments using the pooled control samples generated a linear plot in a 2-color analysis. The slope of the line generated in a 2-color analysis was then used to normalize the ratios of (test:control detection) within each experiment. The normalized ratios from various experiments were then compared and used to identify clustering of gene expression. Thus, the pooled "universal control" sample not only allowed effective relative gene expression determinations in a simple 2-sample comparison, it also allowed multi-sample comparisons across several experiments.

In the present experiments, nucleic acid probes derived from the herein described PRO polypeptide-encoding nucleic acid sequences were used in the creation of the microarray and RNA from the tumor tissues listed above were used for the hybridization thereto. A value based upon the normalized ratio:experimental ratio was designated as a "cutoff ratio". Only values that were above this cutoff ratio were determined to be significant. Table 7 below shows the results of these experiments, demonstrating that various PRO polypeptides of the present invention are significantly overexpressed in various human tumor tissues as compared to a non-cancerous human tissue control. As described above, these data demonstrate that the PRO polypeptides of the present invention are useful not only as diagnostic markers for the presence of one or more cancerous tumors, but also serve as therapeutic targets for the treatment of those tumors.

TABLE 7

| Molecule | is overexpressed in: | as compared to: |
|---|---|---|
| PRO1031 | lung tumor | universal normal control |
| PRO1122 | breast tumor | universal normal control |
| PRO1122 | lung tumor | universal normal control |
| PRO5801 | colon tumor | universal normal control |
| PRO21175 | breast tumor | universal normal control |
| PRO21175 | colon tumor | universal normal control |
| PRO21175 | lung tumor | universal normal control |

Deposit of Material

The following materials have been deposited with the American Type Culture Collection, 10801 University Blvd., Manassas, Va. 20110-2209, USA (ATCC):

| Material | ATCC Dep. No. | Deposit Date |
|---|---|---|
| DNA59294-1381 | 209866 | May 14, 1998 |
| DNA62377-1381-1 | 203552 | Dec. 22, 1998 |
| DNA147531-2821 | PTA-1185 | Jan. 11, 2000 |
| DNA173894-2947 | PTA-2108 | Jun. 20, 2000 |
| DNA115291-2681 | PTA-202 | Jun. 8, 1999 |
| DNA164625-2890 | PTA-1535 | Mar. 21, 2000 |
| DNA119502-2789 | PTA-1082 | Dec. 22, 1999 |
| DNA154095-2998 | PTA-2591 | Oct. 10, 2000 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated polypeptide comprising amino acid residues 1 to 177 of SEQ ID NO:6.

2. A chimeric molecule comprising a polypeptide according to claim 1 fused to a heterologous polypeptide.

3. The chimeric molecule of claim 2, wherein said heterologous polypeptide is an epitope tag sequence or an Fc region of an immunoglobulin.

4. A composition of matter comprising the polypeptide of claim 1 in combination with a carrier.

5. The composition of matter of claim 4, wherein said carrier is a pharmaceutically acceptable carrier.

6. The composition of matter of claim 4, wherein said polypeptide is capable of increasing the proliferation of T-lymphocytes in a mammal.

7. The composition of matter of claim 4 comprising a therapeutically effective amount of said polypeptide.

8. An isolated polypeptide comprising the amino acid sequence of SEQ ID NO:6 encoded by the full-length coding sequence of the cDNA deposited under ATCC accession.

* * * * *